United States Patent
Yang

(10) Patent No.: US 10,933,111 B2
(45) Date of Patent: *Mar. 2, 2021

(54) TREATING DRY EYE DISORDERS

(71) Applicant: Boston Biotechnology US CORP, Cambridge, MA (US)

(72) Inventor: Dan Yang, Kunming (CN)

(73) Assignee: Boston Biotechnology US CORP, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/810,674

(22) Filed: Mar. 5, 2020

(65) Prior Publication Data

US 2020/0215144 A1 Jul. 9, 2020

Related U.S. Application Data

(63) Continuation of application No. 16/636,470, filed as application No. PCT/CN2020/070798 on Jan. 8, 2020.

(30) Foreign Application Priority Data

Jan. 8, 2019 (WO) ................ PCT/CN2019/070856

(51) Int. Cl.
| | | |
|---|---|---|
| A61K 36/00 | (2006.01) |
| A61K 36/889 | (2006.01) |
| A61P 27/04 | (2006.01) |
| A61K 38/13 | (2006.01) |
| A61K 9/00 | (2006.01) |

(52) U.S. Cl.
CPC .......... *A61K 36/889* (2013.01); *A61K 9/0048* (2013.01); *A61K 38/13* (2013.01); *A61P 27/04* (2018.01)

(58) Field of Classification Search
None
See application file for complete search history.

(56) References Cited

U.S. PATENT DOCUMENTS

| 4,608,202 A | * | 8/1986 | Lepper | ...................... C11C 3/04 554/167 |
| 2013/0210912 A1 | * | 8/2013 | Davio | .................. A61K 9/0048 514/530 |
| 2016/0101050 A1 | * | 4/2016 | Lee | ...................... A61K 9/1075 424/400 |

FOREIGN PATENT DOCUMENTS

| CN | 104203215 | 12/2014 |
| CN | 105792848 | 7/2016 |
| CN | 107334868 | 11/2017 |
| WO | WO 2008/106228 | 9/2008 |
| WO | WO 2017/147470 | 8/2017 |

OTHER PUBLICATIONS

Barabino et al., "Animal models of dry eye: a critical assessment of opportunities and limitations," Investigative ophthalmology & visual science, Jun. 2004, 45:1641-1646.
Dong et al., "Cassiae semen: A review of its phytochemistry and pharmacology," Molecular medicine reports, Jun. 29, 2017, 16(3):2331-2346.
Jayasekara et al., "Processing technologies for virgin coconut oil and coconut based confectionaries and beverages," Proceedings of International Coconut Summit, May 7-11, 2007, Kochi, India, 15 pages.
Yang et al., "Current progress on clinical application of cyclosporine A," Int Eye Sci., Mar. 2017, 17(3):463-466 (English Abstract Only).
International Search Report and Written Opinion in International Application No. PCT/CN2019/070856, dated Oct. 10, 2019, 14 pages.
International Search Report and Written Opinion in International Application No. PCT/CN2020/070798, dated Apr. 14, 2020, 14 pages.
Kappally et al., "Coconut Oil—A Review of Potential Applications," Hygeia: journal for drugs and medicines, Oct. 8, 2015, 2(7):34-41.
Leary et al., "AVMA Guidelines for the Euthanasia of Animals. 2013 Edition," The American Veterinary Medical Association, 2013, 102 pages.
Songlin, "Coconut Integrated Processing Technology," China Agricultural Press, Jun. 30, 2007, pp. 161-166 (English Abstract Only).
Sridhar, "Dry Eyes: Diagnosis and Management," U.S. Chinese Journal of Ophthalmology, Mar. 31, 2002, 1(2):4-13.

* cited by examiner

*Primary Examiner* — Qiuwen Mi

(74) *Attorney, Agent, or Firm* — Fish & Richardson P.C.

(57) ABSTRACT

This disclosure is related to compositions and methods for treating dry dye disorders.

20 Claims, 84 Drawing Sheets

FIG. 43

| RT [min] | Molecular Weight | Name | Molecular Weight (predicted) | Δppm | VIP | T-test | Fold change (log2(Prco/Orco)) | Average of Orco | Average of Prco |
|---|---|---|---|---|---|---|---|---|---|
| 3.05 | 114.0685 | 3-Hexenoic acid | 114.0681 | 3 | 1.30992 | 0.00 | -10.59 | 1555.64 | 1.01 |
| 7.152 | 224.1779 | 5,8-Tetradecadienoic acid | 224.1776 | 1 | 1.30485 | 0.00 | -7.22 | 72.84 | 0.49 |
| 4.761 | 117.0582 | Indole | 117.0578 | 2 | 1.32013 | 0.00 | -7.08 | 191.24 | 1.41 |
| 4.761 | 104.0631 | Styrene | 104.0626 | 4 | 1.32266 | 0.00 | -6.98 | 39.09 | 0.31 |
| 8.347 | 453.2861 | LysoPE(16:0/0:0) | 453.2855 | 1 | 1.27166 | 0.00 | -6.81 | 70.21 | 0.63 |
| 2.638 | 126.032 | Hydroxyhydroquinone | 126.0317 | 2 | 1.29315 | 0.00 | -6.76 | 251.41 | 2.32 |
| 4.759 | 100.0531 | Tiglic acid | 100.0524 | 6 | 1.30471 | 0.00 | -6.60 | 51.89 | 0.53 |
| 8.056 | 572.2973 | 1-Palmitoylglycerophosphoinositol | 572.2962 | 2 | 1.24571 | 0.00 | -6.24 | 65.85 | 0.87 |
| 7.879 | 301.2984 | Sphinganine | 301.2981 | 1 | 1.28548 | 0.00 | -6.14 | 260.79 | 3.70 |
| 0.848 | 103.064 | γ-Aminobutryic acid | 103.0633 | 6 | 1.30895 | 0.00 | -6.12 | 18.85 | 0.27 |
| 9.93 | 523.3647 | LysoPC(18:0) | 523.3638 | 2 | 1.24686 | 0.00 | -6.08 | 56.13 | 0.83 |
| 8.207 | 628.3596 | LysoPI(20:0/0:0) | 628.3588 | 1 | 1.23681 | 0.00 | -6.04 | 8.26 | 0.13 |
| 0.836 | 103.1002 | Choline | 103.0997 | 4 | 1.33801 | 0.00 | -5.47 | 583.70 | 13.13 |
| 8.609 | 495.3332 | LysoPC(16:0) | 495.3325 | 1 | 1.24394 | 0.00 | -5.37 | 153.97 | 3.71 |
| 6.394 | 134.1098 | p-Cymene | 134.1096 | 1 | 1.33263 | 0.00 | -5.28 | 3947.29 | 101.52 |
| 6.394 | 170.1308 | Citronellic acid | 170.1307 | 0 | 1.33382 | 0.00 | -5.25 | 15008.76 | 394.36 |
| 9.344 | 481.3176 | LysoPC(15:0) | 481.3168 | 2 | 1.25809 | 0.00 | -5.16 | 21.83 | 0.61 |
| 0.848 | 182.0794 | D-Mannitol | 182.079 | 2 | 1.26496 | 0.00 | -5.15 | 101.20 | 2.84 |
| 8.481 | 523.292 | 1-Oleoylglycerophosphoserine | 523.291 | 2 | 1.24024 | 0.00 | -5.05 | 70.57 | 2.13 |
| 4.848 | 156.1153 | 2-Nonenoic acid | 156.115 | 1 | 1.31522 | 0.00 | -4.95 | 194.67 | 6.32 |
| 4.762 | 131.0738 | 3-Methylindole | 131.0735 | 2 | 1.32172 | 0.00 | -4.93 | 42.89 | 1.40 |
| 0.804 | 174.112 | L-Arginine | 174.1117 | 1 | 1.21541 | 0.00 | -4.76 | 33.33 | 1.23 |
| 0.886 | 135.0548 | Adenine | 135.0545 | 2 | 1.35083 | 0.00 | -4.68 | 14.11 | 0.55 |
| 0.92 | 122.0484 | Niacinamide | 122.048 | 3 | 1.30195 | 0.00 | -4.59 | 22.07 | 0.92 |
| 6.918 | 315.2778 | Dehydrophytosphingosine | 315.2773 | 1 | 1.28427 | 0.00 | -4.22 | 19.18 | 1.03 |

FIG. 43 (Continued)

| | | | | | | | | |
|---|---|---|---|---|---|---|---|---|
| 1.305 | 131.0949 | L-Leucine | 131.0946 | 2 | 1.20314 | 0.00 | -3.51 | 57.81 | 5.08 |
| 9.604 | 200.1779 | lauric acid | 200.1776 | 1 | 1.29273 | 0.00 | -3.44 | 14.55 | 1.34 |
| 9.487 | 436.2595 | DHAP(18:0) | 436.259 | 1 | 1.19592 | 0.00 | -3.30 | 586.71 | 59.77 |
| 6.291 | 184.1466 | 10-hendecenoic acid | 184.1463 | 1 | 1.31142 | 0.00 | -3.28 | 265.66 | 27.43 |
| 9.878 | 635.4535 | PE(14:0/14:0) | 635.4526 | 1 | 1.00121 | 0.00 | -3.13 | 65.15 | 7.43 |
| 0.878 | 115.0637 | L-Proline | 115.0633 | 3 | 1.29547 | 0.00 | -3.10 | 20.30 | 2.36 |
| 9.191 | 392.2333 | CPA(16:0/0:0) | 392.2328 | 1 | 1.23101 | 0.00 | -3.09 | 105.14 | 12.33 |
| 0.86 | 147.0533 | L-Glutamate | 147.0532 | 0 | 1.17512 | 0.00 | -2.60 | 6.35 | 1.05 |
| 1.154 | 123.0324 | Niacin | 123.032 | 3 | 1.15057 | 0.00 | -2.48 | 2.78 | 0.50 |
| 0.891 | 129.0793 | DL-pipecolic acid | 129.079 | 2 | 1.21088 | 0.00 | -2.48 | 4.78 | 0.86 |
| 0.845 | 89.04832 | β-Alanine | 89.0477 | 6 | 1.15679 | 0.00 | -2.44 | 6.10 | 1.12 |
| 11.377 | 310.2874 | cis-gondoic acid | 310.2872 | 1 | 1.31185 | 0.00 | -2.34 | 64.75 | 12.82 |
| 12.039 | 338.3187 | Erucic acid | 338.3185 | 1 | 1.17317 | 0.00 | -2.11 | 28.43 | 6.59 |
| 2.715 | 187.0635 | Indoleacrylic acid | 187.0633 | 0 | 1.13561 | 0.00 | -2.01 | 7.04 | 1.75 |
| 1.841 | 165.0793 | L-Phenylalanine | 165.079 | 1 | 1.17102 | 0.00 | -2.00 | 11.84 | 2.97 |
| 9.121 | 298.2511 | Ricinoleic acid | 298.2508 | 1 | 1.29337 | 0.00 | -1.94 | 42.45 | 11.04 |
| 0.896 | 117.0793 | L-Valine | 117.079 | 2 | 1.14442 | 0.00 | -1.63 | 17.67 | 5.71 |
| 10.687 | 282.2561 | Oleic Acid | 282.2559 | 0 | 1.2361 | 0.00 | -1.61 | 329.72 | 107.77 |
| 10.689 | 226.1934 | Myristoleic acid | 226.1933 | 0 | 1.15467 | 0.00 | -1.53 | 4.93 | 1.71 |
| 9.65 | 302.2249 | Eicosapentaenoic acid | 302.2246 | 1 | 1.17901 | 0.00 | -1.32 | 18.26 | 7.29 |
| 0.912 | 131.0949 | L-Isoleucine | 131.0946 | 2 | 1.00877 | 0.00 | -1.25 | 18.19 | 7.67 |
| 9.537 | 299.2827 | Sphingosine | 299.2824 | 1 | 1.12168 | 0.00 | -0.85 | 22.82 | 12.63 |
| 11.788 | 164.0839 | 3-Phenylbutyric acid | 164.0837 | 1 | 1.13929 | 0.00 | -0.77 | 104.61 | 61.22 |
| 8.609 | 254.2248 | cis-9-palmitoleic acid | 254.2246 | 0 | 1.00975 | 0.00 | -0.77 | 44.50 | 26.16 |
| 16.282 | 634.4582 | PA(10:0/21:0) | 634.4574 | 1 | 1.13896 | 0.00 | -0.60 | 62.08 | 40.96 |
| 10.876 | 283.2876 | Stearamide | 283.2875 | 0 | 1.07961 | 0.00 | 0.70 | 4744.44 | 7689.39 |
| 6.339 | 183.0661 | Phosphocholine | 183.066 | 0 | 1.15393 | 0.00 | 1.06 | 43.83 | 91.29 |
| 12.426 | 456.3816 | DG(12:0/12:0/0:0) | 456.3815 | 0 | 1.31387 | 0.00 | 1.44 | 544.43 | 1473.96 |
| 16.216 | 642.5202 | DG(18:1n9/0:0/20:4n3) | 642.5223 | 3 | 1.20758 | 0.00 | 1.93 | 43.13 | 164.51 |
| 0.765 | 180.0417 | m-Hydroxyphenylpyruvic acid | 180.0423 | 3 | 1.14298 | 0.00 | 2.01 | 3.01 | 12.13 |

FIG. 43 (Continued)

| | | | | | | | |
|---|---|---|---|---|---|---|---|
| 11.757 | 428.3504 | DG(8:0/0:0/14:0) | 428.3502 | 1 | 1.28693 | 0.00 | 2.46 | 269.10 | 1476.65 |
| 11.426 | 440.3297 | Camelledionol | 440.329 | 1 | 1.09976 | 0.00 | 2.53 | 4.34 | 25.00 |
| 9.739 | 436.2806 | Pangamic acid | 436.2785 | 5 | 1.18309 | 0.00 | 2.55 | 2.91 | 17.03 |
| 11.148 | 554.4552 | TG(8:0/8:0/14:0) | 554.4546 | 1 | 1.26666 | 0.00 | 2.56 | 10.20 | 60.08 |
| 10.115 | 330.2772 | MG(16:0/0:0/0:0) | 330.277 | 1 | 1.28227 | 0.00 | 2.76 | 82.91 | 560.29 |
| 10.739 | 280.2405 | Linoleic acid | 280.2402 | 0 | 1.24397 | 0.00 | 3.24 | 2.95 | 27.80 |
| 10.124 | 214.1935 | Tridecanoic acid | 214.1933 | 1 | 1.24984 | 0.00 | 3.29 | 2.16 | 21.15 |
| 11.722 | 582.4865 | TG(12:0/12:0/8:0) | 582.4859 | 1 | 1.18263 | 0.00 | 3.35 | 0.69 | 7.04 |
| 10.777 | 358.3085 | MG(18:0/0:0/0:0) | 358.3083 | 1 | 1.25023 | 0.00 | 3.40 | 11.23 | 118.34 |
| 10.46 | 408.3032 | Ganodosterone | 408.3028 | 1 | 1.3016 | 0.00 | 3.51 | 2.35 | 26.72 |
| 12.549 | 610.5178 | TG(13:0/13:0/8:0) | 610.5172 | 1 | 1.11863 | 0.00 | 3.70 | 0.91 | 11.80 |
| 9.185 | 219.1092 | Pantothenic Acid | 219.1107 | 6 | 1.32599 | 0.00 | 3.77 | 4.94 | 67.31 |
| 4.369 | 148.0527 | Cinnamic acid | 148.0524 | 1 | 1.28382 | 0.00 | 3.92 | 0.43 | 6.49 |
| 5.502 | 162.0683 | Methyl cinnamate | 162.0681 | 1 | 1.25513 | 0.00 | 4.11 | 0.55 | 9.54 |
| 11.808 | 366.3501 | Nervonic acid | 366.3498 | 1 | 1.2384 | 0.00 | 4.24 | 3.00 | 56.82 |
| 8.824 | 372.2881 | DG(8:0/10:0/0:0) | 372.2876 | 1 | 1.26699 | 0.00 | 4.57 | 1.98 | 46.96 |
| 9.188 | 302.246 | MG(0:0/14:0/0:0) | 302.2457 | 1 | 1.29614 | 0.00 | 4.59 | 26.43 | 638.56 |
| 11.373 | 498.3926 | TG(10:0/8:0/8:0) | 498.392 | 1 | 1.28826 | 0.00 | 4.63 | 25.14 | 622.63 |
| 11.71 | 450.348 | Vitamin K1 | 450.3498 | 4 | 1.30455 | 0.00 | 4.70 | 0.33 | 8.56 |
| 11.712 | 428.3658 | Stigmastane-3,6-dione | 428.3654 | 1 | 1.28578 | 0.00 | 4.78 | 0.99 | 27.13 |
| 12.869 | 396.3396 | Ergosterol | 396.3392 | 1 | 1.28092 | 0.00 | 5.02 | 0.45 | 14.66 |
| 10.695 | 424.2983 | LysoPA(18:0e/0:0) | 424.2954 | 7 | 1.24175 | 0.00 | 5.05 | 0.17 | 5.60 |
| 10.663 | 344.293 | MG(17:0/0:0/0:0) | 344.2927 | 1 | 1.26969 | 0.00 | 5.08 | 0.38 | 12.94 |
| 10.355 | 480.2857 | PA(8:0/12:0) | 480.2852 | 1 | 1.24035 | 0.00 | 5.24 | 0.28 | 10.60 |
| 10.965 | 508.3174 | PA(8:0/14:0) | 508.3165 | 2 | 1.25823 | 0.00 | 5.25 | 0.32 | 12.31 |
| 11.886 | 442.3816 | Betulin | 442.3811 | 1 | 1.26139 | 0.00 | 5.25 | 0.26 | 10.10 |
| 9.956 | 310.251 | (R)-2-Hydroxystearic acid | 310.2508 | 1 | 1.26556 | 0.00 | 5.49 | 0.38 | 17.11 |
| 10.162 | 454.3088 | Ubiquinone-4 | 454.3083 | 1 | 1.2808 | 0.00 | 5.72 | 1.24 | 65.46 |
| 13.377 | 384.3395 | Vitamin D3 | 384.3392 | 1 | 1.31213 | 0.00 | 5.90 | 0.29 | 17.64 |
| 7.651 | 424.2256 | PA(8:0/8:0) | 424.2226 | 7 | 1.29752 | 0.00 | 6.09 | 0.33 | 22.23 |

FIG. 43 (Continued)

| | | | | | | | |
|---|---|---|---|---|---|---|---|
| 13.912 | 410.3552 | Delta 8,14 -Sterol | 410.3549 | 1 | 1.29752 | 0.00 | 6.22 | 1.92 | 143.02 |
| 7.652 | 286.2147 | Hexadecanedioic acid | 286.2144 | 1 | 1.29604 | 0.00 | 6.24 | 0.45 | 34.04 |
| 14.297 | 412.3708 | Stigmasterol | 412.3705 | 1 | 1.34041 | 0.00 | 6.38 | 8.66 | 723.37 |
| 11.249 | 426.3501 | Stigmast-22-ene-3,6-dione | 426.3498 | 1 | 1.19498 | 0.00 | 6.41 | 0.84 | 71.05 |
| 9.827 | 316.2618 | MG(0:0/15:0/0:0) | 316.2614 | 1 | 1.30143 | 0.00 | 6.74 | 0.23 | 24.08 |
| 7.597 | 344.2568 | DG(8:0/8:0/0:0) | 344.2563 | 2 | 1.29587 | 0.00 | 6.90 | 0.35 | 41.46 |
| 13.788 | 398.3552 | Campest-4-en-3-one | 398.3549 | 1 | 1.13222 | 0.00 | 7.25 | 1.07 | 162.35 |
| 12.881 | 446.374 | Stigmastentriol | 446.376 | 4 | 1.30093 | 0.00 | 7.73 | 0.43 | 91.98 |

FIG. 44

| RT [min] | Molecular Weight | Name | Molecular Weight (predicted) | Δppm | VIP | T-test | Fold change (log2(Prco/Orco)) | Average of Orco | Average of Prco |
|---|---|---|---|---|---|---|---|---|---|
| 0.867 | 342.1157 | Sucrose | 342.1162 | 1 | 1.60364 | 0.00 | -7.63 | 3847.60 | 19.39 |
| 0.898 | 192.0259 | Citric acid | 192.027 | 5 | 1.39351 | 0.00 | -6.95 | 344.45 | 2.78 |
| 13.165 | 777.5506 | PS(15:0/20:0) | 777.552 | 2 | 1.41824 | 0.00 | -6.84 | 112.87 | 0.98 |
| 8.069 | 572.2956 | 1-Palmitoylglycerophosphoinositol | 572.2962 | 1 | 1.38422 | 0.00 | -6.49 | 1855.14 | 20.65 |
| 0.851 | 182.0779 | D-Mannitol | 182.079 | 6 | 1.45541 | 0.00 | -6.35 | 781.75 | 9.61 |
| 8.35 | 453.2851 | LysoPE(16:0/0:0) | 453.2855 | 1 | 1.49675 | 0.00 | -6.25 | 536.60 | 7.05 |
| 15.162 | 833.6138 | PS(15:0/24:0) | 833.6146 | 1 | 1.46731 | 0.00 | -6.18 | 78.42 | 1.08 |
| 13.597 | 467.2987 | LysoPC(14:0/0:0) | 467.3012 | 5 | 1.29934 | 0.00 | -5.94 | 41.71 | 0.68 |
| 13.466 | 833.6217 | PS(24:0/15:0) | 833.6146 | 9 | 1.33681 | 0.00 | -5.60 | 53.29 | 1.10 |
| 14.619 | 646.5487 | DG(18:1n7/0:0/20:2n6) | 646.5536 | 8 | 1.46251 | 0.00 | -5.58 | 49.49 | 1.03 |
| 9.333 | 600.3269 | LysoPI(18:0/0:0) | 600.3275 | 1 | 1.31772 | 0.00 | -5.48 | 1014.79 | 22.72 |
| 14.065 | 805.5819 | PS(15:0/22:0) | 805.5833 | 2 | 1.39265 | 0.00 | -5.12 | 138.56 | 4.00 |
| 12.212 | 749.5194 | PS(18:0/15:0) | 749.5207 | 2 | 1.2671 | 0.00 | -4.78 | 33.75 | 1.23 |
| 8.485 | 523.2904 | 1-Oleoylglycerophosphoserine | 523.291 | 1 | 1.45178 | 0.00 | -4.69 | 670.23 | 26.05 |
| 6.303 | 302.2089 | xi-8-Hydroxyhexadecanedioic acid | 302.2093 | 1 | 1.5597 | 0.00 | -4.63 | 11.33 | 0.46 |
| 9.346 | 481.3163 | LysoPC(15:0) | 481.3168 | 1 | 1.46846 | 0.00 | -4.51 | 144.79 | 6.33 |
| 0.864 | 260.0291 | D-Glucose 6-phosphate | 260.0297 | 2 | 1.4599 | 0.00 | -4.51 | 53.80 | 2.36 |
| 11.85 | 400.3546 | MG(0:0/21:0/0:0) | 400.3553 | 2 | 1.26978 | 0.00 | -4.23 | 41.25 | 2.19 |
| 0.86 | 180.0623 | α-D-Glucose | 180.0634 | 6 | 1.53884 | 0.00 | -4.04 | 162.71 | 9.89 |
| 14.737 | 396.3962 | Hexacosanoic acid | 396.3967 | 1 | 1.25752 | 0.00 | -3.43 | 11.50 | 1.07 |
| 7.959 | 382.2117 | LysoPA(i-14:0/0:0) | 382.212 | 1 | 1.3816 | 0.00 | -3.24 | 516.24 | 54.50 |
| 12.097 | 470.3599 | TG(8:0/8:0/8:0) | 470.3607 | 2 | 1.36972 | 0.00 | -3.20 | 26.15 | 2.84 |
| 10.441 | 509.3471 | LysoPE(0:0/20:0) | 509.3481 | 2 | 1.28053 | 0.00 | -3.17 | 17.32 | 1.92 |
| 9.507 | 480.2848 | PA(8:0/12:0) | 480.2852 | 1 | 1.3552 | 0.00 | -3.13 | 51.51 | 5.90 |
| 9.494 | 436.2584 | DHAP(18:0) | 436.259 | 1 | 1.3931 | 0.00 | -3.00 | 9474.47 | 1185.36 |
| 0.842 | 169.0492 | Phosphorylcholine | 169.0504 | 7 | 1.48316 | 0.00 | -2.96 | 15.82 | 2.03 |

FIG. 44 (Continued)

| | | | | | | | |
|---|---|---|---|---|---|---|---|
| 9.193 | 412.2488 | LysoPC(10:0) | 412.2464 | 6 | 1.2999 | 0.00 | -2.85 | 42.99 | 5.98 |
| 13.557 | 526.4224 | TG(12:0/8:0/8:0) | 526.4233 | 2 | 1.15517 | 0.00 | -2.54 | 8.68 | 1.50 |
| 9.197 | 410.2430 | LysoPA(16:0/0:0) | 410.2433 | 1 | 1.40727 | 0.00 | -2.45 | 1748.11 | 318.90 |
| 9.896 | 635.4514 | PE(14:0/14:0) | 635.4526 | 2 | 1.06452 | 0.00 | -2.22 | 365.66 | 78.31 |
| 10.481 | 300.2661 | 12-Hydroxystearic acid | 300.2664 | 1 | 1.47987 | 0.00 | -2.18 | 226.72 | 50.10 |
| 0.847 | 243.0867 | Cytidine | 243.0855 | 4 | 1.51072 | 0.00 | -2.14 | 22.64 | 5.13 |
| 10.693 | 282.2553 | Oleic Acid | 282.2559 | 0 | 1.41829 | 0.00 | -2.07 | 20.59 | 4.89 |
| 4.214 | 164.0459 | m-Coumaric acid | 164.0473 | 8 | 1.38003 | 0.00 | -2.01 | 7.26 | 1.80 |
| 0.867 | 172.0122 | Glycerol 3-phosphate | 172.0137 | 8 | 1.39181 | 0.00 | -1.97 | 42.26 | 10.78 |
| 8.022 | 296.2347 | Avenoleic acid | 296.2351 | 2 | 1.40437 | 0.00 | -1.80 | 25.05 | 7.19 |
| 6.668 | 354.1803 | LysoPA(i-12:0/0:0) | 354.1807 | 1 | 1.48986 | 0.00 | -1.78 | 52.22 | 15.24 |
| 14.377 | 179.0570 | Hippuric acid | 179.0582 | 6 | 1.18227 | 0.00 | -1.76 | 84.47 | 25.00 |
| 8.943 | 298.2504 | Ricinoleic acid | 298.2508 | 1 | 1.2302 | 0.00 | -1.45 | 15.90 | 5.81 |
| 9.73 | 228.2079 | Myristic acid | 228.2089 | 4 | 1.3646 | 0.00 | -1.43 | 16.71 | 6.21 |
| 9.363 | 525.3056 | 1-Stearoylglycerophosphoserine | 525.3067 | 2 | 1.54215 | 0.00 | -0.76 | 33.56 | 19.75 |
| 14.462 | 188.1038 | Nonanedioic acid | 188.1049 | 5 | 1.16318 | 0.00 | -0.54 | 44.58 | 30.76 |
| 12.42 | 690.5206 | PA(22:0/13:0) | 690.52 | 1 | 1.63036 | 0.00 | 2.15 | 14.64 | 64.85 |
| 12.374 | 592.4097 | PA(8:0/20:0) | 592.4104 | 1 | 1.44443 | 0.00 | 2.36 | 13.85 | 70.87 |
| 13.092 | 620.4413 | PA(22:0/8:0) | 620.4417 | 1 | 1.34522 | 0.00 | 2.49 | 2.59 | 14.57 |
| 12.219 | 498.4280 | DG(12:0/15:0/0:0) | 498.4284 | 1 | 1.41383 | 0.00 | 3.03 | 0.87 | 7.12 |
| 12.403 | 526.4591 | DG(10:0/0:0/19:0) | 526.4597 | 1 | 1.55413 | 0.00 | 3.05 | 1.88 | 15.50 |
| 9.672 | 438.2756 | LysoPA(18:0/0:0) | 438.2746 | 2 | 1.25185 | 0.00 | 3.24 | 0.63 | 5.96 |
| 12.349 | 664.5040 | DG(20:4n3:0/0/20:4n3) | 664.5067 | 4 | 1.52212 | 0.00 | 3.51 | 1.61 | 18.37 |
| 10.517 | 508.3159 | PA(8:0/14:0) | 508.3165 | 1 | 1.01989 | 0.01 | 3.77 | 1.11 | 15.18 |
| 11.796 | 384.3599 | Cerebronic acid | 384.3603 | 1 | 1.42824 | 0.00 | 3.89 | 63.72 | 945.31 |
| 11.05 | 494.3369 | LysoPA(22:0/0:0) | 494.3372 | 1 | 1.52567 | 0.00 | 4.16 | 2.62 | 46.70 |
| 10.525 | 424.2954 | LysoPA(18:0e/0:0) | 424.2954 | 0 | 1.23205 | 0.00 | 4.27 | 1.10 | 21.38 |
| 12.545 | 512.3159 | 2-Stearoylglycerophosphoglycerol | 512.3114 | 9 | 1.28551 | 0.00 | 4.28 | 3.04 | 58.98 |
| 11.147 | 536.3473 | PA(8:0/16:0) | 536.3478 | 1 | 1.40975 | 0.00 | 4.64 | 1.50 | 37.36 |
| 10.429 | 466.3056 | LysoPA(i-20:0/0:0) | 466.3059 | 1 | 1.11621 | 0.00 | 4.68 | 0.84 | 21.70 |

| | | | | | | | |
|---|---|---|---|---|---|---|---|
| 11.147 | 442.3652 | DG(8:0/0:0/15:0) | 1 | 442.3658 | 1 | 1.36266 | 0.00 | 4.72 | 1.47 | 38.74 |
| 11.021 | 536.3837 | LysoPA(a-25:0/0:0) | 1 | 536.3842 | 1 | 1.52288 | 0.00 | 5.30 | 1.54 | 60.77 |
| 7.646 | 340.2012 | Piperochromenoic acid | 1 | 340.2038 | 8 | 1.50525 | 0.00 | 5.75 | 0.64 | 34.36 |
| 11.646 | 522.3680 | LysoPA(24:0/0:0) | 1 | 522.3685 | 1 | 1.57259 | 0.00 | 7.34 | 0.75 | 121.83 |

| VIP | LipidIon | LipidGroup | Class | FattyAcid | FA1 | FA2 | FA3 | Calc M/z | IonFormula | RT | Prco | Orco | Prco/Orco | Fold change (log2(Prco/Orco)) | T test |
|---|---|---|---|---|---|---|---|---|---|---|---|---|---|---|---|
| 1.94 | Cer(d18:0/16:0+O)+H | Cer(d34:0+O)+H | Cer | d18:0/16:0+O | d18:0 | 16:0+O | | 556.5299 | C34 H70 O4 N1 | 7.01 | 0.210808 | 0.028025 | 7.52343 | 2.911391 | 0.000 |
| 1.83 | Cer(d18:2/20:0+O)+H | Cer(d38:2+O)+H | Cer | d18:2/20:0+O | d18:2 | 20:0+O | | 608.5612 | C38 H74 O4 N1 | 7.45 | 0.183789 | 0.014055 | 13.07633 | 3.708886 | 0.000 |
| 1.78 | Cer(d18:0/20:0)+H | Cer(d38:0)+H | Cer | d18:0/20:0 | d18:0 | 20:0 | | 596.3976 | C38 H78 O3 N1 | 8.39 | 0.020631 | 0.209738 | 0.098266 | -3.34716 | 0.000 |
| 1.77 | Cer(d18:2/17:0+O)+H | Cer(d35:2+O)+H | Cer | d18:2/17:0+O | d18:2 | 17:0+O | | 566.5143 | C35 H68 O4 N1 | 5.64 | 0.068772 | 0.000336 | 204.7024 | 7.677384 | 0.000 |
| 1.58 | Cer(d18:0/24:0)+H | Cer(d42:0)+H | Cer | d18:0/24:0 | d18:0 | 24:0 | | 652.6602 | C42 H86 O3 N1 | 9.07 | 0.026103 | 0.670769 | 0.038915 | -4.68352 | 0.000 |
| 1.48 | Cer(d20:0/24:0)+H | Cer(d44:0)+H | Cer | d20:0/24:0 | d20:0 | 24:0 | | 680.6915 | C44 H90 O3 N1 | 9.40 | 0.008926 | 0.194959 | 0.045786 | -4.44895 | 0.000 |
| 1.46 | Cer(d18:1/17:1)+H | Cer(d35:2)+H | Cer | d18:1/17:1 | d18:1 | 17:1 | | 550.5194 | C35 H68 O3 N1 | 7.27 | 0.008815 | 0.000693 | 12.72753 | 3.669881 | 0.001 |
| 1.46 | Cer(d18:1/16:0+2O)+H | Cer(d34:1+2O)+H | Cer | d18:1/16:0+2O | d18:1 | 16:0+2O | | 570.5092 | C34 H68 O5 N1 | 6.29 | 0.214489 | 0.000698 | 307.1945 | 8.263009 | 0.002 |
| 1.37 | Cer(d18:1/18:0+O)+H | Cer(d36:1+O)+H | Cer | d18:1/18:0+O | d18:1 | 18:0+O | | 582.5456 | C36 H72 O4 N1 | 7.09 | 0.012968 | 0.048125 | 0.269495 | -1.89167 | 0.001 |
| 1.30 | Cer(d18:1/18:0)+H | Cer(d36:1)+H | Cer | d18:1/18:0 | d18:1 | 18:0 | | 582.5456 | C36 H72 O4 N1 | 7.07 | 0.016981 | 0.049689 | 0.341752 | -1.54898 | 0.002 |
| 1.19 | Cer(d18:2/16:0+2O)+H | Cer(d34:2+2O)+H | Cer | d18:2/16:0+2O | d18:2 | 16:0+2O | | 568.4936 | C34 H66 O5 N1 | 5.39 | 0.005126 | 0 | #DIV/0! | #DIV/0! | 5 |
| 1.18 | Cer(d18:2/18:0+O)+H | Cer(d36:2+O)+H | Cer | d18:2/18:0+O | d18:2 | 18:0+O | | 580.5299 | C36 H70 O4 N1 | 6.92 | 0.000934 | 0.010111 | 0.092413 | -3.43581 | 0.005 |
| 1.16 | Cer(d22:0/18:0)+H | Cer(d40:0)+H | Cer | d22:0/18:0 | d22:0 | 18:0 | | 640.6238 | C40 H82 O4 N1 | 8.73 | 0.304571 | 0.088429 | 3.444254 | 1.784192 | 0.007 |
| 1.15 | Cer(d18:1/20:1)+H | Cer(d38:2)+H | Cer | d18:1/20:1 | d18:1 | 20:1 | | 592.5663 | C38 H74 O3 N1 | 8.07 | 0.000749 | 0.010481 | 0.071475 | -3.80642 | 0.007 |
| 1.11 | Cer(d20:2/17:0+O)+H | Cer(d37:2+O)+H | Cer | d20:2/17:0+O | d20:2 | 17:0+O | | 594.5456 | C37 H72 O4 N1 | 6.89 | 0.005852 | 0 | #DIV/0! | #DIV/0! | 0.010 |

FIG. 45 (Continued)

| | | | | | | | | | | | | |
|---|---|---|---|---|---|---|---|---|---|---|---|---|
| 1.08 | Cer(d18:1/20:1)+H | Cer(d38:2)+H | Cer | d18:2/18:0+O | d18:1/20:1 | | 592.5663 | C38 H74 O3 N1 | 7.80 | 0.000749 | 0.009596 | 0.078067 | -3.67914 | 0.013 |
| 1.06 | Cer(d18:2/18:0+O)+H | Cer(d36:2+O)+H | Cer | | d18:2/18:0+O | | 580.5299 | C36 H70 O4 N1 | 6.38 | 0.017006 | 0.041367 | 0.411096 | -1.28245 | 0.015 |
| 1.04 | Cer(d18:2/20:0)+H | Cer(d38:2)+H | Cer | d18:2/20:0 | d18:2/20:0 | | 592.5663 | C38 H74 O3 N1 | 7.52 | 0.000749 | 0.009885 | 0.075784 | -3.72196 | 0.017 |
| 1.93 | CerG1(d24:0/18:0+O)+H | CerG1(d42:0+O)+H | CerG1 | d24:0/18:0+O | d24:0/18:0+O | | 830.708 | C48 H96 O9 N1 | 8.44 | 0.027282 | 0.268977 | 0.101427 | -3.30148 | 0.000 |
| 1.65 | CerG1(d20:0/24:0)+H | CerG1(d44:0)+H | Cer G1 | d20:0/24:0 | d20:0/24:0 | | 842.7443 | C50 H100 O8 N1 | 9.09 | 0.046142 | | #DIV/0! | #DIV/0! | 0.000 |
| 1.92 | CoQ10+H | | Co | Q10 | Q10 | | 863.6912 | C59 H91 O4 | 9.43 | 0.081666 | 0.595451 | 0.137151 | -2.86617 | 0.000 |
| 1.89 | CoQ10+NH4 | | Co | Q10 | Q10 | | 880.7177 | C59 H94 O4 N1 | 9.43 | 0.083472 | 0.468534 | 0.178157 | -2.48878 | 0.000 |
| 1.96 | DG(16:0/18:2)+H | DG(34:2)+H | DG | 16:0/18:2 | 16:0/18:2 | | 593.514 | C37 H69 O5 | 7.10 | 2.337934 | 0.075052 | 31.15087 | 4.961201 | 0.000 |
| 1.95 | DG(12:0/12:0)+NH4 | DG(24:0)+NH4 | DG | 12:0/12:0 | 12:0/12:0 | | 474.4153 | C27 H56 O5 N1 | 5.82 | 18.68295 | 5.64715 | 3.308387 | 1.726125 | 0.000 |
| 1.94 | DG(16:0/18:2)+NH4 | DG(34:2)+NH4 | DG | 16:0/18:2 | 16:0/18:2 | | 610.5405 | C37 H72 O5 N1 | 7.67 | 2.390672 | 0.394508 | 6.059874 | 2.599288 | 0.000 |
| 1.93 | DG(12:0/12:0)+H | DG(24:0)+H | DG | 12:0/12:0 | 12:0/12:0 | | 457.3888 | C27 H53 O5 | 5.81 | 4.105994 | 1.256201 | 3.268581 | 1.708665 | 0.000 |
| 1.92 | DG(8:0/12:0)+H | DG(20:0)+H | DG | 8:0/12:0 | 8:0/12:0 | | 401.3262 | C23 H45 O5 | 4.20 | 0.672082 | 0.088295 | 7.611809 | 2.928239 | 0.000 |
| 1.92 | DG(18:0/12:0)+NH4 | DG(30:0)+NH4 | DG | 18:0/12:0 | 18:0/12:0 | | 558.5092 | C33 H68 O5 N1 | 7.61 | 9.393715 | 4.547239 | 2.065806 | 1.046705 | 0.000 |
| 1.92 | DG(18:1/14:0)+NH4 | DG(32:1)+NH4 | DG | 18:1/14:0 | 18:1/14:0 | | 584.5249 | C35 H70 O5 N1 | 7.63 | 10.39685 | 5.532185 | 1.879345 | 0.910226 | 0.000 |
| 1.92 | DG(12:0/14:0)+H | DG(26:0)+H | DG | 12:0/14:0 | 12:0/14:0 | | 485.4201 | C29 H57 O5 | 6.49 | 3.886055 | 1.179995 | 3.293278 | 1.719524 | 0.000 |
| 1.92 | DG(14:0/18:2)+H | DG(32:2)+H | DG | 14:0/18:2 | 14:0/18:2 | | 565.4827 | C35 H65 O5 | 6.33 | 1.701213 | 0.056634 | 30.03881 | 4.908756 | 0.000 |
| 1.91 | DG(18:1/12:0)+H | DG(30:1)+H | DG | 18:1/12:0 | 18:1/12:0 | | 539.467 | C33 H63 O5 | 7.12 | 3.124702 | 1.163506 | 2.685593 | 1.42524 | 0.000 |
| 1.90 | DG(12:0/14:0)+NH4 | DG(26:0)+NH4 | DG | 12:0/14:0 | 12:0/14:0 | | 502.4466 | C29 H60 O5 N1 | 6.50 | 20.90069 | 6.903316 | 3.027636 | 1.598189 | 0.000 |

FIG. 45 (Continued)

| | | | | | | | | | | | | | |
|---|---|---|---|---|---|---|---|---|---|---|---|---|---|
| 1.90 | DG(10:0/18:2)+NH4 | DG(28:2)+NH4 | DG | 10:0/18:2 | 10:0 18:2 | 526.4466 | C31 H60 O5 N1 | 6.01 | 0.42797 | 0.03271 4 | 13.0822 9 | 3.709543 | 0.00 0 |
| 1.90 | DG(14:0/18:2)+NH4 | DG(32:2)+NH4 | DG | 14:0/18:2 | 14:0 18:2 | 582.5092 | C35 H68 O5 N1 | 7.17 | 1.86287 | 0.29527 1 | 6.30903 | 2.657418 | 0.00 0 |
| 1.90 | DG(18:0/14:0)+NH4 | DG(32:0)+NH4 | DG | 18:0/14:0 | 18:0 14:0 | 586.5405 | C35 H72 O5 N1 | 8.06 | 2.32398 3 | 1.22002 6 | 1.90486 3 | 0.929687 | 0.00 0 |
| 1.90 | DG(10:0/18:1)+NH4 | DG(28:1)+NH4 | DG | 10:0/18:1 | 10:0 18:1 | 528.4623 | C31 H62 O5 N1 | 6.54 | 2.24276 | 0.55764 6 | 4.02177 6 | 2.007833 | 0.00 0 |
| 1.89 | DG(18:1/14:0)+H | DG(32:1)+H | DG | 18:1/14:0 | 18:1 14:0 | 567.4983 | | 7.63 | 1.33108 | 0.68636 8 | 1.93929 8 | 0.955535 | 0.00 0 |
| 1.89 | DG(16:0/12:0)+NH4 | DG(28:0)+NH4 | DG | 16:0/12:0 | 16:0 12:0 | 530.4779 | C31 H64 O5 N1 | 7.08 | 14.937 96 | 6.09905 7 | 2.44922 5 | 1.292325 | 0.00 0 |
| 1.88 | DG(8:0/12:0)+NH4 | DG(20:0)+NH4 | DG | 8:0/12:0 | 8:0 12:0 | 418.3527 | C23 H48 O5 N1 | 4.20 | 1.78118 3 | 0.22493 3 | 7.91883 | 2.985288 | 0.00 0 |
| 1.88 | DG(18:1/12:0)+NH4 | DG(30:1)+NH4 | DG | 18:1/12:0 | 18:1 12:0 | 556.4936 | C33 H66 O5 N1 | 7.12 | 19.94001 | 8.71910 2 | 2.28693 4 | 1.193414 | 0.00 0 |
| 1.88 | DG(16:0/12:0)+H | DG(28:0)+H | DG | 16:0/12:0 | 16:0 12:0 | 513.4514 | | 7.08 | 2.12354 | 0.85312 4 | 2.48913 4 | 1.315644 | 0.00 0 |
| 1.87 | DG(8:0/18:1)+NH4 | DG(26:1)+NH4 | DG | 8:0/18:1 | 8:0 18:1 | 500.4311 | C29 H58 O5 N1 | 5.87 | 2.16133 1 | 0.10164 2 | 21.2641 6 | 4.410352 | 0.00 0 |
| 1.87 | DG(8:0/18:2)+NH4 | DG(26:2)+NH4 | DG | 8:0/18:2 | 8:0 18:2 | 498.4153 | C29 H56 O5 N1 | 5.30 | 0.73259 1 | 0.04171 5 | 17.5616 7 | 4.134358 | 0.00 0 |
| 1.86 | DG(10:0/12:0)+H | DG(22:0)+H | DG | 10:0/12:0 | 10:0 12:0 | 429.3575 | C25 H49 O5 N1 | 5.04 | 1.43503 8 | 0.23468 6 | 6.11471 2 | 2.612285 | 0.00 0 |
| 1.86 | DG(18:2/18:2)+NH4 | DG(36:4)+NH4 | DG | 18:2/18:2 | 18:2 18:2 | 634.5405 | C39 H72 O5 N1 | 7.33 | 4.05541 9 | 1.22669 4 | 3.30597 3 | 1.725075 | 0.00 0 |
| 1.83 | DG(12:0/18:3)+H | DG(30:3)+H | DG | 12:0/18:3 | 12:0 18:3 | 535.4357 | | 4.95 | 0.73098 1 | 0.00117 4 | 624.509 | 9.286579 | 0.00 0 |
| 1.81 | DG(12:0/18:2)+NH4 | DG(30:2)+NH4 | DG | 12:0/18:2 | 12:0 18:2 | 554.4779 | C33 H64 O5 N1 | 6.61 | 3.11723 | 0.59025 8 | 5.31501 4 | 2.410073 | 0.00 0 |
| 1.80 | DG(12:0/18:2)+H | DG(30:2)+H | DG | 12:0/18:2 | 12:0 18:2 | 537.4514 | | 5.85 | 2.18236 | 0.03081 3 | 70.8256 2 | 6.146199 | 0.00 0 |
| 1.69 | DG(16:0/18:1)+NH4 | DG(34:1)+NH4 | DG | 16:0/18:1 | 16:0 18:1 | 612.5562 | C37 H74 O5 N1 | 8.09 | 15.968 11 | 12.2152 7 | 1.30722 6 | 0.386508 | 0.00 0 |
| 1.68 | DG(18:0/18:1)+NH4 | DG(36:1)+NH4 | DG | 18:0/18:1 | 18:0 18:1 | 640.5875 | C39 H78 O5 N1 | 8.49 | 5.50841 9 | 7.07228 1 | 0.77887 5 | -0.36054 | 0.00 0 |

FIG. 45 (Continued)

| | | | | | | | | | | |
|---|---|---|---|---|---|---|---|---|---|---|
| 1.59 | DG(10:0/12:0)+NH4 | DG(22:0)+NH4 | DG | 10:0/12:0 | 10:0/12:0 | 446.384 | C25 H52 O5 N1 | 5.04 | 4.222054 | 0.821875 | 5.137135 | 2.360964 | 0.00 0 |
| 1.53 | DG(18:1/18:2)+NH4 | DG(36:3)+NH4 | DG | 18:1/18:2 | 18:1/18:2 | 636.5562 | C39 H74 O5 N1 | 7.73 | 3.335267 | 1.666327 | 2.001568 | 1.001131 | 0.00 0 |
| 1.47 | DG(18:1/18:2)+H | DG(36:3)+H | DG | 18:1/18:2 | 18:1/18:2 | 619.5296 | C39 H71 O5 | 7.68 | 1.165751 | 0.327111 | 3.563781 | 1.833409 | 0.00 0 |
| 1.42 | DG(18:1/24:0)+NH4 | DG(42:1)+NH4 | DG | 18:1/24:0 | 18:1/24:0 | 724.6814 | C45 H90 O5 N1 | 9.50 | 0.934119 | 0.718293 | 1.300473 | 0.379034 | 0.00 1 |
| 1.39 | DG(16:0/18:1)+H | DG(34:1)+H | DG | 16:0/18:1 | 16:0/18:1 | 595.5296 | C37 H71 O5 | 8.08 | 1.570763 | 1.319181 | 1.190711 | 0.251823 | 0.00 1 |
| 1.01 | DG(12:0/12:0)+NH4 | DG(24:0)+NH4 | DG | 12:0/12:0 | 12:0/12:0 | 474.4153 | C27 H56 O5 N1 | 13.94 | 1.309638 | 1.133745 | 1.155143 | 0.208071 | 0.02 1 |
| 1.88 | LPC(16:0)+H | LPC(16:0)+H | LPC | 16:0 | 16:0 | 496.3398 | C24 H51 O7 N1 P1 | 2.48 | 0.013416 | 0.213664 | 0.062795 | -3.99331 | 0.00 0 |
| 1.81 | LPC(18:1)+H | LPC(18:1)+H | LPC | 18:1 | 18:1 | 522.3554 | C26 H53 O7 N1 P1 | 0.99 | 0.000154 | 0.012616 | 0.012243 | -6.35194 | 0.00 0 |
| 1.37 | LPC(18:1)+H | LPC(18:1)+H | LPC | 18:1 | 18:1 | 522.3554 | C26 H53 O7 N1 P1 | 2.60 | 0.048162 | 1.030177 | 0.046751 | -4.41885 | 0.00 1 |
| 1.31 | LPC(18:2)+H | LPC(18:2)+H | LPC | 18:2 | 18:2 | 520.3398 | C26 H51 O7 N1 P1 | 2.03 | 0.015084 | 0.067832 | 0.222373 | -2.16895 | 0.00 2 |
| 1.88 | LPE(18:1)+H | LPE(18:1)+H | LPE | 18:1 | 18:1 | 480.3085 | C23 H47 O7 N1 P1 | 2.47 | 0.004534 | 0.205303 | 0.022085 | -5.50082 | 0.00 0 |
| 1.39 | PE(18:1/18:1)+H | PE(36:2)+H | PE | 18:1/18:1 | 18:1/18:1 | 744.5538 | C41 H79 O8 N1 P1 | 6.31 | 0.022285 | 0.963425 | 0.023125 | -5.43438 | 0.00 1 |
| 1.83 | So(d18:1)+H | So(d18:1)+H | So | d18:1 | | 300.2897 | C18 H38 O2 N1 | 2.00 | 0.002534 | 0.037552 | 0.067487 | -3.88925 | 0.00 0 |
| 1.54 | So(d18:0)+H | So(d18:0)+H | So | d18:0 | | 302.3054 | C18 H40 O2 N1 | 2.35 | 0.771522 | 0.054162 | 14.24461 | 3.832344 | 0.00 0 |
| 1.52 | So(d18:0)+H | So(d18:0)+H | So | d18:0 | | 302.3054 | C18 H40 O2 N1 | 1.67 | 0.074933 | 0.040296 | 1.859746 | 0.895106 | 0.00 0 |
| 1.13 | So(d18:1)+H | So(d18:1)+H | So | d18:1 | | 300.2897 | C18 H38 O2 N1 | 6.26 | 0.001716 | 0.009035 | 0.190015 | -2.39581 | 0.00 8 |
| 1.97 | TG(18:1/18:1/18:3)+NH4 | TG(54:5)+NH4 | TG | 18:1/18:1/18:3 | 18:1/18:1 | 898.7858 | C57 H104 O6 N1 | 9.90 | 235.9159 | 33.77792 | 6.984324 | 2.80412 | 0.00 0 |
| 1.97 | TG(16:2/18:1/18:1)+NH4 | TG(52:4)+NH4 | TG | 16:2/18:1/18:1 | 16:2/18:1 | 18:1 | 872.7702 | C55 H102 O6 N1 | 9.89 | 168.5289 | 55.11171 | 3.057951 | 1.612565 | 0.00 0 |

FIG. 45 (Continued)

| | | | | | | | | | | | | |
|---|---|---|---|---|---|---|---|---|---|---|---|---|
| 1.96 | TG(18:1/18:1/20 :2)+NH4 | TG(56:4)+ NH4 | TG | 18:1/18:1/2 0:2 | 18:1 | 18:1 | 20:2 | 928.83 28 | C59 H110 O6 N1 | | 18.919 6 | 5.66681 4 | 3.33866 7 | 1.739272 | 0.00 0 |
| 1.96 | TG(18:1/18:1/18 :2)+NH4 | TG(54:4)+ NH4 | TG | 18:1/18:1/1 8:2 | 18:1 | 18:1 | 18:2 | 900.80 15 | C57 H106 O6 N1 | 10.34 | 313.60 83 | 64.7385 2 | 4.84423 | 2.276268 | 0.00 0 |
| 1.96 | TG(18:1/18:1/18 :1)+NH4 | TG(54:3)+ NH4 | TG | 18:1/18:1/1 8:1 | 18:1 | 18:1 | 18:1 | 902.81 71 | C57 H108 O6 N1 | 10.12 | 343.74 6 | 135.646 1 | 2.53413 8 | 1.341495 | 0.00 0 |
| 1.96 | TG(18:1/18:1/20 :3)+NH4 | TG(56:5)+ NH4 | TG | 18:1/18:1/2 0:3 | 18:1 | 18:1 | 20:3 | 926.81 71 | C59 H108 O6 N1 | 10.32 | 6.3128 25 | 1.23584 6 | 5.10809 9 | 2.352786 | 0.00 0 |
| 1.95 | TG(14:0/18:2/18 :3)+NH4 | TG(50:5)+ NH4 | TG | 14:0/18:2/1 8:3 | 14:0 | 18:2 | 18:3 | 842.72 32 | C53 H96 O6 N1 | 9.40 | 4.0162 42 | 0.60359 9 | 6.65392 9 | 2.734206 | 0.00 0 |
| 1.95 | TG(16:0/18:1/18 :2)+NH4 | TG(52:3)+ NH4 | TG | 16:0/18:1/1 8:2 | 16:0 | 18:1 | 18:2 | 874.78 58 | C55 H104 O6 N1 | 10.11 | 458.37 89 | 223.399 4 | 2.05183 6 | 1.036915 | 0.00 0 |
| 1.95 | TG(16:1/16:1/18 :2)+NH4 | TG(50:4)+ NH4 | TG | 16:1/16:1/1 8:2 | 16:1 | 16:1 | 18:2 | 844.73 89 | C53 H98 O6 N1 | 9.64 | 118.91 05 | 43.8374 3 | 2.71253 4 | 1.439641 | 0.00 0 |
| 1.95 | TG(12:0/18:2/18 :2)+NH4 | TG(48:4)+ NH4 | TG | 12:0/18:2/1 8:2 | 12:0 | 18:2 | 18:2 | 816.70 76 | C51 H94 O6 N1 | 9.36 | 143.59 5 | 54.8661 9 | 2.61718 6 | 1.388016 | 0.00 0 |
| 1.94 | TG(28:4/12:0/18 :1)+H | TG(58:5)+ H | TG | 28:4/12:0/1 8:1 | 28:4 | 12:0 | 18:1 | 937.82 19 | C61 H109 O6 | 9.75 | 12.715 9 | 0.11723 6 | 108.464 6 | 6.76108 | 0.00 0 |
| 1.94 | TG(18:1/18:1/18 :2)+H | TG(56:7)+ H | TG | 18:1/18:1/1 8:2 | 18:1 | 18:1 | 18:2 | 905.75 93 | C59 H101 O6 | 10.13 | 14.217 16 | 5.53284 5 | 2.56959 4 | 1.36154 | 0.00 0 |
| 1.94 | TG(18:2/18:2/18 :2)+NH4 | TG(54:6)+ NH4 | TG | 18:2/18:2/1 8:2 | 18:2 | 18:2 | 18:2 | 896.77 02 | C57 H102 O6 N1 | 9.66 | 107.58 7 | 11.0150 8 | 9.76661 8 | 3.287859 | 0.00 0 |
| 1.94 | TG(26:6/8:0/12: 0)+NH4 | TG(46:6)+ NH4 | TG | 26:6/8:0/12 :0 | 26:6 | 8:0 | 12:0 5 | 784.64 | C49 H86 O6 N1 | 4.13 | 0.4875 95 | 0.00074 | 652.089 4 | 9.348926 | 0.00 0 |
| 1.94 | TG(16:1/18:2/18 :2)+NH4 | TG(52:5)+ NH4 | TG | 16:1/18:2/1 8:2 | 16:1 | 18:2 | 18:2 | 870.75 45 | C55 H100 O6 N1 | 9.67 | 8.8893 43 | 1.24802 8 | 7.12271 3 | 2.832427 | 0.00 0 |
| 1.93 | TG(30:3/18:1/18 :1)+H | TG(66:5)+ H | TG | 30:3/18:1/1 8:1 | 30:3 | 18:1 | 18:1 47 | 1049.9 | C69 H125 O6 | 10.56 5 | 9.4411 7 | 0.08348 7 | 113.085 6 | 6.821271 | 0.00 0 |
| 1.93 | TG(18:3/18:2/18 :2)+NH4 | TG(54:7)+ NH4 | TG | 18:3/18:2/1 8:2 | 18:3 | 18:2 | 18:2 | 894.75 45 | C57 H100 O6 N1 | 9.43 | 6.9030 96 | 0.23218 7 | 29.7307 5 | 4.893884 | 0.00 0 |
| 1.93 | TG(18:1/12:0/18 :2)+NH4 | TG(48:3)+ NH4 | TG | 18:1/12:0/1 8:2 | 18:1 | 12:0 | 18:2 | 818.72 32 | C51 H96 O6 N1 | 9.63 | 314.91 26 | 191.559 7 | 1.64394 | 0.717157 | 0.00 0 |
| 1.92 | TG(30:4/12:0/2 0:1)+H | TG(62:5)+ H | TG | 30:4/12:0/2 0:1 | 30:4 | 12:0 | 20:1 45 | 993.88 | C65 H117 O6 | 10.20 | 13.131 85 | 0.14063 5 | 93.3754 2 | 6.54497 | 0.00 0 |
| 1.92 | TG(28:3/8:0/16: 1)+H | TG(52:4)+ H | TG | 28:3/8:0/16 :1 | 28:3 | 8:0 | 16:1 36 | 855.74 | C55 H99 O6 | 9.21 | 16.394 7 | 0.47231 2 | 34.7117 | 5.117351 | 0.00 0 |

FIG. 45 (Continued)

| | | | | | | | | | | | | |
|---|---|---|---|---|---|---|---|---|---|---|---|---|
| 1.92 | TG(19:1/18:1/18:2)+NH4 | TG(55:4)+NH4 | TG | 19:1/18:1/18:2 | 19:1 | 18:1 | 18:2 | 914.8171 | C58H108O6N1 | 10.22 | 1.76355 | 0.30159 | 5.847491 | 2.547818 | 0.00 0 |
| 1.92 | TG(26:3/12:0/18:1)+H | TG(56:4)+H | TG | 26:3/12:0/18:1 | 26:3 | 12:0 | 18:1 | 911.8062 | C59H107O6 | 9.73 | 27.1286 | 0.345627 | 78.49103 | 6.294456 | 0.00 0 |
| 1.92 | TG(26:0/18:1/18:2)+NH4 | TG(62:3)+NH4 | TG | 26:0/18:1/18:2 | 26:0 | 18:1 | 18:2 | 1014.942 | C65H124O6N1 | 11.07 | 6.327842 | 1.808044 | 3.499828 | 1.807284 | 0.00 0 |
| 1.91 | TG(12:0/18:2/18:2)+H | TG(48:4)+H | TG | 12:0/18:2/18:2 | 12:0 | 18:2 | 18:2 | 799.681 | C51H91O6 | 9.35 | 1.801311 | 0.607892 | 2.963206 | 1.567159 | 0.00 0 |
| 1.91 | TG(30:1/12:0/18:1)+Na | TG(60:2)+Na | TG | 30:1/12:0/18:1 | 30:1 | 12:0 | 18:1 | 993.8821 | C63H118O6Na1 | 10.19 | 9.983591 | 0.124979 | 79.88239 | 6.319804 | 0.00 0 |
| 1.91 | TG(30:5/12:0/22:1)+H | TG(64:6)+H | TG | 30:5/12:0/22:1 | 30:5 | 12:0 | 22:1 | 1019.976 | C67H119O6 | 10.20 | 5.905676 | 0.042063 | 140.4013 | 7.133409 | 0.00 0 |
| 1.90 | TG(12:0/12:0/13:1)+H | TG(37:1)+H | TG | 12:0/12:0/13:1 | 12:0 | 12:0 | 13:1 | 651.5558 | C40H75O6 | 8.09 | 2.106818 | 0.09342 | 22.55702 | 4.495505 | 0.00 0 |
| 1.90 | TG(10:0/18:2/18:2)+NH4 | TG(46:4)+NH4 | TG | 10:0/18:2/18:2 | 10:0 | 18:2 | 18:2 | 788.6763 | C49H90O6N1 | 9.05 | 36.01202 | 17.17378 | 2.096919 | 1.068271 | 0.00 0 |
| 1.90 | TG(18:1/17:1/18:1)+NH4 | TG(53:3)+NH4 | TG | 18:1/17:1/18:1 | 18:1 | 17:1 | 18:1 | 888.8015 | C56H106O6N1 | 10.21 | 6.660098 | 2.045848 | 3.255422 | 1.702845 | 0.00 0 |
| 1.90 | TG(20:1/18:1/18:1)+NH4 | TG(56:3)+NH4 | TG | 20:1/18:1/18:1 | 20:1 | 18:1 | 18:1 | 930.8484 | C59H112O6N1 | 10.52 | 43.06707 | 18.27081 | 2.357151 | 1.237044 | 0.00 0 |
| 1.90 | TG(18:1/18:2/20:3)+NH4 | TG(56:6)+NH4 | TG | 18:1/18:2/20:3 | 18:1 | 18:2 | 20:3 | 924.8015 | C59H106O6N1 | 9.92 | 1.079774 | 0.122022 | 8.848996 | 3.145514 | 0.00 0 |
| 1.90 | TG(30:4/18:1/18:1)+H | TG(66:6)+H | TG | 30:4/18:1/18:1 | 30:4 | 18:1 | 18:1 | 1047.931 | C69H123O6 | 10.39 | 4.661511 | 0.039397 | 118.32 | 6.88655 | 0.00 0 |
| 1.89 | TG(30:4/12:0/18:1)+H | TG(60:5)+H | TG | 30:4/12:0/18:1 | 30:4 | 12:0 | 18:1 | 965.8532 | C63H113O6 | 9.97 | 15.76133 | 0.196583 | 80.17634 | 6.325105 | 0.00 0 |
| 1.89 | TG(24:3/12:0/18:1)+H | TG(54:4)+H | TG | 24:3/12:0/18:1 | 24:3 | 12:0 | 18:1 | 883.7749 | C57H103O6 | 9.49 | 34.99514 | 0.4796 | 72.96666 | 6.189166 | 0.00 0 |
| 1.89 | TG(10:0/18:1/18:2)+NH4 | TG(46:3)+NH4 | TG | 10:0/18:1/18:2 | 10:0 | 18:1 | 18:2 | 790.6919 | C49H92O6N1 | 9.34 | 93.45833 | 64.68408 | 1.444843 | 0.530913 | 0.00 0 |
| 1.89 | TG(15:0/18:2/18:2)+NH4 | TG(51:4)+NH4 | TG | 15:0/18:2/18:2 | 15:0 | 18:2 | 18:2 | 858.7545 | C54H100O6N1 | 9.78 | 3.400373 | 1.030287 | 3.300414 | 1.722647 | 0.00 0 |
| 1.89 | TG(18:2/18:2/23:0)+NH4 | TG(59:4)+NH4 | TG | 18:2/18:2/23:0 | 18:2 | 18:2 | 23:0 | 970.8797 | C62H116O6N1 | 10.64 | 0.757989 | 0.152033 | 4.985676 | 2.317789 | 0.00 0 |
| 1.89 | TG(18:1/18:1/24:0)+NH4 | TG(60:2)+NH4 | TG | 18:1/18:1/24:0 | 18:1 | 18:1 | 24:0 | 988.9267 | C63H122O6N1 | 11.06 | 31.41895 | 13.15197 | 2.388916 | 1.256356 | 0.00 0 |

FIG. 45 (Continued)

| | | | | | | | | | | | | |
|---|---|---|---|---|---|---|---|---|---|---|---|---|
| 1.88 | TG(18:1/17:1/18:2)+NH4 | TG(53:4)+NH4 | TG | 18:1/17:1/18:2 | 18:1 | 17:1 | 18:2 | 886.7858 | C56 H104 O6 N1 | 10.00 | 3.526539 | 0.678258 | 5.199403 | 2.378346 | 0.00 0 |
| 1.88 | TG(24:0/18:2/18:2)+NH4 | TG(60:4)+NH4 | TG | 24:0/18:2/18:2 | 24:0 | 18:2 | 18:2 | 984.8954 | C63 H118 O6 N1 | 10.73 | 7.748805 | 2.685525 | 2.885396 | 1.52877 | 0.00 0 |
| 1.88 | TG(18:1/18:1/18:3)+H | TG(54:5)+H | TG | 18:1/18:1/18:3 | 18:1 | 18:1 | 18:3 | 881.7593 | C57 H101 O6 | 9.91 | 1.985626 | 0.291074 | 6.821727 | 2.770137 | 0.00 0 |
| 1.87 | TG(4:0/8:0/16:1)+H | TG(28:1)+H | TG | 4:0/8:0/16:1 | 4:0 | 8:0 | 16:1 | 525.4115 | C31 H57 O6 | 4.71 | 0.078063 | 0.410474 | 0.190177 | -2.39458 | 0.00 0 |
| 1.87 | TG(12:0/14:0/18:2)+NH4 | TG(44:2)+NH4 | TG | 12:0/14:0/18:2 | 12:0 | 14:0 | 18:2 | 764.6763 | C47 H90 O6 N1 | 9.33 | 558.5677 | 428.4964 | 1.303553 | 0.382449 | 0.00 0 |
| 1.87 | TG(19:1/18:1/18:2)+NH4 | TG(55:3)+NH4 | TG | 19:1/18:1/18:2 | 19:1 | 18:1 | 18:2 | 916.8328 | C58 H110 O6 N1 | 10.42 | 1.684555 | 0.473707 | 3.556115 | 1.830302 | 0.00 0 |
| 1.87 | TG(20:0/18:1/20:3)+NH4 | TG(58:4)+NH4 | TG | 20:0/18:1/20:3 | 20:0 | 18:1 | 20:3 | 956.8641 | C61 H114 O6 N1 | 10.54 | 3.841163 | 1.672227 | 2.297034 | 1.199772 | 0.00 0 |
| 1.87 | TG(8:0/8:0/14:1)+NH4 | TG(30:1)+NH4 | TG | 8:0/8:0/14:1 | 8:0 | 8:0 | 14:1 | 570.4728 | C33 H64 O6 N1 | 6.83 | 7.951801 | 1.677073 | 4.741476 | 2.245336 | 0.00 0 |
| 1.87 | TG(25:0/18:2/18:2)+NH4 | TG(61:4)+NH4 | TG | 25:0/18:2/18:2 | 25:0 | 18:2 | 18:2 | 998.9121 | C64 H120 O6 N1 | 10.83 | 0.975357 | 0.158937 | 6.136759 | 2.617477 | 0.00 0 |
| 1.87 | TG(16:1/14:0/16:1)+NH4 | TG(46:2)+NH4 | TG | 16:1/14:0/16:1 | 16:1 | 14:0 | 16:1 | 792.7076 | C49 H94 O6 N1 | 9.61 | 438.2061 | 332.6132 | 1.317465 | 0.397764 | 0.00 0 |
| 1.87 | TG(26:0/18:2/18:2)+NH4 | TG(62:4)+NH4 | TG | 26:0/18:2/18:2 | 26:0 | 18:2 | 18:2 | 1012.927 | C65 H122 O6 N1 | 10.91 | 2.177155 | 0.533538 | 4.080599 | 2.028781 | 0.00 0 |
| 1.86 | TG(8:0/18:1/18:2)+NH4 | TG(44:3)+NH4 | TG | 8:0/18:1/18:2 | 8:0 | 18:1 | 18:2 | 762.6606 | C47 H88 O6 N1 | 9.03 | 283.1044 | 193.6599 | 1.461869 | 0.547814 | 0.00 0 |
| 1.86 | TG(28:3/18:1/18:1)+H | TG(64:5)+H | TG | 28:3/18:1/18:1 | 28:3 | 18:1 | 18:1 | 1021.916 | C67 H121 O6 | 10.38 | 13.16307 | 0.124346 | 105.8581 | 6.725987 | 0.00 0 |
| 1.86 | TG(16:0/18:1/18:1)+NH4 | TG(52:2)+NH4 | TG | 16:0/18:1/18:1 | 16:0 | 18:1 | 18:1 | 876.8015 | C55 H106 O6 N1 | 10.30 | 848.8963 | 561.6223 | 1.511511 | 0.595991 | 0.00 0 |
| 1.86 | TG(16:0/18:1/22:5)+NH4 | TG(56:6)+NH4 | TG | 16:0/18:1/22:5 | 16:0 | 18:1 | 22:5 | 924.8015 | C59 H106 O6 N1 | 9.67 | 3.762705 | 0.657838 | 5.719808 | 2.515967 | 0.00 0 |
| 1.86 | TG(6:0/18:2/18:2)+NH4 | TG(42:4)+NH4 | TG | 6:0/18:2/18:2 | 6:0 | 18:2 | 18:2 | 732.6137 | C45 H82 O6 N1 | 8.36 | 15.26628 | 7.123972 | 2.142943 | 1.099594 | 0.00 0 |
| 1.86 | TG(8:0/18:2/18:2)+NH4 | TG(44:4)+NH4 | TG | 8:0/18:2/18:2 | 8:0 | 18:2 | 18:2 | 760.6425 | C47 H86 O6 N1 | 8.71 | 99.7222 | 48.24532 | 2.066982 | 1.047526 | 0.00 0 |
| 1.86 | TG(25:0/18:1/18:2)+NH4 | TG(61:3)+NH4 | TG | 25:0/18:1/18:2 | 25:0 | 18:1 | 18:2 | 1000.927 | C64 H122 O6 N1 | 10.99 | 2.933686 | 0.699782 | 4.19232 | 2.067742 | 0.00 0 |

FIG. 45 (Continued)

| | | | | | | | | | | | | |
|---|---|---|---|---|---|---|---|---|---|---|---|---|
| 1.86 | TG(30:0/18:1/18:1)+Na | TG(66:2)+Na | TG | 30:0/18:1/18:1 | 30:0 | 18:1 | 1077.976 | C69 H130 O6 Na1 | 10.73 | 4.488947 | 0.05754 3 | 78.0103 8 | 6.285594 | 0.00 0 |
| 1.85 | TG(30:1/12:0/12:0)+Na | TG(54:1)+Na | TG | 30:1/12:0/12:0 | 30:1 | 12:0 | 911.80 38 | C57 H108 O6 Na1 | 9.73 | 26.550 78 | 0.24819 9 | 106.973 8 | 6.741113 | 0.00 0 |
| 1.85 | TG(18:1/18:2/23:0)+NH4 | TG(59:3)+NH4 | TG | 18:1/18:2/23:0 | 18:1 | 23:0 | 972.89 54 | C62 H118 O6 N1 | 10.80 28 | 2.1507 28 | 0.63626 9 | 3.38022 3 | 1.757117 | 0.00 0 |
| 1.85 | TG(4:0/8:0/8:0)+NH4 | TG(20:0)+NH4 | TG | 4:0/8:0/8:0 | 4:0 | 8:0 | 432.33 2 | C23 H46 O6 N1 | 3.73 | 0.0608 29 | 0.16707 9 | 0.36407 3 | -1.4577 | 0.00 0 |
| 1.85 | TG(15:0/18:1/18:1)+NH4 | TG(51:2)+NH4 | TG | 15:0/18:1/18:1 | 15:0 | 18:1 | 862.78 58 | C54 H104 O6 N1 | 10.20 74 | 13.434 29 | 6.94790 5 | 1.93363 9 | 0.951318 | 0.00 0 |
| 1.85 | TG(6:0/8:0/18:1)+NH4 | TG(32:1)+NH4 | TG | 6:0/8:0/18:1 | 6:0 | 8:0 | 598.50 41 | C35 H68 O6 N1 | 6.82 | 2.4284 3 | 0.61721 9 | 3.93447 3 | 1.976171 | 0.00 0 |
| 1.85 | TG(25:6/18:2/18:2)+H | TG(61:10)+H | TG | 25:6/18:2/18:2 | 25:6 | 18:2 | 969.79 06 | C64 H105 O6 | 6.24 | 0.4289 46 | 0 | #DIV/0! | #DIV/0! | 0.00 0 |
| 1.84 | TG(17:0/18:1/18:1)+NH4 | TG(53:2)+NH4 | TG | 17:0/18:1/18:1 | 17:0 | 18:1 | 890.81 71 | C56 H108 O6 N1 | 10.41 75 | 7.0653 75 | 2.92255 8 | 2.41753 | 1.273539 | 0.00 0 |
| 1.84 | TG(6:0/12:0/15:1)+NH4 | TG(33:1)+NH4 | TG | 6:0/12:0/15:1 | 6:0 | 15:1 | 612.51 98 | C36 H70 O6 N1 | 7.64 | 2.9048 37 | 1.11139 9 | 2.61367 6 | 1.38608 | 0.00 0 |
| 1.84 | TG(8:0/12:0/18:3)+NH4 | TG(38:3)+NH4 | TG | 8:0/12:0/18:3 | 8:0 | 18:3 | 678.56 67 | C41 H76 O6 N1 | 8.00 | 12.329 27 | 2.80966 8 | 4.38816 2 | 2.133616 | 0.00 0 |
| 1.84 | TG(18:1/12:0/12:0)+H | TG(42:1)+H | TG | 18:1/12:0/12:0 | 18:1 | 12:0 | 721.63 41 | C45 H85 O6 | 8.11 | 2.8280 38 | 0.76015 3 | 3.72035 6 | 1.895441 | 0.00 0 |
| 1.84 | TG(6:0/8:0/11:0)+NH4 | TG(25:0)+NH4 | TG | 6:0/8:0/11:0 | 6:0 | 8:0 | 502.41 02 | C28 H56 O6 N1 | 5.71 | 0.6575 76 | 0.32404 8 | 2.02925 4 | 1.02095 | 0.00 0 |
| 1.84 | TG(18:1/18:2/24:0)+NH4 | TG(60:3)+NH4 | TG | 18:1/18:2/24:0 | 18:1 | 24:0 | 986.91 1 | C63 H120 O6 N1 | 10.90 44 | 23.136 47 | 8.84749 7 | 2.61502 6 | 1.386826 | 0.00 0 |
| 1.84 | TG(16:0/18:1/24:0)+NH4 | TG(58:1)+NH4 | TG | 16:0/18:1/24:0 | 16:0 | 24:0 | 962.91 1 | C61 H120 O6 N1 | 11.06 12 | 32.524 9 | 17.0070 9 | 1.91238 6 | 0.935373 | 0.00 0 |
| 1.83 | TG(4:0/10:0/16:1)+H | TG(30:1)+H | TG | 4:0/10:0/16:1 | 4:0 | 10:0 | 553.44 63 | C33 H61 O6 | 5.46 | 0.1018 78 | 0.34742 8 | 0.29323 6 | -1.76987 | 0.00 0 |
| 1.83 | TG(26:0/18:1/18:1)+NH4 | TG(62:2)+NH4 | TG | 26:0/18:1/18:1 | 26:0 | 18:1 | 1016.9 58 | C65 H126 O6 N1 | 11.22 | 2.20616 | 2.20616 | 3.50956 7 | 1.811293 | 0.00 0 |
| 1.83 | TG(28:1/18:1/18:1)+NH4 | TG(64:3)+NH4 | TG | 28:1/18:1/18:1 | 28:1 | 18:1 | 1042.9 74 | C67 H128 O6 N1 | 11.23 | 0.4972 22 | 0.13218 2 | 3.76164 8 | 1.911365 | 0.00 0 |
| 1.83 | TG(28:3/12:0/18:1)+H | TG(58:4)+H | TG | 28:3/12:0/18:1 | 28:3 | 12:0 | 939.83 75 | C61 H111 O6 | 9.97 | 31.751 14 | 0.25051 2 | 126.744 8 | 6.985783 | 0.00 0 |

FIG. 45 (Continued)

| | | | | | | | | | | | | |
|---|---|---|---|---|---|---|---|---|---|---|---|---|
| 1.83 | TG(18:1/12:0/18:2)+H | TG(48:3)+H | TG | 18:1/12:0/18:2 | 18:1 | 12:0 | 18:2 | 801.6967 | C51 H93 O6 | 9.63 | 1.683974 | 0.772757 | 2.179177 | 1.123783 | 0.00 0 |
| 1.82 | TG(16:1/8:0/8:0)+H | TG(32:1)+H | TG | 16:1/8:0/8:0 | 16:1 | 8:0 | 8:0 | 581.4776 | C35 H65 O6 | 5.74 | 1.47064 | 3.634555 | 0.404627 | -1.30533 | 0.00 0 |
| 1.82 | TG(26:0/16:0/20:0)+NH4 | TG(62:0)+NH4 | TG | 26:0/16:0/20:0 | 26:0 | 16:0 | 20:0 | 1020.989 | C65 H130 O6 N1 | 11.45 | 0.352801 | 0.110602 | 3.189809 | 1.67347 | 0.00 0 |
| 1.82 | TG(4:0/12:0/16:1)+H | TG(32:1)+H | TG | 4:0/12:0/16:1 | 4:0 | 12:0 | 16:1 | 581.4776 | C35 H65 O6 | 6.13 | 0.813814 | 2.403433 | 0.338605 | -1.56232 | 0.00 0 |
| 1.82 | TG(18:1/18:1/21:0)+NH4 | TG(57:2)+NH4 | TG | 18:1/18:1/21:0 | 18:1 | 18:1 | 21:0 | 946.8797 | C60 H116 O6 N1 | 10.80 | 2.815368 | 1.138039 | 2.473878 | 1.306774 | 0.00 0 |
| 1.82 | TG(18:1/18:1/21:2)+NH4 | TG(57:4)+NH4 | TG | 18:1/18:1/21:2 | 18:1 | 18:1 | 21:2 | 942.8484 | C60 H112 O6 N1 | 10.43 | 0.194703 | 0.066015 | 2.94937 | 1.560407 | 0.00 0 |
| 1.82 | TG(26:0/16:0/18:1)+NH4 | TG(60:1)+NH4 | TG | 26:0/16:0/18:1 | 26:0 | 16:0 | 18:1 | 990.9423 | C63 H124 O6 N1 | 11.22 | 9.957052 | 3.847537 | 2.587907 | 1.371786 | 0.00 0 |
| 1.82 | TG(12:0/12:0/18:3)+H | TG(42:3)+H | TG | 12:0/12:0/18:3 | 12:0 | 12:0 | 18:3 | 717.6028 | C45 H81 O6 | 7.61 | 4.078346 | 1.824166 | 2.235732 | 1.160747 | 0.00 0 |
| 1.82 | TG(15:0/18:1/18:2)+NH4 | TG(51:3)+NH4 | TG | 15:0/18:1/18:2 | 15:0 | 18:1 | 18:2 | 860.7702 | C54 H102 O6 N1 | 9.99 | 9.626581 | 3.576398 | 2.691698 | 1.428516 | 0.00 0 |
| 1.82 | TG(18:1/17:2/18:2)+NH4 | TG(53:5)+NH4 | TG | 18:1/17:2/18:2 | 18:1 | 17:2 | 18:2 | 884.7702 | C56 H102 O6 N1 | 10.12 | 0.609849 | 0.051866 | 11.75811 | 3.555583 | 0.00 0 |
| 1.82 | TG(18:1/18:1/21:1)+NH4 | TG(57:3)+NH4 | TG | 18:1/18:1/21:1 | 18:1 | 18:1 | 21:1 | 944.8641 | C60 H114 O6 N1 | 10.62 | 0.470297 | 0.182851 | 2.572041 | 1.362914 | 0.00 0 |
| 1.81 | TG(27:0/16:0/18:1)+NH4 | TG(61:1)+NH4 | TG | 27:0/16:0/18:1 | 27:0 | 16:0 | 18:1 | 1004.958 | C64 H126 O6 N1 | 11.29 | 0.687764 | 0.217351 | 3.164311 | 1.661891 | 0.00 0 |
| 1.81 | TG(18:1/18:1/23:0)+NH4 | TG(59:2)+NH4 | TG | 18:1/18:1/23:0 | 18:1 | 18:1 | 23:0 | 974.911 | C62 H120 O6 N1 | 10.98 | 5.065707 | 1.869135 | 2.710188 | 1.438393 | 0.00 0 |
| 1.81 | TG(27:0/18:1/18:2)+NH4 | TG(63:3)+NH4 | TG | 27:0/18:1/18:2 | 27:0 | 18:1 | 18:2 | 1028.958 | C66 H126 O6 N1 | 11.15 | 0.452122 | 0.083713 | 5.400872 | 2.433192 | 0.00 0 |
| 1.81 | TG(8:0/14:0/18:3)+H | TG(40:3)+H | TG | 8:0/14:0/18:3 | 8:0 | 14:0 | 18:3 | 706.5938 | C43 H80 O6 N1 | 8.34 | 8.253042 | 3.750394 | 2.200584 | 1.137884 | 0.00 0 |
| 1.81 | TG(25:0/18:1/18:1)+NH4 | TG(61:2)+NH4 | TG | 25:0/18:1/18:1 | 25:0 | 18:1 | 18:1 | 1002.942 | C64 H124 O6 N1 | 11.14 | 3.778317 | 1.025303 | 3.685072 | 1.881693 | 0.00 0 |
| 1.80 | TG(12:0/12:0/18:2)+NH4 | TG(42:2)+NH4 | TG | 12:0/12:0/18:2 | 12:0 | 12:0 | 18:2 | 736.6425 | C45 H86 O6 N1 | 9.01 | 548.5717 | 411.6145 | 1.332732 | 0.414386 | 0.00 0 |
| 1.80 | TG(28:0/18:1/18:1)+NH4 | TG(64:2)+NH4 | TG | 28:0/18:1/18:1 | 28:0 | 18:1 | 18:1 | 1044.989 | C67 H130 O6 N1 | 11.37 | 0.613877 | 0.197986 | 3.100556 | 1.632527 | 0.00 0 |

FIG. 45 (Continued)

| | | TG | 8:0/12:0/20:5 | 8:0 | 12:0 | 20:5 | 685.5402 | 8.28 | 61.55544 | 47.28621 | 1.301763 | 0.380467 | 0.00 0 |
|---|---|---|---|---|---|---|---|---|---|---|---|---|---|
| 1.80 | TG(8:0/12:0/20:5)+H | TG(40:5)+H | | | | | | | | | | | |
| 1.79 | TG(16:0/18:1/18:2)+H | TG(52:3)+H | TG | 16:0/18:1/18:2 | 16:0 | 18:1 | 18:2 | 857.7593 | 10.12 | 2.055046 | 3.924811 | 0.523603 | -0.93346 | 0.00 0 |
| 1.79 | TG(18:1/18:2/22:0)+NH4 | TG(58:3)+NH4 | TG | 18:1/18:2/22:0 | 18:1 | 18:2 | 22:0 | 958.8797 | 10.71 | 11.98553 | 6.630198 | 1.807718 | 0.85417 | 0.00 0 |
| 1.79 | TG(28:0/16:0/18:1)+NH4 | TG(62:1)+NH4 | TG | 28:0/16:0/18:1 | 28:0 | 16:0 | 18:1 | 1018.974 | 11.36 | 1.269918 | 0.477834 | 2.657655 | 1.410154 | 0.00 0 |
| 1.79 | TG(6:0/8:0/14:1)+NH4 | TG(28:1)+NH4 | TG | 6:0/8:0/14:1 | 6:0 | 8:0 | 14:1 | 542.4415 | 6.28 | 1.630516 | 0.217479 | 7.497355 | 2.906382 | 0.00 0 |
| 1.78 | TG(25:0/16:0/18:1)+NH4 | TG(59:1)+NH4 | TG | 25:0/16:0/18:1 | 25:0 | 16:0 | 18:1 | 976.9267 | 11.14 | 3.765051 | 1.337617 | 2.814745 | 1.493004 | 0.00 0 |
| 1.77 | TG(6:0/18:1/18:2)+NH4 | TG(42:3)+NH4 | TG | 6:0/18:1/18:2 | 6:0 | 18:1 | 18:2 | 734.6293 | 8.70 | 86.01817 | 54.06703 | 1.590954 | 0.669892 | 0.00 0 |
| 1.76 | TG(6:0/8:0/8:0)+NH4 | TG(22:0)+NH4 | TG | 6:0/8:0/8:0 | 6:0 | 8:0 | 8:0 | 460.3633 | 4.53 | 0.837826 | 1.464531 | 0.572078 | -0.80572 | 0.00 0 |
| 1.76 | TG(29:1/18:1/18:1)+NH4 | TG(65:3)+NH4 | TG | 29:1/18:1/18:1 | 29:1 | 18:1 | 18:1 | 1056.989 | 10.90 | 1.042577 | 0.496296 | 2.100715 | 1.07088 | 0.00 0 |
| 1.76 | TG(18:1/24:0/24:1)+NH4 | TG(66:2)+NH4 | TG | 18:1/24:0/24:1 | 18:1 | 24:0 | 24:1 | 1073.021 | 11.51 | 0.140093 | 0.053921 | 2.598171 | 1.377497 | 0.00 0 |
| 1.76 | TG(8:0/18:1/18:1)+NH4 | TG(44:2)+NH4 | TG | 8:0/18:1/18:1 | 8:0 | 18:1 | 18:1 | 764.6763 | 9.03 | 40.44261 | 28.33067 | 1.427524 | 0.513511 | 0.00 0 |
| 1.76 | TG(18:1/18:1/22:0)+NH4 | TG(58:2)+NH4 | TG | 18:1/18:1/22:0 | 18:1 | 18:1 | 22:0 | 960.8954 | 10.89 | 32.23334 | 16.61434 | 1.940071 | 0.956109 | 0.00 0 |
| 1.76 | TG(16:0/18:1/23:0)+NH4 | TG(57:1)+NH4 | TG | 16:0/18:1/23:0 | 16:0 | 18:1 | 23:0 | 948.8954 | 10.98 | 4.633015 | 2.183871 | 2.121469 | 1.085064 | 0.00 0 |
| 1.76 | TG(11:0/8:0/18:2)+NH4 | TG(37:2)+NH4 | TG | 11:0/8:0/18:2 | 11:0 | 8:0 | 18:2 | 666.5667 | 8.06 | 2.518413 | 1.515393 | 1.661889 | 0.732824 | 0.00 0 |
| 1.75 | TG(6:0/8:0/12:0)+NH4 | TG(26:0)+NH4 | TG | 6:0/8:0/12:0 | 6:0 | 8:0 | 12:0 | 516.4259 | 3.89 | 0.618205 | 0.110912 | 5.573843 | 2.478672 | 0.00 0 |
| 1.75 | TG(18:0/18:1/18:1)+NH4 | TG(54:2)+NH4 | TG | 18:0/18:1/18:1 | 18:0 | 18:1 | 18:1 | 904.8328 | 10.51 | 222.7095 | 154.3892 | 1.442524 | 0.528594 | 0.00 0 |
| 1.74 | TG(8:0/14:0/18:3)+H | TG(40:3)+H | TG | 8:0/14:0/18:3 | 8:0 | 14:0 | 18:3 | 689.5715 | 7.11 | 1.910298 | 1.196708 | 1.596294 | 0.674726 | 0.00 0 |
| 1.74 | TG(10:0/12:0/18:2)+NH4 | TG(40:2)+NH4 | TG | 10:0/12:0/18:2 | 10:0 | 12:0 | 18:2 | 708.6137 | 8.67 | 394.4357 | 306.9304 | 1.285098 | 0.361878 | 0.00 0 |

FIG. 45 (Continued)

| | | | | | | | | | | | |
|---|---|---|---|---|---|---|---|---|---|---|---|
| 1.73 | TG(20:0/18:2/18:2)+H | TG(56:4)+H | TG | 20:0/18:2/18:2 | 20:0 | 18:2 | 18:2 | 911.8062 | C59 H107 O6 | 10.70 | 7.202238 | 10.03157 | 0.717957 | -0.47803 | 0.00 0 |
| 1.73 | TG(18:1/14:0/23:0)+NH4 | TG(55:1)+NH4 | TG | 18:1/14:0/23:0 | 18:1 | 14:0 | 23:0 | 920.8641 | C58 H114 O6 N1 | 10.80 | 4.373572 | 2.165833 | 2.019349 | | 0.00 0 |
| 1.73 | TG(8:0/12:0/14:1)+NH4 | TG(34:1)+NH4 | TG | 8:0/12:0/14:1 | 8:0 | 12:0 | 14:1 | 626.5354 | C37 H72 O6 N1 | 7.81 | 110.191 | 80.65471 | 1.366194 | 1.01389 | 0.00 0 |
| 1.72 | TG(18:0/16:0/16:0)+Na | TG(50:0)+Na | TG | 18:0/16:0/16:0 | 18:0 | 16:0 | 16:0 | 857.7569 | C53 H102 O6 Na1 | 10.50 | 3.145527 | 5.310465 | 0.592326 | 0.450163 | 0.00 0 |
| 1.72 | TG(19:0/12:0/12:0)+NH4 | TG(43:0)+NH4 | TG | 19:0/12:0/12:0 | 19:0 | 12:0 | 12:0 | 754.6919 | C46 H92 O6 N1 | 9.42 | 10.66589 | 15.11144 | 0.705815 | -0.75554 | 0.00 0 |
| 1.71 | TG(18:0/12:0/16:0)+Na | TG(46:0)+Na | TG | 18:0/12:0/16:0 | 18:0 | 12:0 | 16:0 | 801.6943 | C49 H94 O6 Na1 | 10.06 | 5.932032 | 16.20576 | 0.366046 | -0.50264 | 0.00 0 |
| 1.71 | TG(8:0/12:0/18:2)+NH4 | TG(38:2)+NH4 | TG | 8:0/12:0/18:2 | 8:0 | 12:0 | 18:2 | 680.5824 | C41 H78 O6 N1 | 8.28 | 620.4019 | 506.5436 | 1.224776 | -1.4499 | 0.00 0 |
| 1.70 | TG(8:0/9:0/10:0)+NH4 | TG(27:0)+NH4 | TG | 8:0/9:0/10:0 | 8:0 | 9:0 | 10:0 | 530.4415 | C30 H60 O6 N1 | 6.37 | 5.236492 | 3.334623 | 1.570346 | 0.292517 | 0.00 0 |
| 1.70 | TG(24:3/18:1/18:1)+NH4 | TG(60:5)+NH4 | TG | 24:3/18:1/18:1 | 24:3 | 18:1 | 18:2 | 982.8797 | C63 H116 O6 N1 | 10.55 | 0.338172 | 0.088982 | 3.800458 | 0.651077 | 0.00 0 |
| 1.70 | TG(6:0/12:0/20:5)+H | TG(38:5)+H | TG | 6:0/12:0/20:5 | 6:0 | 12:0 | 20:5 | 657.5089 | C41 H69 O6 | 7.87 | 25.96122 | 21.08588 | 1.231218 | 1.926173 | 0.00 0 |
| 1.69 | TG(26:0/18:1/24:0)+NH4 | TG(68:1)+NH4 | TG | 26:0/18:1/24:0 | 26:0 | 18:1 | 24:0 | 1103.068 | C71 H140 O6 N1 | 11.77 | 0.063858 | 0.016841 | 3.792151 | 0.300087 | 0.00 0 |
| 1.69 | TG(18:1/12:0/23:0)+NH4 | TG(53:1)+NH4 | TG | 18:1/12:0/23:0 | 18:1 | 12:0 | 23:0 | 892.8357 | C56 H110 O6 N1 | 10.62 | 4.486957 | 2.436585 | 1.841494 | 1.923016 | 0.00 0 |
| 1.67 | TG(18:0/16:0/16:0)+Na | TG(50:1)+Na | TG | 18:1/12:0/23:0 | 18:1 | 12:0 | 23:0 | 855.7428 | C53 H100 O6 Na1 | 10.28 | 17.38933 | 29.83463 | 0.582857 | 0.880877 | 0.00 0 |
| 1.67 | TG(16:0/16:0/16:0)+NH4 | TG(48:0)+NH4 | TG | 16:0/16:0/16:0 | 16:0 | 16:0 | 16:0 | 824.7702 | C51 H102 O6 N1 | 10.30 | 133.4463 | 207.5435 | 0.642987 | -0.77879 | 0.00 0 |
| 1.66 | TG(6:0/12:0/18:1)+NH4 | TG(36:1)+NH4 | TG | 6:0/12:0/18:1 | 6:0 | 12:0 | 18:1 | 654.5667 | C39 H76 O6 N1 | 7.86 | 14.04952 | 8.188815 | 1.715695 | -0.63715 | 0.00 0 |
| 1.65 | TG(8:0/12:0/18:1)+NH4 | TG(38:1)+NH4 | TG | 8:0/12:0/18:1 | 8:0 | 12:0 | 18:1 | 682.5984 | C41 H80 O6 N1 | 8.28 | 65.69804 | 37.35315 | 1.758835 | 0.778793 | 0.00 0 |
| 1.65 | TG(18:1/14:0/24:0)+NH4 | TG(56:1)+NH4 | TG | 18:1/14:0/24:0 | 18:1 | 14:0 | 24:0 | 934.8797 | C59 H116 O6 N1 | 10.89 | 38.94792 | 24.52161 | 1.588313 | 0.81462 | 0.00 0 |
| 1.64 | TG(18:0/12:0/16:0)+NH4 | TG(46:0)+NH4 | TG | 18:0/12:0/16:0 | 18:0 | 12:0 | 16:0 | 796.7389 | C49 H98 O6 N1 | 10.06 | 310.3821 | 489.4434 | 0.634153 | -0.6571 | 0.00 0 |

FIG. 45 (Continued)

| | | TG | | | | | | | | | | | |
|---|---|---|---|---|---|---|---|---|---|---|---|---|---|
| 1.64 | TG(6:0/8:0/12:0)+NH4 | TG(26:0)+NH4 | 6:0/8:0/12:0 | 6:0 | 8:0 | 12:0 | 516.4259 | C29H58O6 N1 | 4.77 | 1.393072 | 14.87284 | 0.093666 | -3.41634 | 0.00 0 |
| 1.64 | TG(8:0/8:0/18:1)+NH4 | TG(34:1)+NH4 | 8:0/8:0/18:1 | 8:0 | 8:0 | 18:1 | 626.5354 | C37H72O6 N1 | 7.44 | 6.32692 | 3.997472 | 1.582748 | 0.662431 | 0.00 0 |
| 1.62 | TG(16:0/17:0/18:1)+NH4 | TG(51:1)+NH4 | 16:0/17:0/18:1 | 16:0 | 17:0 | 18:1 | 864.8015 | C54H106O6N1 | 10.41 | 8.155174 | 5.069951 | 1.60853 | 0.685744 | 0.00 0 |
| 1.62 | TG(12:0/12:0/14:0)+Na | TG(38:0)+Na | 12:0/12:0/14:0 | 12:0 | 12:0 | 14:0 | 689.5691 | C41H78O6 Na1 | 9.72 | 0.337376 | 0.996718 | 0.338488 | -1.56283 | 0.00 0 |
| 1.62 | TG(16:0/16:0/16:0)+Na | TG(48:0)+Na | 16:0/16:0/16:0 | 16:0 | 16:0 | 16:0 | 829.7256 | C51H98O6 Na1 | 10.28 | 2.546413 | 7.858206 | 0.324045 | -1.62573 | 0.00 0 |
| 1.62 | TG(12:0/14:0/18:3)+H | TG(44:3)+H | 12:0/14:0/18:3 | 12:0 | 14:0 | 18:3 | 745.6341 | C47H85O6 N1 | 8.04 | 3.210866 | 1.363211 | 2.355371 | 1.235955 | 0.00 0 |
| 1.62 | TG(17:0/12:0/12:0)+NH4 | TG(41:0)+NH4 | 17:0/12:0/12:0 | 17:0 | 12:0 | 12:0 | 726.6606 | C44H88O6 N1 | 9.11 | 16.88557 | 23.44484 | 0.720224 | -0.47348 | 0.00 0 |
| 1.62 | TG(17:0/17:0/17:0)+NH4 | TG(51:0)+NH4 | 17:0/17:0/17:0 | 17:0 | 17:0 | 17:0 | 866.8171 | C54H108O6 N1 | 10.62 | 5.218084 | 3.627036 | 1.438666 | 0.524731 | 0.00 0 |
| 1.61 | TG(16:1/16:1/18:1)+NH4 | TG(50:3)+NH4 | 16:1/16:1/18:1 | 16:1 | 16:1 | 18:1 | 846.7545 | C53H100O6 N1 | 9.88 | 277.6014 | 163.6339 | 1.696489 | 0.762552 | 0.00 0 |
| 1.61 | TG(26:0/18:1/24:1)+NH4 | TG(68:2)+NH4 | 26:0/18:1/24:1 | 26:0 | 18:1 | 24:1 | 1101.052 | C71H138O6 N1 | 11.65 | 0.042411 | 0.010676 | 3.972628 | 1.990094 | 0.00 0 |
| 1.60 | TG(20:0/18:1/18:1)+NH4 | TG(56:2)+NH4 | 20:0/18:1/18:1 | 20:0 | 18:1 | 18:1 | 932.8641 | C59H114O6 N1 | 10.70 | 49.57836 | 36.08276 | 1.374017 | 0.458399 | 0.00 0 |
| 1.59 | TG(18:1/17:1/20:3)+NH4 | TG(55:5)+NH4 | 18:1/17:1/20:3 | 18:1 | 17:1 | 20:3 | 912.8045 | C58H106O6 N1 | 10.01 | 1.080565 | 0.067532 | 16.00132 | 4.000119 | 0.00 0 |
| 1.59 | TG(8:0/12:0/18:1)+NH4 | TG(38:1)+NH4 | 8:0/12:0/18:1 | 8:0 | 12:0 | 18:1 | 682.598 | C41H80O6 N1 | 8.63 | 1115.604 | 984.1616 | 1.133558 | 0.180858 | 0.00 0 |
| 1.58 | TG(6:0/8:0/8:0)+Na | TG(22:0)+Na | 6:0/8:0/8:0 | 6:0 | 8:0 | 8:0 | 465.3187 | C25H46O6 Na1 | 4.53 | 1.153706 | 1.721239 | 0.670276 | -0.57717 | 0.00 0 |
| 1.58 | TG(26:0/18:1/20:0)+NH4 | TG(64:1)+NH4 | 26:0/18:1/20:0 | 26:0 | 18:1 | 20:0 | 1047.005 | C67H132O6 N1 | 11.50 | 0.182518 | 0.083245 | 2.192557 | 1.132614 | 0.00 0 |
| 1.58 | TG(18:1/20:2/20:3)+NH4 | TG(58:6)+NH4 | 18:1/20:2/20:3 | 18:1 | 20:2 | 20:3 | 952.8328 | C61H110O6 N1 | 10.18 | 0.108484 | 0.005705 | 19.00691 | 4.248452 | 0.00 0 |
| 1.57 | TG(6:0/12:0/12:0)+H | TG(30:0)+H | 6:0/12:0/12:0 | 6:0 | 12:0 | 12:0 | 555.4619 | | 5.69 | 2.072005 | 0.022769 | 91.01849 | 6.508088 | 0.00 0 |
| 1.57 | TG(16:1/16:1/17:1)+NH4 | TG(49:3)+NH4 | 16:1/16:1/17:1 | 16:1 | 16:1 | 17:1 | 832.7389 | C52H98O6 N1 | 9.74 | 5.849407 | 3.446359 | 1.604178 | 0.681834 | 0.00 0 |

FIG. 45 (Continued)

| | | | | | | | | | | | | |
|---|---|---|---|---|---|---|---|---|---|---|---|---|
| 1.56 | TG(6:0/8:0/12:0)+NH4 | TG(26:0)+NH4 | TG | 6:0/8:0/12:0 | | | | 516.4259 | C29 H58 O6 N1 | 5.30 | 10.04993 | 14.5967 2 | 0.68850 6 | -0.53846 | 0.00 0 |
| 1.56 | TG(28:0/18:1/24:0)+NH4 | TG(70:1)+NH4 | TG | 28:0/18:1/24:0 | | | | 1131.099 | C73 H144 O6 N1 | 11.89 | 0.001654 | 0.00087 3 | 13.3501 7 | 3.738786 | 0.00 0 |
| 1.56 | TG(11:0/12:0/18:2)+NH4 | TG(41:2)+NH4 | TG | 11:0/12:0/18:2 | | | | 722.6293 | C44 H84 O6 N1 | 8.83 | 5.575514 | 4.08795 | 1.36389 3 | 0.447728 | 0.00 0 |
| 1.56 | TG(8:0/13:0/18:2)+NH4 | TG(39:2)+NH4 | TG | 8:0/13:0/18:2 | | | | 694.598 | C42 H80 O6 N1 | 8.47 | 3.588726 | 2.68999 1 | 1.33410 3 | 0.415871 | 0.00 0 |
| 1.54 | TG(10:0/12:0/18:1)+NH4 | TG(40:1)+NH4 | TG | 10:0/12:0/18:1 | | | | 710.6293 | C43 H84 O6 N1 | 8.67 | 45.53787 | 32.4662 1 | 1.40262 3 | 0.488128 | 0.00 0 |
| 1.54 | TG(12:0/14:0/23:0)+NH4 | TG(49:0)+NH4 | TG | 12:0/14:0/23:0 | | | | 838.7858 | C52 H104 O6 N1 | 10.43 | 8.624185 | 6.55791 7 | 1.31508 | 0.39515 | 0.00 0 |
| 1.53 | TG(18:0p/24:0/18:0)+NH4 | TG(66:1p)+NH4 | TG | 18:0p/24:0/18:0 | | | | 1059.041 | C69 H136 O5 N1 | 11.06 | 0.056114 | 0.03660 8 | 1.53284 4 | 0.616211 | 0.00 0 |
| 1.53 | TG(15:0/16:1/16:1)+NH4 | TG(47:2)+NH4 | TG | 15:0/16:1/16:1 | | | | 806.7232 | C50 H96 O6 N1 | 9.73 | 13.20056 | 9.55176 8 | 1.38200 2 | 0.46676 | 0.00 0 |
| 1.52 | TG(18:0/12:0/14:0)+NH4 | TG(44:0)+NH4 | TG | 18:0/12:0/14:0 | | | | 768.7076 | C47 H94 O6 N1 | 9.82 | 833.9653 | 1156.16 2 | 0.72132 2 | -0.47128 | 0.00 0 |
| 1.52 | TG(18:1/24:0/24:0)+NH4 | TG(66:1)+NH4 | TG | 18:1/24:0/24:0 | | | | 1075.036 | C69 H136 O6 N1 | 11.64 | 0.150569 | 0.07104 5 | 2.11933 4 | 1.083611 | 0.00 0 |
| 1.51 | TG(20:0e/16:0/18:1)+NH4 | TG(54:1e)+NH4 | TG | 20:0e/16:0/18:1 | | | | 892.8692 | C57 H114 O5 N1 | 10.63 | 0.041424 | 0.01612 6 | 2.56869 5 | 1.361036 | 0.00 0 |
| 1.51 | TG(8:0/10:0/18:2)+NH4 | TG(36:2)+NH4 | TG | 8:0/10:0/18:2 | | | | 652.5511 | C39 H74 O6 N1 | 7.86 | 184.7022 | 145.845 5 | 1.26642 4 | 0.34076 | 0.00 0 |
| 1.50 | TG(15:0/16:0/18:1)+NH4 | TG(49:1)+NH4 | TG | 15:0/16:0/18:1 | | | | 836.7702 | C52 H102 O6 N1 | 10.19 | 14.74763 | 11.267 2 | 1.30892 | 0.38838 | 0.00 0 |
| 1.49 | TG(18:1/18:1/18:1)+H | TG(54:3)+H | TG | 18:1/18:1/18:1 | | | | 885.7906 | C57 H105 O6 | 10.32 | 1.39283 | 2.20041 6 | 0.63298 5 | -0.65976 | 0.00 0 |
| 1.49 | TG(8:0/12:0/14:1)+H | TG(34:1)+H | TG | 8:0/12:0/14:1 | | | | 609.5089 | C37 H69 O6 | 6.73 | 1.642782 | 3.62010 9 | 0.45379 4 | -1.13989 | 0.00 0 |
| 1.48 | TG(11:0/18:1/18:2)+NH4 | TG(47:3)+NH4 | TG | 11:0/18:1/18:2 | | | | 804.7076 | C50 H94 O6 N1 | 9.47 | 2.938065 | 1.68621 4 | 1.74240 3 | 0.801079 | 0.00 0 |
| 1.48 | TG(18:1/12:0/12:0)+NH4 | TG(42:1)+NH4 | TG | 18:1/12:0/12:0 | | | | 738.6645 | C45 H88 O6 N1 | 9.30 | 1309.745 | 1201.11 9 | 1.09043 7 | 0.124907 | 0.00 0 |
| 1.47 | TG(6:0/8:0/18:1)+NH4 | TG(32:1)+NH4 | TG | 6:0/8:0/18:1 | | | | 598.5041 | C35 H68 O6 N1 | 7.32 | 21.55151 | 14.6895 6 | 1.46713 1 | 0.552998 | 0.00 0 |

FIG. 45 (Continued)

| | | | | | | | | | | | | |
|---|---|---|---|---|---|---|---|---|---|---|---|---|
| 1.46 | TG(8:0/8:0/8:0)+Na | TG(24:0)+Na | TG | 8:0/8:0/8:0 | 8:0 | 8:0 | 8:0 | 493.35 | C27 H50 O6 Na1 | 5.31 | 27.5678 | 23.97109 | 1.150044 | 0.201688 | 0.00 0 |
| 1.45 | TG(6:0/11:0/12:0)+NH4 | TG(29:0)+NH4 | TG | 6:0/11:0/12:0 | 6:0 | 11:0 | 12:0 | 558.47 28 | C32 H64 O6 N1 | 6.98 | 32.918 64 | 23.8723 3 | 1.37894 5 | 0.463565 | 0.00 0 |
| 1.43 | TG(8:0/12:0/12:0)+NH4 | TG(32:0)+NH4 | TG | 8:0/12:0/12:0 | 8:0 | 12:0 | 12:0 | 600.51 98 | C35 H70 O6 N1 | 7.73 | 5065.3 75 | 5417.05 8 | 0.93507 9 | -0.09684 | 0.00 0 |
| 1.43 | TG(16:0/12:0/14:0)+NH4 | TG(42:0)+NH4 | TG | 16:0/12:0/14:0 | 16:0 | 12:0 | 14:0 | 740.67 63 | C45 H90 O6 N1 | 8.77 | 6.6680 9 | 8.45948 9 | 0.78823 9 | -0.3433 | 0.00 0 |
| 1.42 | TG(40:2)+Na | TG(40:2)+Na | TG | 10:0/12:0/18:2 | 10:0 | 12:0 | 18:2 | 713.56 91 | C43 H78 O6 Na1 | 8.68 | 29.820 08 | 25.8911 1 | 1.15175 | 0.203827 | 0.00 0 |
| 1.42 | TG(25:0/18:1/24:1)+NH4 | TG(67:2)+NH4 | TG | 25:0/18:1/24:1 | 25:0 | 18:1 | 24:1 | 1087.0 36 | C70 H136 O6 N1 | 11.57 | 0.1044 5 | 0.00190 | 54.8209 1 | 5.776654 | 0.00 0 |
| 1.41 | TG(8:0/8:0/21:6)+Na | TG(37:6)+Na | TG | 8:0/8:0/21:6 | 8:0 | 8:0 | 21:6 | 663.45 95 | C40 H64 O6 Na1 | 7.35 | 120.07 11 | 86.3472 | 1.39056 9 | 0.475667 | 0.00 0 |
| 1.40 | TG(6:0/12:0/18:1)+NH4 | TG(36:1)+NH4 | TG | 6:0/12:0/18:1 | 6:0 | 12:0 | 18:1 | 654.56 67 | C39 H76 O6 N1 | 8.25 | 435.63 31 | 378.963 3 | 1.14953 9 | 0.201055 | 0.00 0 |
| 1.40 | TG(20:1/18:1/20:3)+NH4 | TG(58:5)+NH4 | TG | 20:1/18:1/20:3 | 20:1 | 18:1 | 20:3 | 954.84 84 | C61 H112 O6 N1 | 10.37 | 0.2127 53 | 0.05151 | 4.13035 4 | 2.046264 | 0.00 0 |
| 1.40 | TG(18:1/18:1/22:6)+H | TG(58:8)+H | TG | 18:1/18:1/22:6 | 18:1 | 18:1 | 22:6 | 931.77 49 | C61 H103 O6 | 10.15 | 0.1844 35 | 0.03200 1 | 5.76336 4 | 2.526911 | 0.00 0 |
| 1.40 | TG(15:0/16:1/18:1)+NH4 | TG(49:2)+NH4 | TG | 15:0/16:1/18:1 | 15:0 | 16:1 | 18:1 | 834.75 45 | C52 H100 O6 N1 | 9.98 | 17.524 7 | 12.2908 1 | 1.42583 8 | 0.51181 | 0.00 0 |
| 1.40 | TG(12:0/13:0/18:2)+NH4 | TG(43:2)+NH4 | TG | 12:0/13:0/18:2 | 12:0 | 13:0 | 18:2 | 750.66 06 | C46 H88 O6 N1 | 9.15 | 7.7707 63 | 5.53477 1 | 1.40398 8 | 0.489531 | 0.00 1 |
| 1.40 | TG(18:0/16:0/18:1)+NH4 | TG(52:1)+NH4 | TG | 18:0/16:0/18:1 | 18:0 | 16:0 | 18:1 | 878.81 71 | C55 H108 O6 N1 | 10.51 | 270.63 49 | 226.139 6 | 1.19676 | 0.259134 | 0.00 1 |
| 1.39 | TG(16:0/18:1/18:1)+NH4 | TG(52:2)+NH4 | TG | 16:0/18:1/18:1 | 16:0 | 18:1 | 18:1 | 876.80 15 | C55 H106 O6 N1 | 10.79 | 3.9623 16 | 2.46946 9 | 1.60452 | 0.682143 | 0.00 1 |
| 1.39 | TG(25:0/12:0/16:1)+NH4 | TG(53:0)+NH4 | TG | 25:0/12:0/16:1 | 25:0 | 12:0 | 16:0 | 894.84 84 | C56 H112 O6 N1 | 10.81 | 2.5394 79 | 1.83484 6 | 1.38402 9 | 0.468874 | 0.00 1 |
| 1.39 | TG(8:0/9:0/18:1)+NH4 | TG(35:1)+NH4 | TG | 8:0/9:0/18:1 | 8:0 | 9:0 | 18:1 | 640.55 11 | C38 H74 O6 N1 | 8.09 | 14.695 4 | 12.1986 3 | 1.20467 7 | 0.268646 | 0.00 1 |
| 1.38 | TG(12:0/12:0/20:5)+H | TG(44:5)+H | TG | 12:0/12:0/20:5 | 12:0 | 12:0 | 20:5 | 741.60 28 | C47 H81 O6 | 9.02 | 32.538 49 | 27.0267 7 | 1.20393 6 | 0.267758 | 0.00 1 |
| 1.38 | TG(8:0/12:0/12:0)+NH4 | TG(32:0)+NH4 | TG | 8:0/12:0/12:0 | 8:0 | 12:0 | 12:0 | 600.51 98 | C35 H70 O6 N1 | 7.73 | 4978.4 14 | 5245.71 8 | 0.94904 3 | -0.07545 | 0.00 1 |

FIG. 45 (Continued)

| | | | | | | | | | | | | | |
|---|---|---|---|---|---|---|---|---|---|---|---|---|---|
| 1.37 | TG(8:0/9:0/10:0)+Na | TG | 8:0/9:0/10:0 | 8:0 | 9:0 | 10:0 | 535.3969 | C30 H56 O6 Na1 | 6.37 | 2.070672 | 2.335135 | 0.886746 | -0.17341 | 0.00 1 |
| 1.37 | TG(18:1/14:0/18:3)+H | TG | 18:1/14:0/18:3 | 18:1 | 14:0 | 18:3 | 827.7123 | C53 H95 O6 | 8.73 | 2.33126 | 0.709342 | 3.287029 | 1.716784 | 0.00 1 |
| 1.36 | TG(6:0/8:0/12:0)+NH4 | TG | 6:0/8:0/12:0 | 6:0 | 8:0 | 12:0 | 516.4259 | C29 H58 O6 N1 | 6.05 | 370.249 | 456.1036 | 0.81176 | -0.30086 | 0.00 1 |
| 1.36 | TG(18:1/14:0/18:1)+NH4 | TG | 18:1/14:0/18:1 | 18:1 | 14:0 | 18:1 | 848.7702 | C53 H102 O6 N1 | 10.09 | 709.3062 | 633.6737 | 1.11935 | 0.162668 | 0.00 1 |
| 1.34 | TG(16:0e/24:1/24:1)+NH4 | TG | 16:0e/24:1/24:1 | 16:0e | 24:1 | 24:1 | 1031.01 | C67 H132 O5 N1 | 10.91 | 0.02492 | 0.014861 | 1.67694 | 0.745835 | 0.00 1 |
| 1.34 | TG(16:0/12:0/18:1)+Na | TG | 16:0/12:0/18:1 | 16:0 | 12:0 | 18:1 | 799.6786 | C49 H92 O6 Na1 | 9.81 | 24.39555 | 38.96428 | 0.6261 | -0.67553 | 0.00 1 |
| 1.33 | TG(16:0p/24:0/24:1)+NH4 | TG | 16:0p/24:0/24:1 | 16:0p | 24:0 | 24:1 | 1031.01 | C67 H132 O5 N1 | 10.90 | 0.021593 | 0.014221 | 1.51835 | 0.60251 | 0.00 1 |
| 1.33 | TG(28:1/18:1/24:0)+NH4 | TG | 28:1/18:1/24:0 | 28:1 | 18:1 | 24:0 | 1129.083 | C73 H142 O6 N1 | 11.74 | 0.009641 | 0.002847 | 3.39450 | 1.763202 | 0.00 1 |
| 1.33 | TG(15:1/16:0/16:0)+NH4 | TG | 15:1/16:0/16:0 | 15:1 | 16:0 | 16:0 | 808.7389 | C50 H98 O6 N1 | 9.96 | 22.42222 | 17.57468 | 1.27582 | 0.351431 | 0.00 1 |
| 1.33 | TG(30:1/18:1/18:1)+NH4 | TG | 30:1/18:1/18:1 | 30:1 | 18:1 | 18:1 | 1071.05 | C69 H132 O6 N1 | 11.37 | 0.051151 | 0.018028 | 2.83848 | 1.505123 | 0.00 1 |
| 1.32 | TG(16:2/18:1/18:1)+NH4 | TG | 16:2/18:1/18:1 | 16:2 | 18:1 | 18:1 | 872.7702 | C55 H102 O6 N1 | 10.62 | 0.433291 | 0.585447 | 0.74010 | -0.43419 | 0.00 1 |
| 1.29 | TG(16:0/12:0/14:0)+NH4 | TG | 16:0/12:0/14:0 | 16:0 | 12:0 | 14:0 | 740.6763 | C45 H90 O6 N1 | 1.61 | 3.44646 | 1.274429 | 2.70432 | 1.435271 | 0.00 2 |
| 1.28 | TG(8:0/10:0/12:0)+NH4 | TG | 8:0/10:0/12:0 | 8:0 | 10:0 | 12:0 | 572.4885 | C33 H66 O6 N1 | 7.24 | 3450.409 | 3732.197 | 0.92449 | -0.11326 | 0.00 2 |
| 1.28 | TG(8:0/8:0/18:2)+NH4 | TG | 8:0/8:0/18:2 | 8:0 | 8:0 | 18:2 | 624.5198 | C37 H70 O6 N1 | 7.37 | 31.71686 | 25.10301 | 1.26346 | 0.337389 | 0.00 2 |
| 1.28 | TG(18:0/18:0/18:1)+NH4 | TG | 18:0/18:0/18:1 | 18:0 | 18:0 | 18:1 | 906.8484 | C57 H112 O6 N1 | 10.70 | 99.10934 | 82.99824 | 1.19411 | 0.255941 | 0.00 2 |
| 1.27 | TG(15:0/12:0/12:0)+NH4 | TG | 15:0/12:0/12:0 | 15:0 | 12:0 | 12:0 | 698.6293 | C42 H84 O6 N1 | 8.77 | 24.85167 | 31.91402 | 0.77870 | -0.36085 | 0.00 2 |
| 1.26 | TG(18:0/12:0/22:3)+H | TG | 18:0/12:0/22:3 | 18:0 | 12:0 | 22:3 | 857.7593 | C55 H101 O6 | 8.61 | 0.253449 | 0.702236 | 0.36091 | -1.47026 | 0.00 3 |
| 1.24 | TG(8:0/12:0/18:1)+H | TG | 8:0/12:0/18:1 | 8:0 | 12:0 | 18:1 | 665.5715 | C41 H77 O6 | 7.29 | 3.030264 | 1.200769 | 2.52360 | 1.335485 | 0.00 3 |

FIG. 45 (Continued)

| | | | | | | | | | | | | |
|---|---|---|---|---|---|---|---|---|---|---|---|---|
| 1.24 | TG(8:0/12:0/18:1)+NH4 | TG(38:1)+NH4 | TG | 8:0/12:0/18:1 | 8:0 | 12:0 | 18:1 | 682.598 | C41 H80 O6 N1 | 10.73 | 3.794284 | 14.58862 | 0.260085 | -1.94294 | 0.00 3 |
| 1.23 | TG(27:0/18:1/18:1)+NH4 | TG(63:2)+NH4 | TG | 27:0/18:1/18:1 | 27:0 | 18:1 | 18:1 | 1030.974 | C66 H128 O6 N1 | 11.30 | 0.498665 | 0.217922 | 2.288279 | 1.194263 | 0.00 3 |
| 1.23 | TG(16:0/13:0/14:0)+NH4 | TG(43:0)+NH4 | TG | 16:0/13:0/14:0 | 16:0 | 13:0 | 14:0 | 754.6919 | C46 H92 O6 N1 | 9.71 | 30.04357 | 34.49344 | 0.870994 | -0.19927 | 0.00 3 |
| 1.23 | TG(8:0/8:0/12:0)+NH4 | TG(28:0)+NH4 | TG | 8:0/8:0/12:0 | 8:0 | 8:0 | 12:0 | 544.4572 | C31 H62 O6 N1 | 12.85 | 29.40913 | 32.74152 | 0.898222 | -0.15486 | 0.00 3 |
| 1.22 | TG(16:0/12:0/14:0)+NH4 | TG(42:0)+NH4 | TG | 16:0/12:0/14:0 | 16:0 | 12:0 | 14:0 | 740.6763 | C45 H90 O6 N1 | 9.55 | 2047.3 | 2338.95 | 0.875333 | -0.1921 | 0.00 4 |
| 1.22 | TG(8:0/12:0/18:3)+H | TG(38:3)+H | TG | 8:0/12:0/18:3 | 8:0 | 12:0 | 18:3 | 661.5402 | C41 H73 O6 N1 | 6.83 | 4.567345 | 2.772048 | 1.647648 | 0.720408 | 0.00 4 |
| 1.22 | TG(8:0/8:0/12:0)+NH4 | TG(28:0)+NH4 | TG | 8:0/8:0/12:0 | 8:0 | 8:0 | 12:0 | 544.4572 | C31 H62 O6 N1 | 4.94 | 1.530339 | 0.437999 | 3.493932 | 1.804851 | 0.00 4 |
| 1.22 | TG(8:0/8:0/12:0)+NH4 | TG(28:0)+NH4 | TG | 8:0/8:0/12:0 | 8:0 | 8:0 | 12:0 | 544.4572 | C31 H62 O6 N1 | 10.91 | 7.55101 | 22.34954 | 0.337864 | -1.56548 | 0.00 4 |
| 1.22 | TG(8:0/8:0/8:0)+NH4 | TG(24:0)+NH4 | TG | 8:0/8:0/8:0 | 8:0 | 8:0 | 8:0 | 488.3946 | C27 H54 O6 N1 | 5.31 | 35.99698 | 24.46783 | 1.471197 | 0.55699 | 0.00 4 |
| 1.21 | TG(18:1/12:0/14:0)+NH4 | TG(44:1)+NH4 | TG | 18:1/12:0/14:0 | 18:1 | 12:0 | 14:0 | 766.6919 | C47 H92 O6 N1 | 12.11 | 3.399689 | 1.573594 | 2.160462 | 1.11134 | 0.00 4 |
| 1.21 | TG(16:0/8:0/12:0)+NH4 | TG(36:0)+NH4 | TG | 16:0/8:0/12:0 | 16:0 | 8:0 | 12:0 | 656.5824 | C39 H78 O6 N1 | 8.58 | 4721.767 | 5112.342 | 0.923601 | -0.11466 | 0.00 4 |
| 1.21 | TG(12:0/14:0/14:0)+NH4 | TG(40:0)+NH4 | TG | 12:0/14:0/14:0 | 12:0 | 14:0 | 14:0 | 712.645 | C43 H86 O6 N1 | 9.26 | 2962.506 | 3221.584 | 0.919581 | -0.12095 | 0.00 4 |
| 1.20 | TG(6:0/12:0/18:1)+NH4 | TG(36:1)+NH4 | TG | 6:0/12:0/18:1 | 6:0 | 12:0 | 18:1 | 654.5667 | C39 H76 O6 N1 | 6.31 | 0.835654 | 0.463115 | 1.804421 | 0.851536 | 0.00 4 |
| 1.20 | TG(26:0/16:0/24:0)+NH4 | TG(66:0)+NH4 | TG | 26:0/16:0/24:0 | 26:0 | 16:0 | 24:0 | 1077.052 | C69 H138 O6 N1 | 11.71 | 0.031333 | 0.011627 | 2.694824 | 1.430191 | 0.00 4 |
| 1.20 | TG(8:0/12:0/12:0)+NH4 | TG(32:0)+NH4 | TG | 8:0/12:0/12:0 | 8:0 | 12:0 | 12:0 | 600.5198 | C35 H70 O6 N1 | 5.47 | 22.42918 | 9.660047 | 2.321851 | 1.215275 | 0.00 5 |
| 1.20 | TG(12:0/12:0/14:0)+NH4 | TG(38:0)+NH4 | TG | 12:0/12:0/14:0 | 12:0 | 12:0 | 14:0 | 684.6137 | C41 H82 O6 N1 | 9.96 | 13.72065 | 5.869796 | 2.337501 | 1.224967 | 0.00 5 |
| 1.17 | TG(6:0/8:0/12:0)+NH4 | TG(26:0)+NH4 | TG | 6:0/8:0/12:0 | 6:0 | 8:0 | 12:0 | 516.4259 | C29 H58 O6 N1 | 13.82 | 2.470605 | 3.867888 | 0.638748 | -0.64668 | 0.00 6 |
| 1.17 | TG(12:0/12:0/12:0)+NH4 | TG(36:0)+NH4 | TG | 12:0/12:0/12:0 | 12:0 | 12:0 | 12:0 | 656.5824 | C39 H78 O6 N1 | 7.47 | 52.78527 | 29.77038 | 1.773088 | 0.826258 | 0.00 6 |

FIG. 45 (Continued)

| | | | | | | | | | | |
|---|---|---|---|---|---|---|---|---|---|---|
| 1.17 | TG(10:0/12:0/18:1)+NH4 | TG(40:1)+NH4 | TG | 10:0/12:0/18:1 | 10:0 | 12:0 | 18:1 | 710.6293 | C43 H84 O6 N1 | 8.98 | 613.7414 | 560.9213 | 1.094167 | 0.129832 | 0.006 |
| 1.16 | TG(15:1/12:0/18:1)+NH4 | TG(45:2)+NH4 | TG | 15:1/12:0/18:1 | 15:1 | 12:0 | 18:1 | 778.6919 | C48 H92 O6 N1 | 9.45 | 12.38522 | 8.784843 | 1.409837 | 0.495528 | 0.006 |
| 1.16 | TG(26:0/18:0/24:0)+NH4 | TG(68:0)+NH4 | TG | 26:0/18:0/24:0 | 26:0 | 18:0 | 24:0 | 1105.083 | C71 H142 O6 N1 | 11.79 | 0.007717 | 0.002658 | 2.903558 | 1.537818 | 0.006 |
| 1.16 | TG(19:1/12:0/12:0)+NH4 | TG(43:1)+NH4 | TG | 19:1/12:0/12:0 | 19:1 | 12:0 | 12:0 | 752.6763 | C46 H90 O6 N1 | 8.68 | 3.381498 | 2.586846 | 1.307196 | 0.386469 | 0.006 |
| 1.16 | TG(6:0/18:1/18:1)+NH4 | TG(42:2)+NH4 | TG | 6:0/18:1/18:1 | 6:0 | 18:1 | 18:1 | 736.6415 | C45 H86 O6 N1 | 8.70 | 14.97946 | 11.92237 | 1.256416 | 0.329315 | 0.007 |
| 1.15 | TG(16:0/12:0/12:0)+NH4 | TG(40:0)+NH4 | TG | 16:0/12:0/12:0 | 16:0 | 12:0 | 12:0 | 712.6425 | C43 H86 O6 N1 | 9.52 | 23.91589 | 18.06991 | 1.323521 | 0.404381 | 0.007 |
| 1.13 | TG(8:0/10:0/12:0)+NH4 | TG(30:0)+NH4 | TG | 8:0/10:0/12:0 | 8:0 | 10:0 | 12:0 | 572.4885 | C33 H66 O6 N1 | 9.12 | 37.68943 | 17.86144 | 2.11011 | 1.077312 | 0.008 |
| 1.13 | TG(15:0/8:0/12:0)+NH4 | TG(35:0)+NH4 | TG | 15:0/8:0/12:0 | 15:0 | 8:0 | 12:0 | 642.5667 | C38 H76 O6 N1 | 7.97 | 28.66496 | 35.55694 | 0.806171 | -0.31084 | 0.008 |
| 1.12 | TG(29:0/18:1/18:1)+NH4 | TG(65:2)+NH4 | TG | 29:0/18:1/18:1 | 29:0 | 18:1 | 18:1 | 1059.005 | C68 H132 O6 N1 | 11.44 | 0.089116 | 0.018492 | 4.819254 | 2.26881 | 0.009 |
| 1.12 | TG(18:1/12:0/12:0)+H | TG(42:1)+H | TG | 18:1/12:0/12:0 | 18:1 | 12:0 | 12:0 | 721.6341 | C45 H85 O6 | 9.32 | 3.250756 | 2.674417 | 1.215501 | 0.281551 | 0.010 |
| 1.12 | TG(16:0/18:1/18:1)+H | TG(52:2)+H | TG | 16:0/18:1/18:1 | 16:0 | 18:1 | 18:1 | 859.7749 | C55 H103 O6 | 10.31 | 1.358613 | 0.971597 | 1.398337 | 0.483705 | 0.010 |
| 1.12 | TG(8:0/12:0/12:0)+Na | TG(32:0)+Na | TG | 8:0/12:0/12:0 | 8:0 | 12:0 | 12:0 | 605.4752 | C35 H66 O6 Na1 | 7.92 | 98.8043 | 19.96894 | 4.947899 | 2.306816 | 0.010 |
| 1.11 | TG(30:1/18:1/22:1)+NH4 | TG(70:3)+NH4 | TG | 30:1/18:1/22:1 | 30:1 | 18:1 | 22:1 | 1127.068 | C73 H140 O6 N1 | 11.54 | 0.006483 | 0.000552 | 11.73689 | 3.552978 | 0.010 |
| 1.11 | TG(8:0/12:0/12:0)+NH4 | TG(32:0)+NH4 | TG | 8:0/12:0/12:0 | 8:0 | 12:0 | 12:0 | 600.5198 | C35 H70 O6 N1 | 10.58 | 356.2704 | 838.5154 | 0.424882 | -1.23486 | 0.010 |
| 1.11 | TG(8:0/12:0/14:1)+H | TG(34:1)+H | TG | 8:0/12:0/14:1 | 8:0 | 12:0 | 14:1 | 609.5089 | C37 H69 O6 | 6.43 | 5.052327 | 6.467424 | 0.781196 | -0.35624 | 0.010 |
| 1.09 | TG(4:0/12:0/20:3)+H | TG(36:3)+H | TG | 4:0/12:0/20:3 | 4:0 | 12:0 | 20:3 | 633.5089 | C39 H69 O6 N1 | 6.38 | 3.330138 | 1.593176 | 2.072201 | 1.051164 | 0.012 |
| 1.09 | TG(20:0e/18:1/20:0e)+NH4 | TG(62:2e)+NH4 | TG | 20:0e/18:1/20:0e | 20:0e | 18:1 | 24:1 | 1002.979 | C65 H128 O5 N1 | 10.72 | 0.030434 | 0.018781 | 1.620466 | 0.696409 | 0.012 |
| 1.08 | TG(9:0/18:1/18:2)+NH4 | TG(45:3)+NH4 | TG | 9:0/18:1/18:2 | 9:0 | 18:1 | 18:2 | 776.6763 | C48 H90 O6 N1 | 9.19 | 1.554594 | 1.064993 | 1.459723 | 0.545694 | 0.012 |

FIG. 45 (Continued)

| | | | | | | | | | | | | |
|---|---|---|---|---|---|---|---|---|---|---|---|---|
| 1.08 | TG(8:0/10:0/12:0)+Na | TG(30:0)+Na | TG | 8:0/10:0/12:0 | 8:0 | 10:0 | 12:0 | 577.4439 | C33 H62 O6 Na1 | 7.32 | 25.62578 | 16.6423 | 1.53979 | 0.622735 | 0.012 |
| 1.08 | TG(15:1/14:0/16:0)+NH4 | TG(45:1)+NH4 | TG | 15:1/14:0/16:0 | 15:1 | 14:0 | 16:0 | 780.7076 | C48 H94 O6 N1 | 9.71 | 26.07527 | 22.2541 | 1.17170 | 0.228606 | 0.013 |
| 1.07 | TG(12:0/12:0/14:0)+NH4 | TG(38:0)+NH4 | TG | 12:0/12:0/14:0 | 12:0 | 12:0 | 14:0 | 684.6137 | C41 H82 O6 N1 | 7.75 | 40.9195 | 30.6508 | 1.33502 | 0.416863 | 0.014 |
| 1.07 | TG(10:0/12:0/18:1)+NH4 | TG(40:1)+NH4 | TG | 10:0/12:0/18:1 | 10:0 | 12:0 | 18:1 | 710.6293 | C43 H84 O6 N1 | 3.79 | 2.660236 | 0.597978 | 4.44872 | 2.153391 | 0.014 |
| 1.07 | TG(16:0/12:0/14:0)+NH4 | TG(42:0)+NH4 | TG | 16:0/12:0/14:0 | 16:0 | 12:0 | 14:0 | 740.6763 | C45 H90 O6 N1 | 4.68 | 3.40398 | 0.425385 | 8.00208 | 3.000376 | 0.014 |
| 1.05 | TG(12:0/14:0/14:0)+NH4 | TG(40:0)+NH4 | TG | 12:0/14:0/14:0 | 12:0 | 14:0 | 14:0 | 712.6405 | C43 H86 O6 N1 | 1.93 | 19.88129 | 10.6665 | 1.86389 | 0.898319 | 0.016 |
| 1.05 | TG(25:0/18:1/20:0)+NH4 | TG(63:1)+NH4 | TG | 25:0/18:1/20:0 | 25:0 | 18:1 | 20:0 | 1032.989 | C66 H130 O6 N1 | 11.44 | 0.078384 | 0.040092 | 1.95485 | 0.967059 | 0.016 |
| 1.05 | TG(8:0/12:0/14:0)+NH4 | TG(34:0)+NH4 | TG | 8:0/12:0/14:0 | 8:0 | 12:0 | 14:0 | 628.5511 | C37 H74 O6 N1 | 4.95 | 11.49572 | 22.2951 | 0.51561 | -0.95563 | 0.017 |
| 1.04 | TG(6:0/12:0/14:1)+NH4 | TG(32:1)+NH4 | TG | 6:0/12:0/14:1 | 6:0 | 12:0 | 14:1 | 598.5041 | C35 H68 O6 N1 | 7.56 | 21.19037 | 3.507466 | 6.04151 | 2.59491 | 0.017 |
| 1.04 | TG(20:1p/18:1/20:13:0)+H | TG(61:2p)+H | TG | 20:1p/18:1/20:1 | 20:1p | 18:1 | 23:0 | 969.9209 | C64 H121 O5 | 10.76 | 0.007144 | 0.002389 | 2.99037 | 1.580326 | 0.017 |
| 1.04 | TG(8:0/12:0/12:0)+NH4 | TG(32:0)+NH4 | TG | 8:0/12:0/12:0 | 8:0 | 12:0 | 14:0 | 600.5198 | C35 H70 O6 N1 | 1.41 | 119.4956 | 202.623 | 0.58974 | -0.76184 | 0.018 |
| 1.04 | TG(8:0/10:0/12:0)+NH4 | TG(30:0)+NH4 | TG | 8:0/10:0/12:0 | 8:0 | 10:0 | 12:0 | 572.4885 | C33 H66 O6 N1 | 13.00 | 171.1726 | 186.0398 | 0.92008 | -0.12016 | 0.018 |
| 1.03 | TG(18:0/12:0/14:0)+NH4 | TG(44:0)+NH4 | TG | 18:0/12:0/14:0 | 18:0 | 12:0 | 14:0 | 768.7076 | C47 H94 O6 N1 | 13.29 | 0.706845 | 0.390397 | 1.81058 | 0.856458 | 0.018 |
| 1.03 | TG(17:0/8:0/18:1)+NH4 | TG(43:1)+NH4 | TG | 17:0/8:0/18:1 | 17:0 | 8:0 | 18:1 | 752.6763 | C46 H90 O6 N1 | 9.13 | 3.921817 | 4.809203 | 0.81548 | -0.29428 | 0.019 |
| 1.02 | TG(8:0/12:0/18:1)+NH4 | TG(38:1)+NH4 | TG | 8:0/12:0/18:1 | 8:0 | 12:0 | 18:1 | 682.5981 | C41 H80 O6 N1 | 3.25 | 0.265479 | 0.698937 | 0.37983 | -1.39656 | 0.020 |
| 1.00 | TG(8:0/10:0/12:0)+NH4 | TG(30:0)+NH4 | TG | 8:0/10:0/12:0 | 8:0 | 10:0 | 12:0 | 572.4885 | C33 H66 O6 N1 | 7.24 | 3655.287 | 3886.301 | 0.94055 | -0.08841 | 0.022 |
| 1.00 | TG(8:0/12:0/18:1)+NH4 | TG(38:1)+NH4 | TG | 8:0/12:0/18:1 | 8:0 | 12:0 | 18:1 | 682.5981 | C41 H80 O6 N1 | 10.01 | 3.300144 | 11.25839 | 0.29312 | -1.77039 | 0.022 |
| 1.00 | TG(12:0/14:0/14:0)+NH4 | TG(40:0)+NH4 | TG | 12:0/14:0/14:0 | 12:0 | 14:0 | 14:0 | 712.6405 | C43 H86 O6 N1 | 3.42 | 0.619558 | 1.412087 | 0.43875 | -1.18852 | 0.023 |

FIG. 45 (Continued)

| | | | | | | | | | | | |
|---|---|---|---|---|---|---|---|---|---|---|---|
| 1.83 | ZyE(24:1)+H | ZyE(24:1)+H | ZyE | 24:1 | 24.1 | 733.6857 | C51 H89 O2 | 9.43 | 0.1053 36 | 0.00037 4 | 281.812 9 | 8.138594 | 0.00 0 |
| 1.52 | ZyE(28:2)+H | ZyE(28:2)+H | ZyE | 28:2 | 28.2 | 787.7327 | C55 H95 O2 | 11.02 | 0.0069 26 | 0.03047 3 | 0.22728 9 | -2.1374 | 0.00 0 |

FIG. 46

| VIP | Lipid Ion | Lipid Group | Class | FattyAcid | FA1 | FA2 | FA3 | FA4 | Calc M/z | IonFormula | RT | Prco | Orco | Prco/Orco | Fold change (log2(Proc/Orco)) | T.test |
|---|---|---|---|---|---|---|---|---|---|---|---|---|---|---|---|---|
| 1.48 | CL(18:1/18:1/18:1/20:0)-H | CL(74:3)-H | CL | 18:1/18:1/18:1/20:0 | | | 18:1 | 20:0 | 1486.0745 | C83 H155 O17 P2 | 7.296 | 0 | 14.648323 | 0 | n.a. | 0.00 0 |
| 1.55 | cPA(18:1)-H | cPA(18:1)-H | cPA | 18:1 | 18:1 | | | | 417.24115 | C21 H38 O6 N0 P1 | 2.232 | 0.0849812 | 5.9441 | 0.0142967 | -6.13 | 0.00 0 |
| 1.67 | DGDG(16:0/18:2)+HCOO | DGDG(34:2)+HCOO | DGDG | 16:0/18:2 | 16:0 | 18:2 | | | 961.61053 | C50 H89 O17 | 6.563 | 0.4194472 | 23.976559 | 0.0174941 | -5.84 | 0.00 0 |
| 1.65 | DGDG(18:2/18:2)+HCOO | DGDG(36:4)+HCOO | DGDG | 18:2/18:2 | 18:2 | 18:2 | | | 985.61053 | C52 H89 O17 | 6.21 | 1.0764838 | 21.461557 | 0.0501587 | -4.32 | 0.00 0 |
| 1.62 | DGDG(18:0/18:1)+HCOO | DGDG(36:1)+HCOO | DGDG | 18:0/18:1 | 18:0 | 18:1 | | | 991.65748 | C52 H95 O17 | 7.47 | 0.0013948 | 26.511125 | 5.261E-05 | -14.21 | 0.00 0 |
| 1.55 | DGDG(18:1/18:1)+HCOO | DGDG(36:2)+HCOO | DGDG | 18:1/18:1 | 18:1 | 18:1 | | | 989.64183 | C52 H93 O17 | 7.256 | 0.6375599 | 94.39694 | 0.006754 | -7.21 | 0.00 0 |
| 1.52 | DGDG(16:0/18:1)+HCOO | DGDG(34:1)+HCOO | DGDG | 16:0/18:1 | 16:0 | 18:1 | | | 963.62618 | C50 H91 O17 | 7.005 | 0 | 58.225714 | 0 | n.a. | 0.00 0 |
| 1.28 | DGMG(19:5)+HCOO | DGMG(19:5)+HCOO | DGMG | 19:5 | 19:5 | | | | 731.34956 | C35 H55 O16 | 7.26 | 185.96066 | 100.39053 | 1.8523725 | 0.89 | 0.00 0 |
| 1.68 | dMePE(12:0/12:0)-H | dMePE(24:0)-H | dMePE | 12:0/12:0 | 12:0 | 12:0 | | | 606.41403 | C31 H61 O8 N1 P1 | 5.579 | 1.2382573 | 19.123705 | 0.0647499 | -3.95 | 0.00 0 |
| 1.61 | dMePE(18:1/18:1)-H | dMePE(36:2)-H | dMePE | 18:1/18:1 | 18:1 | 18:1 | | | 770.57053 | C43 H81 O8 N1 P1 | 8.207 | 3.3364604 | 80.564758 | 0.0414134 | -4.59 | 0.00 0 |

FIG. 46 (Continued)

| | | | | | | | | | | | | |
|---|---|---|---|---|---|---|---|---|---|---|---|---|
| 1.59 | dMePE(14:0 /14:0)-H | dMePE(2 8:0)-H | dMePE | 14:0/14: 0 | 14:0 | 14:0 | | 662.4763 | C35 H69 O8 N1 P1 | 6.925 | 2.1328876 | 15.701319 | 0.135884 13 | -2.88 | 0.00 0 |
| 1.61 | LdMePE(18: 1)-H | LdMePE( 18:1)-H | LdMeP E | 18:1 | 18:1 | | | 506.32522 | C25 H49 O7 N1 P1 | 2.581 | 0.4245358 | 11.205717 | 0.037788 56 | -4.72 | 0.00 0 |
| 1.49 | LdMePE(12: 0)-H | LdMePE( 12:0)-H | LdMeP E | 12:0 | 12:0 | | | 424.24697 | C19 H39 O7 N1 P1 | 1.296 | 6926.0005 77 | 3576.1705 | 1.936717 07 | 0.95 | 0.00 0 |
| 1.47 | LdMePE(10: 0)-H | LdMePE( 10:0)-H | LdMeP E | 10:0 | 10:0 | | | 396.21567 | C17 H35 O7 N1 P1 | 1.037 | 27.412704 | 13.021227 | 2.105232 | 1.07 | 0.00 0 |
| 1.57 | LPC(16:0)+ HCOO | LPC(16:0 )+HCOO | LPC | 16:0 | 16:0 | | | 540.3307 | C25 H51 O9 N1 P1 | 2.464 | 3.5671682 | 23.058437 | 0.154710 12 | -2.69 | 0.00 0 |
| 1.50 | LPC(18:1)+ HCOO | LPC(18:1 )+HCOO | LPC | 18:1 | 18:1 | | | 566.34635 | C27 H53 O9 N1 P1 | 2.584 | 9.1284897 | 136.18501 | 0.067036 01 | -3.90 | 0.00 0 |
| 1.46 | LPC(10:0)+ HCOO | LPC(10:0 )+HCOO | LPC | 10:0 | 10:0 | | | 456.2368 | C19 H39 O9 N1 P1 | 1.035 | 91.309368 | 45.073017 | 2.025811 | 1.02 | 0.00 0 |
| 1.43 | LPC(13:0)+ HCOO | LPC(13:0 )+HCOO | LPC | 13:0 | 13:0 | | | 498.28375 | C22 H45 O9 N1 P1 | 1.495 | 23.582354 | 11.986369 | 1.967430 09 | 0.98 | 0.00 0 |
| 1.39 | LPC(11:0)+ HCOO | LPC(11:0 )+HCOO | LPC | 11:0 | 11:0 | | | 470.25245 | C20 H41 O9 N1 P1 | 1.144 | 13.329542 | 6.8768137 | 1.938331 11 | 0.95 | 0.00 0 |
| 1.09 | LPC(14:0)+ HCOO | LPC(14:0 )+HCOO | LPC | 14:0 | 14:0 | | | 512.2994 | C23 H47 O9 N1 P1 | 1.756 | 27.412213 | 19.836792 | 1.381887 4 | 0.47 | 0.00 3 |
| 1.67 | LPE(18:1)-H | LPE(18:1 )-H | LPE | 18:1 | 18:1 | | | 478.29392 | C23 H45 O7 N1 P1 | 2.471 | 3.1514141 | 74.719986 | 0.042176 3 | -4.57 | 0.00 0 |
| 1.60 | LPE(16:0)-H | LPE(16:0 )-H | LPE | 16:0 | 16:0 | | | 452.27827 | C21 H43 O7 N1 P1 | 2.336 | 0.8322149 | 10.483624 | 0.079382 4 | -3.66 | 0.00 0 |
| 1.32 | LPG(18:1)- H | LPG(18:1 )-H | LPG | 18:1 | 18:1 | | | 509.2885 | C24 H46 O9 N0 P1 | 0.966 | 1.347416 7 | 0 | #DIV/0! | #DIV/0! | 0.00 0 |
| 1.00 | LPG(18:1)- H | LPG(18:1 )-H | LPG | 18:1 | 18:1 | | | 509.2885 | C24 H46 O9 N0 P1 | 1.871 | 0.065608 7 | 3.518175 9 | 0.018648 5 | -5.74 | 0.00 7 |
| 1.42 | LPI(18:0)-H | LPI(18:0) -H | LPI | 18:0 | 18:0 | | | 599.32019 | C27 H52 O12 N0 P1 | 2.388 | 0.31160 98 | 7.558572 8 | 0.041226 | -4.60 | 0.00 0 |
| 1.40 | LPI(18:1)-H | LPI(18:1) -H | LPI | 18:1 | 18:1 | | | 597.30454 | C27 H50 O12 N0 P1 | 1.829 | 0.157001 8 | 13.688958 | 0.011469 2 | -6.45 | 0.00 0 |

FIG. 46 (Continued)

| | | | | | | | | | | | | |
|---|---|---|---|---|---|---|---|---|---|---|---|---|
| 1.36 | LPI(16:0)-H | LPI(16:0)-H | LPI | 16:0 | 16:0 | | 571.28889 | C25 H48 O12 N0 P1 | 1.722 | 0.5389098 | 11.816497 | 0.0456066 | -4.45 | 0.000 |
| 1.34 | LPMe(25:2)-H | LPMe(25:2)-H | LPMe | 25:2 | 25:2 | | 545.36127 | C29 H54 O7 N0 P1 | 3.654 | 14.555422 | 1.0454898 | 13.922109 | 3.80 | 0.000 |
| 1.69 | MGDG(18:0/18:1)+HCOO | MGDG(3 6:1)+HCOO | MGDG | 18:0/18:1 | 18:0 | 18:1 | 829.60465 | C46 H85 O12 | 8.005 | 4.6451642 | 25.514287 | 0.1820613 | -2.46 | 0.000 |
| 1.67 | MGDG(18:2/18:2)+HCOO | MGDG(3 6:4)+HCOO | MGDG | 18:2/18:2 | 18:2 | 18:2 | 823.5577 | C46 H79 O12 | 6.728 | 11.439462 | 484.94074 | 0.0235894 | -5.41 | 0.000 |
| 1.64 | MGDG(18:1/18:1)+HCOO | MGDG(3 6:2)+HCOO | MGDG | 18:1/18:1 | 18:1 | 18:1 | 827.589 | C46 H83 O12 | 7.574 | 47.594867 | 327.24209 | 0.1454424 | -2.78 | 0.000 |
| 1.57 | MGDG(18:1/18:2)+HCOO | MGDG(3 6:3)+HCOO | MGDG | 18:1/18:2 | 18:1 | 18:2 | 825.57335 | C46 H81 O12 | 7.102 | 4.1518459 | 343.10877 | 0.0121007 | -6.37 | 0.000 |
| 1.54 | MGDG(16:0/18:2)+HCOO | MGDG(3 4:2)+HCOO | MGDG | 16:0/18:2 | 16:0 | 18:2 | 799.5577 | C44 H79 O12 | 7.057 | 2.6735234 | 32.918639 | 0.0812161 | -3.62 | 0.000 |
| 1.37 | MGDG(16:0/18:1)+HCOO | MGDG(3 4:1)+HCOO | MGDG | 16:0/18:1 | 16:0 | 18:1 | 801.57335 | C44 H81 O12 | 7.561 | 13.265179 | 32.893212 | 0.4032801 | -1.31 | 0.000 |
| 1.67 | MGMG(18:2)+HCOO | MGMG(1 8:2)+HCOO | MGMG | 18:2 | 18:2 | | 561.32804 | C28 H49 O11 | 2.11 | 0.0948809 | 9.9938061 | 0.0094944 | -6.72 | 0.000 |
| 1.15 | MGMG(10:4)+HCOO | MGMG(1 0:4)+HCOO | MGMG | 10:4 | 10:4 | | 445.17154 | C20 H29 O11 | 10.095 | 240.74721 | 48.90584 | 4.9226678 | 2.30 | 0.001 |
| 1.02 | MGMG(10:4)+HCOO | MGMG(1 0:4)+HCOO | MGMG | 10:4 | 10:4 | | 445.17154 | C20 H29 O11 | 9.564 | 144.09271 | 69.593259 | 2.0704981 | 1.05 | 0.006 |
| 1.01 | MGMG(10:4)+HCOO | MGMG(1 0:4)+HCOO | MGMG | 10:4 | 10:4 | | 445.17154 | C20 H29 O11 | 9.861 | 124.19751 | 59.750861 | 2.0785894 | 1.06 | 0.007 |

FIG. 46 (Continued)

| | | | | | | | | | | | |
|---|---|---|---|---|---|---|---|---|---|---|---|
| 1.67 | OAHFA(18:2/34:5)-H | OAHFA(52:7)-H | OAHFA | 18:2/34:5 | 18:2 | 34:5 | | 775.66098 | C52 H87 O4 | 9.022 | 2.047594 | 28.096318 | 0.0728777 | -3.78 | 0.00 0 |
| 1.60 | OAHFA(18:2/25:1)-H | OAHFA(43:3)-H | OAHFA | 18:2/25:1 | 18:2 | 25:1 | | 657.58273 | C43 H77 O4 | 8.42 | 9.5452303 | 30.2253 78 | 0.3158018 | -1.66 | 0.00 0 |
| 1.52 | OAHFA(18:1/31:4)-H | OAHFA(49:5)-H | OAHFA | 18:1/31:4 | 18:1 | 31:4 | | 737.64533 | C49 H85 O4 | 8.918 | 15.311234 | 0.5461186 | 28.036463 | 4.81 | 0.00 0 |
| 1.44 | OAHFA(18:2/33:3)-H | OAHFA(51:5)-H | OAHFA | 18:2/33:3 | 18:2 | 33:3 | | 765.67663 | C51 H89 O4 | 9.216 | 11.290996 | 0.6934626 | 16.282054 | 4.03 | 0.00 0 |
| 1.33 | OAHFA(18:2/21:1)-H | OAHFA(39:3)-H | OAHFA | 18:2/21:1 | 18:2 | 21:1 | | 601.52013 | C39 H69 O4 | 7.967 | 95.865659 | 38.819847 | 2.469501 2 | 1.30 | 0.00 0 |
| 1.32 | OAHFA(16:0/20:0)-H | OAHFA(36:0)-H | OAHFA | 16:0/20:0 | 16:0 | 20:0 | | 565.52013 | C36 H69 O4 | 8.108 | 115.47824 | 42.332138 | 2.7279094 | 1.45 | 0.00 0 |
| 1.30 | OAHFA(18:2/18:1)-H | OAHFA(36:3)-H | OAHFA | 18:2/18:1 | 18:2 | 18:1 | | 559.47318 | C36 H63 O4 | 7.048 | 69.390954 | 23.404916 | 2.9648025 | 1.57 | 0.00 0 |
| 1.30 | OAHFA(18:1/35:4)-H | OAHFA(53:5)-H | OAHFA | 18:1/35:4 | 18:1 | 35:4 | | 793.70793 | C53 H93 O4 | 9.5 | 7.2482549 | 1.1307811 | 6.4099541 | 2.68 | 0.00 1 |
| 1.25 | OAHFA(18:2/26:1)-H | OAHFA(44:3)-H | OAHFA | 18:2/26:1 | 18:2 | 26:1 | | 671.59838 | C44 H79 O4 | 8.547 | 0.2521112 | 5.1437774 | 0.0490128 | -4.35 | 0.00 0 |
| 1.24 | OAHFA(20:2/25:0)-H | OAHFA(45:2)-H | OAHFA | 20:2/25:0 | 20:2 | 25:0 | | 687.62968 | C45 H83 O4 | 9.11 | 0.3536387 | 1.791289 | 0.1974214 | -2.34 | 0.00 0 |
| 1.22 | OAHFA(18:2/30:2)-H | OAHFA(48:4)-H | OAHFA | 18:2/30:2 | 18:2 | 30:2 | | 725.64533 | C48 H85 O4 | 8.845 | 10.246925 | 2.9390766 | 3.4864437 | 1.80 | 0.00 0 |
| 1.20 | OAHFA(18:1/34:4)-H | OAHFA(52:5)-H | OAHFA | 18:1/34:4 | 18:1 | 34:4 | | 779.69228 | C52 H91 O4 | 9.346 | 0.9341818 | 19.049801 | 0.0490389 | -4.35 | 0.00 1 |
| 1.16 | OAHFA(18:2/30:3)-H | OAHFA(48:5)-H | OAHFA | 18:2/30:3 | 18:2 | 30:3 | | 723.62968 | C48 H83 O4 | 8.699 | 0.1442285 | 2.92041 | 0.0493864 | -4.34 | 0.00 0 |
| 1.15 | OAHFA(18:2/23:0)-H | OAHFA(41:2)-H | OAHFA | 18:2/23:0 | 18:2 | 23:0 | | 631.56708 | C41 H75 O4 | 8.41 | 1.6223747 | 3.7110232 | 0.4372706 | -1.19 | 0.00 1 |
| 1.14 | OAHFA(18:2/32:4)-H | OAHFA(50:6)-H | OAHFA | 18:2/32:4 | 18:2 | 32:4 | | 749.64533 | C50 H85 O4 | 8.804 | 0.6519846 | 6.8471046 | 0.0952205 | -3.39 | 0.00 2 |
| 1.12 | OAHFA(18:1/30:2)-H | OAHFA(48:3)-H | OAHFA | 18:1/30:2 | 18:1 | 30:2 | | 727.66098 | C48 H87 O4 | 9.201 | 16.754625 | 188.1569 6 | 0.089046 | -3.49 | 0.00 2 |
| 1.09 | OAHFA(18:2/32:3)-H | OAHFA(50:5)-H | OAHFA | 18:2/32:3 | 18:2 | 32:3 | | 751.66098 | C50 H87 O4 | 9.047 | 5.3262753 | 73.540449 | 0.0724265 | -3.79 | 0.00 3 |
| 1.07 | OAHFA(18:2/36:5)-H | OAHFA(54:7)-H | OAHFA | 18:2/36:5 | 18:2 | 36:5 | | 803.69228 | C54 H91 O4 | 9.147 | 2.3703646 | 0.3551806 | 6.6736885 | 2.74 | 0.00 4 |

FIG. 46 (Continued)

| | | | | | | | | | | | | | | | |
|---|---|---|---|---|---|---|---|---|---|---|---|---|---|---|---|
| 1.34 | PA(18:1/14:0)-H | PA(32:1)-H | 18:1/14:0 | 18:1 | 14:0 | PA | 645.45008 | | C35 H66 O8 N0 P1 | 7.616 | 52.88168 | 177.71731 | 0.2975603 | -1.75 | 0.00 0 |
| 1.27 | PA(18:1/18:2)-H | PA(36:3)-H | 18:1/18:2 | 18:1 | 18:2 | PA | 697.48138 | | C39 H70 O8 N0 P1 | 7.502 | 237.11243 | 524.77384 | 0.4518374 | -1.15 | 0.00 0 |
| 1.13 | PA(18:1/18:1)-H | PA(36:2)-H | 18:1/18:1 | 18:1 | 18:1 | PA | 699.49703 | | C39 H72 O8 N0 P1 | 7.731 | 652.00651 | 1700.8014 | 0.3833525 | -1.38 | 0.00 2 |
| 1.51 | PAF(10:0e)+HCOO | PAF(10:0e)+HCOO | 10:0e | 10:0e | | PAF | 484.2681 | | C21 H43 O9 N1 P1 | 1.296 | 323362.285 | 164727.63 | 1.9645936 | 0.97 | 0.00 0 |
| 1.66 | PC(18:1/14:0)+HCOO | PC(32:1)+HCOO | 18:1/14:0 | 18:1 | 14:0 | PC | 776.54471 | | C41 H79 O10 N1 P1 | 7.533 | 1.0224337 | 281.92644 | 0.0036266 | -8.11 | 0.00 0 |
| 1.65 | PC(18:0/18:1)+HCOO | PC(36:1)+HCOO | 18:0/18:1 | 18:0 | 18:1 | PC | 832.60731 | | C45 H87 O10 N1 P1 | 8.975 | 21.382818 | 389.1255 | 0.054951 | -4.19 | 0.00 0 |
| 1.62 | PC(16:0/18:1)+HCOO | PC(34:1)+HCOO | 16:0/18:1 | 16:0 | 18:1 | PC | 804.57601 | | C43 H83 O10 N1 P1 | 8.249 | 75.649184 | 1441.3567 | 0.0524847 | -4.25 | 0.00 0 |
| 1.61 | PC(18:1/18:1)+HCOO | PC(36:2)+HCOO | 18:1/18:1 | 18:1 | 18:1 | PC | 830.59166 | | C45 H85 O10 N1 P1 | 8.237 | 252.5188 | 4312.2277 | 0.0585588 | -4.09 | 0.00 0 |
| 1.38 | PC(16:0/18:1)+HCOO | PC(34:1)+HCOO | 16:0/18:1 | 16:0 | 18:1 | PC | 804.57601 | | C43 H83 O10 N1 P1 | 8.291 | 51.775977 | 1240.7724 | 0.0417288 | -4.58 | 0.00 0 |
| 1.25 | PC(18:1/18:1)+HCOO | PC(36:2)+HCOO | 18:1/18:1 | 18:1 | 18:1 | PC | 830.59166 | | C45 H85 O10 N1 P1 | 8.338 | 198.24915 | 3484.6913 | 0.0568915 | -4.14 | 0.00 0 |
| 1.19 | PC(18:1/18:2)+HCOO | PC(36:3)+HCOO | 18:1/18:2 | 18:1 | 18:2 | PC | 828.57601 | | C45 H83 O10 N1 P1 | 7.697 | 74.251839 | 370.96298 | 0.2001598 | -2.32 | 0.00 1 |
| 1.68 | PE(18:1/18:1)-H | PE(36:2)-H | 18:1/18:1 | 18:1 | 18:1 | PE | 742.53923 | | C41 H77 O8 N1 P1 | 7.56 | 183.73244 | 2669.8679 | 0.0688171 | -3.86 | 0.00 0 |
| 1.68 | PE(18:0/18:1)-H | PE(36:1)-H | 18:0/18:1 | 18:0 | 18:1 | PE | 744.55488 | | C41 H79 O8 N1 P1 | 8.011 | 24.960866 | 332.23958 | 0.0751291 | -3.73 | 0.00 0 |
| 1.68 | PE(18:1/24:0)-H | PE(42:1)-H | 18:1/24:0 | 18:1 | 24:0 | PE | 828.64878 | | C47 H91 O8 N1 P1 | 9.232 | 27.149767 | 368.88038 | 0.0736005 | -3.76 | 0.00 0 |

FIG. 46 (Continued)

| | | | | | | | | | | |
|---|---|---|---|---|---|---|---|---|---|---|
| 1.68 | PE(16:0/18:1)-H | PE(34:1)-H | PE | 16:0/18:1 | 16:0 | 18:1 | 716.523 58 | C39 H75 O8 N1 P1 | 7.528 | 51.8403 04 | 1082.47 02 | 0.04789 07 | -4.38 | 0.00 0 |
| 1.68 | PE(18:1/14:0)-H | PE(32:1)-H | PE | 18:1/14:0 | 18:1 | 14:0 | 688.492 28 | C37 H71 O8 N1 P1 | 6.972 | 10.8381 55 | 258.229 29 | 0.04197 11 | -4.57 | 0.00 0 |
| 1.68 | PE(12:0/14:0)-H | PE(26:0)-H | PE | 12:0/14:0 | 12:0 | 14:0 | 606.414 03 | C31 H61 O8 N1 P1 | 5.579 | 1.23710 2 | 19.1566 14 | 0.06457 83 | -3.95 | 0.00 0 |
| 1.66 | PE(26:0/18:1)-H | PE(44:1)-H | PE | 26:0/18:1 | 26:0 | 18:1 | 856.680 08 | C49 H95 O8 N1 P1 | 9.564 | 5.11295 3 | 60.9551 67 | 0.08388 05 | -3.58 | 0.00 0 |
| 1.65 | PE(20:1/18:1)-H | PE(38:2)-H | PE | 20:1/18:1 | 20:1 | 18:1 | 770.570 53 | C43 H81 O8 N1 P1 | 8.024 | 2.27534 86 | 43.0377 87 | 0.05286 86 | -4.24 | 0.00 0 |
| 1.63 | PE(18:1/18:1)-H | PE(36:2)-H | PE | 18:1/18:1 | 18:1 | 18:1 | 742.539 23 | C41 H77 O8 N1 P1 | 6.348 | 7.74586 34 | 286.844 14 | 0.02700 37 | -5.21 | 0.00 0 |
| 1.63 | PE(18:1/18:2)-H | PE(36:3)-H | PE | 18:1/18:2 | 18:1 | 18:2 | 740.523 58 | C41 H75 O8 N1 P1 | 7.109 | 28.0574 25 | 329.107 5 | 0.08525 31 | -3.55 | 0.00 0 |
| 1.62 | PE(16:0/18:1)-H | PE(34:1)-H | PE | 16:0/18:1 | 16:0 | 18:1 | 716.523 58 | C39 H75 O8 N1 P1 | 6.322 | 0.53188 39 | 12.9773 1 | 0.04098 57 | -4.61 | 0.00 0 |
| 1.61 | PE(18:1/18:2)-H | PE(36:3)-H | PE | 18:1/18:2 | 18:1 | 18:2 | 740.523 58 | C41 H75 O8 N1 P1 | 5.865 | 0.79384 49 | 27.9776 98 | 0.02837 42 | -5.14 | 0.00 0 |
| 1.61 | PE(20:0/18:1)-H | PE(38:1)-H | PE | 20:0/18:1 | 20:0 | 18:1 | 772.586 18 | C43 H83 O8 N1 P1 | 8.442 | 23.6520 74 | 72.0793 96 | 0.32813 92 | -1.61 | 0.00 0 |
| 1.60 | PE(18:1/12:0)-H | PE(30:1)-H | PE | 18:1/12:0 | 18:1 | 12:0 | 660.460 98 | C35 H67 O8 N1 P1 | 4.785 | 0.01086 97 | 19.9284 17 | 0.00054 54 | -10.84 | 0.00 1 |
| 1.58 | PE(18:1/14:0)-H | PE(32:1)-H | PE | 18:1/14:0 | 18:1 | 14:0 | 688.492 28 | C37 H71 O8 N1 P1 | 5.46 | 0.16540 19 | 12.3344 29 | 0.01340 98 | -6.22 | 0.00 0 |
| 1.45 | PE(18:1/22:0)-H | PE(40:1)-H | PE | 18:1/22:0 | 18:1 | 22:0 | 800.617 48 | C45 H87 O8 N1 P1 | 8.841 | 31.8377 09 | 94.3133 02 | 0.33757 39 | -1.57 | 0.00 0 |
| 1.20 | PE(18:1/12:0)-H | PE(30:1)-H | PE | 18:1/12:0 | 18:1 | 12:0 | 660.460 98 | C35 H67 O8 N1 P1 | 6.362 | 55.2289 71 | 93.2223 05 | 0.59244 37 | -0.76 | 0.00 0 |
| 1.62 | PEt(16:0/18:1)-H | PEt(34:1)-H | PEt | 16:0/18:1 | 16:0 | 18:1 | 701.512 68 | C39 H74 O8 N0 P1 | 7.134 | 6.68147 42 | 97.9293 75 | 0.06822 75 | -3.87 | 0.00 0 |
| 1.59 | PEt(18:1/18:1)-H | PEt(36:2)-H | PEt | 18:1/18:1 | 18:1 | 18:1 | 727.528 33 | C41 H76 O8 N0 P1 | 7.202 | 1.88951 05 | 277.156 29 | 0.00681 75 | -7.20 | 0.00 0 |
| 1.58 | PEt(18:1/18:2)-H | PEt(36:3)-H | PEt | 18:1/18:2 | 18:1 | 18:2 | 725.512 68 | C41 H74 O8 N0 P1 | 6.499 | 0.00153 68 | 13.1229 23 | 0.00011 71 | -13.06 | 0.00 0 |
| 1.28 | PEt(18:0/18:1)-H | PEt(36:1)-H | PEt | 18:0/18:1 | 18:0 | 18:1 | 729.543 98 | C41 H78 O8 N0 P1 | 7.59 | 5.85702 26 | 25.8881 85 | 0.22624 31 | -2.14 | 0.00 0 |

FIG. 46 (Continued)

| | | | | | | | | | | |
|---|---|---|---|---|---|---|---|---|---|---|
| 1.63 | PG(16:0/18:1)-H | PG(34:1)-H | PG | 16:0/18:1 | 16:0 | 18:1 | 747.51816 | C40 H76 O10 N0 P1 | 6.771 | 9.6213667 | 244.3468 | 0.0393759 | -4.67 | 0.00 0 |
| 1.60 | PG(16:0/14:0)-H | PG(30:0)-H | PG | 16:0/14:0 | 16:0 | 14:0 | 693.47121 | C36 H70 O10 N0 P1 | 6.126 | 0.3444593 | 18.717888 | 0.0184027 | -5.76 | 0.00 0 |
| 1.58 | PG(16:0/16:0)-H | PG(32:0)-H | PG | 16:0/16:0 | 16:0 | 16:0 | 721.50251 | C38 H74 O10 N0 P1 | 6.705 | 1.1173414 | 54.29032 | 0.0205809 | -5.60 | 0.00 0 |
| 1.56 | PG(18:0/18:1)-H | PG(36:1)-H | PG | 18:0/18:1 | 18:0 | 18:1 | 775.54946 | C42 H80 O10 N0 P1 | 7.257 | 17.816703 | 242.17116 | 0.0735707 | -3.76 | 0.00 0 |
| 1.50 | PG(18:0/18:0)-H | PG(34:0)-H | PG | 18:0/18:0 | 18:0 | 16:0 | 749.53381 | C40 H78 O10 N0 P1 | 7.221 | 1.3731062 | 88.047976 | 0.0155595 | -6.00 | 0.00 0 |
| 1.06 | PG(16:0/12:0)-H | PG(28:0)-H | PG | 16:0/12:0 | 16:0 | 12:0 | 665.43991 | C34 H66 O10 N0 P1 | 5.496 | 11.626929 | 25.810197 | 0.4504781 | -1.15 | 0.00 4 |
| 1.53 | PI(18:0/18:1)-H | PI(36:1)-H | PI | 18:0/18:1 | 18:0 | 18:1 | 863.56551 | C45 H84 O13 N0 P1 | 7.131 | 3.9905104 | 382.65763 | 0.0104284 | -6.58 | 0.00 0 |
| 1.53 | PI(18:0/14:0)-H | PI(32:0)-H | PI | 18:0/14:0 | 18:0 | 14:0 | 809.51856 | C41 H78 O13 N0 P1 | 6.567 | 0.196321 | 49.839985 | 0.0039399 | -7.99 | 0.00 0 |
| 1.52 | PI(18:1/12:0)-H | PI(30:1)-H | PI | 18:1/12:0 | 18:1 | 12:0 | 779.47161 | C39 H72 O13 N0 P1 | 5.248 | 0.0399586 | 25.657047 | 0.0015574 | -9.33 | 0.00 0 |
| 1.51 | PI(16:0/18:1)-H | PI(34:1)-H | PI | 16:0/18:1 | 16:0 | 18:1 | 835.53421 | C43 H80 O13 N0 P1 | 6.631 | 18.046646 | 566.72768 | 0.0318436 | -4.97 | 0.00 0 |
| 1.50 | PI(18:1/14:0)-H | PI(32:1)-H | PI | 18:1/14:0 | 18:1 | 14:0 | 807.50291 | C41 H76 O13 N0 P1 | 6.042 | 0.0760551 | 40.420973 | 0.0018816 | -9.05 | 0.00 0 |
| 1.50 | PI(18:1/18:1)-H | PI(36:2)-H | PI | 18:1/18:1 | 18:1 | 18:1 | 861.54986 | C45 H82 O13 N0 P1 | 6.691 | 7.3691942 | 273.47238 | 0.0269468 | -5.21 | 0.00 0 |

FIG. 46 (Continued)

| 1.49 | PI(16:0/12:0)-H | PI(28:0)-H | PI | 16:0/12:0 | 16:0 | 12:0 | | 753.45596 | C37 H70 O13 N0 P1 | 5.296 | 2.0747475 | 214.83931 | 0.0096572 | -6.69 | 0.00 0 |
|---|---|---|---|---|---|---|---|---|---|---|---|---|---|---|---|
| 1.49 | PI(18:0/12:0)-H | PI(30:0)-H | PI | 18:0/12:0 | 18:0 | 12:0 | | 781.48726 | C39 H74 O13 N0 P1 | 5.972 | 2.8440762 | 261.48616 | 0.0108766 | -6.52 | 0.00 0 |
| 1.24 | PI(16:0/18:2)-H | PI(34:2)-H | PI | 16:0/18:2 | 16:0 | 18:2 | | 833.51856 | C43 H78 O13 N0 P1 | 6.164 | 26.732486 | 157.48112 | 0.1697504 | -2.56 | 0.00 0 |
| 1.16 | PI(18:1/18:2)-H | PI(36:3)-H | PI | 18:1/18:2 | 18:1 | 18:2 | | 859.53421 | C45 H80 O13 N0 P1 | 6.208 | 3.9011119 | 21.987596 | 0.1774233 | -2.49 | 0.00 1 |
| 1.04 | PMe(17:1/18:1)-H | PMe(35:2)-H | PMe | 17:1/18:1 | 17:1 | 18:1 | | 699.49703 | C39 H72 O8 N0 P1 | 8.189 | 868.79363 | 2476.2123 | 0.3508559 | -1.51 | 0.00 5 |

| Test Name | September 28, 2017 | August 30, 2018 | April 8, 2019 |
|---|---|---|---|
| NIKBUT (OD): first/average | 5.35 sec / 9.26 sec | 2.48 sec / 10.76 sec | N.D. / N.D. |
| NIKBUT (OS): first/average | 2.93 sec / 6.61 sec | 10.13 sec / 12.20 sec | 8.67 sec / 11.61 sec |
| Eye dryness level (OD) | 1 | 1 | 0 |
| Eye dryness level (OS) | 2 | 1 | 1 |
| Upper Meibo-Scan (OD) | Missing > 2/3 | N/A | N/A |
| Lower Meibo-Scan (OD) | Missing > 2/3 | Missing < 1/3 | Missing < 1/3 |
| Upper Meibo-Scan (OS) | Missing > 2/3 | N/A | N/A |
| Lower Meibo-Scan (OS) | Missing > 2/3 | Missing < 1/3 | Missing < 1/3 |

FIG. 54

| Test Name | May 17, 2018 | September 28, 2019 |
|---|---|---|
| Upper Meibo-Scan (OD) | Missing > 2/3 | 1/3 < Missing < 2/3 |
| Lower Meibo-Scan (OD) | Missing > 2/3 | 1/3 < Missing < 2/3 |
| Upper Meibo-Scan (OS) | Missing > 2/3 | 1/3 < Missing < 2/3 |
| Lower Meibo-Scan (OS) | 1/3 < Missing < 2/3 | 1/3 < Missing < 2/3 |

FIG. 55

TREATING DRY EYE DISORDERS

CLAIM OF PRIORITY

This application is a continuation-in-part application of and claims priority to U.S. application Ser. No. 16/636,470, filed on Feb. 4, 2020, which claims priority to international Application No. PCT/CN2020/070798, filed on Jan. 8, 2020, which claims priority to international Application No. PCT/CN2019/070856 under 35 U.S. Code § 119, filed on Jan. 8, 2019. The entire contents of the foregoing are incorporated herein by reference.

TECHNICAL FIELD

This disclosure is related to compositions and methods for treating dry dye disorders.

BACKGROUND

Dry eye disorder (e.g., dry eye syndrome) is a common eye disease. It is the condition of having dry eyes. Some common symptoms of dry eye disorders include e.g., irritation, redness, discharge, inflammation, easily fatigued eyes, and blurred vision. In some severe cases, scarring of the cornea may occur. Dry eye disorder affects about 5-34% of the population worldwide. In China, it affects at least 17% of people.

Treatments for dry eye disorder usually involves artificial tear eye drops. The application of artificial tear eye drops usually can provide temporary relief of dry eye disorder. In most cases, artificial tear eye drops need to be periodically reapplied. This can be inconvenient, particularly if the need to reapply eye drops occurs too frequently. In fact, it is quite common for a patient to have to apply artificial tear solution ten to twenty times over the course of the day. Such dosing is cumbersome and time-consuming, and increases the exposure of the eye to preservative agents present in many artificial tears. In addition, for patients with severe dry eye disorders or chronic dry eye disorders, the application of artificial tear eye drops is usually ineffective. There remains a need for safe and effective therapies to treat dry eye disorders.

SUMMARY

This disclosure is related to compositions and methods for treating dry dye disorders.

In one aspect, the present disclosure provides methods of treating or alleviating symptoms of a dry eye disorder, asthenopia, impaired vision, blurred vision, photophobia, astigmatism, and/or blepharitis. The methods involve identifying a subject having the dry eye disorder, asthenopia, impaired vision, blurred vision, photophobia, astigmatism, and/or blepharitis; and administering to the subject in need thereof an effective amount of a pharmaceutical composition comprising deacidified coconut oil.

In some embodiments, the dry eye disorder is dry eye syndrome. In some embodiments, the composition is administered to the patient's eye as an eye drop.

In some embodiments, the composition consists essentially of deacidified coconut oil.

In some embodiments, the deacidified coconut oil administered to the patient is made by a process comprising one or more the following steps: providing coconut oil; mixing the coconut oil with a basic solution (pH>8), thereby obtaining a mixture comprising a water phase and an oil phase; separating the water phase and the oil phase from the mixture; and collecting deacidified coconut oil from the oil phase.

In some embodiments, the process further includes one or more of the following steps: mixing coconut meat or coconut powder with a base, thereby obtaining a coconut meat mixture; heating and pressing the coconut meat mixture, thereby obtaining an extract; and collecting coconut oil from the extract.

In some embodiments, prior to administering the pharmaceutical composition to the subject, artificial tear eye drops are administered to the subject.

In some embodiments, the methods further include one or more of the following steps: orally administering to the subject an effective amount of a composition comprising one, two, or all of the following ingredients: wolfberries (*Lycium barbarum* or *Lycium chinense*) or a wolfberry extract; *Astragalus* root or an *Astragalus* root extract; chrysanthemum or a chrysanthemum extract to the subject.

In some embodiments, the methods involve orally administering an effective amount of wolfberries (*Lycium barbarum* or *Lycium chinense*) or a wolfberry extract to the subject.

In some embodiments, the methods involve orally administering an effective amount of *Astragalus* root or an *Astragalus* root extract to the subject.

In some embodiments, the methods involve orally administering an effective amount of chrysanthemum or a chrysanthemum extract to the subject.

In some embodiments, the methods further involve administering a heat therapy to the eye of the subject.

In some embodiments, the heat therapy comprises applying a thermal pad comprising a herb composition on the eye of the subject.

In some embodiments, the herb composition contains Cassiae semen and borneol.

In some embodiments, the weight percentage of Cassiae semen in the herb composition is from 50% to 90%.

In some embodiments, the weight percentage of borneol in the herb composition is from 10% to 50%.

In one aspect, the disclosure provides a pharmaceutical composition comprising deacidified coconut oil. In some embodiments, the pharmaceutical composition consists of deacidified coconut oil.

In some embodiments, the deacidified coconut oil is made by a process comprising one or more of the following steps: providing coconut oil; mixing the coconut oil with a basic solution (pH>8), thereby obtaining a mixture comprising a water phase and an oil phase; separating the water phase and the oil phase from the mixture; and collecting deacidified coconut oil from the oil phase.

In some embodiments, the process further comprises: mixing coconut meat or coconut powder with a base, thereby obtaining a coconut meat mixture; heating and pressing the coconut meat mixture, thereby obtaining an extract; and collecting coconut oil from the extract.

In one aspect, the present disclosure provides methods of improving the efficacy of an artificial tear eye drops in a subject. The methods involve administering an artificial tear eye drop to the subject; and administering to the subject an effective amount of a composition comprising deacidified coconut oil after the artificial tear eye drop is administered to the subject.

In some embodiments, the composition consists essentially of deacidified coconut oil.

In some embodiments, the composition comprising deacidified coconut oil is administered within 1, 2, 3, 4, 5, 6, 7, 8, 9, or 10 minutes after the artificial tear eye drop is administered to the subject.

In one aspect, the present disclosure provides a herb composition comprising:
(1) wolfberries (*Lycium barbarum* or *Lycium chinense*) or a wolfberry extract;
(2) *Astragalus* root or an *Astragalus* root extract; and
(3) *chrysanthemum* or a *chrysanthemum* extract.

In some embodiments, the ratio of (1), (2), and (3) is about 1:1:1.

In one aspect, the present disclosure provides a thermal pad comprising a herb composition. In some embodiments, the herb composition comprises Cassiae semen and borneol.

In some embodiments, the weight percentage of Cassiae semen in the herb composition is from 50% to 90%.

In some embodiments, the weight percentage of borneol in the herb composition is from 10% to 50%.

In one aspect, the present disclosure provides methods of making a composition comprising deacidified coconut oil. The methods involve mixing coconut meat or coconut powder with a base or a basic solution, thereby obtaining a coconut meat mixture; heating and pressing the coconut meat mixture, thereby obtaining an extract; and collecting the coconut oil from the extract.

In some embodiments, the methods further involve after collecting coconut oil from the extract, mixing the coconut oil with a basic solution (pH>7), thereby obtaining a mixture comprising a water phase and an oil phase; separating the water phase and the oil phase from the mixture; and collecting deacidified coconut oil from the oil phase.

In some embodiments, the methods further involve filtering the deacidified coconut oil through membrane filtration, thereby obtaining a filtered deacidified coconut oil; and sterilizing the filtered deacidified coconut oil.

In one aspect, the present disclosure provides methods of making a composition comprising deacidified coconut oil. The methods involve mixing coconut oil with a base or a basic solution, thereby obtaining a mixture; and collecting deacidified coconut oil.

In some embodiments, the methods involve mixing coconut oil with a basic solution; separating the water phase and the oil phase from the mixture; and collecting deacidified coconut oil.

In some embodiments, the methods further involve filtering the deacidified coconut oil through membrane filtration, thereby obtaining a filtered deacidified coconut oil; and sterilizing the filtered deacidified coconut oil.

In one aspect, the disclosure also relates to a composition comprising deacidified coconut oil and cyclosporine.

In one aspect, the disclosure provides a method of treating or alleviating symptoms of a dry eye disorder, asthenopia, impaired vision, blurred vision, photophobia, astigmatism, and/or blepharitis, comprising identifying a subject having the dry eye disorder, asthenopia, impaired vision, blurred vision, photophobia, astigmatism, and/or blepharitis; and administering to the subject in need thereof an effective amount of a pharmaceutical composition comprising deacidified coconut oil and cyclosporine.

In some embodiments, the method further comprises administering an effective amount of cyclosporine to the subject.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIG. 43 summarizes the differences between the deacidified coconut oil (Prco) group and the original coconut oil (Orco) group detected under ECL+ model (metabolite analysis), showing retention time (RT), molecular weight (detected), name, molecular weight (predicated), Appm, VIP, P value for T-test, fold change (log 2(Prco/Orco)), average of Orco, and average of Prco.

FIG. 44 summarizes the differences between the deacidified coconut oil (Prco) group and the original coconut oil (Orco) group detected under ECL− model (metabolite analysis), showing retention time (RT), molecular weight (detected), name, molecular weight (predicated), Appm, VIP, P value for T-test, fold change (log 2(Prco/Orco)), average of Orco, and average of Prco.

FIG. 45 summarizes the differences between the deacidified coconut oil (Prco) group and the original coconut oil (Orco) group detected under ECL+ model (lipidomics analysis), showing VIP, lipid ion, lipid group, class, fatty acid, FA1, FA2, FA3, calculated m/z, ion formula, retention time (RT), average of Prco, average of Orco, Prco/Orco, fold change (log 2(Prco/Orco)), P value for T-test.

FIG. 46 summarizes the differences between the deacidified coconut oil (Prco) group and the original coconut oil (Orco) group detected under ECL− model (lipidomics analysis), showing VIP, lipid ion, lipid group, class, fatty acid, FA1, FA2, FA3, FA4, calculated m/z, ion formula, retention time (RT), average of Prco, average of Orco, Prco/Orco, fold change (log 2(Prco/Orco)), P value for T-test.

FIG. 49 shows an eye ball structure with dry eye disease. Lack of tears is shown in black and while.

FIG. 54 summarizes the ocular surface inspection reports of patient 1. NIKBUT is noninvasive Keratograph tear breakup time. N.D. stands for not detected. N/A stands for not applicable.

FIG. 55 summarizes the ocular surface inspection reports of patient 2.

DETAILED DESCRIPTION

Figure 1:
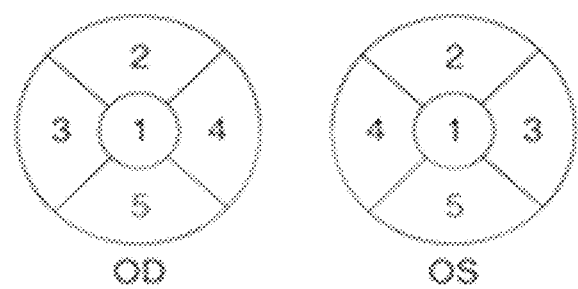
FIG. 1 is a schematic diagram showing 5 regions of the cornea of eye. Number 1-5 are exemplary scores indicating the percentage of colored area within each region.

This disclosure relates to the diagnosis, alleviation, cure, and treatment of dry eye disorders. Particularly, the disclosure provides an ophthalmic composition for treating dry eye disorders. The ophthalmic composition can comprise, consist essentially of, or consist of deacidified coconut oil. As used herein, the term "deacidified coconut oil" refers to coconut oil (which can be prepared as described herein or commercially obtained) that has been at least partially deacidified by treating the coconut oil with a base. The deacidification process causes a change in the chemical compositions of the coconut oil so that the deacidified coconut oil causes less irritation to the eye when it is administered to the eye of a subject. As used herein, the term "coconut oil" refers to an oil composition that is collected or derived from coconut, or a composition that has ingredients that are essentially the same as the oil derived from coconut.

The ophthalmic composition comprising coconut oil described herein can provide relief, e.g., long-term relief, for dry eye disorders. Regular coconut oil (e.g., virgin coconut oil) has irritants and is unsuitable for use as eye drops. The deacidified coconut oil can be administered to the subject alone or in combination with artificial tear eye drops. When it is used in combination with artificial tears, the deacidified coconut oil eye drop can also greatly enhance the efficacy of the artificial tears.

The present disclosure also provides herb tea compositions and heat therapies. The herb tea and heat therapies can be use alone or in combination with deacidified coconut oil eye drops. The herb tea and heat therapies can improve the therapeutic effects of deacidified coconut oil eye drops.

Together, the methods described herein can provide rapid relief of symptoms of dry eye disorders and improve the effects of artificial tear eye drops. Particularly, the methods described herein can provide a relatively long-term effect, obviating the need of administering artificial tear eye drops 10-20 times per day.

Dry Eye Disorders

The tear film is a consistent layer of tears on the surface of the eye. It is essential to keep the eyes healthy, comfortable and seeing well. Tears bathe the eye's surface to keep it moist and wash away dust, debris and microorganisms. The normal tear film typically has three important components: a lipid component, a watery component, and a mucous-like (mucin) component. Each tear component is produced by different glands on or near the eye. The lipid component is produced by meibomian glands in the eyelids. The watery component is produced by lacrimal glands located behind the outer aspect of the upper eyelids. The mucin component is produced by goblet cells in the conjunctiva that covers the white of the eye (sclera).

In order to remain transparent, cornea has no blood vessels. The oxygen and nutrients needed by its surface cells are transported by tears, as are its metabolic wastes. Tears can clean up normal shed epithelial debris, metabolized carbon dioxide and water. It delivers nutrients from the limbus blood vessels and oxygen exchanged from the air to the cornea. Therefore, the tear is equivalent to the blood of the cornea and it is the necessary foundation of a healthy cornea.

Figure 47:
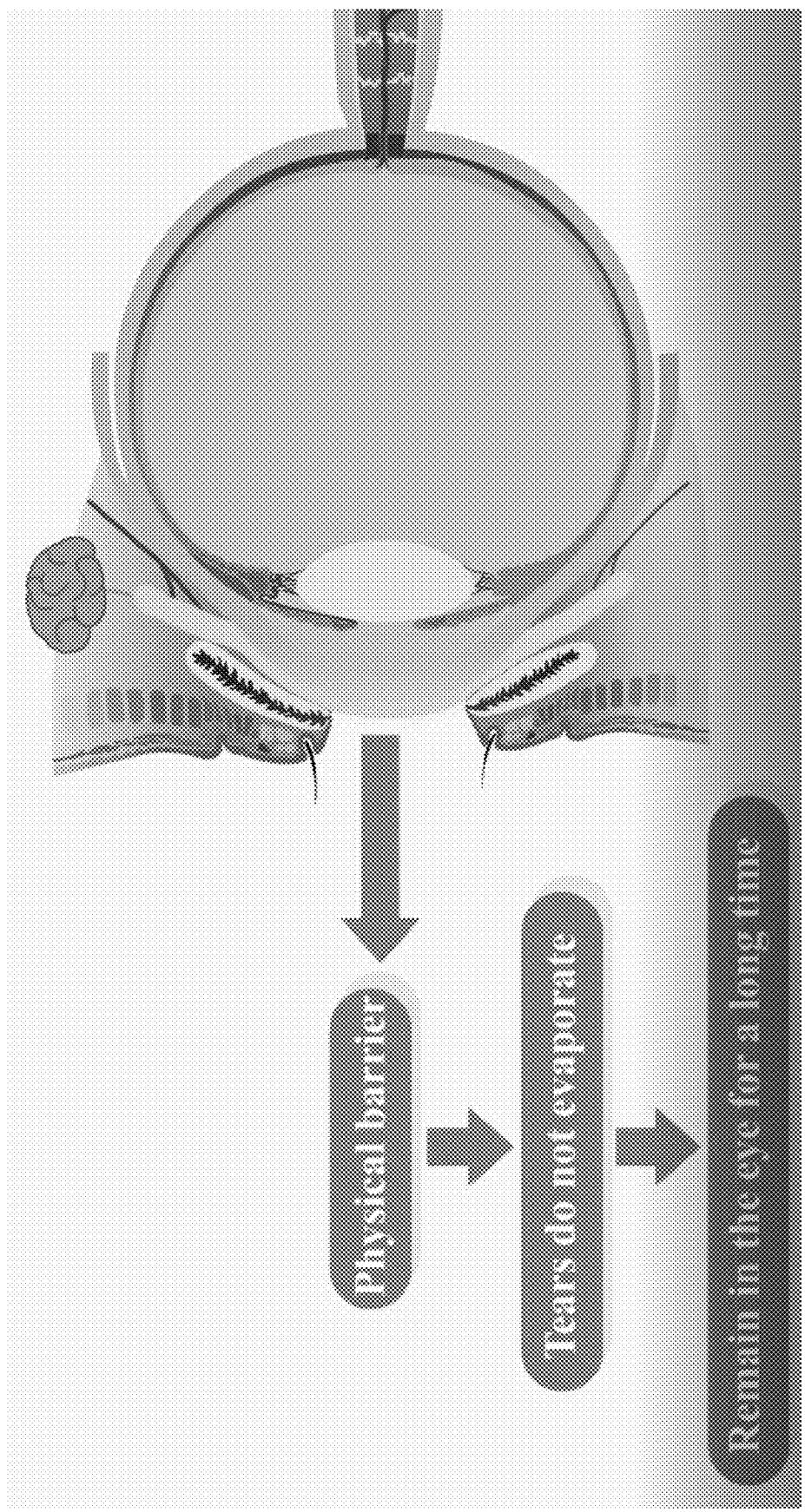
FIG. 47 shows an eye ball structure. The lipid is located on top of the tear.
Figure 48:
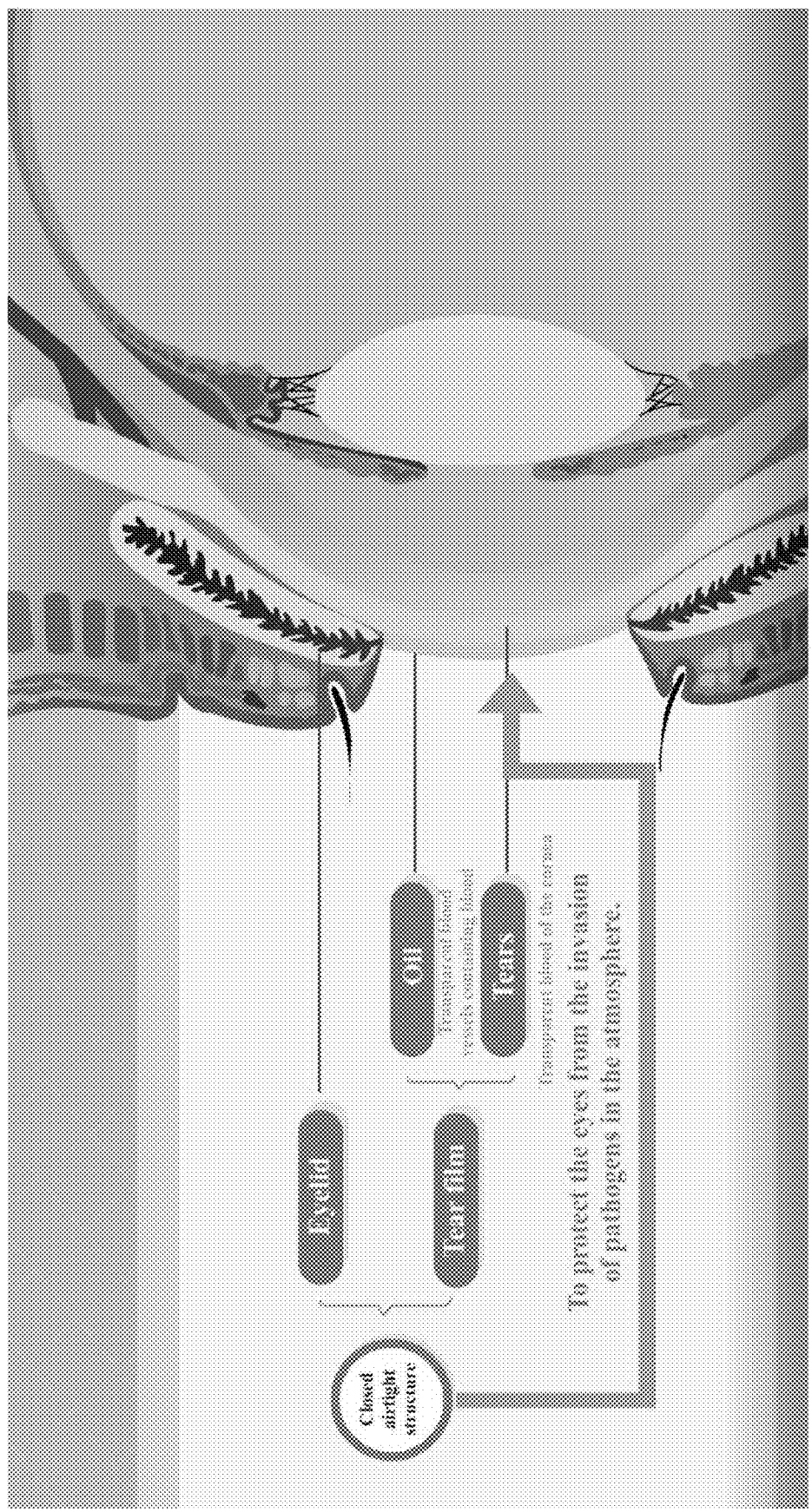
FIG. 48 shows a closed airtight structure comprising eyelid and the tear film.

As shown in FIG. 47, the lipid component provides a physical barrier such that tears do not drip out of the eye. In addition, the physical barrier can keep the tears from evaporation. Because oxygen is fat-soluble, oxygen can freely pass through the lipid layer into tears to supply the cornea for metabolism. In addition, the tear film and eyelid closed together can form a closed airtight structure (FIG. 48), to protect the eyes from the invasion of pathogens in the atmosphere. Therefore, if the tear is equivalent to the blood of the cornea, the lipid layer is equivalent to transparent blood vessels.

Figure 49:
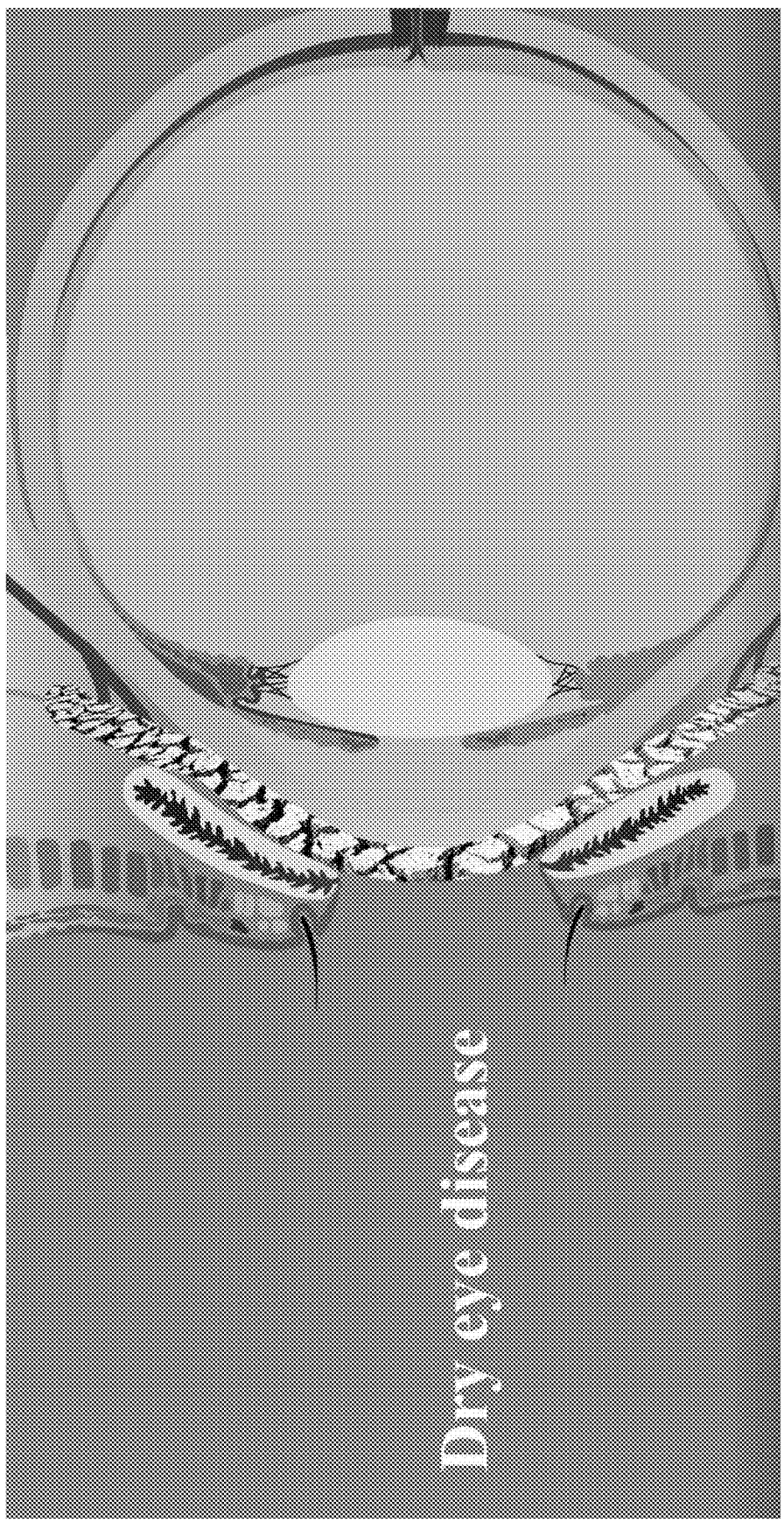

A problem with any of these sources of tear film components can result in tear instability and dry eyes (FIG. 49). For example, if the meibomian glands cannot produce or secrete enough oil (meibum), the tear film may evaporate too quickly—a condition called "evaporative dry eye" or "meibomian gland dysfunction."

Dry eye disorder refers to a lack of sufficient lubrication and moisture on the surface of the eye, or dysfunction of the tear film. Dry eye disorder can be temporary, acute, or chronic. Chronic dry eye disorders include e.g., dry eye syndrome, keratitis sicca, keratoconjunctivitis sicca, dysfunctional tear syndrome, lacrimal keratoconjunctivitis, evaporative tear deficiency, aqueous tear deficiency, meibomian gland dysfunction, and LASIK-induced neurotrophic epitheliopathy (LNE). Dry eye syndrome is caused by a chronic a chronic lack of sufficient lubrication and moisture on the surface of the eye. Keratitis sicca refers to dryness and inflammation of the cornea. Keratoconjunctivitis sicca refers to dry eye that affects both the cornea and the conjunctiva. Dysfunctional tear syndrome generally refers to inadequate quality of tears.

Consequences of dry eye disorders range from subtle but constant eye irritation to significant inflammation and even scarring of the front surface of the eye. Symptoms of dry eye disorders (e.g., dry eye syndrome) include, e.g., burning sensation, itchiness, aching sensations, heavy eyes, fatigued eyes, sore eyes, dryness sensation, red eyes, photophobia (sensitivity to light), blurred vision, inflammation, and a foreign body sensation. The foreign body sensation is a common symptom. It refers to the feeling that grit or some other object or material is "in" the eye. In some cases, watery eyes can also be a symptom of dry eye syndrome. This is because dryness on the eye's surface sometimes will over-stimulate production of the watery component of tears as a protective mechanism. However, this "reflex tearing" cannot stay on the eye long enough to correct the underlying dry eye condition. In some cases, dry eye disorders can affect the outcomes of LASIK (laser-assisted in situ keratomileusis) and cataract surgery. In severe cases, vision can be substantially impaired.

Dry eye occurs when the eye does not produce enough tears or when the tears evaporate too quickly. There can be many causes for dry eye disorders, including e.g., contact lens use, meibomian gland dysfunction, allergies, pregnancy, Sjögren's syndrome, vitamin A deficiency, LASIK surgery, and certain medications such as antihistamines, some blood pressure medication, hormone replacement therapy, and antidepressants.

Skilled practitioners will appreciate that diagnosis can be mostly based on the symptoms. In some cases, tests can be performed to determine whether the quantity and the quality of the tears are sufficient. A slit lamp examination is often used to diagnose dry eyes and to document any damage to the eye. The Schirmer's test can measure the amount of moisture bathing the eye. This test is useful for determining the severity of the condition. A tear breakup time (TBUT) test measures the time it takes for tears to break up in the eye. The tear breakup time can be determined after placing a drop of fluorescein in the cul-de-sac. Thus, in some aspects, this disclosure also provides methods of identifying a subject having dry eye disorders and dye eye symptoms (e.g., from mild to severe dry eye symptoms).

Many factors can increase the risk of dry eye disorders. These factors include, e.g., computer use, contact lens wear, aging, menopause, air conditioning, air heating, arid climates, dry or windy weather conditions, smoking, diabetes, thyroid-associated diseases, lupus, rheumatoid arthritis, Sjogren's syndrome, medications (e.g., antihistamines, antidepressants, blood pressure medications and birth control pills), eyelid problems (e.g., lagophthalmos), LASIK, and corneal refractive surgery, etc.

Without wishing to be bound by theory, it is believed that the deacidified coconut oil can form an oil film and cover the tears. The oil film can form a physical barrier on the surface of the eye, protecting the human eye from pathogens such as bacteria, microorganisms and dust. The oil film can reduce the evaporation rate and maintain the surface tension of human tears, therefore keeping the tears on the eye surface. The tears can then deliver the nourishment to the cornea properly, and remove the metabolic waste. In the meantime, oxygen can enter the tears through the oil film, and reach to the cornea. In addition, dry eyelids can scratch the surface of cornea when blinking and generate small wounds. For example, some of the small wounds can form at the corneal epithelium due to lack of nutrition and apoptotic shedding. Some small wounds can form by scratching between corneal epithelium and contact lenses, orthokeratology lenses, or beautiful pupils. The oil film can cover the small wounds, reduce the risk of developing subsequence corneal diseases, relieve the symptoms of foreign matter sensation, grit sensation, dryness, itching, pain and redness, as well as maintain the proper eye function. The oil film can relieve eye pain, photophobia, astigmatism, blurred vision, and redness of the eyes caused by damaged corneal epithelial cells. The oil firm can also relieves the symptoms of itchiness, eyelid redness, and pain in the outer eye of patients with blepharitis.

The oil film has an adjuvant effect on corneal diseases and pathological reactions caused by lack of nutrients such as oxygen, glucose and amino acids due to corneal metabolic disorders. Eyelid inflammation can be caused by demodex, a type of arachnid mites that live hear hair follicles and sebaceous glands. The oil film can reduce the oxygen supply the pathogen (e.g., bacteria or the parasite) needs, forming an anoxic environment to kill the pathogen.

The present disclosure provides methods of treating or alleviating symptoms of a dry eye disorder, asthenopia, impaired vision, blurred vision, photophobia, astigmatism, and/or blepharitis as described herein. The methods involve identifying a subject having the dry eye disorder, asthenopia, impaired vision, blurred vision, photophobia, astigmatism, and/or blepharitis; and administering to the subject in need thereof an effective amount of a pharmaceutical composition comprising deacidified coconut oil.

The disclosure provides a method of treating or alleviating symptoms of a dry eye disorder, asthenopia, impaired vision, blurred vision, photophobia, astigmatism, and/or blepharitis as described herein, comprising identifying a subject having the dry eye disorder, asthenopia, impaired vision, blurred vision, photophobia, astigmatism, and/or blepharitis; and administering to the subject in need thereof an effective amount of a pharmaceutical composition comprising deacidified coconut oil and cyclosporine.

Deacidified Coconut Oil

Coconut oil is an edible, non-toxic oil extracted from the kernel or meat of mature coconuts harvested from the coconut palm (*Cocos nucifera*). It is characterized by high content of saturated fat. It is slow to be oxidized and, thus, resistant to rancidification. It can last up to six months at 24° C. without spoiling.

Coconut oil is 99% fat (or lipid), composed mainly of saturated fats (82% of total). In some cases, coconut oil includes one or more of the following fatty acids: octanoic acid (e.g., caprylic acid) (C8:0), citric acid, dodecanoic acid (e.g., lauric acid) (C12:0), tetradecanoic acid (e.g., myristic acid) (C14:0), hexadecanoic acid (e.g., palmitic acid) (C16:0), octadecyl acid (C18:0), and/or octadecenoic acid (e.g., oleic acid) (C18:1). In some cases, about half of the saturated fat content of coconut oil is lauric acid (e.g., about 41.8 grams per 100 grams), while other significant saturated fats are myristic acid (e.g., about 16.7 grams per 100 grams), palmitic acid (e.g., about 8.6 grams per 100 grams), and caprylic acid (e.g., about 6.8 grams per 100 grams). Mono-unsaturated fats can be, e.g., about 5% to 10% (e.g., 6%) of total composition, and polyunsaturated fats can be, e.g., about 1% to 5% (e.g., 2%). Coconut oil also may also include phytosterols.

Coconut oil can be extracted through dry or wet processing. Dry processing requires that the meat or kernel be extracted from the shell and dried using fire, sunlight, or kilns to create copra. The copra is pressed or dissolved with solvents, producing the coconut oil and a high-protein, high-fiber mash.

The all-wet process uses raw coconut rather than dried copra, and the protein in the coconut creates an emulsion of oil and water. The more challenging step is breaking up the emulsion to recover the oil. This used to be done by prolonged boiling, but this produces a discolored oil and is not economical. Modern techniques use centrifuges and pre-treatments with heat. Despite numerous variations and technologies, wet processing may be less viable than dry processing due to a 10-15% lower yield, even taking into account the losses due to spoilage and pests with dry processing.

Virgin coconut oil refers to coconut oil extracted from coconuts without subjecting to substantial chemical or physical changes. The virgin coconut oil is closer to its natural form (Jayasekara et al., "Processing technologies for virgin coconut oil and coconut based confectionaries and beverages." Proceedings of International Coconut Summit (2007): 7-11). Virgin coconut oil is typically extracted by cold compression or cold milling of copra with a moisture content of around six percent. After using processes such as fermentation, churning (centrifugal separation), and refrigeration, the oil is separated from the water or moisture. In some cases, virgin coconut oil can be extracted directly by cold compression of fresh dried coconut meat. This process is called micro expelling.

It has been determined that that unmodified coconut oil and virgin coconut oil has irritants and are not suitable for being used in an ophthalmic composition, such as eye drops. However, when modified as described herein, e.g., via deacidification, coconut oil can be applied to the eye. The present disclosure provides deacidified coconut oil compositions, which are different from the unmodified coconut oil and virgin coconut oil in the composition, and are safe to be used in ophthalmic compositions. The deacidified coconut oil can be made by the methods described herein. In some embodiments, the deacidified coconut oil is made by a process comprising mixing the coconut oil with a basic solution (pH>7); separating the water phase and the oil phase from the mixture; and collecting deacidified coconut oil from the oil phase.

While not intending to be bound by any theory, it is believed that the deacidification process removes soluble ingredients (e.g., free glycerol) and soluble fatty acids in the coconut oil. Thus, it is likely that the deacidified fatty acids contain a higher percentage of lipids that are resistant to deacidification (or resistant to saponification) and/or a higher percentage of insoluble fatty acids (fatty acids with a relatively long hydrocarbon carbon chain, e.g., with C10 or higher). The deacidified coconut oil is more stable and is less likely to cause irritation when it is administered to eyes.

The pH of the ophthalmic solution is preferably 6.0 to 8.5, more preferably 7.0 to 8.0. A pH of lower than 6.0 tends to cause eye irritation, while a pH of higher than 8.5 is out of the physiological pH range. In some embodiments, the pH of the ophthalmic solution is about 7.

In some embodiments, the ophthalmic solution does not contain any preservatives, such as antimicrobial preservatives (e.g., antibiotics, sorbic acid, sodium sorbate and sorbates, benzoic acid, sodium benzoate and benzoates, hydroxybenzoate and derivatives, sulfur dioxide and sulfites, nitrite, nitrate, lactic acid, propionic acid and/or sodium propionate) or antioxidants (e.g., ascorbic acid, sodium ascorbate, butylated hydroxytoluene, butylated hydroxyanisole, gallic acid and sodium gallate, sulfur dioxide and sulfites, and/or tocopherols).

In some embodiments, the deacidified coconut oil has an enriched level of Stigmastentriol as compared to original coconut oil (e.g., the log 2 of the ratio between the deacidified coconut oil and the original coconut oil is at least or about 5, 6, 7, 8, 9, 10, or 11). In some embodiments, the deacidified coconut oil has an enriched level of Campest-4-en-3-one as compared to original coconut oil (e.g., the log 2 of the ratio between the deacidified coconut oil and the original coconut oil is at least or about 4, 5, 6, 7, 8, 9, or 10). In some embodiments, the deacidified coconut oil has an enriched level of Stigmasterol as compared to original coconut oil (e.g., the log 2 of the ratio between the deacidified coconut oil and the original coconut oil is at least or about 3, 4, 5, 6, 7, 8, or 9). In some embodiments, the deacidified coconut oil has an enriched level of Stigmast-22-ene-3,6-dione as compared to original coconut oil (e.g., the log 2 of the ratio between the deacidified coconut oil and the original coconut oil is at least or about 3, 4, 5, 6, 7, 8, or 9). In some embodiments, the deacidified coconut oil has an enriched level of ubiquinone-4 as compared to original coconut oil (e.g., the log 2 of the ratio between the deacidified coconut oil and the original coconut oil is at least or about 3, 4, 5, 6, 7, 8, or 9). In some embodiments, the deacidified coconut oil has an enriched level of Vitamin D3 as compared to original coconut oil (e.g., the log 2 of the ratio between the deacidified coconut oil and the original coconut oil is at least or about 3, 4, 5, 6, 7, 8, or 9).

In some embodiments, the deacidified coconut oil has a decreased level of 3-hexenoic acid as compared to original coconut oil (e.g., the log 2 of the ratio is less than or about −7, −8, −9, −10, −11, −12, or −13). In some embodiments, the deacidified coconut oil has a decreased level of 5,8-tetradecadienoic acid as compared to original coconut oil (e.g., the log 2 of the ratio is less than or about −4, −5, −6, −7, −8, −9, or −10). In some embodiments, the deacidified coconut oil has a decreased level of Indole as compared to original coconut oil (e.g., the log 2 of the ratio is less than or about −4, −5, −6, −7, −8, −9, or −10). In some embodiments, the deacidified coconut oil has a decreased level of isolecucine as compared to original coconut oil (e.g., the log 2 of the ratio is less than or about 0, −1, or −2). In some embodiments, the deacidified coconut oil has a decreased level of valine as compared to original coconut oil (e.g., the log 2 of the ratio is less than or about 0, −1, −2, −3, or −4). In some embodiments, the deacidified coconut oil has a decreased level of glutamate as compared to original coconut oil (e.g., the log 2 of the ratio is less than or about 0, −1, −2, −3, −4, −5, or −6). In some embodiments, the deacidified coconut oil has a decreased level of beta-alanine as compared to original coconut oil (e.g., the log 2 of the ratio is less than or about 0, −1, −2, −3, −4, −5, or −6).

In some embodiments, the deacidified coconut oil has an enriched level of Piperochromenoic acid as compared to original coconut oil (e.g., the log 2 of the ratio between the deacidified coconut oil and the original coconut oil is at least or about 3, 4, 5, 6, 7, 8, or 9). In some embodiments, the deacidified coconut oil has an enriched level of LysoPA(a-25:0/0:0) as compared to original coconut oil (e.g., the log 2 of the ratio between the deacidified coconut oil and the original coconut oil is at least or about 2, 3, 4, 5, 6, 7, 8, or 9). In some embodiments, the deacidified coconut oil has an enriched level of LysoPA(24:0/0:0) as compared to original coconut oil (e.g., the log 2 of the ratio between the deacidified coconut oil and the original coconut oil is at least or about 3, 4, 5, 6, 7, 8, 9, or 10).

In some embodiments, the deacidified coconut oil has a decreased level of sucrose as compared to original coconut oil (e.g., the log 2 of the ratio is less than or about −5, −6, −7, −8, −9, −10, or −11). In some embodiments, the deacidified coconut oil has a decreased level of citric acid as compared to original coconut oil (e.g., the log 2 of the ratio is less than or about −4, −5, −6, −7, −8, −9, −10, or −11). In some embodiments, the deacidified coconut oil has a decreased level of mannitol as compared to original coconut oil (e.g., the log 2 of the ratio is less than or about −3, −4, −5, −6, −7, −8, −9, −10, or −11). In some embodiments, the deacidified coconut oil has a decreased level of glucose or glucose-6-phosphate as compared to original coconut oil (e.g., the log 2 of the ratio is less than or about −1, −2, −3, −4, −5, −6, or −7).

In some embodiments, the deacidified coconut oil comprises at least 1, 2, 3, 4, 5, 6, 7, 8, 9, 10, 11, 12, 13, 14, 15, 16, 17, 18, 19, 20, or all of Stigmastentriol, Campest-4-en-3-one, DG(8:0/8:0/0:0), MG(0:0/15:0/0:0), Stigmast-22-ene-3,6-dione, Stigmasterol, Hexadecanedioic acid, Delta 8,14-Sterol, PA(8:0/8:0), Vitamin D3, Ubiquinone-4, (R)-2-Hydroxysterculic acid, Betulin, PA(8:0/14:0), PA(8:0/12:0), MG(17:0/0:0/0:0), LysoPA(18:0e/0:0), Ergosterol, Stigmastane-3,6-dione, Vitamin K1, TG(10:0/8:0/8:0), MG(0:0/14:0/0:0), DG(8:0/10:0/0:0), Nervonic acid, Methyl cinnamate, Cinnamic acid, Pantothenic Acid, TG(13:0/13:0/8:0), Ganodosterone, MG(18:0/0:0/0:0), TG(12:0/12:0/8:0), Tridecanoic acid, Linoleic acid, MG(16:0/0:0/0:0), TG(8:0/8:0/14:0), Pangamic acid, Camelledionol, DG(8:0/0:0/14:0), m-Hydroxyphenylpyruvic acid, DG(18:1n9/0:0/20:4n3), DG(12:0/12:0/0:0), Phosphocholine, Stearamide, LysoPA(24:0/0:0), Piperochromenoic acid, LysoPA(a-25:0/0:0), DG(8:0/0:0/15:0), LysoPA(i-20:0/0:0), PA(8:0/16:0), 2-Stearoylglycerophosphoglycerol, LysoPA(18:0e/0:0), LysoPA(22:0/0:0), Cerebronic acid, PA(8:0/14:0), DG(20:4n3/0:0/20:4n3), LysoPA(18:0/0:0), DG(10:0/0:0/19:0), DG(12:0/15:0/0:0), PA(22:0/8:0), PA(8:0/20:0), and PA(22:0/13:0). In some embodiments, these chemicals have a higher concentration as compared to original coconut oil.

In some embodiments, the deacidified coconut oil has an enriched level of DG as compared to original coconut oil (e.g., the log 2 of the ratio between the deacidified coconut oil and the original coconut oil is at least or about 0, 1, 2, 3, 4, 5, 6, 7, 8, or 9). In some embodiments, the deacidified coconut oil has an enriched level of ChE as compared to original coconut oil (e.g., the log 2 of the ratio between the deacidified coconut oil and the original coconut oil is at least or about 0, 1, 2, or 3). In some embodiments, the deacidified coconut oil has an enriched level of ZyE or StE as compared to original coconut oil (e.g., the log 2 of the ratio between the deacidified coconut oil and the original coconut oil is at least or about 0, 1, 2, or 3).

In some embodiments, the deacidified coconut oil has a decreased level of LPE as compared to original coconut oil (e.g., the log 2 of the ratio is less than or about −2, −3, −4, −5, −6, −7, or −8). In some embodiments, the deacidified coconut oil has a decreased level of PE as compared to original coconut oil (e.g., the log 2 of the ratio is less than or about −2, −3, −4, −5, −6, −7, or −8). In some embodiments, the deacidified coconut oil has a decreased level of Co as compared to original coconut oil (e.g., the log 2 of the ratio is less than or about −1, −2, −3, or −4). In some embodiments, the deacidified coconut oil has a decreased level of LPC as compared to original coconut oil (e.g., the log 2 of the ratio is less than or about −1, −2, −3, −4, −5, −6, −7, or −8). In some embodiments, the deacidified coconut oil has a decreased level of CerG1 as compared to original coconut oil (e.g., the log 2 of the ratio is less than or about −1, −2, −3, −4, or −5).

In some embodiments, the deacidified coconut oil has an enriched level of LdMePE as compared to original coconut oil (e.g., the log 2 of the ratio between the deacidified coconut oil and the original coconut oil is at least or about 1, 2, 3, 4, 5, 6, or 7). In some embodiments, the deacidified coconut oil has an enriched level of PAF as compared to original coconut oil (e.g., the log 2 of the ratio between the deacidified coconut oil and the original coconut oil is at least or about 1, 2, 3, 4, or 5). In some embodiments, the deacidified coconut oil has an enriched level of DGMG as compared to original coconut oil (e.g., the log 2 of the ratio between the deacidified coconut oil and the original coconut oil is at least or about 1, 2, 3, 4, or 5). In some embodiments, the deacidified coconut oil has an enriched level of MGMG as compared to original coconut oil (e.g., the log 2 of the ratio between the deacidified coconut oil and the original coconut oil is at least or about 1, 2, 3, 4, or 5). In some embodiments, the deacidified coconut oil has an enriched level of LPMe as compared to original coconut oil (e.g., the log 2 of the ratio between the deacidified coconut oil and the original coconut oil is at least or about 1, 2, 3, 4, 5, 6, or 7).

In some embodiments, the deacidified coconut oil has a decreased level of DGDG as compared to original coconut oil (e.g., the log 2 of the ratio is less than or about −3, −4, −5, −6, −7, −8, or −9). In some embodiments, the deacidified coconut oil has a decreased level of cPA as compared to original coconut oil (e.g., the log 2 of the ratio is less than or about −3, −4, −5, −6, −7, −8, or −9). In some embodiments, the deacidified coconut oil has a decreased level of LPI as compared to original coconut oil (e.g., the log 2 of the ratio is less than or about −2, −3, −4, −5, −6, −7, or −8). In some embodiments, the deacidified coconut oil has a decreased level of LPE as compared to original coconut oil (e.g., the log 2 of the ratio is less than or about −1, −2, −3, −4, −5, −6, or −7). In some embodiments, the deacidified coconut oil has a decreased level of PC as compared to original coconut oil (e.g., the log 2 of the ratio is less than or about −1, −2, −3, −4, −5, −6, or −7). In some embodiments, the deacidified coconut oil has a decreased level of dMePE as compared to original coconut oil (e.g., the log 2 of the ratio is less than or about −1, −2, −3, −4, −5, −6, or −7). In some embodiments, the deacidified coconut oil has a decreased level of MGDG as compared to original coconut oil (e.g., the log 2 of the ratio is less than or about −1, −2, −3, −4, −5, −6, or −7). In some embodiments, the deacidified coconut oil has a decreased level of PI as compared to original coconut oil (e.g., the log 2 of the ratio is less than or about −1, −2, −3, −4, −5, −6, or −7). In some embodiments, the deacidified coconut oil has a decreased level of PE as compared to original coconut oil (e.g., the log 2 of the ratio is less than or about −1, −2, −3, −4, or −5). In some embodiments, the deacidified coconut oil has a decreased level of PG as compared to original coconut oil (e.g., the log 2 of the ratio is less than or about −1, −2, −3, −4, or −5). In some embodiments, the deacidified coconut oil has a decreased level of PMe as compared to original coconut oil (e.g., the log 2 of the ratio is less than or about 0, −1, or −2). In some embodiments, the deacidified coconut oil has a decreased level of LPG as compared to original coconut oil (e.g., the log 2 of the ratio is less than or about 0, −1, or −2). In some embodiments, the deacidified coconut oil has a decreased level of PEt as compared to original coconut oil (e.g., the log 2 of the ratio is less than or about 0, −1, or −2).

In some embodiments, the deacidified coconut oil comprises at least 1, 2, 3, 4, 5, 6, 7, 8, 9, or all of DG, ChE, ZyE, StE, LdMePE, PAF, DGMG, MGMG, LPMe and CL. In some embodiments, these chemicals have a higher concentration as compared to original coconut oil.

In some embodiments, the deacidified coconut oil does not comprise (e.g., a detectable amount of) cardiolipin (CL) (18:1/18:1/18:1/20:0) or digalactosyldiacylglycerol (DGDG) (16:0/18:1). In some embodiments, the methods described herein (e.g., lipidomics analysis) cannot detect CL(18:1/18:1/18:1/20:0)-H or DGDG (16:0/18:1)+HCOO from the deacidified coconut oil.

Cyclosporine

Cyclosporine ophthalmic solution (or emulsion) is a prescription eye drop that helps patients increase their eyes' natural ability to produce tears. It is used to treat a type of chronic dry eye condition caused by inflammation. Cyclosporine is also available in oral and injectable formulations that are used to treat various conditions including treatment or prevention of rejection of transplanted organs, psoriasis, and rheumatoid arthritis. Following oral administration or injection, cyclosporine is absorbed in the blood stream and works systemically to suppress the body's immune system. However, cyclosporine eye drop emulsion is thought to work differently. Cyclosporine is believed to work locally in the eye as a partial modulator of the immune system. Tear production is thought to be decreased when lymphocytes, a type of white blood cell of the immune system, die and accumulate in the tear glands. Cyclosporine reverses this condition, increasing tear production. Cyclosporine does not produce its effect immediately. An increase in tear production may not be noticed until 3 to 6 months after starting treatment.

Because cyclosporine is not soluble in water, the composition described herein (e.g., deacidified coconut oil) can be used as a solvent for cyclosporine. In some embodiments, cyclosporine can be used for dry eye treatment at a concentration of about or at least 0.01 mg/ml, e.g., about or at least 0.05 mg/ml, 0.1 mg/ml, 0.2 mg/ml, 0.3 mg/ml, 0.4 mg/ml, 0.5 mg/ml, 0.6 mg/ml, 0.7 mg/ml, 0.8 mg/ml, 0.9 mg/ml, 1.0 mg/ml, 1.5 mg/ml, 2 mg/ml, 3 mg/ml, 4 mg/ml, 5 mg/ml, or 10 mg/ml. In some embodiments, the concentration is about or at least 0.5 mg/ml.

In some embodiments, the concentration for cyclosporine is about or at least 0.01%, e.g., about or at least 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, or 1% (weight percentage or volume percentage). In some embodiments, the concentration is less than 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, or 1% (weight percentage or volume percentage).

In some embodiments, the concentration is from 0.01% to 0.1% (weight percentage or volume percentage), e.g., 0.05% or 0.09%.

In some embodiments, the solution can additionally comprise DMSO and/or olive oil.

In some embodiments, cyclosporine can be used for dry eye treatment in combination with one or more artificial tear (e.g., carboxymethylcellulose, dextran, glycerin, hypromellose, polyethylene glycol 400 (PEG 400), polysorbate, polyvinyl alcohol, povidone, or propylene glycol), lubricant, unprocessed coconut oil samples as described herein, deacidified coconut oil samples as described herein, or any dry eye treatment compounds known in the art.

Herb Tea

The present disclosure provides herb tea compositions for treating dry eye disorders. In some embodiments, the herb tea composition comprises one or more of the following ingredients:

(1) wolfberries (*Lycium barbarum* or *Lycium chinense*) or a wolfberry extract;

(2) *Astragalus* root or an *Astragalus* root extract;

(3) chrysanthemum or a chrysanthemum extract to the subject.

Wolfberries (also known as "goji" in Chinese) are the fruit of either *Lycium barbarum* or *Lycium chinense*. The fruit has been used as an ingredient in traditional Chinese medicine.

*Astragalus* root (also known as "huangqi" in Chinese) is the root of *Astragalus propinquus*. It is commonly used in traditional Chinese medicine. Chemical constituents of the roots include polysaccharides and triterpenoids (such as astragalosides), as well as isoflavones (including e.g., kumatakenin, calycosin, and formononetin) and their glycosides and malonates.

*Chrysanthemum* (also known as "juhua" in Chinese) are flowering plants of the genus *Chrysanthemum* in the family *Asteraceae*. Chrysanthemum can be used in the tea and is also widely used in traditional Chinese medicine.

In some embodiments, the herb tea composition (e.g., for one serving) can comprise about or at least 1 gram, e.g., about or at least 2, 3, 4, 5, 6, 7, 8, 9, 10, 11, 12, 13, 14, 15, 16, 17, 18, 19, 20, 30, 40, or 50 grams of wolfberries (e.g., 10 g). In some embodiments, the herb tea composition (e.g., for one serving) can comprise about or at least 1 gram, e.g., about or at least 2, 3, 4, 5, 6, 7, 8, 9, 10, 11, 12, 13, 14, 15, 16, 17, 18, 19, 20, 30, 40, or 50 grams of *Astragalus* root (e.g., 10 g). In some embodiments, the herb tea composition (e.g., for one serving) can comprise about or at least 1 gram, e.g., about or at least 2, 3, 4, 5, 6, 7, 8, 9, 10, 11, 12, 13, 14, 15, 16, 17, 18, 19, 20, 30, 40, or 50 grams of *Chrysanthemum* (or *Chrysanthemum* flowers) (e.g., 10 g).

In some embodiments, the weight percentage of wolfberries in the herb tea composition is at least or about 10%, e.g., at least or about 20%, 30%, 40%, 50%, 60%, 70%, 80%, or 90%. In some embodiments, the herb tea composition comprises wolfberries, and the weight percentage of wolfberries in the herb tea composition is less than 10%, 20%, 30%, 40%, 50%, 60%, 70%, 80%, or 90%.

In some embodiments, the weight percentage of *Astragalus* root in the herb tea composition is about or at least 10%, e.g., about or at least 20%, 30%, 40%, 50%, 60%, 70%, 80%, or 90%. In some embodiments, the weight percentage of *Astragalus* root in the herb tea composition is less than 10%, 20%, 30%, 40%, 50%, 60%, 70%, 80%, or 90%.

In some embodiments, the weight percentage of *Chrysanthemum* (or *Chrysanthemum* flowers) in the herb tea composition is about or at least 10%, e.g., about or at least 20%, 30%, 40%, 50%, 60%, 70%, 80%, or 90%. In some embodiments, the weight percentage of *Chrysanthemum* (or *Chrysanthemum* flowers) in the herb tea composition is less than 10%, 20%, 30%, 40%, 50%, 60%, 70%, 80%, or 90%.

In some embodiments, the ratio of three ingredients (1), (2), and (3) is about 1:1:1, 2:1:1, 1:2:1, 1:1:2, 1:2:2, 2:1:2, or 2:2:1.

The herb tea compositions can be administered to the subject as needed. The subject can drink herb tea several times per day, e.g., about or at least 1 time (e.g., about or at least 2, 3, 4, 5, 6, 7, 8, 9, or 10 times) per day. In some embodiments, the subject can drink the herb tea periodically for an extended period of time, e.g., about or at least 1, 2, 3, 4, 5, 6, 7, 8, 9, or 10 weeks, or about or at least 1, 2, 3, 4, 5, 6, 7, 8, 9, 10, 11, or 12 months. In some embodiments, the subject can drink herb tea prior to or after the administration of deacidified coconut oil eye drops.

In some embodiments, for convenience, the herb tea composition can be placed in herb tea pods. These herb tea pods can be used as single-serve containers (e.g., tea cup, tea pods, K-cup, tea capsule). The powder of the herb tea composition can be stored in the single-serve containers. In some embodiments, the containers are filled with nitrogen to increase storage time. The nitrogen can prevent wolfberries powder from forming an aggregate. The containers can be further sealed. In some embodiments, the herb tea pods can be used in an appropriate coffee machine or tea maker.

In some embodiments, the extracts of wolfberries, *Astragalus* roots, or chrysanthemum can be used. In some embodiments, the extracts can be made in the form of pills, tablets or capsules. The pills, tablets or capsules can be administered on a regimen of 1 to 4 times per day, preferably once or twice per day. This dosing regimen can be adjusted to provide the optimal therapeutic response.

Heat Therapies

Also provided herein are heat therapies. The heat therapies can be used alone or in combination with other methods described herein (e.g., deacidified coconut oil eye drops and/or herb tea) to treat dry eye disorders. In some embodiments, a thermal pad comprising an herb composition is used. As used herein, the term "thermal pad" or "heat pad" refers to a pad used for warming of parts of the body in order to provide therapeutic effects. The thermal pad can have a shape of pre-formed square or rectangle. Thermal pads can be filled with medical compositions (e.g., herb compositions).

In some embodiments, the herb composition comprises Cassiae semen and/or borneol.

Cassiae semen (also known as "Juemingzi" in Chinese) is the dry and mature seed of *Cassia obtusifolia* or *Cassia tora*, which belong to the *Cassia* genus of Leguminosae. It is cultivated in Korea, Japan and China, and is commonly consumed as a roasted tea. In traditional Chinese medicine, it has been used in treatments for hyperlipemia, diabetes mellitus, Alzheimer's disease, acute liver injury, inflammation, photophobia, headache, dizziness and hypertension. A detailed description of Cassiae semen can be found e.g., in Dong et al. "Cassiae semen: A review of its phytochemistry and pharmacology." Molecular medicine reports 16.3 (2017): 2331-2346, which is incorporated herein by reference in its entirety.

Borneol is a bicyclic organic compound and a terpene derivative. It can be found in several species of *Heterotheca, Artemisia, Callicarpa, Dipterocarpaceae, Blumea balsamifera* and *Kaempferia galanga*. In some cases, the borneol resin refers to the resin obtained from *Dryobalanops aromatica* or from *Blumea balsamifera*. The typical form of borneol is in thin, semi-opaque, whitish angular pieces or crystals. Borneol (as a crude resin) is used internally and externally in the practice of Chinese medicine.

The disclosure provides a thermal pad comprising Cassiae semen and/or borneol that can be used to treat dry eye disorders or alleviate symptoms of dry eye disorders.

In some embodiments, the thermal pad comprises about or at least 50 g, e.g., about or at least 100 g, 150 g, 200 g, 250 g, 300 g, 350 g, 400 g, 450 g, or 500 g of Cassiae semen (e.g., 200 g). In some embodiments, the thermal pad comprises about or at least 50 g, e.g., about or at least 60 g, 70, 80 g, 90 g, 100 g, 150 g, 200 g, 250 g, 300 g, 350 g, 400 g, 450 g, or 500 g of borneol (e.g., 80 g).

In some embodiments, the herb composition in the thermal pad is about or at least 50 g, e.g., about or at least 100 g, 150 g, 200 g, 250 g, 300 g, 350 g, 400 g, 450 g, or 500 g. In some embodiments, the weight percentage of Cassiae semen in the herb composition is about or at least 10%, e.g., about or at least 20%, 30%, 40%, 50%, 60%, 70%, 80%, or 90%. In some embodiments, the weight percentage of borneol in the herb composition is about or at least 10%, e.g., about or at least 20%, 30%, 40%, 50%, 60%, 70%, 80%, or 90%. In some embodiments, the weight percentage of Cassiae semen in the herb composition is less than 90%, e.g., less than 10%, 20%, 30%, 40%, 50%, 60%, 70%, or 80%. In some embodiments, the weight percentage of borneol in the herb composition is less than 90%, e.g., less than 10%, 20%, 30%, 40%, 50%, 60%, 70%, or 80%.

In some embodiments, the weight ratio of Cassiae semen to Borneol is about 5:1, 5:2, 5:3, 5:4, 1:1, 4:5, 3:5, 2:5, or 1:5. In some embodiments, the weight ratio of Cassiae semen to Borneol is about 4:1, 3:1, 2:1, 1:1, 1:2, 1:3, or 1:4.

In some embodiments, the thermal pad has a size or a volume of at least or about 100 mm$^3$, e.g., at least or about 200 mm$^3$, 300 mm$^3$, 400 mm$^3$, 500 mm$^3$, 600 mm$^3$, 700 mm$^3$, 800 mm$^3$, 900 mm$^3$, or 1000 mm$^3$.

In some embodiments, the thermal pad is heated (e.g., in a steamer) for a sufficient period of time (e.g., about or at least 5 minutes, 10 minutes, or 15 minutes). When the temperature on the surface of thermal pad reaches an appropriate temperature (e.g., from 40 to 70° C., from 40 to 65° C., from 40 to 60° C., from 45 to 70° C., from 45 to 65° C., from 45 to 60° C., from 50 to 70° C., from 50 to 65° C., or from 50 to 60° C., e.g., about 40, 41, 42, 43, 44, 45, 46, 47, 48, 49, 50, 51, 52, 53, 54, 55, 56, 57, 58, 59, or 60° C.), the thermal pad can be placed on the eyes of the subject for a sufficient period of time (e.g., about or at least 5, 10, 15, 20, 25, or 30 minutes). In some embodiments, the thermal pad is big enough to cover the eye affected by dry eye syndrome, or both eyes of the subject.

The heat therapies can be administered to the subject once per day, twice per day, or three times per day. In some embodiments, the heat therapies are administered to the patient in the morning, or in the evening, or both. For patients with severe symptoms, the heat therapies can be additionally administered to the patient around noon. In some embodiments, the heat therapies are administered to the subject several times a week, e.g., once per week, twice per week, three times per week, four times per week, five times per week, six times per week, or seven times per week, or more.

In some embodiments, the heat therapies are administered to the patients prior to or after the administration of deacidified coconut oil eye drops. In some embodiments, the thermal pad can be in the form a flexible eye cover. In some embodiments, the size of thermal pad is adjustable, and/or is sized to fit the head of the subject.

In some embodiments, eye massage are performed before or after the heat therapy. The heat therapies and/or eye massage can increase the secretion of lipids from meibomian glands, increase the flow in the meibomian gland ducts, and resolve the clogging of meibomian gland ducts.

Methods of Treating Dry Eye Disorders and Various Eye Diseases

The methods described herein include methods for the treatment of disorders associated with dry eye disorders (e.g., dry eye syndrome, keratitis sicca, keratoconjunctivitis sicca, dysfunctional tear syndrome, lacrimal keratoconjunctivitis, evaporative tear deficiency, or aqueous tear deficiency). In some embodiments, the disorder is chronic. In some embodiments, the disorder is dry eye syndrome. Generally, the methods include administering a therapeutically effective amount of the composition as described herein (e.g., deacidified coconut oil), to a subject who is in need of, or who has been determined to be in need of, such treatment.

As used in this context, to "treat" means to ameliorate at least one symptom of the dry eye disorder. Often, the treatment can result in a reduction of irritation, dryness sensation, burning sensation, itchiness, or pain. In some aspects, the methods described herein can also be used to increase tear production, improve the quantity and/or quality of tear, reduce ocular discomfort, improve ocular surface health, protect the ocular surface during environmentally challenging conditions (e.g., dry or windy conditions), increase the amount or concentration of one or more lacrimal proteins on the ocular surface (e.g., epithelial growth factor, lactoferin, lacritin, prolactin, adrenocorticotropic, leucine enkephalin, ALS2CL, ARHGEF19, KIAA1109, PLXNAL POLL, WIPI1, ZMIZ2 or other proteins of the tear proteome), or enhance tear clearance.

The terms "subject" and "patient" are used interchangeably throughout the specification and describe an animal, human or non-human, to whom treatment according to the methods of the present invention is provided. Veterinary and non-veterinary applications are contemplated by the present invention. Human patients can be adult humans or juvenile humans (e.g., humans below the age of 18 years old). In addition to humans, patients include but are not limited to mice, rats, hamsters, guinea-pigs, rabbits, ferrets, cats, dogs, and primates. Included are, for example, non-human primates (e.g., monkey, chimpanzee, gorilla, and the like), rodents (e.g., rats, mice, gerbils, hamsters, ferrets, rabbits), lagomorphs, swine (e.g., pig, miniature pig), equine, canine, feline, bovine, and other domestic, farm, and zoo animals.

In some embodiments, the subject is a human. The human subject can be a male or a female (e.g., a post-menopausal woman). In some embodiments, the human patient is at least or about 30 years old, e.g., at least or about 35, 40, 45, 50, 55, 60, 65, 70, 75, or 80 years old. In some embodiments, the patient can have the dry eye disorder for at least 1, 2, 3, 4, 5, 6, 7, 8, 9, or 10, or more, years.

In some embodiments, the deacidified coconut oil eye drops are administered after the subject is treated by artificial tear eye drops. While not intending to be bound by any theory, it is believed that the deacidified coconut oil can form a lipid layer, and the lipid layer can keep the tear film from evaporating too quickly and increase lubrication. Various artificial tear eye drops are known in the art. Examples of artificial tear can include, but are not limited to, water and/or buffered, isotonic saline solutions. In some embodiments, the aqueous solutions can contain water-soluble polymers that render the solutions more viscous and thus less easily shed by the eye. In some embodiments, artificial tear compositions can include one or more of the following ingredients: carboxymethyl cellulose, polyvinyl alcohol, hydroxypropyl methylcellulose (a.k.a. HPMC or hypromellose), hydroxypropyl cellulose and hyaluronic acid (a.k.a. hyaluronan, HA). In some embodiments, artificial tear compositions can include one or more of the following ingredients: carboxymethylcellulose, dextran, glycerin, hypromellose, polyethylene glycol 400 (PEG 400), polysorbate, polyvinyl alcohol, povidone, and propylene glycol. In some embodiments, artificial tear compositions can include polyvinyl alcohol (e.g., 0.1% to 1%, e.g., about 0.5% by volume percentage) and/or povidone (e.g., 0.1% to 1%, e.g., about 0.6% by volume percentage).

In some embodiments, the deacidified coconut oil eye drop is administered before, during, or after the artificial tear eye drop is administered to the subject.

In some embodiments, the deacidified coconut oil eye drop is administered within a period of time after the artificial tear eye drop is administered to the subject, e.g., within 1, 2, 3, 4, 5, 6, 7, 8, 9, or 10 minutes. In some embodiments, the period of time is from 1 to 30 minutes, from 1 to 20 minutes, from 1 to 15 minutes, from 1 to 10 minutes, from 1 to 5 minutes, from 5 to 20 minutes, from 5 to 15 minutes, from 5 to 10 minutes, or from 10 to 20 minutes.

In some embodiments, the deacidified coconut oil eye drop is administered before, during, or after the cyclosporine is administered to the subject. In some embodiments, the deacidified coconut oil eye drop is administered within a period of time after the cyclosporine is administered to the subject, e.g., within 1, 2, 3, 4, 5, 6, 7, 8, 9, or 10 minutes. In some embodiments, the period of time is from 1 to 30 minutes, from 1 to 20 minutes, from 1 to 15 minutes, from 1 to 10 minutes, from 1 to 5 minutes, from 5 to 20 minutes, from 5 to 15 minutes, from 5 to 10 minutes, or from 10 to 20 minutes.

In some embodiments, a composition comprising deacidified coconut oil and cyclosporine is administered to the subject.

The deacidified coconut oil and the compositions described herein can be used in combination with some other methods (e.g., medical procedures), compositions, or mediations to treat dry eye disorders. For example, artificial tear solutions, saline, topical steroids, topical immunosuppressants (e.g., ciclospori), diquafosol, lifitegrast, or ciclosporin can be administered to the subjects along with the deacidified coconut oil. In some embodiments, an anti-inflammation medication (e.g., cyclosporine or corticosteroids) is administered to the subject in order to reduce eyelid inflammation and/or to control cornea inflammation (e.g., cyclosporine). In some embodiments, antibiotics can be administered to the subject. In some embodiments, the hydroxypropyl cellulose (Lacrisert) insert can be administered to a subject between the lower eyelid and the eyeball. The insert can dissolve slowly, releasing a substance to lubricate the eye. In some embodiments, tear-stimulating drugs (e.g., cholinergics, pilocarpine, or cevimeline) can be administered to a subject to help increase tear production. These drugs can be available as pills, gel or eyedrops.

In some embodiments, procedures can be performed to close the tear ducts to reduce tear loss. This procedure can be done by partially or completely closing the tear ducts, which are designed to drain tears away. In some embodiments, tear ducts can be plugged with tiny silicone plugs (punctal plugs). These are removable. In some embodiments, tear ducts can be plugged with a procedure that uses heat (e.g., thermal cautery).

In some embodiments, a subject can wear special contact lenses (e.g., scleral lenses or bandage lenses). The special contact lens can protect the surface of the eyes and trap moisture. In some embodiments, these contact lenses are covered by deacidified coconut oil described herein.

In some embodiments, procedures can be performed to unblock oil glands. In some embodiments, the procedure is LipiFlow thermal pulsation. During the treatment, a device that is similar to an eyecup is placed over the affected eye. It can deliver a gentle, warm massage to the lower eyelid.

In some embodiments, light therapy or eyelid massage can be performed. In some embodiments, a technique called intense-pulsed light therapy followed by massage of the eyelids can be used to treat severe dry eyes.

In some embodiments, tarsorrhaphy can be performed in addition to the administration of the pharmaceutical compositions described herein. The tarsorrhaphy procedure can reduce the palpebral fissure (eyelid separation), leading to a reduction in tear evaporation.

In some embodiments, the methods described herein does not cause irritation to the subject.

In some embodiments, the methods described herein can improve Schirmer's test score by at least 10%, e.g., at least 20%, 30%, 40%, 50%, 60%, 70%, 80%, or 90%. For example, some patients can have ≥15 mm wetting after 5 minutes in a Schirmer's test.

In some embodiments, the methods described herein can increase tear secretion by at least 10%, e.g., at least 20%, 30%, 40%, 50%, 60%, 70%, 80%, or 90%. In some embodiments, the methods described herein can reduce corneal fluorescein sodium staining score by at least 10%, e.g., at least 20%, 30%, 40%, or 50%.

Methods of Making Deacidified Coconut Oil

The present disclosure provides methods of making a composition comprising deacidified coconut oil. The methods can involve one or more the following steps: mixing coconut meat, coconut copra or coconut powder with a base; heating and pressing the coconut meat mixture, thereby obtaining an extract; collecting the coconut oil from the extract; mixing the coconut oil with a basic solution (pH>7), thereby obtaining a mixture comprising a water phase and an oil phase; separating the water phase and the oil phase from the mixture; and/or collecting deacidified coconut oil from the oil phase.

The coconut meat, coconut copra or coconut powder are readily available and can be obtained commercially. In some embodiments, the coconut meat, coconut copra or coconut powder are dried coconut meat, coconut copra or coconut powder. In some embodiments, the methods also involve producing coconut meat, coconut copra or coconut powder from coconuts. Methods of producing coconut meat, coconut copra or coconut powder are known in the art. For example, the methods can involve removing the shell of coconuts, breaking the shell up, and/or drying. Copra can be made by smoke drying, sun drying, or kiln drying. During sun drying, halved nuts are drained of water, and left with the meat facing the sky. They can then be washed to remove mold-creating contaminants. After a few days, the meat can be removed from the shell with ease, and the drying process is complete after three to five more days (up to seven in total). Sun drying is often combined with kiln drying, eight hours of exposure to sunlight means the time spent in a kiln can be reduced by a day and the hot air the shells are exposed to in the kiln is more easily able to remove the remaining moisture. This process can also be reversed, partially drying the copra in the kiln and finishing the process with sunlight.

In some embodiments, the methods can involve filtering the deacidified coconut oil through membrane filtration, thereby obtaining a filtered deacidified coconut oil. In some instances, the filtered deacidified coconut oil may be sterilized, e.g., using heat sterilization methods known in the art.

In some embodiments of making deacidified coconut oil, the coconut meat or coconut powder is dried in a suitable dryer (e.g., a solar dyer, a forced drought tray-type dryer or a vacuum dryer).

In some embodiments, the coconut meat or coconut powder is collected, and is mixed with a base (e.g., sodium carbonate powder). In some embodiments, the base is a dried powder. In some embodiments, the base is an aqueous solution. The base can be NaOH, KOH, $Mg(OH)_2$, $Ca(OH)_2$, $Na_2CO_3$, $NaHCO_3$, $Na_2CO_3$, $K_2CO_3$, or $KHCO_3$. In some embodiments, the coconut meat or coconut powder can be mixed with a chemical compound, wherein if the compound is mixed with water, it will generate a base aqueous solution. In some embodiments, the chemical compound is CaO.

The mixture is then heated to an appropriate temperature (e.g., about 60 to 90, 70 to 80, or 70 to 75° C.) in an appropriate apparatus. In some embodiments, the temperature is about or at least 60, e.g., about or at least 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, or 95° C. In some embodiments, the temperature is below 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, or 95° C. Skilled practitioners will appreciate that any suitable apparatus may be used, e.g., a heating apparatus such as a steam-jacketed kettle.

The heated coconut meat or coconut powder is then pressed, by e.g., an expeller, a hand-pressing machine, a screw type oil press, hydraulic pressing, or a hydraulic jack type oil press.

The extract is then cooled (e.g., to room temperature, or to a temperature that is about or below 20° C., e.g., about or below 19, 18, 17, 16, 15, 14, 13, 12, 11, 10, 9, 8, 7, 6, 5, 4, 3, 2, or 1° C.). In some embodiments, the extract is cooled to a temperature that is above or at least 10° C., e.g., about or at least 9, 8, 7, 6, 5, 4, 3, 2, 1, or 0° C. During the cooling process, the water phase and the oil phase are separated. Skilled practitioners will appreciate that cooling can be performed using any active or passive cooling method, e.g., refrigeration or allowing the mixture to cool to ambient temperature. The coconut oil can be collected from the oil phase. In some embodiments, the temperature is cooled to below the melting point of the coconut oil (e.g., around 20, 19, 18, 17, 16, 15, 14, 13, 12, 11, 10° C.). The coconut oil is then solidified, facilitating the collection of the coconut oil from the extract. In some embodiments, the cooling process can be operated in a refrigerator, in a cooled room, or in a cooling apparatus.

In some embodiments, the coconut oil is treated with a base solution. The base aqueous solution can be e.g., the aqueous solution of NaOH, KOH, $Mg(OH)_2$, $Ca(OH)_2$, $Na_2CO_3$, $NaHCO_3$, $Na_2CO_3$, $K_2CO_3$, or $KHCO_3$, or any combination thereof. In some embodiments, the pH of the solution can be, e.g., from 7.5 to 11, from 7.5 to 10, from 7.5 to 9, from 8 to 11, from 8 to 10, from 8 to 9, or from 9 to 11. In some embodiments, the aqueous solution is a saturated solution (e.g., at the room temperature, at the standard condition, or at 20 or 25° C.). In some embodiments, the solution is a saturated solution of sodium bicarbonate. The amount of the base solution should be sufficient to react with all acids that are free to react with the base. In some embodiments, the weight ratio of the extract to the sodium bicarbonate solution is equal to or less than about 1:1, e.g., equal to or less than about 1:1.1, 1:1.2, 1:1.3, 1:1.4, 1:1.5, 1:1.6, 1:1.7, 1:1.8, 1:1.9, 1:2, 1:3, 1:4, or 1:5.

In some embodiments, the starting material is regular coconut oil (e.g., coconut oil that can be obtained commercially, virgin coconut oil, untreated coconut oil). The regular coconut oil can be treated with a base (e.g., NaOH, KOH, $Mg(OH)_2$, $Ca(OH)_2$, $Na_2CO_3$, $NaHCO_3$, $Na_2CO_3$, $K_2CO_3$, or $KHCO_3$) or a basic solution as described herein (e.g., the aqueous solution of NaOH, KOH, $Mg(OH)_2$, $Ca(OH)_2$, $Na_2CO_3$, $NaHCO_3$, $Na_2CO_3$, $K_2CO_3$, or $KHCO_3$, or any combination thereof) and processed as described above and/or as described elsewhere herein.

The mixture is then cooled (e.g., to room temperature), or to a temperature that is below 20, 19, 18, 17, 16, 15, 14, 13, 12, 11, 10, 9, 8, 7, 6, 5, 4, 3, 2, or 1° C. In some embodiments, the extract is cooled to a temperature that is above 10, 9, 8, 7, 6, 5, 4, 3, 2, 1, or 0° C. In some embodiments, the temperature is cooled to below the melting point of the deacidified coconut oil (e.g., around 20, 19, 18, 17, 16, 15, 14, 13, 12, 11, 10° C.). In some embodiments, the coconut oil is solidified, facilitating the collection. In some embodiments, the cooling process can be operated in a refrigerator, in a cooled rom, or in a cooling apparatus.

In some embodiments, the coconut oil can be then collected and filtered, e.g., through a membrane under a pressure. In some embodiments, the filter size is at least or about 5, e.g., at least or about 6, 7, 8, 9, 10, 11, 12, 13, 14, 15, 16, 17, 18, 19, or 20 nm. In some embodiments, the filter size is less than 5, 6, 7, 8, 9, 10, 11, 12, 13, 14, 15, 16, 17, 18, 19, or 20 nm. In some embodiments, the filter size is from 10 to 15 nm, from 5 to 20 nm, or from 10 to 20 nm. In some embodiments, the pressure is greater than 1 $kg/cm^2$ (1 $kg/cm^2$=98.0665 kPa). In some embodiments, the pressure is less than 2 $kg/cm^2$, less than 3 $kg/cm^2$, or 4 $kg/cm^2$.

The filtered coconut oil may be sterilized (e.g., at a temperature above 100, 110, 120, 130, 140, or 150° C., or at about 134° C.). In some embodiments, the temperature is less than 100, 110, 120, 130, 140, or 150° C. Skilled practitioners will appreciate that any art-known method of sterilization may be utilized.

In some embodiments, the methods increase the amount of Stigmastentriol (e.g., the log 2 of the ratio between the deacidified coconut oil and the original coconut oil is at least or about 5, 6, 7, 8, 9, 10, or 11). In some embodiments, the methods increase the amount of Campest-4-en-3-one (e.g., the log 2 of the ratio between the deacidified coconut oil and the original coconut oil is at least or about 4, 5, 6, 7, 8, 9, or 10). In some embodiments, the methods increase the amount of Stigmasterol (e.g., the log 2 of the ratio between the deacidified coconut oil and the original coconut oil is at least or about 3, 4, 5, 6, 7, 8, or 9). In some embodiments, the methods increase the amount of Stigmast-22-ene-3,6-dione (e.g., the log 2 of the ratio between the deacidified coconut oil and the original coconut oil is at least or about 3, 4, 5, 6, 7, 8, or 9). In some embodiments, the methods increase the amount of ubiquinone-4 (e.g., the log 2 of the ratio between the deacidified coconut oil and the original coconut oil is at least or about 3, 4, 5, 6, 7, 8, or 9). In some embodiments, the methods increase the amount of Vitamin D3 (e.g., the log 2 of the ratio between the deacidified coconut oil and the original coconut oil is at least or about 3, 4, 5, 6, 7, 8, or 9).

In some embodiments, the methods decrease 3-hexenoic acid (e.g., the log 2 of the ratio between the deacidified coconut oil and the original coconut oil is less than or about −7, −8, −9, −10, −11, −12, or −13). In some embodiments, the methods decrease 5, 8-tetradecadienoic acid (e.g., the log 2 of the ratio between the deacidified coconut oil and the original coconut oil is less than or about −4, −5, −6, −7, −8, −9, or −10). In some embodiments, the methods decrease Indole (e.g., the log 2 of the ratio between the deacidified coconut oil and the original coconut oil is less than or about −4, −5, −6, −7, −8, −9, or −10). In some embodiments, the methods decrease isolecucine (e.g., the log 2 of the ratio between the deacidified coconut oil and the original coconut oil is less than or about 0, −1, or −2). In some embodiments, the methods decrease valine (e.g., the log 2 of the ratio between the deacidified coconut oil and the original coconut oil is less than or about 0, −1, −2, −3, or −4). In some embodiments, the methods decrease glutamate (e.g., the log 2 of the ratio between the deacidified coconut oil and the original coconut oil is less than or about 0, −1, −2, −3, −4, −5, or −6). In some embodiments, the methods decrease beta-alanine (e.g., the log 2 of the ratio between the deacidified coconut oil and the original coconut oil is less than or about 0, −1, −2, −3, −4, −5, or −6).

In some embodiments, the methods increase the amount of Piperochromenoic acid (e.g., the log 2 of the ratio between the deacidified coconut oil and the original coconut oil is at least or about 3, 4, 5, 6, 7, 8, or 9). In some embodiments, the methods increase the amount of LysoPA (a-25:0/0:0) (e.g., the log 2 of the ratio between the deacidified coconut oil and the original coconut oil is at least or about 2, 3, 4, 5, 6, 7, 8, or 9). In some embodiments, the methods increase the amount of LysoPA(24:0/0:0) (e.g., the log 2 of the ratio between the deacidified coconut oil and the original coconut oil is at least or about, 4, 5, 6, 7, 8, 9, or 10).

In some embodiments, the methods decrease sucrose (e.g., the log 2 of the ratio between the deacidified coconut oil and the original coconut oil is less than or about 5, −6, −7, −8, −9, −10, or −11). In some embodiments, the methods decrease citric acid (e.g., the log 2 of the ratio between the deacidified coconut oil and the original coconut oil is less than or about −4, −5, −6, −7, −8, −9, −10, or −11). In some embodiments, the methods decrease mannitol (e.g., the log 2 of the ratio between the deacidified coconut oil and the original coconut oil is less than or about −3, −4, −5, −6, −7, −8, −9, −10, or −11). In some embodiments, the methods decrease glucose (e.g., the log 2 of the ratio between the deacidified coconut oil and the original coconut oil is less than or about −1, −2, −3, −4, −5, −6, or −7).

In some embodiments, the methods increase the amount of DG (e.g., the log 2 of the ratio between the deacidified coconut oil and the original coconut oil is at least or about 0, 1, 2, 3, 4, 5, 6, 7, 8, or 9). In some embodiments, the methods increase the amount of ChE (e.g., the log 2 of the ratio between the deacidified coconut oil and the original coconut oil is at least or about 0, 1, 2, or 3). In some embodiments, the methods increase the amount of ZyE (e.g., the log 2 of the ratio between the deacidified coconut oil and the original coconut oil is at least or about 0, 1, 2, or 3).

In some embodiments, the methods decrease LPE (e.g., the log 2 of the ratio between the deacidified coconut oil and the original coconut oil is less than or about −2, −3, −4, −5, −6, −7, or −8). In some embodiments, the methods decrease PE (e.g., the log 2 of the ratio between the deacidified coconut oil and the original coconut oil is less than or about −2, −3, −4, −5, −6, −7, or −8). In some embodiments, the methods decrease Co (e.g., the log 2 of the ratio between the deacidified coconut oil and the original coconut oil is less than or about −1, −2, −3, or −4). In some embodiments, the methods decrease LPC (e.g., the log 2 of the ratio between the deacidified coconut oil and the original coconut oil is less than or about −1, −2, −3, −4, −5, −6, −7, or −8). In some embodiments, the methods decrease CerG1 (e.g., the log 2 of the ratio between the deacidified coconut oil and the original coconut oil is less than or about −1, −2, −3, −4, or −5).

In some embodiments, the methods increase the amount of LdMePE (e.g., the log 2 of the ratio between the deacidified coconut oil and the original coconut oil is at least or about 1, 2, 3, 4, 5, 6, or 7). In some embodiments, the methods increase the amount of PAF (e.g., the log 2 of the ratio between the deacidified coconut oil and the original coconut oil is at least or about 1, 2, 3, 4, or 5). In some embodiments, the methods increase the amount of DGMG (e.g., the log 2 of the ratio between the deacidified coconut oil and the original coconut oil is at least or about 1, 2, 3, 4, or 5). In some embodiments, the methods increase the amount of MGMG (e.g., the log 2 of the ratio between the deacidified coconut oil and the original coconut oil is at least or about 1, 2, 3, 4, or 5). In some embodiments, the methods increase the amount of LPMe (e.g., the log 2 of the ratio between the deacidified coconut oil and the original coconut oil is at least or about 1, 2, 3, 4, 5, 6, or 7).

In some embodiments, the methods decrease DGDG (e.g., the log 2 of the ratio between the deacidified coconut oil and the original coconut oil is less than or about −3, −4, −5, −6, −7, −8, or −9). In some embodiments, the methods decrease cPA (e.g., the log 2 of the ratio between the deacidified coconut oil and the original coconut oil is less than or about −3, −4, −5, −6, −7, −8, or −9). In some embodiments, the methods decrease LPI (e.g., the log 2 of the ratio between the deacidified coconut oil and the original coconut oil is less than or about −2, −3, −4, −5, −6, −7, or −8). In some embodiments, the methods decrease LPE (e.g., the log 2 of the ratio between the deacidified coconut oil and the original coconut oil is less than or about −1, −2, −3, −4, −5, −6, or −7). In some embodiments, the methods decrease PC (e.g., the log 2 of the ratio between the deacidified coconut oil and the original coconut oil is less than or about −1, −2, −3, −4, −5, −6, or −7). In some embodiments, the methods decrease dMePE (e.g., the log 2 of the ratio between the deacidified coconut oil and the original coconut oil is less than or about −1, −2, −3, −4, −5, −6, or −7). In some embodiments, the methods decrease MGDG (e.g., the log 2 of the ratio between the deacidified coconut oil and the original coconut oil is less than or about −1, −2, −3, −4, −5, −6, or −7). In some embodiments, the methods decrease PI (e.g., the log 2 of the ratio between the deacidified coconut oil and the original coconut oil is less than or about −1, −2, −3, −4, −5, −6, or −7). In some embodiments, the methods decrease PE (e.g., the log 2 of the ratio between the deacidified coconut oil and the original coconut oil is less than or about −1, −2, −3, −4, or −5). In some embodiments, the methods decrease PG (e.g., the log 2 of the ratio between the deacidified coconut oil and the original coconut oil is less than or about −1, −2, −3, −4, or −5). In some embodiments, the methods decrease PMe (e.g., the log 2 of the ratio between the deacidified coconut oil and the original coconut oil is less than or about 0, −1, or −2). In some embodiments, the methods decrease LPG (e.g., the log 2 of the ratio between the deacidified coconut oil and the original coconut oil is less than or about 0, −1, or −2). In some embodiments, the methods decrease PEt (e.g., the log 2 of the ratio between the deacidified coconut oil and the original coconut oil is less than or about 0, −1, or −2).

Dosage

An "effective amount" is an amount sufficient to effect beneficial or desired results. For example, a therapeutic amount is one that achieves the desired therapeutic effect. This amount can be the same or different from a prophylactically effective amount, which is an amount necessary to prevent onset of disease or disease symptoms. An effective amount can be administered in one or more administrations, applications or dosages. The compositions (e.g., deacidified coconut oil or herb tea) can be administered one from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the therapeutic compounds described herein can include a single treatment or a series of treatments.

Dosage, toxicity and therapeutic efficacy of the therapeutic compositions can be determined by standard pharmaceutical procedures in experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50.

The data obtained from cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized.

Skilled practitioners will appreciate, however, that the specific dose level for any particular patient will depend upon a variety of factors. Such factors include the age, body weight, general health, sex, and diet of the patient. Other factors include the time and route of administration, rate of excretion, drug combination, and the type and severity of the particular disease undergoing therapy.

In the treatment of the disorders as described herein, an appropriate dosage level of deacidified coconut oil can be about 1 to 10 drops, 1 to 9 drops, 1 to 8 drops, 1 to 7 drops, 1 to 6 drops, 1 to 5 drops, 1 to 4 drops, 1 to 3 drops, 1 to 2 drops, 2 to 5 drops, 3 to 5 drops, or 2 to 3 drops per administration. For example, 1, 2, 3, 4, 5, 6, 7, 8, 9, 10 (e.g., 1 or 2) drops of the deacidified coconut oil can be administered to the subject. Each drop can be, e.g., 0.1 to 1 ml, 0.1 to 0.9 ml, 0.1 to 0.8 ml, 0.1 to 0.7 ml, 0.1 to 0.6 ml, 0.1 to 0.5 ml, 0.1 to 0.4 ml, 0.1 to 0.3 ml, 0.1 to 0.2 ml, 0.2 to 1 ml, 0.2 to 0.8 ml, 0.2 to 0.7 ml, 0.3 to 1 ml, 0.3 to 0.8 ml, 0.3 to 0.7 ml, 0.4 to 1 ml, 0.4 to 0.9 ml, 0.4 to 0.8 ml, 0.4 to 0.7 ml, 0.4 to 0.6 ml, 0.1 to 0.5 ml, 0.5 to 1 ml, or 0.1 to 1 ml. In some embodiments, each drop is about 0.05 ml. The deacidified coconut oil can be administered to the subject about or at least 1 times per day, e.g., at least 2, 3, 4, 5, 6, 7, 8, 9, 10, 11, or 12 times per day, or about or at least 2, 3, 4, 5, 6, 7, 8, 9, 10, 11, or 12 times every 1, 2, 3, 4, 5, 6, 7, 8, 9, 10, 11, or 12 hours. In some embodiments, deacidified coconut oil can be administered to the subject less than 3, 4, 5, 6, 7, 8, 9, 10, 11, or 12 times per day. In some embodiments, deacidified coconut oil can be administered to the subject 1 to 10 times, 1 to 9 times, 1 to 8 times, 1 to 7 times, 1 to 6 times, 1 to 5 times, 1 to 4 times, 1 to 3 times, 1 to 2 times, 2 to 5 times, 3 to 5 times, or 2 to 3 times per day.

In some embodiments, the deacidified coconut oil drop is administered to the subject every 4, 5, 6, 7, 8, 9 or 10 hours. In some embodiments, the therapeutic effects (e.g., relief of symptoms of dry eye disorders) of deacidified coconut oil eye drop can last e.g., 1 to 12 hours, 1 to 11 hours, 1 to 10 hours, 1 to 9 hours, 1 to 8 hours, 1 to 7 hours, 1 to 6 hours, 1 to 5 hours, 1 to 4 hours, 1 to 3 hours, 1 to 2 hours, 2 to 12 hours, 2 to 11 hours, 2 to 10 hours, 2 to 9 hours, 2 to 8 hours, 2 to 7 hours, 2 to 6 hours, 2 to 5 hours, 3 to 12 hours, 3 to 10 hours, 3 to 8 hours, 3 to 6 hours, or 4 to 6 hours. In some embodiments, the therapeutic effects can last about or about or at least 2, 3, 4, 5, 6, 7, 8, 9, 10, 11, or 12 hours, 1 day, 2 days, 3 days, 4 days, or 5 days (e.g., about or at least 6 hours, 12 hours, or 1 day).

In some embodiments, the length of the treatment period is between 2 days and 1 year, including e.g., about or at least 2 days, 3 days, 4 days, 5 days, 6 days, 7 days, 10 days, 12 days, 15 days, 20 days, 28 days, 5 weeks, 6 weeks, 7 weeks, or 8 weeks.

In some embodiments, the composition described herein is administered to the subject twice a day. In some embodiments, about or at least 10 uL is administered to one eye for each administration.

Pharmaceutical Compositions and Methods of Administration

The methods described herein include the use of an ophthalmic compositions comprising deacidified coconut oil as an active ingredient or a composition comprising the active agents of the herb tea described herein.

The compositions can include a pharmaceutically acceptable carrier. As used herein, the language "pharmaceutically acceptable carrier" includes saline, solvents, dispersion media, coatings, antibacterial and antifungal agents, isotonic and absorption delaying agents, and the like, compatible with pharmaceutical administration.

Oral compositions (e.g., compositions comprising active agents of the herb tea described herein) generally include an inert diluent or an edible carrier. For the purpose of oral therapeutic administration, the active agents can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

In some embodiments, the active agents are prepared with carriers that will protect the therapeutic compounds against rapid elimination from the body. Biodegradable, biocompatible polymers can be used, such as ethylene vinyl acetate, polyanhydrides, polyglycolic acid, collagen, polyorthoesters, and polylactic acid. Such formulations can be prepared using standard techniques, or obtained commercially.

In some embodiments, the active agents are prepared in a nebulized form. Thus, the deacidified coconut oil can be administered to a subject as sprays. In some embodiments, the deacidified coconut oil can be added to contacts. Thus, the deacidfied coconut oil is administered to a subject, when the subject wears the contacts.

In some embodiments, the pharmaceutical composition consists of or consists essentially of deacidified coconut oil. In some embodiments, the pharmaceutical composition can optionally have various ingredients other than deacidified coconut oil, such as sugars, electrolytes, amino acids, vitamins, lipids, and medicinal additives. Examples of these ingredients include sugars such as glucose, maltose, etc., oligosaccharides, mannitol, and sugar alcohols such as sorbitol; electrolytes such as sodium chloride, sodium hydrogenphosphate, potassium chloride, magnesium sulfate, and calcium chloride; amino acids such as glycine and alanine; vitamins such as thiamin hydrochloride, sodium riboflavin phosphate, pyridoxine hydrochloride, nicotinic acid amide, folic acid, biotin, vitamin A, L-ascorbic acid, and $\alpha$-glycosyl ascorbic acid; and derivatives of these. These ingredients may be compounded in suitable combinations as needed.

In some embodiments, the pharmaceutical composition can include preservatives such as methyl parahydroxybenzoate, sodium dehydroacetate, and benzalkonium chloride; stabilizers such as sodium edetate and sodium hydrogensulfite; buffers such as borax, boric acid, and sodium hydrogencarbonate; thickeners such as methyl cellulose, carboxymethyl cellulose, chondroitin sulfuric acid, polyvinyl alcohol, and pullulan; and dissolution improvers such as Polysorbate 80.

In some embodiments, the compositions can additionally include one or more of the following ingredients: carboxymethyl cellulose, polyvinyl alcohol, hydroxypropyl methylcellulose (a.k.a. HPMC or hypromellose), hydroxypropyl cellulose and hyaluronic acid (a.k.a. hyaluronan, HA). In some embodiments, the compositions can additionally include one or more of the following ingredients: carboxymethylcellulose, dextran, glycerin, hypromellose, polyethylene glycol 400 (PEG 400), polysorbate, polyvinyl alcohol, povidone, and propylene glycol.

Skilled practitioners will appreciate that other compositions that can be used to treat dry eye can be included in the pharmaceutical compositions or the treatments described herein. For example, artificial tear solutions, saline, steroids, immunosuppressants (e.g., ciclospori), diquafosol, lifitegrast, or ciclosporin can be included in the pharmaceutical compositions or can be administered to the subjects with the pharmaceutical compositions comprising deacidified coconut oil.

The pharmaceutical compositions can be included in a container, pack, or dispenser together with instructions for administration. In some embodiments, the kit also include artificial tears.

EXAMPLES

The invention is further described in the following examples, which do not limit the scope of the invention described in the claims.

Example 1: Coconut Oil Extraction and Deacidification

The coconut meat or coconut powder was collected, and was mixed with sodium carbonate powder. The mixture was then heated to about 70° C. and then was screw pressed. The extract was then cooled to about 5° C. The water phase and the oil phase were separated. The coconut oil was collected. The coconut oil was then mixed with a saturated solution of sodium bicarbonate (the weight ratio of the extract to the sodium bicarbonate solution is about 1:1.1). The mixture was then cooled to about 5° C. The coconut oil was then collected and was then filtered through 13 nm membrane filtration under a pressure not greater than 4 kg/cm' (about 392.266 kPa). The filtered coconut oil was then sterilized at about 134° C. and stored for future use.

Both the sodium carbonate powder and the saturated solution of sodium bicarbonate were used to deacidify the coconut oil. Some coconut oil was also prepared without the deacidification process for comparison purpose.

Example 2: Testing Deacidified Coconut Oil Eye Drops in Human Subjects Safety The deacidified coconut oil eye drops were tested in ten subjects after their consent. Among them, four were healthy subjects, and six had dry eye syndromes. None of the subjects, including the four healthy subjects, experienced any irritation or discomfort. Only in some of these cases, immediately after the deacidified coconut oil was applied to the eye, some patients experienced mild blurred visions for a short period of time (e.g., seeing colored stripes around strong light). The patterns of stripes was similar to those on soap bubbles, which are caused by the thin film interference. The mild blurred vision was typically resolved within hours or just a few days. Among the subjects with dry eye syndromes, the deacidified coconut oil eye drops were administered to the subjects for an extended period of time. No adverse effects were observed. The results at least suggest the deacidified coconut oil was generally safe and not toxic to human.

For comparison purposes, coconut oil without deacidification was also tested in at least two human subjects. The coconut oil immediately caused irritation, redness, and blisters. The results suggest that coconut oil without deacidification is not suitable for being used as eye drops.

Furthermore, coconut oil (cold-pressed) was purchased from the company Haizhiye (Hainan Province, China). The coconut oil was extracted without being heated and the deacidification process. The coconut oil was also known as virgin coconut oil. The coconut oil (cold-pressed) was tested in one human subject. The coconut oil (cold-pressed) immediately caused strong irritation in the eyes. The results indicate that coconut oil (cold-pressed) cannot be used as eye drops.

The results above indicate that the regular coconut oil has irritants for eyes and is not suitable for being used as eye drops, and the deacidification process can effectively remove the irritants.

Efficacy

Six patients with dry eye syndromes were treated with deacidified coconut oil eye drops after their consent. The symptoms were alleviated in all of the six cases. These cases are described in more detail below:

Case 1: A 52 year-old male patient received a surgery in 2007 to prevent trichiasis. After the operation, the patient started to have the sensation of dryness in both eyes. In 2012, it was determined that the tarsal glands had shrunk by two thirds of its size, and the patient was diagnosed as having dry eye syndrome. The tarsal glands may be damaged during the surgery in 2007. The patient experienced the symptoms of dry eye syndrome several times a year. The patient had the sensation of dryness, pain, and severe itching, and could not perform normal daily functions, including e.g., using the cellphone or the computer. Other symptoms included headache, insomnia, sensitivity to light and wind, and difficulties to open eyes. The patient were prescribed with artificial tear eye drops. However, the treatments were not effective. The quality of the patient's life was severely affected.

In 2017, the patient was treated with deacidified coconut oil eye drop. The deacidified coconut oil eye drop was administered along with the artificial tear eye drops. The artificial tear eye drops were administered to the patient first, and then the deacidified coconut oil eye drops were administered. After one year's treatment, the patient's right eye was fully recovered. The symptoms for the left eye was not yet fully recovered, but significant improvements were observed. Particularly, immediately after the treatment, certain symptoms, including e.g., extreme itchiness, headache, insomnia, sensitivity to light and wind were resolved. In the following check-up in the Department of Ophthalmology at Yunnan No. 2 People's Hospital, it was determined that the patient's right eye was found to be normal, and the patient's left eye was diagnosed as having only mild dry eye syndrome.

Case 2: The female patient was 47 years old. She had dry eye syndrome for at least 5 years before being treated with deacidified coconut oil eye drop. The dry eye syndrome caused great discomfort, and the disease severely affected her work performance. The patient was treated by various treatments (including artificial tear eye drops), but there was no improvement in her symptoms. In early 2018, she was treated with deacidified coconut oil eye drop (one administration per day, one eye drop for one administration). The deacidified coconut oil eye drop was administered along with artificial tear eye drops. The treatment immediately alleviated her pain. She continued to use the deacidified coconut oil eye drops. The sensation of dryness and pain were resolved during the treatment period.

Case 3: The patient was a 56 years old female. She had dry eye syndrome for at least 6 years before being treated with deacidified coconut oil eye drops. She was also diagnosed of chronic keratoconjunctivitis. Her symptoms included dryness and redness in her eyes. In early 2018, she was treated with deacidified coconut oil eye drops. The deacidified coconut oil eye drops were administered along with artificial tear eye drops. The treatment alleviated the symptoms of the dry eye syndrome. The redness in the eyes was resolved.

Case 4: The patient was a 52-year-old female. She had moderate dry eye syndrome for years. After being treated with deacidified coconut oil eye drops along with artificial tear eye drops, the symptoms for dry every syndrome were resolved.

Case 5: The patient was a woman, who was more than 70 years old. She had severe dry eye syndrome for several years. After being treated with deacidified coconut oil eye drops along with artificial tear eye drops, her symptoms were resolved.

Case 6: The patient was a man, who was more than 60 year old. He had dry eye syndrome for a few years. After being treated with deacidified coconut oil eye drops along with artificial tear eye drops, his symptoms were resolved as well.

As all of these cases had chronic dry eye syndrome for years, the results before and after the treatment with deacidified coconut oil drops suggest that deacidified coconut oil drops are effective for treating dry eye disorders.

Example 3: Methods of Making Herb Tea and Herb Tea Pod

Wolfberries, *Astragalus* root, and *chrysanthemum* flower were cleaned, dried, and were sterilized by heat. The mixture was then grinded to powder, and was stored in a container. For making herb tea pods for being used as single-serve containers (e.g., tea cup, K-cup, tea capsule), the powder was stored in the single-serve containers, and then the containers were filled with nitrogen to increase storage time. The containers were then sealed and can be used in appropriate coffee machines or tea makers.

Example 4: Methods of Making Thermal Pads

About 200 g Cassiae semen and about 80 g borneol were added to a cotton bag with the size of 22 cm×11 cm. Before using, the bag was heated in a steamer for a sufficient period of time (e.g., about 10 minutes). The bag should not be immersed in the water in the steamer. After heating, the bag was left on a container at the room temperature. When the temperature dropped to about 46° C., the bag can be placed on the eyes of a human subject as a thermal pad.

Example 5: Testing Herb Tea and Thermal Pads in Human Subjects

The patient had dry eye syndrome for years and was being treated with deacidified coconut oil for an extended period of time.

During the period when the patient was administered with deacidified coconut oil, the patient also took the herb tea for treating dry eye disorders. Wolfberries (about 10 g), *Astragalus* root (about 10 g), and *chrysanthemum* flower (about 10 g) were mixed with about 2 cups of hot water. After it was cooled to appropriate temperature, the herb tea was then orally administered to the patient at least once per day.

The patient also received heat therapy several times a week using the heat pad comprising Cassiae semen and borneol.

By comparing the symptoms before and after the herb tea treatment and the heat therapy, it was determined that the herb tea and the heat therapy significantly improved the efficacy of deacidified coconut oil eye drops.

Example 6: Testing Deacidified Coconut Oil Eye Drops in Animal Models for Dry Eye Syndromes Animal models for dry eye syndromes can be placed into 4 groups. The first group is treated with artificial tear eye drops. The second group is treated with deacidified coconut oil eye drops. The third group is treated with deacidified coconut oil eye drops along with artificial tear eye drops. The fourth group does not receive any treatments, and is used as a control group.

The animal models can be any animal models for dry eye syndromes that are known in the art. Numerous animal models for dry eye syndromes are known in the art, and are described for example in Barabino, et al. "Animal models of dry eye: a critical assessment of opportunities and limitations," Investigative ophthalmology & visual science 45.6 (2004): 1641-1646, which is incorporated herein by reference in its entirety.

In this example, the animal model can be a rabbit model. Because of the large exposed ocular surface in rabbits compared with mice, standard dry eye clinical tests such as tear break-up time and fluorescein or rose bengal staining of the ocular surface can be much more easily performed in rabbits. An autoimmune disease in rabbits resembling Sjögren's syndrome can be induced by injecting into the lacrimal gland autologous peripheral blood lymphocytes proliferated in culture with epithelial cells obtained from the contralateral excised gland. The injection can trigger a continuous decrease in tear production and stability.

In the first group, the artificial tear eye drops are administered to the eyes of the animal twice per day. In the second group, the deacidified coconut oil eye drops are administered to the eyes of the animal twice per day. In the third group, the artificial tear eye drops are administered to the eyes of the animal first and then the deacidified coconut oil eye drops are administered to the eyes of the animal. Two administrations are performed in a day.

A Schirmer's test can be used to determine whether there is any improvement in dry eye syndromes. The Schirmer's test determines whether the eye produces enough tears to keep it moist. It uses paper strips inserted into the eye for several minutes to measure the production of tears. The exact procedure may vary somewhat. Most often, this test includes placing a small strip of filter paper inside the lower eyelid (inferior fornix). The eyes are closed for 5 minutes. The paper is then removed and the amount of moisture is measured. Sometimes a topical anesthetic is placed into the eye before the filter paper to prevent tearing due to the irritation from the paper. The use of the anesthetic ensures that only basal tear secretion is being measured.

It is expected that the deacidified coconut oil eye drops and the combination of the deacidified coconut oil eye drops and the artificial tear eye drops can alleviate symptoms of dry eye syndromes.

Example 7: Testing Deacidified Coconut Oil Eye Drops in a Clinic Trial

Human patients with dry eye syndromes can be placed into 5 groups. The first group is treated with artificial tear eye drops. The second group is treated with deacidified coconut oil eye drops. The third group is treated with deacidified coconut oil eye drops along with artificial tear eye drops. For the fourth group, in addition to be treated with the combination of deacidified coconut oil eye drops and artificial tear eye drops, the fourth group also receives the herb tea treatment and the heat therapy. The fifth group is not treated with anything, and is used as a control group.

In the first group, the artificial tear eye drops are administered to the eyes of the subject twice per day. In the second group, the deacidified coconut oil eye drops are administered to the eyes of the subject twice per day. In the third group, the artificial tear eye drops are administered to the eyes of the subject first and then the deacidified coconut oil eye drops are administered to the eyes or the subject twice per day. The procedure for the fourth group is identical to the third group, except that the subjects in the fourth group are also treated with herb tea and heat therapy. The clinical trial can last 2 to 6 weeks.

The responses to the treatments are recorded. In some cases, Schirmer's test can be used to provide an objective evaluation of dry eye symptoms. In a Schirmer's test, 15 mm wetting of the paper after 5 minutes indicates normal, 14-9 mm wetting of the paper after 5 minutes indicates mild dry eye syndrome, 8-4 mm wetting of the paper after 5 minutes indicates moderate dry eye syndrome, and <4 mm wetting of the paper after 5 minutes indicates severe dry eye syndrome.

It is expected that the deacidified coconut oil eye drops and the combination of the deacidified coconut oil eye drops and the artificial tear eye drops can alleviate symptoms of dry eye syndromes, and the herb tea and heat therapy can further improve the efficacy of the deacidified coconut oil eye drops.

Example 8: A Pilot Efficacy Study on Dry Eye in Mice

Experiments were performed to determine the efficacy of the deacidified coconut oil composition. Biodecs001 was the deacidified coconut oil described herein, and was used in the following experiments.

The following materials were used in the following examples.

C57BL/6SLAC mice were purchased from Shanghai Slack Co., Ltd.

Scopolamine hydrobromide was purchased from Sigma-Aldrich (Lot Number: SLBD0119V).

Cyclosporine eye drops were obtained from Yunnan Biotech Biotechnology Co., Ltd.

Polyvinyl alcohol eye drops (artificial tears) were purchased from JOINN Laboratories (Suzhou) Inc. and manufactured by Hubei Yuanda Everyday Bright Eyes Pharmaceutical Co., Ltd. (Lot Number: 190103).

Sodium Chloride Injection was purchased from Shijiazhuang No. 4 Pharmaceutical Co., Ltd. (Lot Number: 1805303204).

Mouse feed was purchased from Beijing Keaoxieli Feed Co., Ltd. (Lot Number: 19043323, 19073113).

8.1 Experimental Design

Fifty-nine healthy female C57BL/6SLAC mice were selected for experiments. Mice that were healthy and with normal eyes were randomly divided into age-matched control group (8 animals/group) and test groups (51 animals) according to body weight on Day −1 (one day before the study period). Forty mice with similar right eye corneal fluorescein sodium staining score and tear secretion were divided into five groups (8 animals/group) according to the right eye corneal fluorescein sodium staining score on Day 5. Each mice was given a unique animal number. The grouping and treatment plans of mice are shown in the table below:

TABLE 1

| No. | Group | Modelling treatment | | Test/Control Article | Dosing | No. of animal | Animal ID▼ |
|---|---|---|---|---|---|---|---|
| | | Humidity | Scopolamine hydrobromide | | | | |
| 1 | Age-matched control group | D 1-D 17, normal humidity environment | — | — | — | 8 | 1921241~1921248 |
| 2 | Model control group | D 1-D 17, low humidity environment | D 1-D 17, 2 time/day, 0.75 mg/eye/ time, 0.3 mL/ | — | — | 8 | 1921249~1921256 |
| 3 | Negative control group | | | Saline | D 6-D 17, 2 time/day, | 8 | 1921257~1921264 |

TABLE 1-continued

| | | Modelling treatment | | | | | |
|---|---|---|---|---|---|---|---|
| No. | Group | Humidity | Scopolamine hydrobromide | Test/Control Article | Dosing | No. of animal | Animal ID▼ |
| 4 | Cyclosporine + artificial tears + test composition group* | | eye/time, subcutaneous injection | Cyclosporine + artificial tears + test composition* | 10 μL/eye, right eye | 8 | 1921265~1921272 |
| 5 | Artificial tears + test composition group# | | | Artificial tears + test composition* | | 8 | 1921273~1921280 |
| 6 | Test composition group | | | Test composition | | 8 | 1921281~1921288 |

In Table 1, "-" means that there was no treatment. "◆" means that the first and the last animals of each group were involved in this study in batches. "*" means that the eyes of mice in group 4 were given cyclosporine first, 20 minutes later artificial tears were added, and one minute later test composition were added. "#" means that the eyes of mice in group 5 were given artificial tears first, one minute later test composition were added.

Test/control compositions were dosed to the right eye by topical instillation, at a frequency of twice daily (about 8 hours apart) for 12 consecutive days (10 μL/eye/time). 10 μL test/control compositions including artificial tears or cyclosporine eye drop, were drawn with a pipette, and then dropped on the exposed cornea of the mice. After at least 10 seconds, eyelid was gently closed. Any spilled liquid was gently wiped off with sterile gauzes. The application, dose level, frequency and duration of dosing selected for this study was based on relevant reference information.

All animals of all groups were observed once daily during the study period (Day 1-Day 17). The animal's death or near-death, mental state, behavioral activities, feeding and fecal traits were observed by the cage. Body weights of all the animals in all groups were obtained at the time of receipt, the end of the quarantine period and the end of the last ophthalmic examination.

Tear secretion from the right eye of all the animals in all groups were measured by the following method on Day −1 (one day before the study period), Day 5, Day 9, Day 13 and Day 17. The phenol red cotton thread was clamped by clean, toothless tweezers and fixed in the middle of the lower eyelid conjunctival sac of mice for 30 seconds. Under the microscope, the length of the cotton dyeing was measured with a ruler and the picture was photographed.

Corneal fluorescein sodium staining test of the right eye of all the animals in all groups was performed as follows on Day −1, Day 5, Day 9, Day 13 and Day 17. All animals were awake when examined. The examiner described the results of each animal without being informed of the animal's identity, and the results of the examination was recorded by another person. About 1.5 minutes after the sodium fluorescein solution (1.5 μL, 0.5%) was dipped into the conjunctival sac of animals, the conjunctival sacs of the mice were washed with 1.25 ml saline every 10 seconds for 3 times, then the liquid around the animal's eyes was wiped with paper each time. About 5 minutes after corneal staining, the ocular surface was observed and photos were taken by slit lamp microscope with cobalt blue filter, and the staining content of corneal was graded by the modified NEI fluorescent staining grading method. According to this method, the cornea of eye is divided into 5 regions, and the staining score of each region is up to 4. "0" indicates that corresponding area is not clearly colored, and "1" indicates that the dotted colored area is 1 to 25% of the corresponding area, and "2", "3", "4" indicates percentages of 26%-50%, 51%~75%, 76%~100% respectively. The total score of each eye is up to 20 (FIG. 1). The total score of corneal staining for each eye can be calculated.

According to the protocol, during the study period, the animals would be euthanized by excessive carbon dioxide inhalation and thoracic opening if they developed severe eye abnormalities or in extremis. There were no animals in this experiment with irreversible signs and no animals were euthanized. After the last inspection, all surviving animals were euthanized by excessive carbon dioxide inhalation.

For the quantity of tears fluid and total score of corneal fluorescein sodium staining of all groups at different time point, the means and standard deviations were calculated with software SPSS, and the group difference on each time point were analyzed by the following statistical procedures: A Levene's test was performed to test for variance homogeneity. If the result showed no significance ($p>0.05$), a one-way analysis of variance (ANOVA) was performed. If ANOVA showed significance (p 0.05), a Dunnett's test was performed for multiple comparisons. If ANOVA showed no significance ($p>0.05$), no more statistical tests were performed. In the case of heterogeneity of variance at $p \leq 0.05$, a Kruskal-Wallis nonparametric test was performed. If the Kruskal-Wallis nonparametric test showed significance ($p \leq 0.05$), a further Mann-Whitney test was performed for multiple comparisons. Pre- and post-modelling of the group animals were compared using statistical methods of independent sample T test.

8.2 Results (Clinical Observations)

During the study (Day 1-Day 17), no animal death was seen in all groups in the dosing period, no abnormal clinical signs (other than ocular signs) were seen. On Day 4 (before treatment) after the modelling, animal with temporary number 3 was found dead. On Day 5 (also before treatment), animal with temporary number 59 was found dead after corneal staining examination. In such case, the corpse was disposed as medical waste, and no biopsy were carried out.

Four out of 8 treated eyes in the test composition group (Animal 1921281-1921284) on Day 13-Day 17, and the other 4 treated eyes (Animal 1921285-1921288) on Day 16-Day 17 were observed with sparse hairing in the ocular region. Four out of 8 treated eyes (Animal 1921273-1921276) on Day 13-Day 17, and the other 4 treated eyes (Animal 1921277-1921280) on Day 16-Day 17 were noted also with sparse hairing in the ocular region, and the incidence rate and time were the same with the Test composition group. Four out of 8 treated eyes in the cyclosporine+artificial tears+test composition group (Animal 1921269-1921272) on Day 12-Day 17, and the other 4 treated eyes (Animal 1921265~1921268) on Day 13-Day 17 were all seen with eyelid bloating, reduced hairing in ocular region, with or without peri-ocular skin redness. Other than signs described above, the untreated eyes in the three groups mentioned above and the age-matched control group, the model control group and the negative control group had no abnormal ocular signs.

Peri-ocular sparse hairing was seen in all treated eyes in the test composition group, but not seen in treated eyes in the negative control group with the same dosing frequency, cycle, and volume with the test composition group, thus this abnormality was considered to be due to the overflow of excess test composition to the peri-ocular region, which indicated the test composition could incite irritation to the peri-ocular skin and the dosing amount should be considered accordingly to prevent over-flow. Since the peri-ocular sparse hairing in all treated eyes in the artificial tears+test composition group had the same incidence rate and time with the test composition group, giving artificial lacrimal fluid alone might have no effect on the peri-ocular skin. Peri-ocular hair loss, bloated eyelid, sparse hairing, with or without periocular skin redness were noted in the treated eyes in the cyclosporine+artificial tears+test composition group, and not seen in the rest 6 groups. Therefore, this might be related to the over-flow of excess cyclosporine, or both cyclosporine and test composition to the peri-ocular skin, indicating that the cyclosporine was significantly irritative to the peri-ocular skin and eyelid.

8.3 Results (Body Weight)

Figure 2:
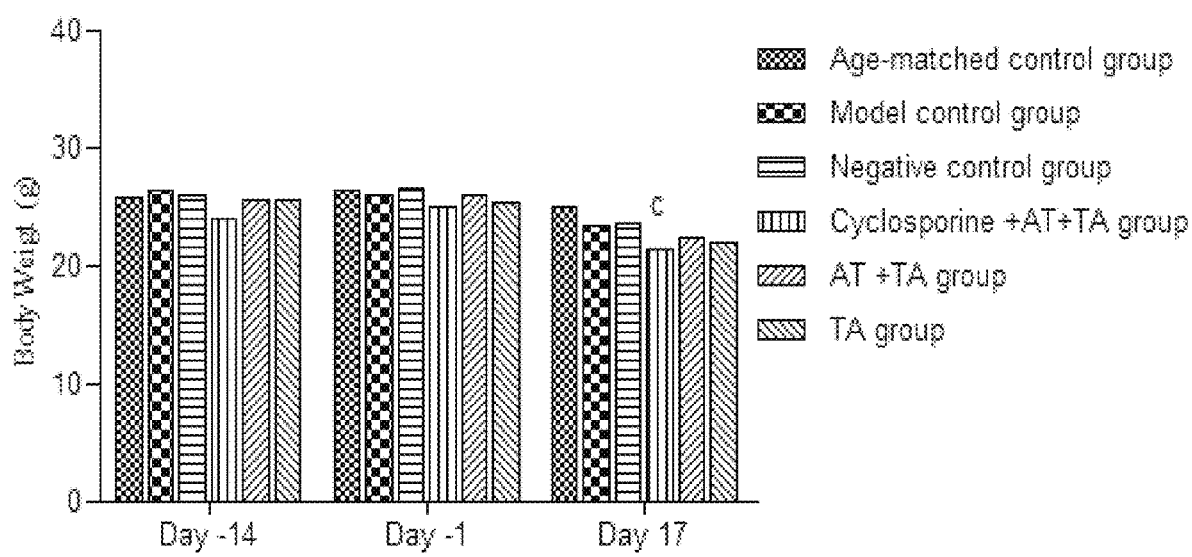
FIG. 2 is a bar histogram showing average body weight of mice in each group. "c" indicates that compared with Negative control group, "the differences were statistically significant ($p<0.05$). AT indicates artificial tears TA indicates test composition.

Body weight are summarized in FIG. 2. Before testing (Day−1), all animals in all groups showed no statistically significant difference in weight (p>0.05).

At the end of the observation period (Day 17), all animals in all groups had weight loss compared to Day −1, which could be a result of that the tested mice were all retired breeder mice, which were in old age, and the change of feed while entering the study (the animals ate reproduction feed before purchase and sustaining feed after purchase). Moreover, on Day 17, the animals in cyclosporine+artificial tears+test composition group had significantly reduction in weight (p<0.05) compared to time-matched negative control group, which could be due to irritation related issues caused by cyclosporine. The rest of animals in other groups showed no significant difference in weight (p>0.05).

8.4 Results (Tear Secretion)

Figure 3:
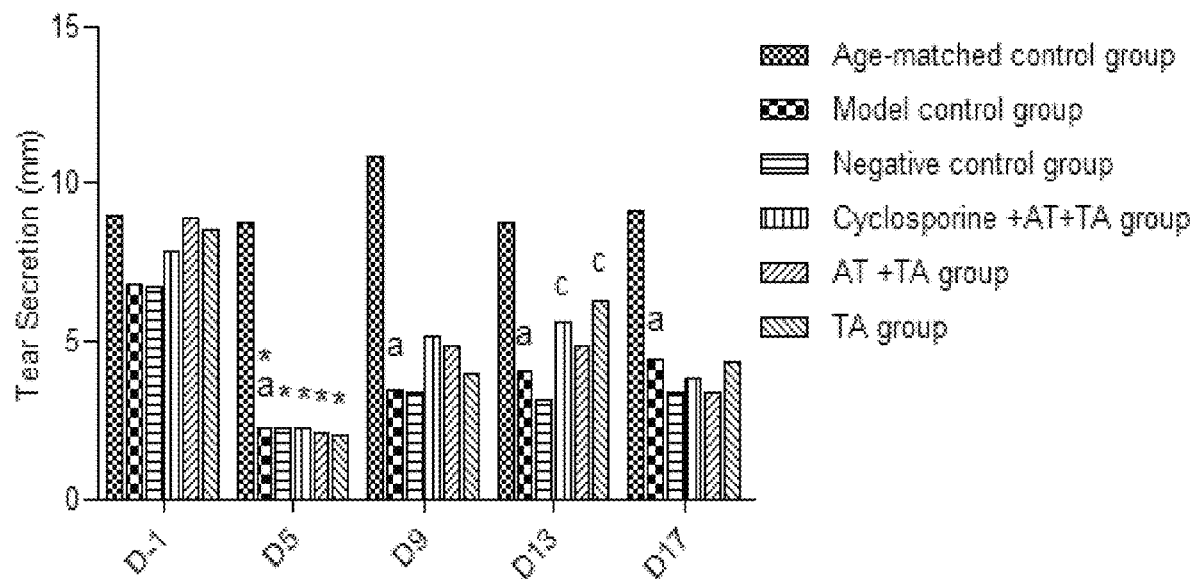
FIG. 3 is a bar histogram showing average tear secretion of mice in each group. "a" indicates that compared with Age-matched control group, "c" indicates that compared with Negative control group, "*" indicates that compared with that before modeling, the differences were statistically significant ($p<0.05$). AT indicates artificial tears TA indicates test composition.

The data of tear secretion are summarized in FIG. 3. Before testing (Day−1), the lacrimal secretion volume in the right eyes of all animals in all groups showed no statistical difference (p>0.05).

After modelling treatment and before test composition treatment (Day 5), except that the right eyes of the age-matched control groups showed no significant difference in lacrimal secretion volume compared to Day −1, the rest of the groups showed significant decrease (p<0.05) in the lacrimal secretion volume in the right eyes, which indicated low environmental humidity and scopolamine successfully induced an reduction in the lacrimal secretion amount, and no significant difference (p>0.05) was seen among all modelling groups.

After treatment, the specific result of lacrimal secretion in all groups of animal are as following:

Age-matched control group: On Day 9, Day 13, Day 17, the lacrimal secretion of right eyes were 10.81±2.36 mm, 8.75±2.52 mm, 9.13±1.58 mm, respectively.

Model control group: On Day 9, Day 13, Day 17, the lacrimal secretion of the right eyes were 3.44±1.59 mm, 4.00±1.07 mm, and 4.38±2.57 mm, respectively, which were significantly lower than that of the age-matched control group on the respective days (p<0.05). The result indicated that low environmental humidity and scopolamine induced reduction in lacrimal secretion, which was stably maintained throughout the study period.

Negative control group: On Day 9, Day 13, Day 17, the lacrimal secretion of the right eyes were 3.38±1.51 mm, 3.13±1.92 mm, and 3.38±1.94 mm, respectively, which were all significantly lower than that of the age-matched control group on the respective days (p<0.05). In addition, the results showed no statistically significant difference compared to the modelling control group on the respective days (p>0.05), which indicated that normal saline had no effect on the mouse lacrimal secretion.

Test composition group (Test article group or TA group): On Day 9, Day 13, Day 17, the lacrimal secretion of the right eyes were respectively 3.94±2.43 mm, 6.2 5±1.98 mm, and 4.31±3.26 mm, and the results on Day 9 and Day 13 were both higher than those of the model control group and the negative control group on the respective days, among which the Day 13 result had statistically significant difference compared to that of the negative control group (p<0.05), but the result on Day 17 showed no statistically significant difference when compared to the modelling control group and negative control group (p>0.05). The result suggested that the test composition used alone effectively improved the mouse lacrimal secretion to a certain degree on the 8th dosing day (Day 13).

Artificial tears+test composition group (AT+TA group): On Day 9, Day 13, Day 17, the lacrimal secretion of the right eyes were 4.81±2.24 mm, 4.88±1.48 mm, and 3.31±1.53 mm, respectively. The result on Day 9 and Day 13 were both higher than those of the modelling control group and the negative control group on the respective days, and the result on Day 17 was lower than both the model control group and negative group on the respective days, with no statistical significance in difference (p>0.05).

Cyclosporine+artificial tears+test composition group (Cyclosporine+AT+TA group): On Day 9, Day 13, Day 17, the lacrimal secretion of the right eyes were 5.13±1.81 mm, 5.63±1.36 mm, and 3.81±1.33 mm, respectively. Among them, the results on both Day 9 and Day 13 were higher than the model control group and negative control group on the respective days, in which the result on Day 13 had significant difference compared to negative control group (p<0.05), and the result of Day 17 showed no statistically significant difference compared with the model control group and negative control group on the respective days (p>0.05). The results showed combining three drugs in treatment could at certain level increase the lacrimal secretion of the mice on the 8th dosing day (Day 13). Compared with the test composition group, this group showed no significant difference among respective time points in the right eye (p>0.05).

8.5 Results (Corneal Fluorescein Sodium Staining Test)

Figure 4:
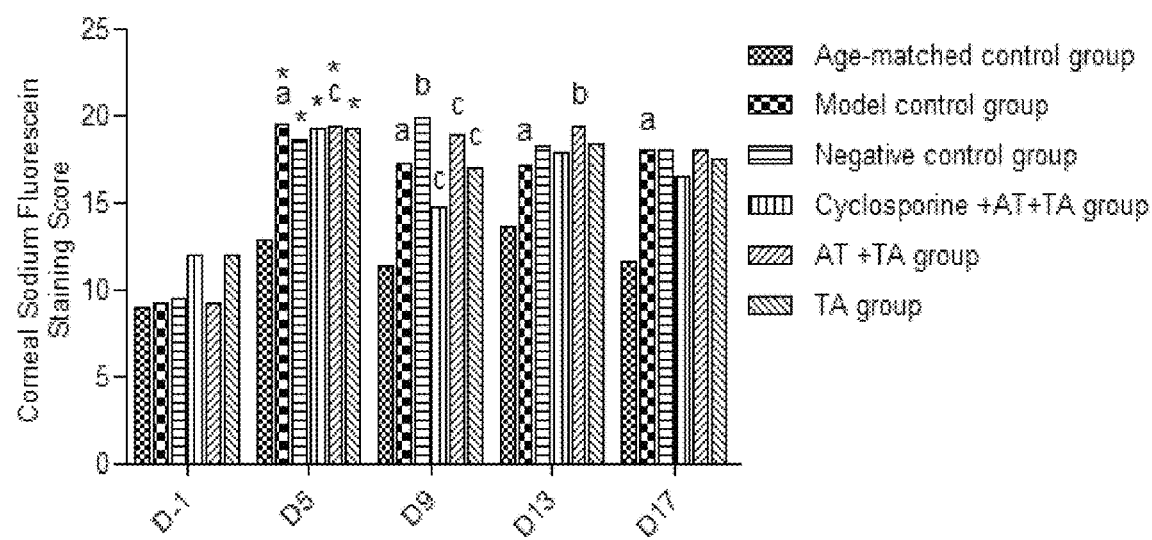
FIG. 4 is a bar histogram showing average corneal sodium fluorescein staining score of mice in each group. "a" indicates that compared with Age-matched control group, "b" indicates that compared with Model control group, "c" indicates that compared with Negative control group, "*" indicates that compared with that before modelling, the differences were statistically significant ($p<0.05$). AT indicates artificial tears TA indicates test composition.
Figure 5:
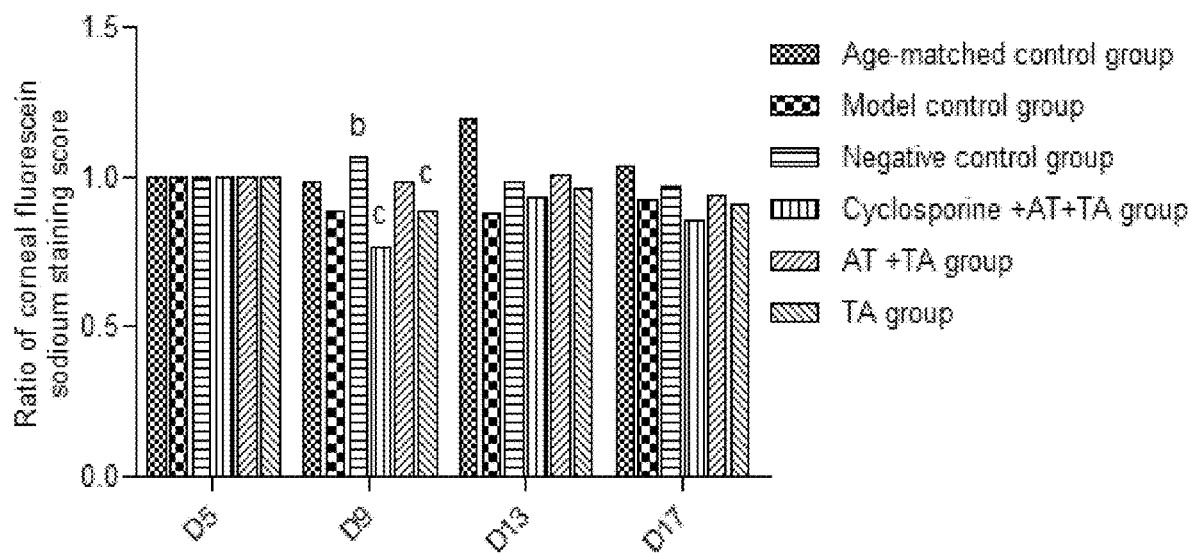
FIG. 5 is a bar histogram showing ratio of corneal fluorescein sodium staining score of mice in each group. "b" indicates that compared with Model control group, "c" indicates that compared with Negative control group, the differences were statistically significant ($p<0.05$). AT indicates artificial tears TA indicates test composition.

Staining scores of corneal sodium fluorescein are summarized in FIG. 4, and ratio of the staring scores are summarized in FIG. 5. Before modelling (Day −1), the corneal fluorescein sodium staining scores of the right eyes of all animals in all groups showed no statistically significant difference (p>0.05).

After modelling and before treatment (Day 5), except that the staining scores of the right eyes of the age-matched control group showed no significant difference compared to those on Day −1, the rest of the groups showed an significant increase in the staining scores in the right eye (p<0.05), which indicated that low environmental humidity and scopolamine successfully induced an increase of the mouse corneal fluorescein sodium staining scores, and exacerbated the loss of corneal epithelium in the mice. Except that the staining score of the negative control group was significantly lower than that of the artificial tears+test composition group (AT+TA group), the rest of the modelling groups showed no significant inter-group difference (p>0.05). To reduce the effect of inter-group difference before treatment on the following analysis, within a particular group, each post-treatment result was divided by the result on Day 5 (before treatment) and a scoring value was calculated. The value could indicate the relative ratio of the pre- and post-treatment results. As shown in FIG. 5, no significant difference was found (p>0.05), while the average of scoring values of each group were all 1.

After treatment, the specifics of the corneal fluorescein sodium staining scores, and calculated scoring values are as follows:

Age-matched control group: On Day 9, Day 13, Day 17, the staining scores of the right eyes were 11.4±4.1, 13.6±3.4, and 11.6±3.1, respectively, while the average of the scoring value comparing pre-/post-treatment during the dosing period were fluctuating in 1.0-1.2.

Model control group: On Day 9, Day 13, Day 17, the staining scores of the right eyes were 17.3±2.3, 17.1±2.7, and 18.0±1.7, respectively, with the average scoring value comparing pre-/post-treatment fluctuating between 0.9-1.0. Compared to the age-matched control group on the specific days, the staining scores increased significantly (p<0.05), which indicated that low environmental humidity and scopolamine induced increase in the mouse corneal staining scores, which were stably maintained in the whole treatment period.

Negative control group: On Day 9, Day 13, Day 17, the staining scores of the right eyes were 19.9±0.4, 18.3±2.1, and 18.0±2.2, respectively. Compared to the modelling group, the scores on Day 9 showed a significant increase, but those on Day 13 and Day 17 showed no statistical difference (p>0.05). The reason of the difference on Day 9 was not clear, which could be derived from systematic errors. However, considering the data on Day 13 and Day 17, the saline solution was thought to have no significant impact on the mouse corneal fluorescein sodium staining scores. The average scoring value comparing pre-/post-treatment during the dosing period fluctuated around 1.0-1.1.

Test composition group (Test Article group): On Day 9, Day 13, Day 17, the staining scores of the right eyes were 17.0±2.9, 18.4±2.3, and 17.5±2.8, respectively. The average of staining scoring value comparing pre-/post-treatment fluctuated around 0.9-1.0. On Day 9, the staining score and the scoring value were both lower than those of the model control group and the negative control group. Only in comparing with the negative control group, statistically significant difference was found (p<0.05). At the rest of the time points, no significant difference was observed when compared to the model and the negative control group on respective days (p>0.05). The results indicated that by using test composition alone on the 4th dosing day (Day 9), the mouse fluorescence staining scores showed a certain reducing effect.

Artificial tears+test composition group (Artificial tears+test article group): On Day 9, Day 13, Day 17, the staining scores of the right eyes were 18.9±1.4, 19.4±0.9, and 18.0±4.5, respectively, while the average scoring values comparing pre-/post-treatment were about 1.0. On Day 9 the staining score was significantly lower than the negative control group (p<0.05), but the average scoring value showed no significant difference compared with the negative control group (p>0.05). In addition, the scores together with the scoring values were all higher than those of the model control group. On Day 13, the staining score was significantly higher than the model control group, but the scoring value was not significantly different to the model control group (p>0.05). At the rest of the time points, this group showed no statistical difference when compared to the model control group, the negative control group, and the test composition group at respective time points (p>0.05).

Cyclosporine+artificial tears+test composition group (Cyclosporine+AT+TA group): On Day 9, Day 13, Day 17, the staining scores of the right eyes were 14.8±6.2, 17.9±2.1, 16.5±2.7, respectively, while the scoring values comparing pre-/post-treatment fluctuated around 0.8-0.9. On Day 9, the staining score and the average scoring value were both lower than those of the model control group, the negative control group, the test composition group and the artificial tears+test composition group, but only significantly different than those of the negative control group (p<0.05). The rest of the time points showed no significant difference than those of the modelling groups at respective time points (p>0.05). The results showed that by combining the three drugs, the treatment can reduce the mouse corneal staining score.

8.6 Conclusion

Amount of tear secretion: During the study, on Day 5, Day 9, Day 13, Day 17, model control group and negative control group had a statistically significant drop (p<0.05) in tear secretion compared to time-matched age-matched control group. On Day 13, compared to time-matched negative control group, the test composition group and the cyclosporine+artificial tears+test composition group showed a rise in amount of lacrimination which is statistically significant (p<0.05).

Corneal fluorescein sodium staining scores: During the study, on Day 5, Day 9, Day 13, Day 17, the model control group and negative control group showed significantly higher scores in corneal fluorescein sodium staining than the time-matched age-matched control group (p<0.05). On Day 9, compared to the time-matched negative control group, the test composition group, artificial tears+test composition group and the cyclosporine+artificial tears+test composition group showed significantly lower scores (p<0.05) in corneal fluorescein sodium staining.

General clinical observation: During the study, no animal deaths were confirmed related to the test composition, and all animals in the age-matched control group, model control group, and negative control group showed no abnormal clinical signs, and the rest of the animals in other groups showed no abnormal sign besides ocular signs. All animals in the test composition group and artificial tears+test composition group showed decreased hairing around the peri-ocular region in the treated eyes that might due to the overflow of excess test composition to the peri-ocular region, which started from Day 12 or Day 16, and lasted until the end of the observation period. All animals in the cyclosporine+artificial tears+test composition group showed eyelid bloating, losing hair around ocular region, and with or without skin redness around the ocular region in the treated eye that might due to the overflow of excess cyclosporine or both of cyclosporine and test composition to the peri-ocular region, which lasted from Day 12 or Day 13 until the end of observation. All untreated eyes in animals above showed no abnormal clinical signs.

Conclusion: Under the circumstances in this study, the test composition Biodecs001 used alone or combined with artificial tears, cyclosporine eye drops (twice per day, 10 µL per eye in each dose, consecutively for 12 days) could increase the lacrimal secretion and decrease the corneal fluorescein sodium staining scores of the dry eye mouse model induced by drying stress to a certain degree.

Example 9: An Eye Irritation Study of Biodecs001 with 14-Day Instillation in New Zealand White Rabbits 9.1 Experimental Design The following materials were used in the following examples.

New Zealand White Rabbits (SPF Grade) were purchased from Dongfang Breeding Co., Ltd. Rabbit growth reproduction feed was purchased from Beijing Keaoxieli Feed Co., Ltd., and Pizhou Xiaohe Technology Development Co., Ltd. (Lot Number: 19044111, 20190325).

Within 24 hours prior to the 1$^{st}$ dosing (Day −1), slit lamp microscopy and sodium fluorescein examination were applied to all healthy animals; any animal with eye irritation, ocular defect, or pre-existing injury was excluded. Twelve animals with normal eyes and similar body weight were selected for experiments.

Through a computer-generated randomization procedure, the twelve animals were randomly assigned to respective treatment groups according to the body weight measured within 24 hours prior to the 1$^{st}$ dosing (Day −1), as shown in Table 2.

TABLE 2

Group assignment

| Group | Dosing Treatment | | Dosing Volume(µL/ eye/time) | Number of animals |
|---|---|---|---|---|
| | Right eye | Left eye | | |
| 1 | — | Saline | 50 | 4 |
| 2 | — | Biodecs001 eye drops | 50 | 4 |
| 3 | — | Artificial tears * + Biodecs001 eye drops | 50 + 50 (about 1 minute apart) | 4 |

In Table 2, "-" means the right eye of animals was not treated with any composition. "*" means gave the artificial tears first, and then test composition for animals from Group 3.

Compositions were dosed to the left eye by topical administration, at a frequency of once daily for 14 consecutive days (50 µL/eye/time). 50 µL test/control compositions were drawn with a pipette, and 100 µL composition was dropped into the conjunctiva sac by pulling out the lower eyelid of the animal. Then, the lower eyelid was gently closed and remained for 10 seconds. The application, dose level, frequency and duration of dosing selected for this study was based on relevant reference information and the request of the guidance to support the subsequent toxicity studies and/or clinical trials.

All animals of all groups were observed daily. During the 14-day dosing period, all animals were observed twice daily (before the first instillation in the morning and one time in the afternoon), At Day −1 (within 24 hours pre-experiment) and the non-dosing period, all animals were observed once daily. Observation included signs of mortality, morbidity, behavior, respiration, secretion, excretion, pain and/or distress (e.g. repeated pawing or rubbing of the eye, excessive blinking, and excessive tearing) and so on.

Body weight of all animals of all groups were obtained on Day −1, Day 7, Day 14, and Day 17.

Both eyes of all animals of all groups in conscious condition were examined by an experienced examiner with a slit lamp microscope under observer-masked condition. The animals were brought to the examiner at a random order and the examiner graded each animal without knowing the animal ID and someone else was responsible for grade recording. The examination time points are: Day −1 (within 24 hours), prior to administration during Day 1 to Day 14 and 1, 2, 4, 24, 48, 72 hours post-final instillation on Day 14. The following examinations were performed.

A. Slit lamp examination: The cornea, iris, conjunctiva, edema, and ocular secretions were observed with a slit lamp and scored according to the eye irritation response score (shown in Table 3).

B. Sodium fluorescein examination: After examination A, cornea epithelial change with fluorescein staining was observed with moist sodium fluorescein indicator paper. The Corneal Staining (% Area) was scored according to the Modified MacDonald-Shadduck Scoring System as described in Table 4. No other abnormal eye symptoms were found during the examination.

TABLE 3

Modified Draize Scoring System of Eye Irritation

Cornea
Opacity: degree of density (readings should be taken from most dense area)*

| | |
|---|---|
| No ulceration or opacity | 0 |
| Scattered or diffuse areas of opacity (other than slight dulling of normal lustre): details of iris clearly visible | 1 |
| Easily discernible translucent area; details of iris slightly obscured | 2 |
| Nacrous area; no details of iris visible; size of pupil barely discernible | 3 |
| Opaque cornea; iris not discernible through the opacity | 4 |

Maximum possible: 4; * the area of corneal opacity should be noted
Iris

| | |
|---|---|
| Normal | 0 |
| Markedly deepened rugae, congestion, swelling, moderate circumcorneal hyperaemia; or injection; iris reactive to light (a sluggish reaction is considered to be an effect) | 1 |
| Hemorrhage, gross destruction, or no reaction to light | 2 |

Maximum possible: 2
Conjunctivae
Redness (refers to palpebral and bulbar conjunctivae; excluding cornea and iris)

| | |
|---|---|
| Normal | 0 |
| Some blood vessels hyperaemic (injected) | 1 |
| Diffuse, crimson colour; individual vessels not easily discernible | 2 |
| Diffuse beefy red | 3 |

Maximum possible: 3
Chemosis
Swelling (refers to lids and/or nictating membranes)

| | |
|---|---|
| Normal | 0 |
| Some swelling above normal | 1 |
| Obvious swelling, with partial eversion of lids | 2 |
| Swelling, with lids about half closed | 3 |
| Swelling, with lids more than half closed | 4 |

Maximum possible: 4
Discharge

| | |
|---|---|
| No discharge | 0 |
| Any amount different from normal (does not include small amounts observed in inner canthus of normal animals) | 1 |
| Discharge with moistening of lids and hairs just adjacent to the lids | 2 |

TABLE 3-continued

Modified Draize Scoring System of Eye Irritation

| | |
|---|---|
| Discharge with moistening of lids and hairs, and considerable area around the eye | 3 |
| Maximum possible: 3 | |

TABLE 4

Modified MacDonald-Shadduck Scoring System

Corneal Staining (% Area)

| | |
|---|---|
| No area of fluorescein staining. | 0 |
| 1% to 25% area of fluorescein staining. | 1 |
| 26% to 50% area of fluorescein staining. | 2 |
| 51% to 75% area of fluorescein staining. | 3 |
| 76% to 100% area of fluorescein staining. | 4 |

According to the protocol, animals with either of the following eye lesions post-instillation should be euthanized: 1) perforation or significant corneal ulceration including staphyloma; 2) blood in the anterior chamber of the eye; 3) grade 4 corneal opacity; 4) absence of a light reflex (iridial response grade 2) which persists for 72 hours.

Body weights should be obtained prior to euthanizing in extremis. In accordance with the *AVMA Guidelines for the Euthanasia of Animals:* 2013 Edition (the American Veterinary Medical Association, 2013), rabbits could be euthanized by an intramuscular injection of Zoletil 50 (8 mg/kg, 50 mg/mL) and Xylazine Hydrochloride Injection (5 mg/kg, 100 mg/mL) and followed by femoral artery exsanguinations and thoracic opening method.

There were no animals with irreversible symptoms in the study, thus no animals was euthanized. All survival animals were transferred back to the holding colony on Day 18.

For the body weights of all groups at different time point, with software SPSS the means and standard deviations were calculated, and the group difference on each time point were analyzed by the following statistical procedures: A Levene's test was performed to test for variance homogeneity. If the result showed no significance (p>0.05), a one-way analysis of variance (ANOVA) was performed. If ANOVA showed significance (p≤0.05), a Dunnett's test was performed for multiple comparisons. If ANOVA showed no significance (p>0.05), statistical tests ended. In the case of heterogeneity of variance at p≤0.05, a Kruskal-Wallis nonparametric test was performed. If the Kruskal-Wallis nonparametric test showed significance (p≤0.05), a further Mann-Whitney test was performed for multiple comparisons.

The total treatment-related ocular reaction grading scores (cornea, iris, conjunctiva, chemosis and discharge) of each animal's each eye at each examination time point were added, the group average scores (GAS) at each time point were calculated, and eventually eye irritation was classified based on the method described in Table 5.

TABLE 5

Criteria of Eye Irritation Scores

| Score Range | Classification |
|---|---|
| 0-3 | No Irritation |
| 4-8 | Mild Irritation |
| 9-12 | Medium Irritation |
| 13-16 | Severe Irritation |

The treatment-related eye irritation effects of test composition/vehicle were evaluated in conjunction with daily observations, the nature and severity of lesions, and their reversibility or lack of reversibility.

9.2 Results (Clinical Observations)

No mortality and abnormal clinical signs were noted in any animal throughout the study.

9.3 Results (Body Weight)

Figure 6:
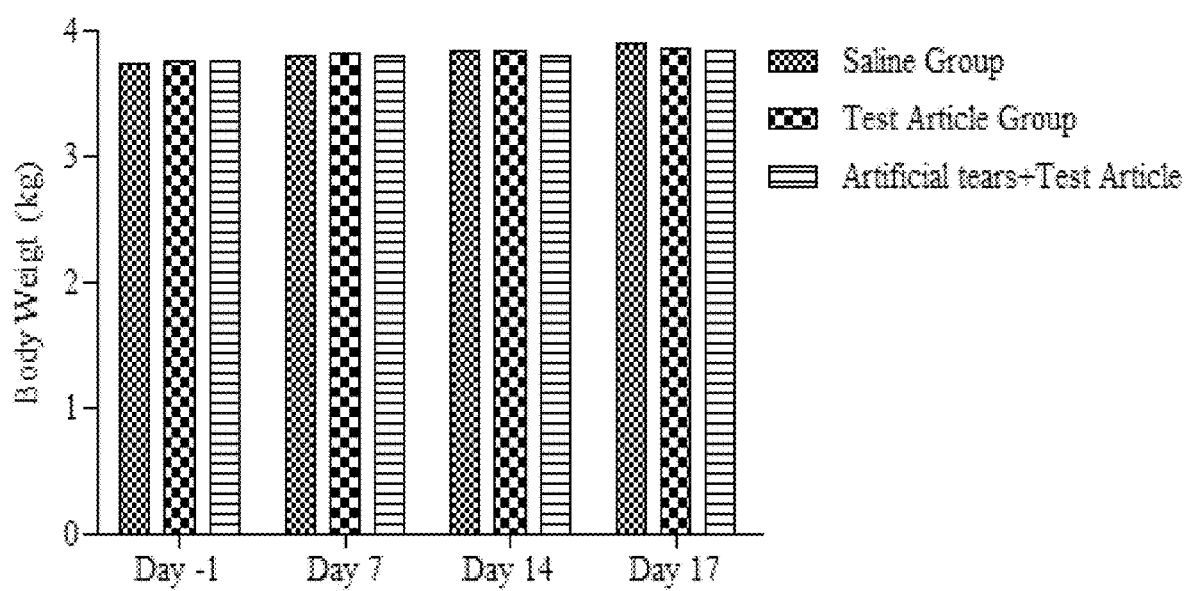
FIG. 6 is a bar histogram showing average body weight of mice in each group.

Body weight are summarized in FIG. 6. No statistically significant difference in body weights was noted between all 3 groups on Days −1, 7, 14, and 17 (p>0.05).

9.4 Results (Ophthalmic Observation-Slit Lamp Examination)

The eye irritation scores in both eyes of all animals from each group were zero throughout the study. According to the Criteria of Eye Irritation Scores, the eye irritation of all animals from each group at each examination time point was classified as no irritation.

9.5 Results (Ophthalmic Observation-Sodium Fluorescein Examination)

Staining score of corneal sodium fluorescein are summarized in Tables 6-12.

During the 14-day dosing period and the non-dosing observation period, some animals in the saline group, test composition group and artificial tear+test composition group were observed with sodium fluorescein staining in the cornea of unilateral or bilateral eyes, and the staining scores were mostly 1, only 1 left eye of test composition group scored 2 on Day 3. And at the end of observation, the corneal fluorescence staining score of all eyes was 0. There were no statistical differences (p>0.05) in the corneal fluorescence staining scores of eyes between the 3 groups except that the left eye scores of saline group is significantly higher than that of test composition group and artificial tears+test composition group on Day 9 (saline group: 1.00±0.00 points, test composition group: 0.25±0.50 points, artificial tears+test composition group, 0.00±0.00; p<0.05). The corneal staining difference between groups mentioned above was lack of time-response relationship, and was considered to be not associated with the use of test composition or the combined-use of artificial tears and test composition.

TABLE 6

Summary of Corneal Sodium Fluorescein Staining Score (Day −1 to Day 2)

| Group | Dosing Treatment | | D −1 | | D 1 | | D 2 | |
|---|---|---|---|---|---|---|---|---|
| | | | OD | OS | OD | OS | OD | OS |
| 1 | Saline | Mean ± SD | 0.00 ± 0.00 | 0.00 ± 0.00 | 0.00 ± 0.00 | 0.25 ± 0.50 | 0.00 ± 0.00 | 0.00 ± 0.00 |
| | | n | 4 | 4 | 4 | 4 | 4 | 4 |
| 2 | Biodecs001 eye drops | Mean ± SD | 0.00 ± 0.00 | 0.00 ± 0.00 | 0.00 ± 0.00 | 0.50 ± 0.58 | 0.00 ± 0.00 | 0.50 ± 0.58 |
| | | n | 4 | 4 | 4 | 4 | 4 | 4 |

TABLE 6-continued

Summary of Corneal Sodium Fluorescein Staining Score (Day −1 to Day 2)

| Group | Dosing Treatment | | D −1 OD | D −1 OS | D 1 OD | D 1 OS | D 2 OD | D 2 OS |
|---|---|---|---|---|---|---|---|---|
| 3 | Artificial tears * + Biodecs001 eye drops | Mean ± SD n | 0.00 ± 0.00 4 | 0.00 ± 0.00 4 | 0.00 ± 0.00 4 | 0.00 ± 0.00 4 | 0.00 ± 0.00 4 | 0.25 ± 0.50 4 |

Note:
"n" means the number of animal eyes.

TABLE 7

Summary of Corneal Sodium Fluorescein Staining Score (Day 3 to Day 5)

| Group | Dosing Treatment | | D 3 OD | D 3 OS | D 4 OD | D 4 OS | D 5 OD | D 5 OS |
|---|---|---|---|---|---|---|---|---|
| 1 | Saline | Mean ± SD n | 0.50 ± 0.58 4 | 0.75 ± 0.50 4 | 0.00 ± 0.00 4 | 0.00 ± 0.00 4 | 0.00 ± 0.00 4 | 0.00 ± 0.00 4 |
| 2 | Biodecs001 eye drops | Mean ± SD n | 0.00 ± 0.00 4 | 1.00 ± 0.82 4 | 0.00 ± 0.00 4 | 0.00 ± 0.00 4 | 0.00 ± 0.00 4 | 0.25 ± 0.50 4 |
| 3 | Artificial tears * + Biodecs001 eye drops | Mean ± SD n | 0.25 ± 0.50 4 | 0.00 ± 0.00 4 | 0.25 ± 0.50 4 | 0.00 ± 0.00 4 | 0.00 ± 0.00 4 | 0.00 ± 0.00 4 |

Note:
"n" means the number of animal eyes.

TABLE 8

Summary of Corneal Sodium Fluorescein Staining Score (Day 6 to Day 8)

| Group | Dosing Treatment | | D 6 OD | D 6 OS | D 7 OD | D 7 OS | D 8 OD | D 8 OS |
|---|---|---|---|---|---|---|---|---|
| 1 | Saline | Mean ± SD n | 0.00 ± 0.00 4 | 0.00 ± 0.00 4 | 0.75 ± 0.50 4 | 0.50 ± 0.58 4 | 0.00 ± 0.00 4 | 0.00 ± 0.00 4 |
| 2 | Biodecs001 eye drops | Mean ± SD n | 0.00 ± 0.00 4 | 0.00 ± 0.00 4 | 0.25 ± 0.50 4 | 0.00 ± 0.00 4 | 0.00 ± 0.00 4 | 0.00 ± 0.00 4 |
| 3 | Artificial tears * + Biodecs001 eye drops | Mean ± SD n | 0.00 ± 0.00 4 | 0.00 ± 0.00 4 | 1.00 ± 0.00 4 | 0.50 ± 0.58 4 | 0.00 ± 0.00 4 | 0.00 ± 0.00 4 |

Note:
"n" means the number of animal eyes.

TABLE 9

Summary of Corneal Sodium Fluorescein Staining Score (Day 9 to Day 11)

| Group | Dosing Treatment | | D 9 OD | D 9 OS | D 10 OD | D 10 OS | D 11 OD | D 11 OS |
|---|---|---|---|---|---|---|---|---|
| 1 | Saline | Mean ± SD n | 0.50 ± 0.58 4 | 1.00 ± 0.00 4 | 0.00 ± 0.00 4 | 0.50 ± 0.58 4 | 0.00 ± 0.00 4 | 0.75 ± 0.50 4 |
| 2 | Biodecs001 eye drops | Mean ± SD n | 0.00 ± 0.00 4 | 0.25 ± 0.50* 4 | 0.25 ± 0.50 4 | 0.25 ± 0.50 4 | 0.25 ± 0.50 4 | 0.25 ± 0.50 4 |
| 3 | Artificial tears * + Biodecs001 eye drops | Mean ± SD n | 0.00 ± 0.00 4 | 0.00 ± 0.00* 4 | 0.00 ± 0.00 4 | 0.25 ± 0.50 4 | 0.00 ± 0.00 4 | 0.00 ± 0.00 4 |

Note:
"n" means the number of animal eyes.

TABLE 10

Summary of Corneal Sodium Fluorescein Staining Score (Day 12 to Day 14)

| Group | Dosing Treatment | | D 12 OD | D 12 OS | D 13 OD | D 13 OS | D 14-before dosing OD | D 14-before dosing OS |
|---|---|---|---|---|---|---|---|---|
| 1 | Saline | Mean ± SD | 0.25 ± 0.50 | 0.75 ± 0.50 | 0.25 ± 0.50 | 0.50 ± 0.58 | 0.00 ± 0.00 | 0.50 ± 0.58 |
|  |  | n | 4 | 4 | 4 | 4 | 4 | 4 |
| 2 | Biodecs001 eye drops | Mean ± SD | 0.00 ± 0.00 | 0.25 ± 0.50 | 0.00 ± 0.00 | 0.50 ± 0.58 | 0.50 ± 0.58 | 0.00 ± 0.00 |
|  |  | n | 4 | 4 | 4 | 4 | 4 | 4 |
| 3 | Artificial tears * + Biodecs001 eye drops | Mean ± SD | 0.00 ± 0.00 | 0.25 ± 0.50 | 0.00 ± 0.00 | 0.25 ± 0.50 | 0.00 ± 0.00 | 0.25 ± 0.50 |
|  |  | n | 4 | 4 | 4 | 4 | 4 | 4 |

Note:
"n" means the number of animal eyes.

TABLE 11

Summary of Corneal Sodium Fluorescein Staining Score (Day 14)

| Group | Dosing Treatment | | D 14-1 hours after dosing OD | D 14-1 hours after dosing OS | D 14-2 hours after dosing OD | D 14-2 hours after dosing OS | D 14-4 hours after dosing OD | D 14-4 hours after dosing OS |
|---|---|---|---|---|---|---|---|---|
| 1 | Saline | Mean ± SD | 0.00 ± 0.00 | 0.00 ± 0.00 | 0.00 ± 0.00 | 0.50 ± 0.58 | 0.00 ± 0.00 | 0.25 ± 0.50 |
|  |  | n | 4 | 4 | 4 | 4 | 4 | 4 |
| 2 | Biodecs001 eye drops | Mean ± SD | 0.00 ± 0.00 | 0.00 ± 0.00 | 0.25 ± 0.50 | 0.00 ± 0.00 | 0.00 ± 0.00 | 0.25 ± 0.50 |
|  |  | n | 4 | 4 | 4 | 4 | 4 | 4 |
| 3 | Artificial tears * + Biodecs001 eye drops | Mean ± SD | 0.00 ± 0.00 | 0.25 ± 0.50 | 0.00 ± 0.00 | 0.25 ± 0.50 | 0.00 ± 0.00 | 0.00 ± 0.00 |
|  |  | n | 4 | 4 | 4 | 4 | 4 | 4 |

Note:
"n" means the number of animal eyes.

TABLE 12

Summary of Corneal Sodium Fluorescein Staining Score (Day 15 to Day 17)

| Group | Dosing Treatment | | D 15 OD | D 15 OS | D 16 OD | D 16 OS | D 17 OD | D 17 0 |
|---|---|---|---|---|---|---|---|---|
| 1 | Saline | Mean ± SD | 0.00 ± 0.00 | 0.25 ± 0.50 | 0.25 ± 0.50 | 0.00 ± 0.00 | 0.00 ± 0.00 | 0.00 ± 0.00 |
|  |  | n | 4 | 4 | 4 | 4 | 4 | 4 |
| 2 | Biodecs001 eye drops | Mean ± SD | 0.00 ± 0.00 | 0.00 ± 0.00 | 0.00 ± 0.00 | 0.00 ± 0.00 | 0.00 ± 0.00 | 0.00 ± 0.00 |
|  |  | n | 4 | 4 | 4 | 4 | 4 | 4 |
| 3 | Artificial tears * + Biodecs001 eye drops | Mean ± SD | 0.00 ± 0.00 | 0.00 ± 0.00 | 0.00 ± 0.00 | 0.00 ± 0.00 | 0.00 ± 0.00 | 0.00 ± 0.00 |
|  |  | n | 4 | 4 | 4 | 4 | 4 | 4 |

Note:
"n" means the number of animal eyes.

9.6 Conclusion

No mortality and abnormal clinical signs were noted in any animals throughout the study. No statistically significant difference in body weights was noted between all 3 groups on Days −1, 7, 14, and 17.

The eye irritation scores in both eyes of all animals from each group were zero throughout the study. According to the Criteria of Eye Irritation Scores, the eye irritation of all animals from each group at each examination time point was classified as no irritation. Sodium fluorescein staining in the cornea of unilateral or bilateral eyes was observed in some animals from all 3 groups during the study, The staining scores were mostly 1 and without time-response relationship, thus the corneal staining signs were considered to be not associated with the use of Biodecs001 eye drops or the combined-use of artificial tears and Biodecs001 eye drops.

Under the conditions of this study, Biodecs001 topically administered once daily to New Zealand White Rabbits for 14 consecutive days, either alone or after the instillation of artificial tears, did not cause eye irritation.

Example 10: Metabolite Analysis of Coconut Oil Samples 10.1 Sample Preparation, Instrumental Parameters and Data Analysis A total of 20 coconut oil samples (divided into two groups: unprocessed coconut oil group and the deacidified coconut oil group) were tested by LC-MS with positive and negative ion modes, and compared between groups according to the test data. The analysis is designed primarily to analyze small, polar metabolites such as amino acids, nucleic acids, sugars and small organic acids that are typically part of primary metabolism.

The samples (100 µL) were transferred into a 1.5 mL centrifuge tube, then 300 µL methanol and 10 µL dichlorophenylalanine (2.8 mg/mL) were added to the tube. Next, the tube was vortexed for 30 seconds and incubated at −20° C. for 1 hour. Next, the tube was centrifuged at 12,000 RPM (4° C.) for 15 minutes. After the centrifugation, 200 µL supernatant was transferred to a vial for inspection.

LC-MS instrument platform (Thermo, Ultimate 3000LC, Q Exactive) and chromatographic column Hyper gold C18 (100×2.1 mm 1.9 µm) were used in chromatographic separation under conditions of the follows: column temperature: 40° C.; flow rate: 0.35 mL/min; mobile phase A: water+5% acetonitrile+0.1% formic acid; mobile phase B: acetonitrile+0.1% formic acid; injection volume: 10 µL; Automatic injector temperature: 4° C. Mobile phase gradient elution procedure is shown in Table 13.

TABLE 13

Mobile phase gradient elution procedure

| Time (min) | Flow rate (mL/min) | A (%) | B (%) |
|---|---|---|---|
| 0 | 0.3 | 100 | 0 |
| 0 | 0.3 | 100 | 0 |
| 1.5 | 0.3 | 80 | 20 |
| 9.5 | 0.3 | 0 | 100 |
| 14.5 | 0.3 | 0 | 100 |
| 14.6 | 0.3 | 100 | 0 |
| 18 | 0.3 | 100 | 0 |

Mass spectrometry analysis was performed using the following parameters:

ESI+: Heater Temp 300° C.; Sheath Gas Flow rate, 45arb; Aux Gas Flow Rate, 15 arb; Sweep Gas Flow Rate, 1arb; spray voltage, 3.0 KV; Capillary Temp, 350° C.; S-Lens RF Level, 30%. ESI−: Heater Temp 300° C., Sheath Gas Flow rate, 45arb; Aux Gas Flow Rate, 15arb; Sweep Gas Flow Rate, 1arb; spray voltage, 3.2 KV; Capillary Temp, 350° C.; S-Lens RF Level, 60%. Scan mode: Full Scan (m/z 70~1050) and data-dependent second-order mass spectrometry scanning (dd-ms2, TopN=10); Resolution: 70,000 (MS1) & 17,500 (MS2). Collision mode: high energy collision dissociation (HCD).

The data was analyzed by performing feature extraction and preprocessed with compound discoverer software (Thermo), and then normalized and edited into two-dimensional data matrix by excel 2010 software, including molecular weight, retention time (RT) and peak intensity. The data after editing were performed Multivariate Analysis (MVA) using SIMCA-P software (Umetrics AB, Umea, Sweden).

10.2 Chromatogram

Figure 7:
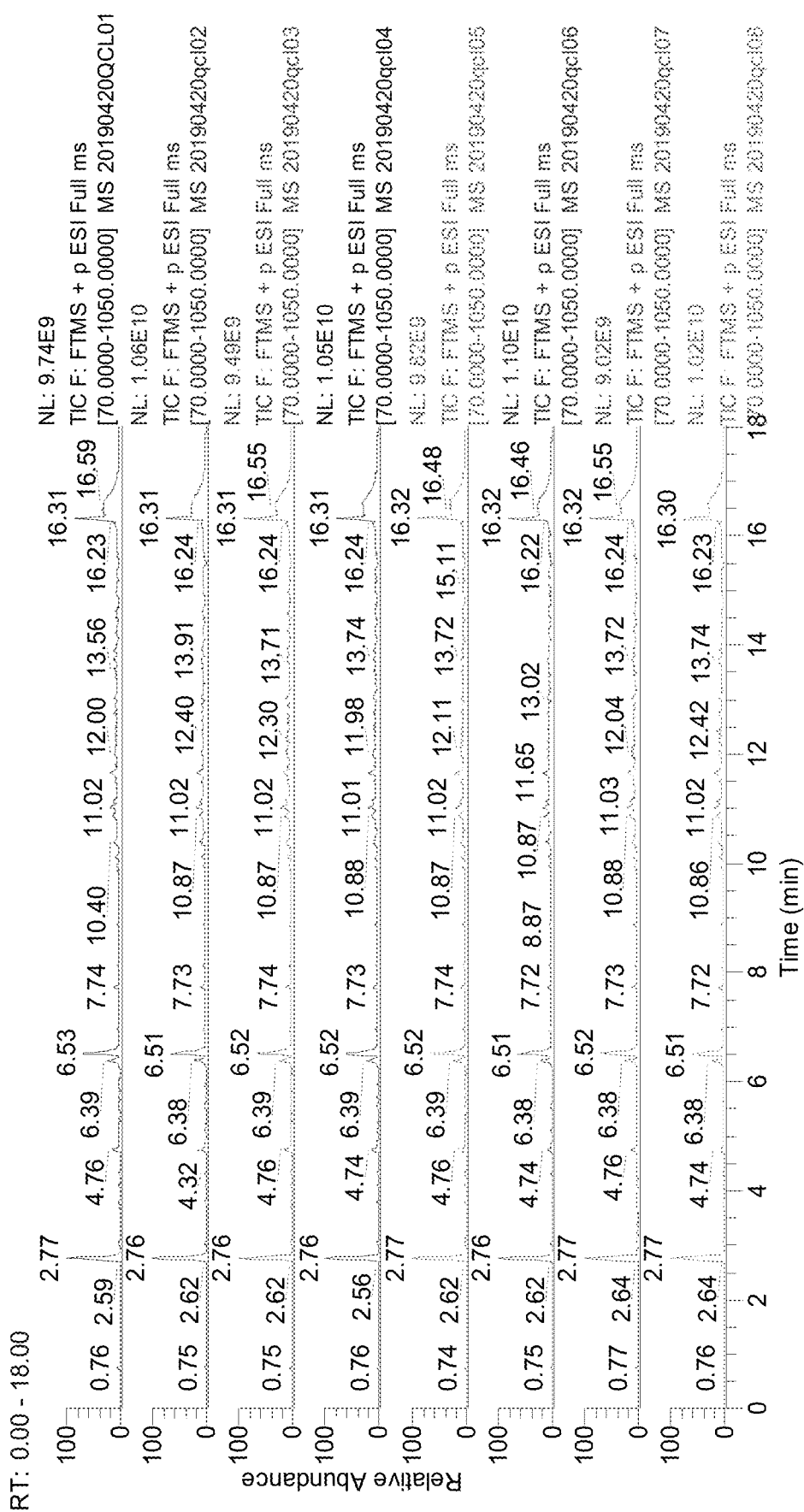
FIG. 7 shows the total ion chromatogram of QC (ESL+).
Figure 8:
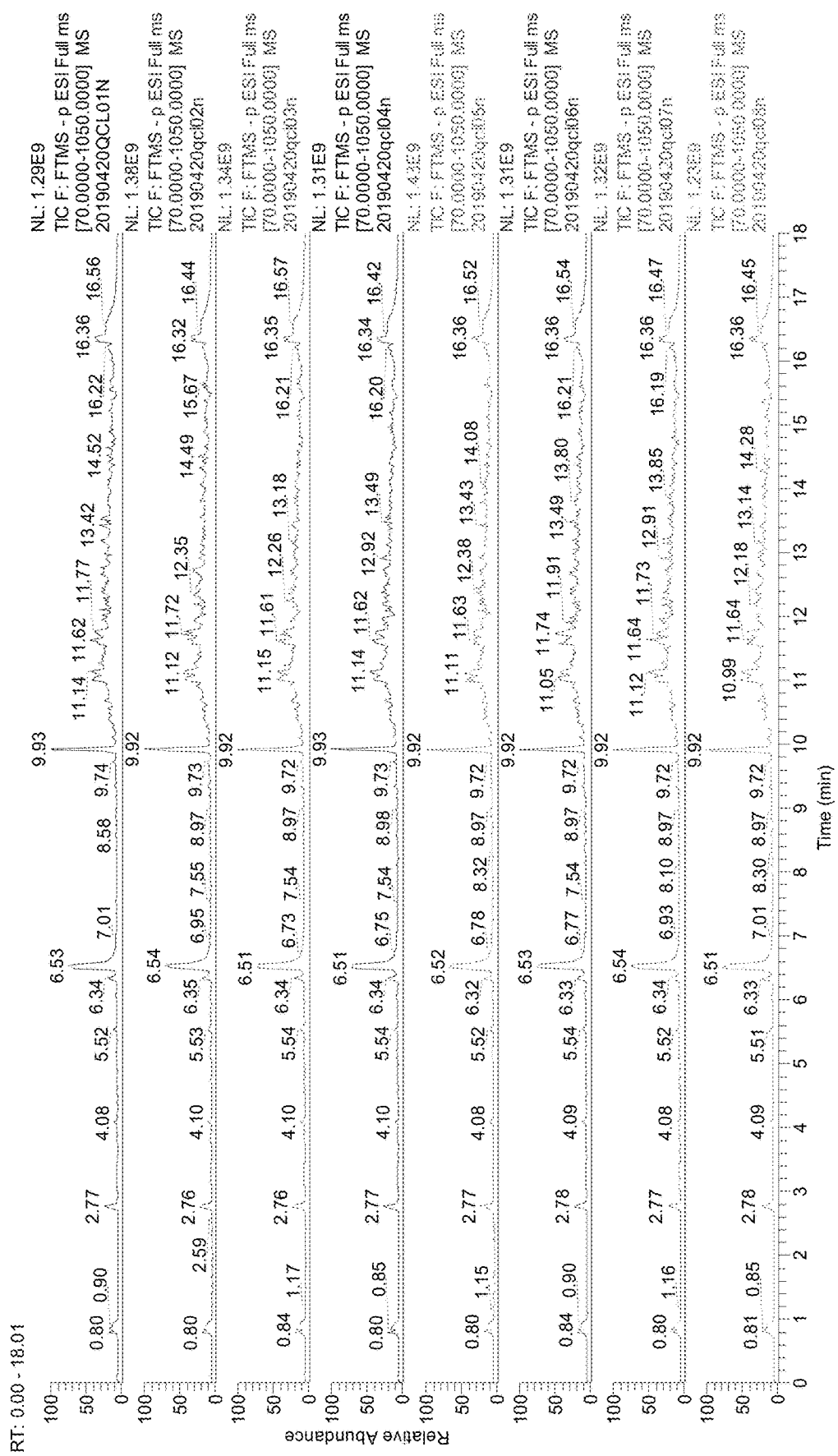
FIG. 8 shows the total ion chromatogram of QC (ESL-).
Figure 9:
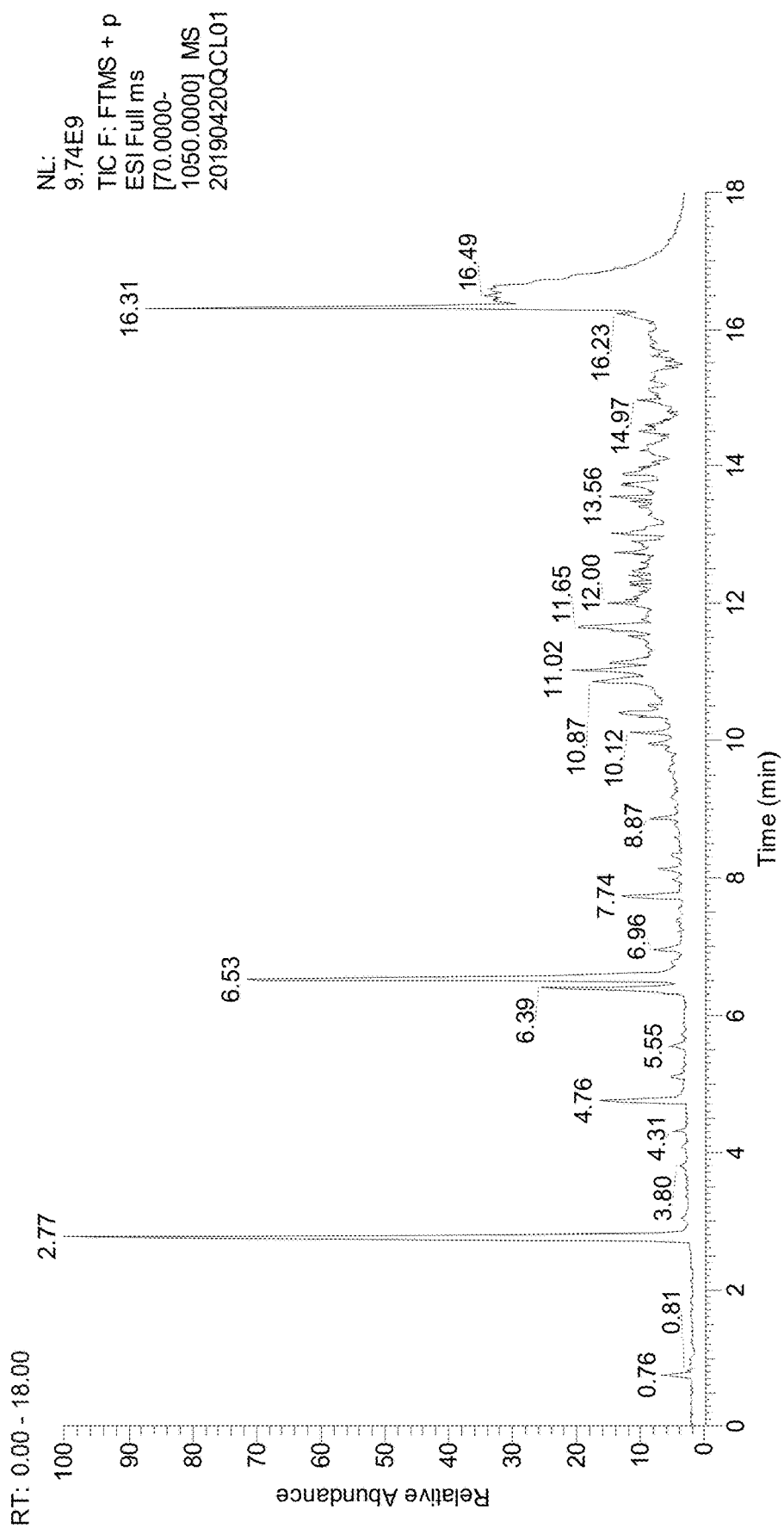
FIG. 9 shows an exemplary total ion chromatogram of a sample of the QC group (ECL+).
Figure 10:
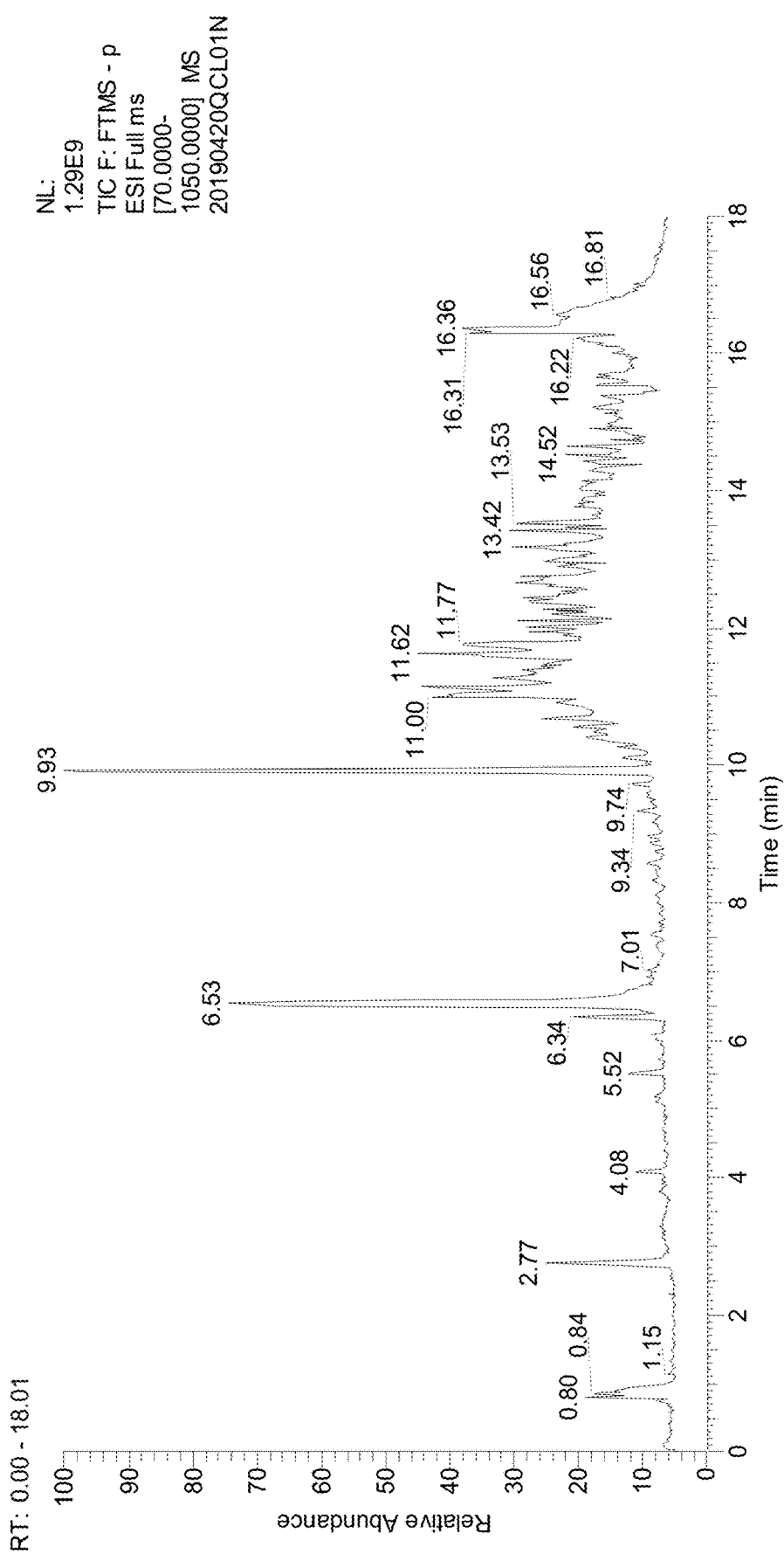
FIG. 10 shows an exemplary total ion chromatogram of a sample of the QC group (ECL-).
Figure 11:
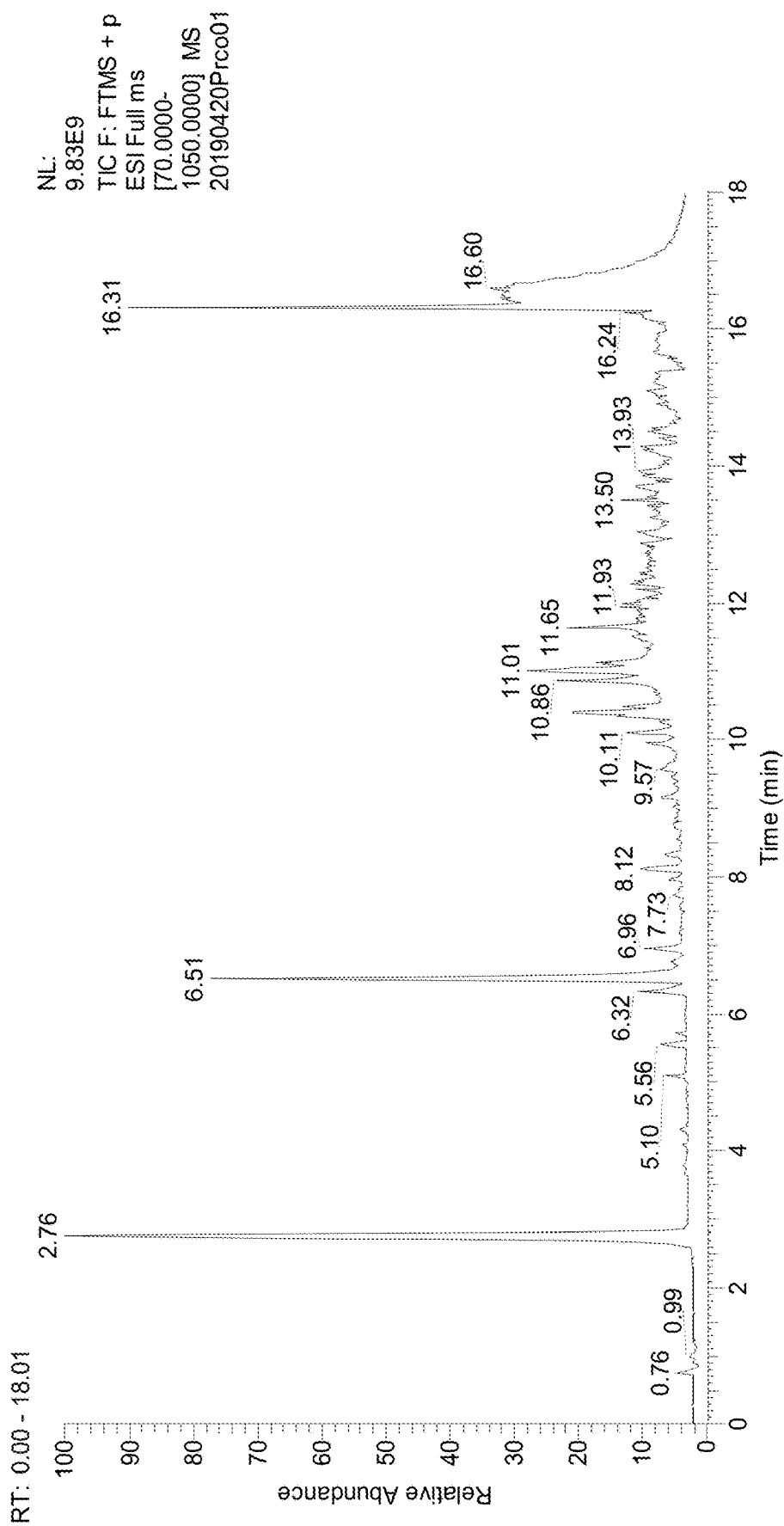
FIG. 11 shows an exemplary total ion chromatogram of a sample of the deacidified coconut oil (Prco) group (ECL+).
Figure 12:
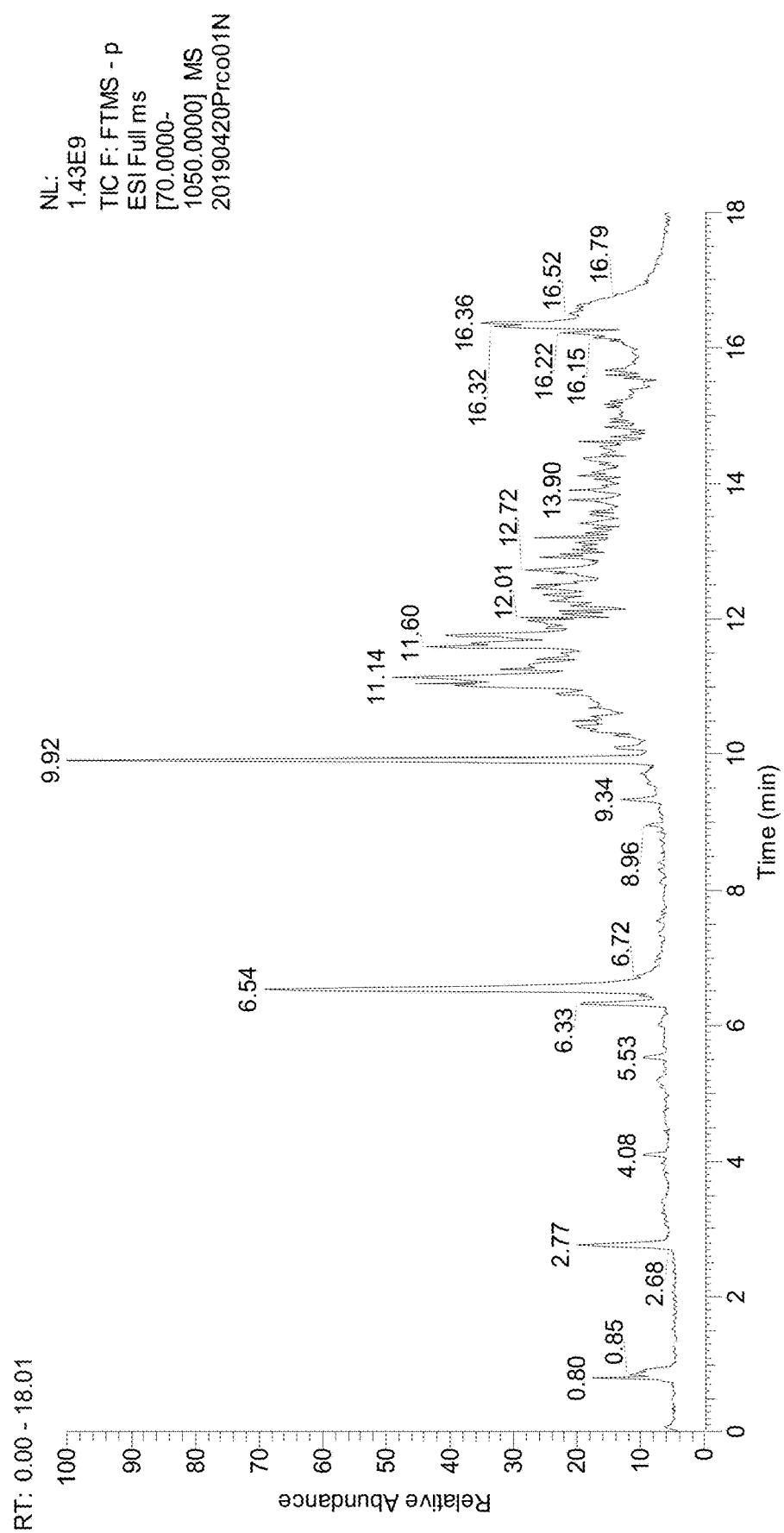
FIG. 12 shows an exemplary total ion chromatogram of a sample of the deacidified coconut oil group (ECL-).
Figure 13:
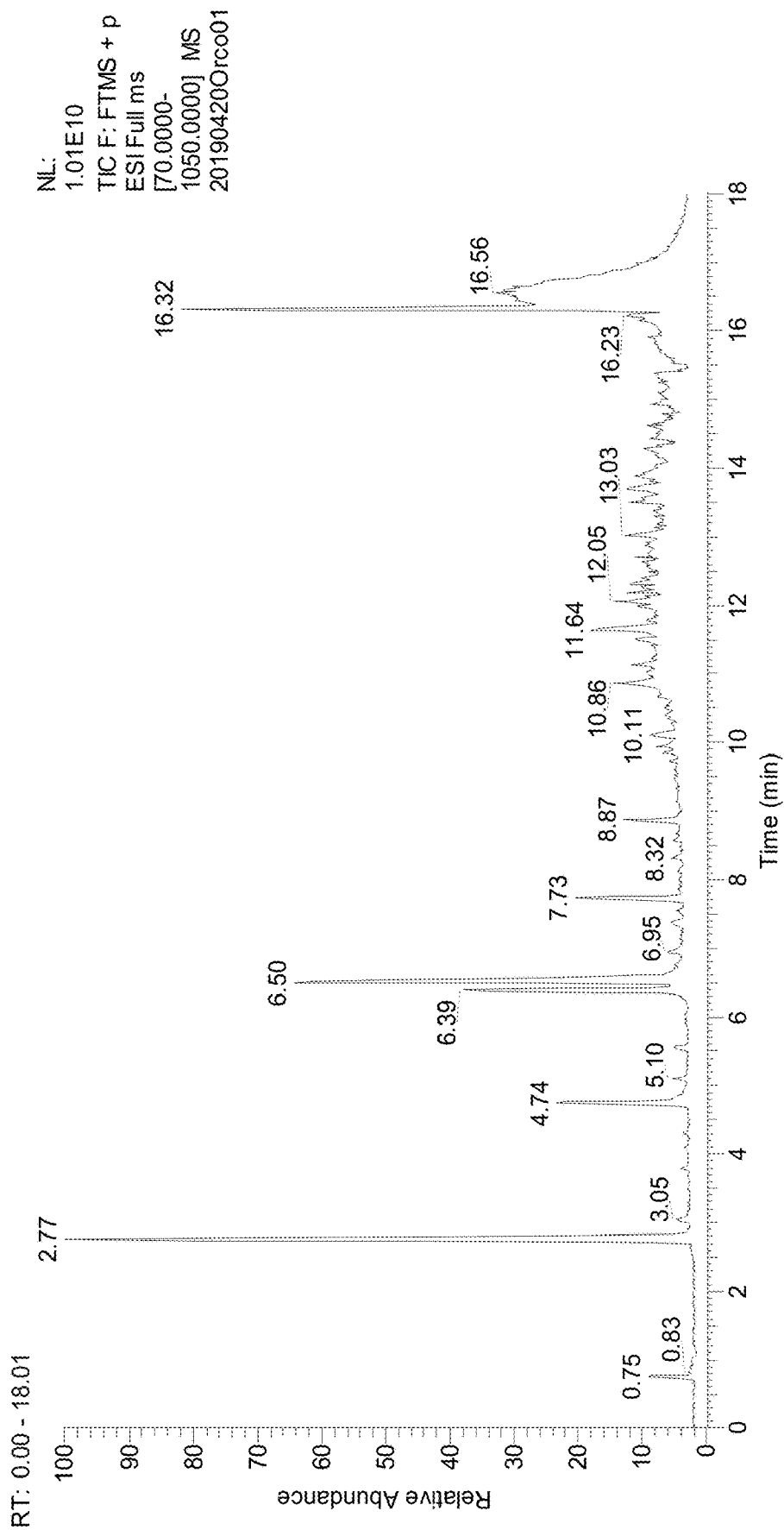
FIG. 13 shows an exemplary total ion chromatogram of a sample of the original coconut oil (Orco) group (ECL+).
Figure 14:
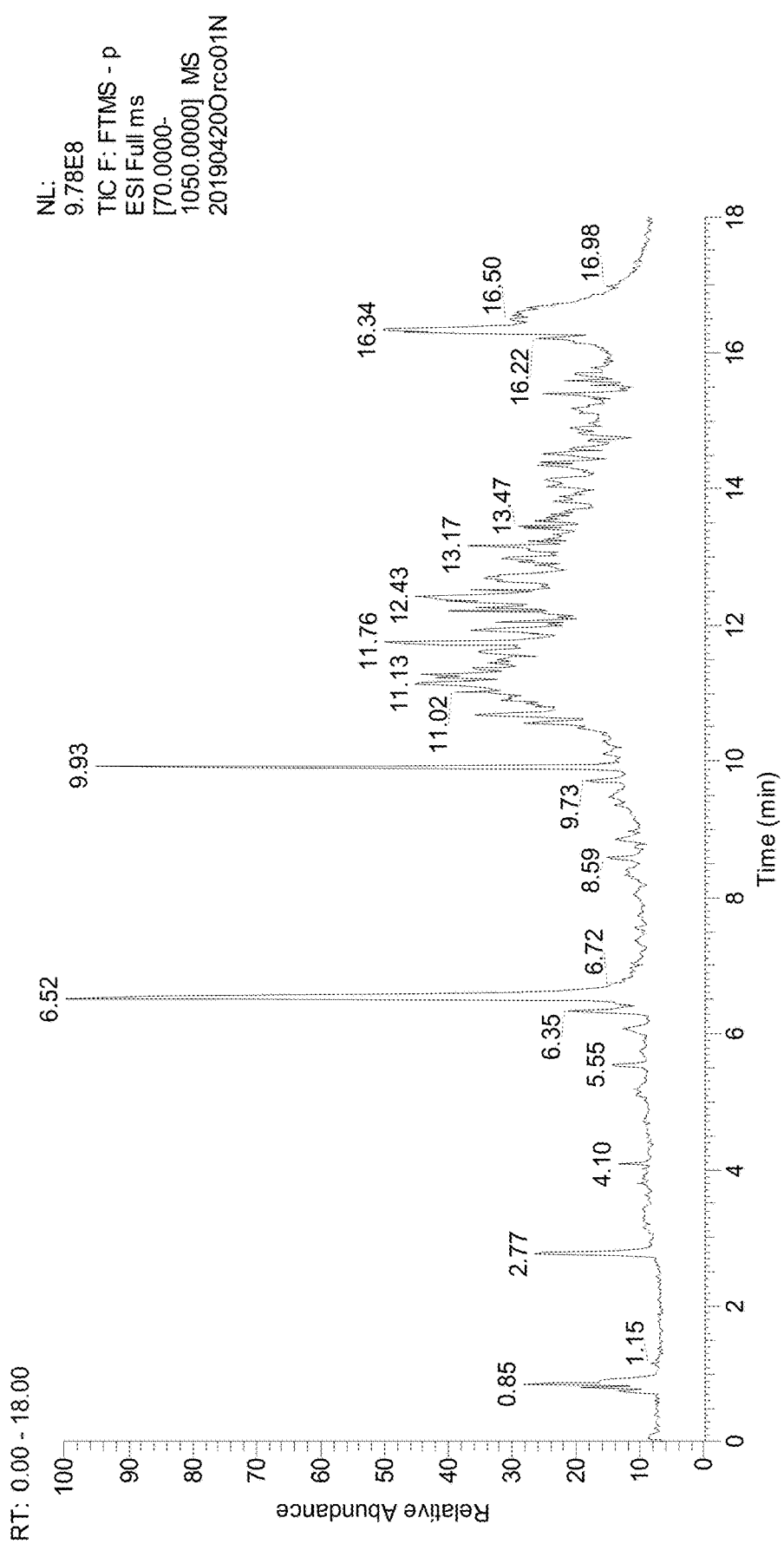
FIG. 14 shows an exemplary total ion chromatogram of a sample of the original coconut oil group (ECL-).

The total ion chromatogram (TIC) of QC samples was overlapped, as shown in FIGS. 7-8, which showed that the retention time reproducibility of the instrument was good and the instrument was stable, so the results of instrument analysis and data had high reliability. A sample of TIC (FIGS. 9-14) for each group of samples is listed separately.

QC sample is the mixture of different and equal samples after sample extraction. The QC sample was injected after a certain number of sample detections. The stability of the instrument can be investigated through the overlapping of the QC chromatogram. (ESI+) represents the positive ion detection mode, that is, in the detection process, the mass analyzer only scans the positive ion and filters out the negative ion, so as to obtain the information of positive ion; (ESI−) represents the mode of negative ion detection, that is, during the detection process, the mass analyzer only scans negative charge ions and filters out positive charge ions, so as to obtain information of negative charge ions.

10.3 PCA Analysis of all Samples

Principal component analysis was carried out on the sample reflecting the overall differences between groups of samples and the size of the group in the degree of variation between samples. Before using SMICA-P software to perform the analysis, the data set was normalized in order to obtain more intuitive and reliable results. The purpose of normalization is to make the variable scale (a digital features, such as mean and standard deviation) on the same level. This prevents the signals of certain ingredients that are too high or too low from masking other differences.

Figure 15:
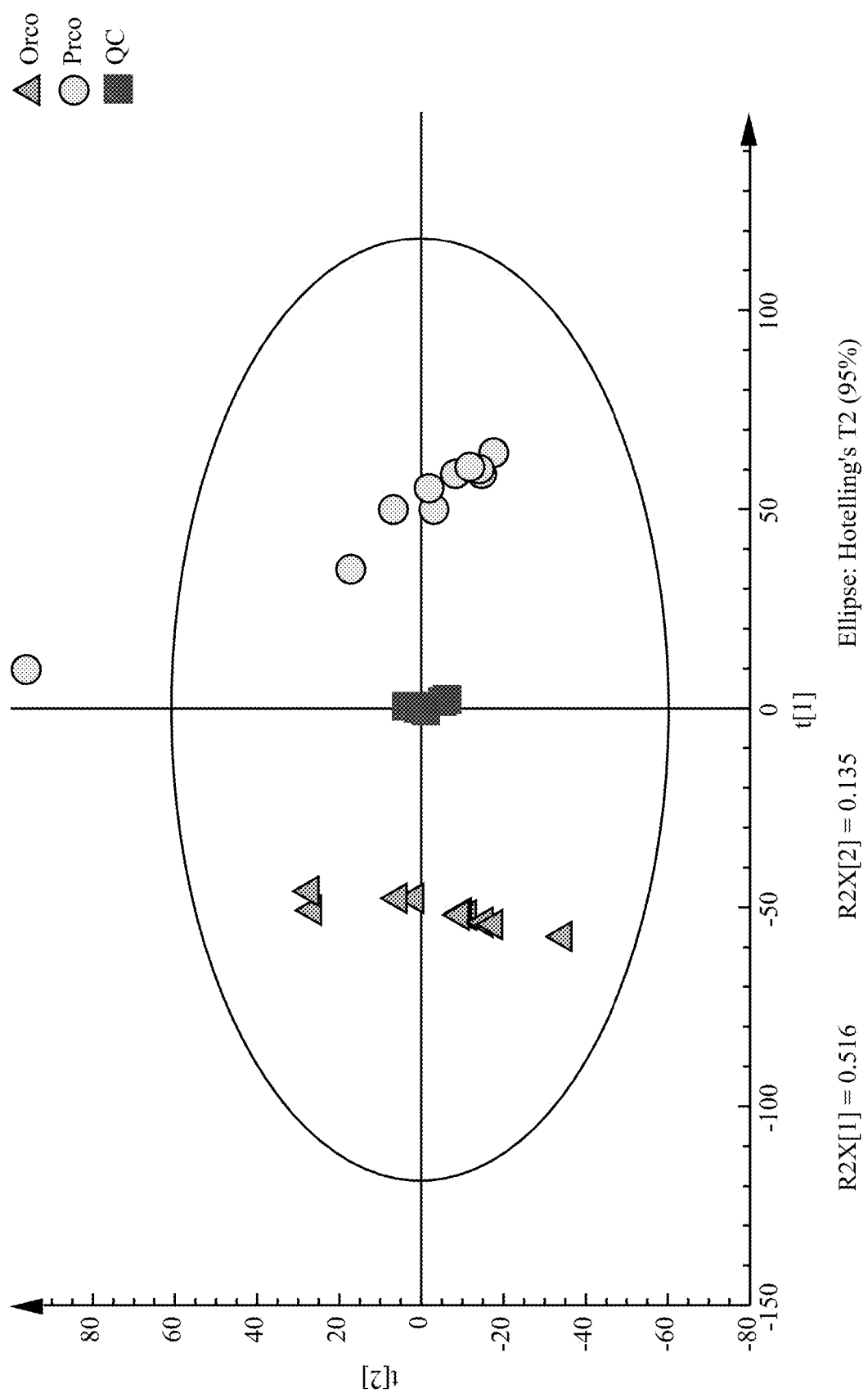
FIG. 15 shows the PCA scores plot of all samples (ESI+).
Figure 16:
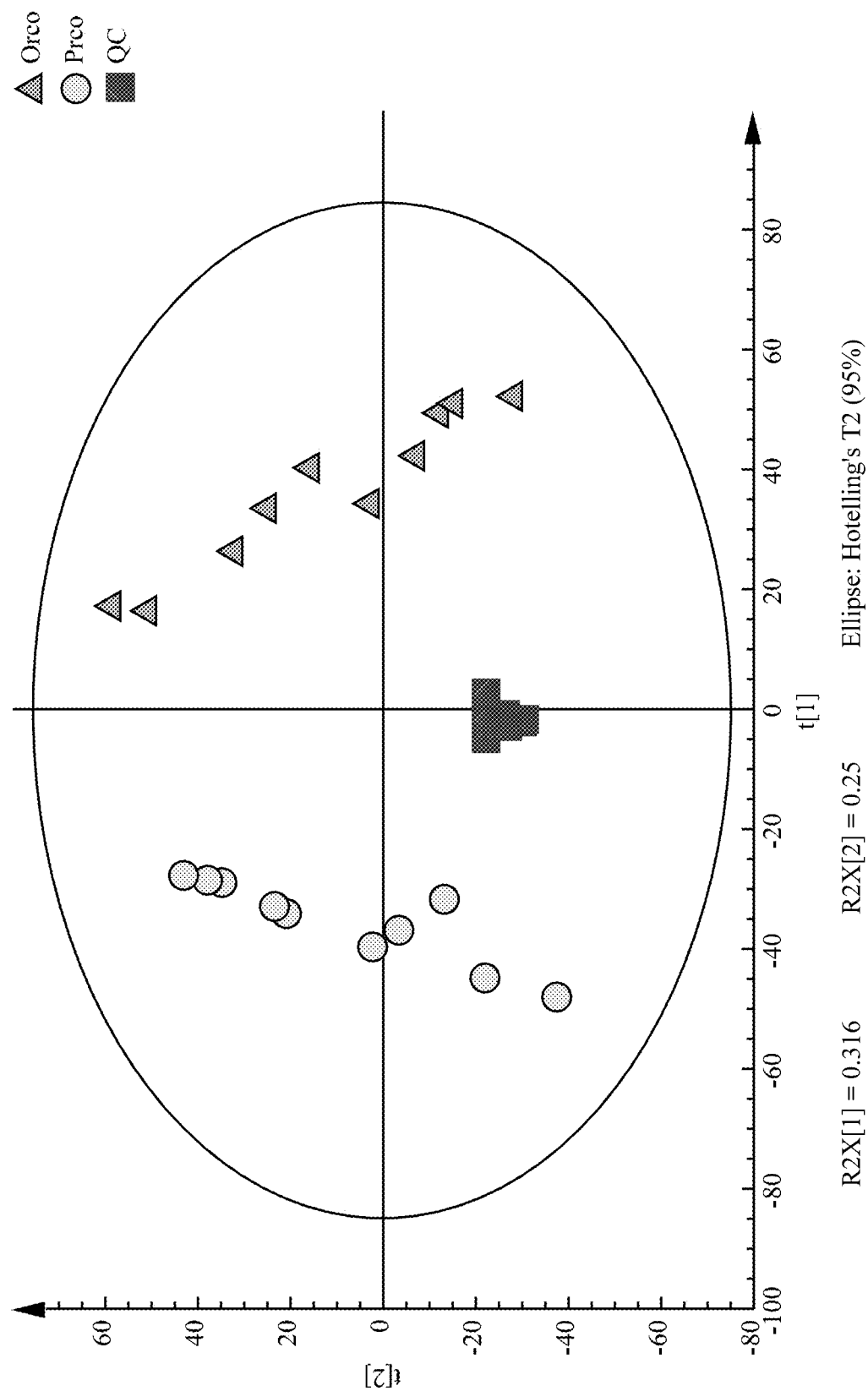
FIG. 16 shows the PCA scores plot of all samples (ESI-).

In order to distinguish whether there were differences between the two groups, the PCA modeling method was used to analyze the samples. In this analysis, a total of 3 principal components were obtained in the positive mode, with cumulative $R^2X=0.715$ and $Q^2=0.605$. In the negative mode, a total of 2 principal components were obtained, with cumulative $R^2X=0.565$ and $Q^2=0.467$. PCA Scores plot under ESL+ and ESL−modes are shown in FIG. 15 and FIG. 16, respectively.

Figure 17:
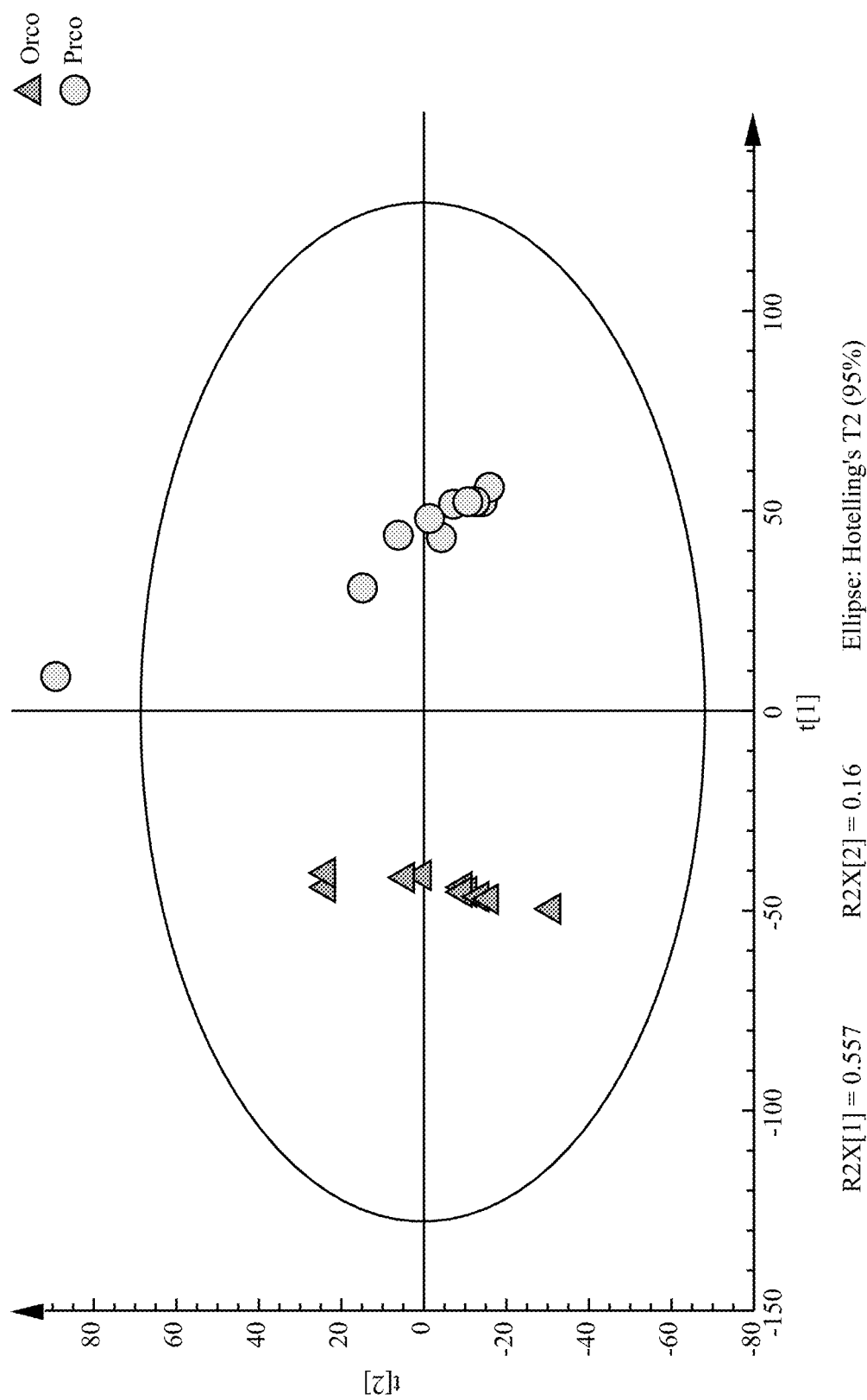
FIG. 17 shows the PCA scores plot of both the Prco and Orco groups (ESI+).
Figure 18:
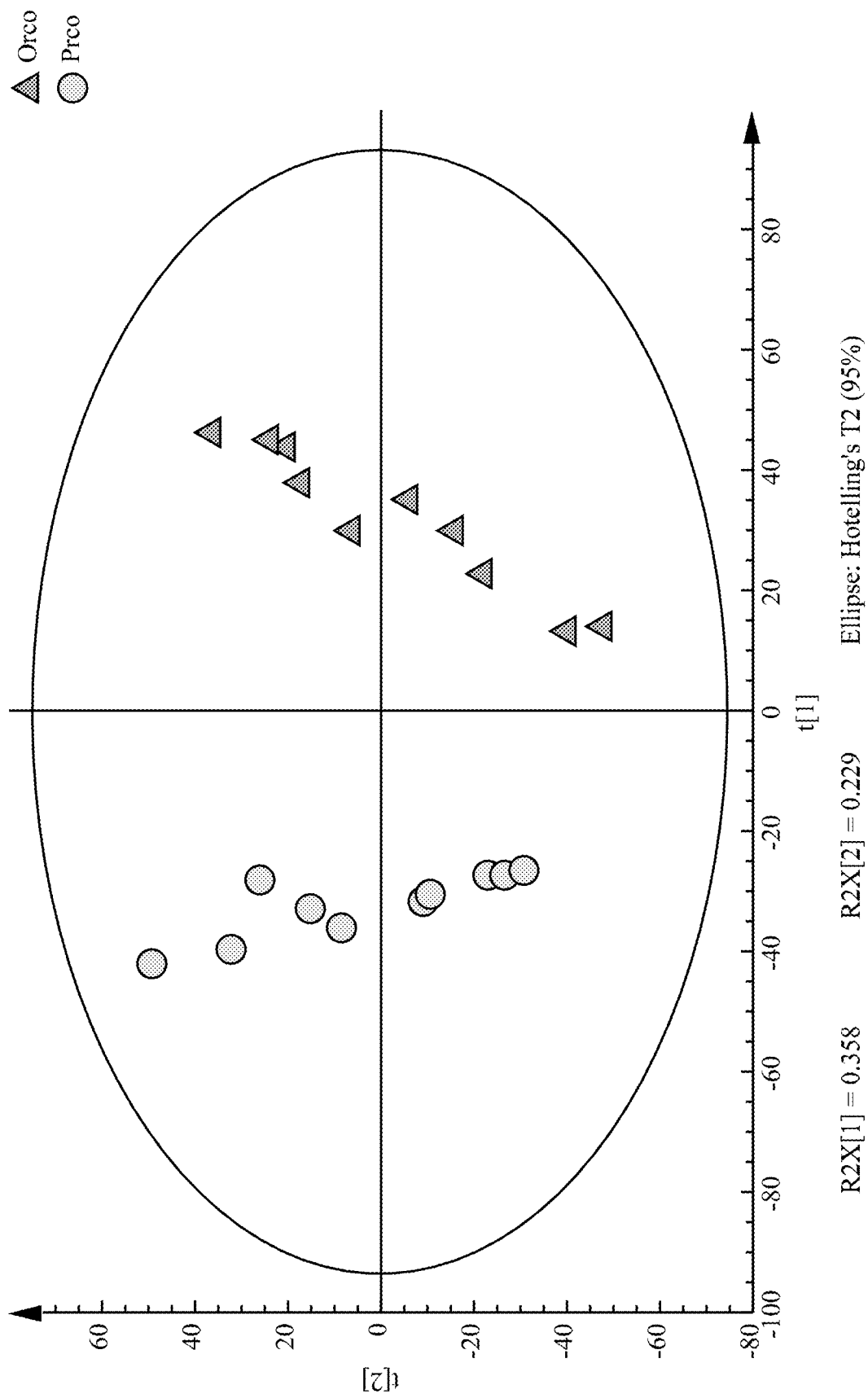
FIG. 18 shows the PCA scores plot of both the Prco and Orco groups (ESI-).
Figure 19A:
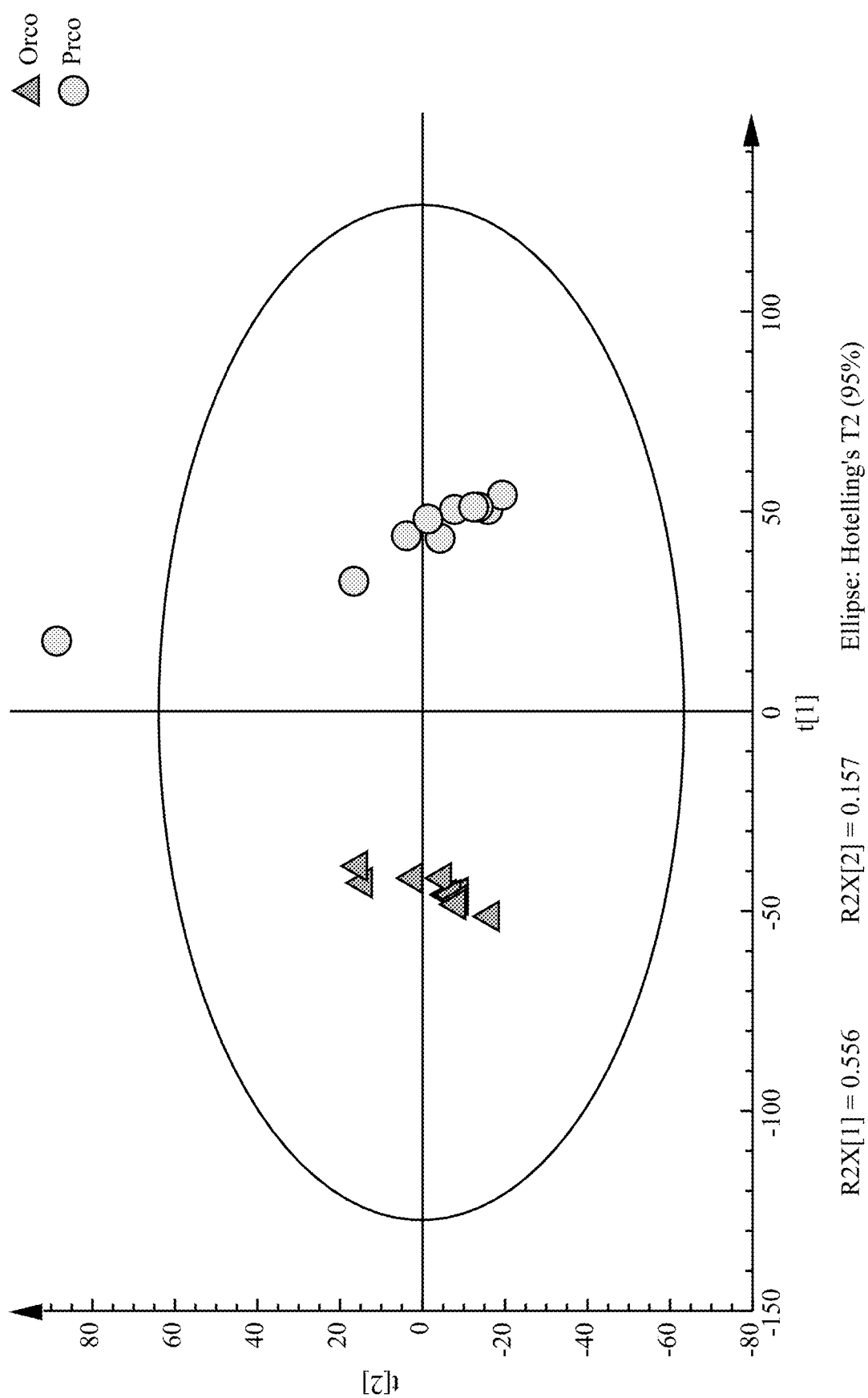
FIG. 19A shows the PLS-DA scores plot of both the Prco and Orco group (ESI+).
Figure 19B:
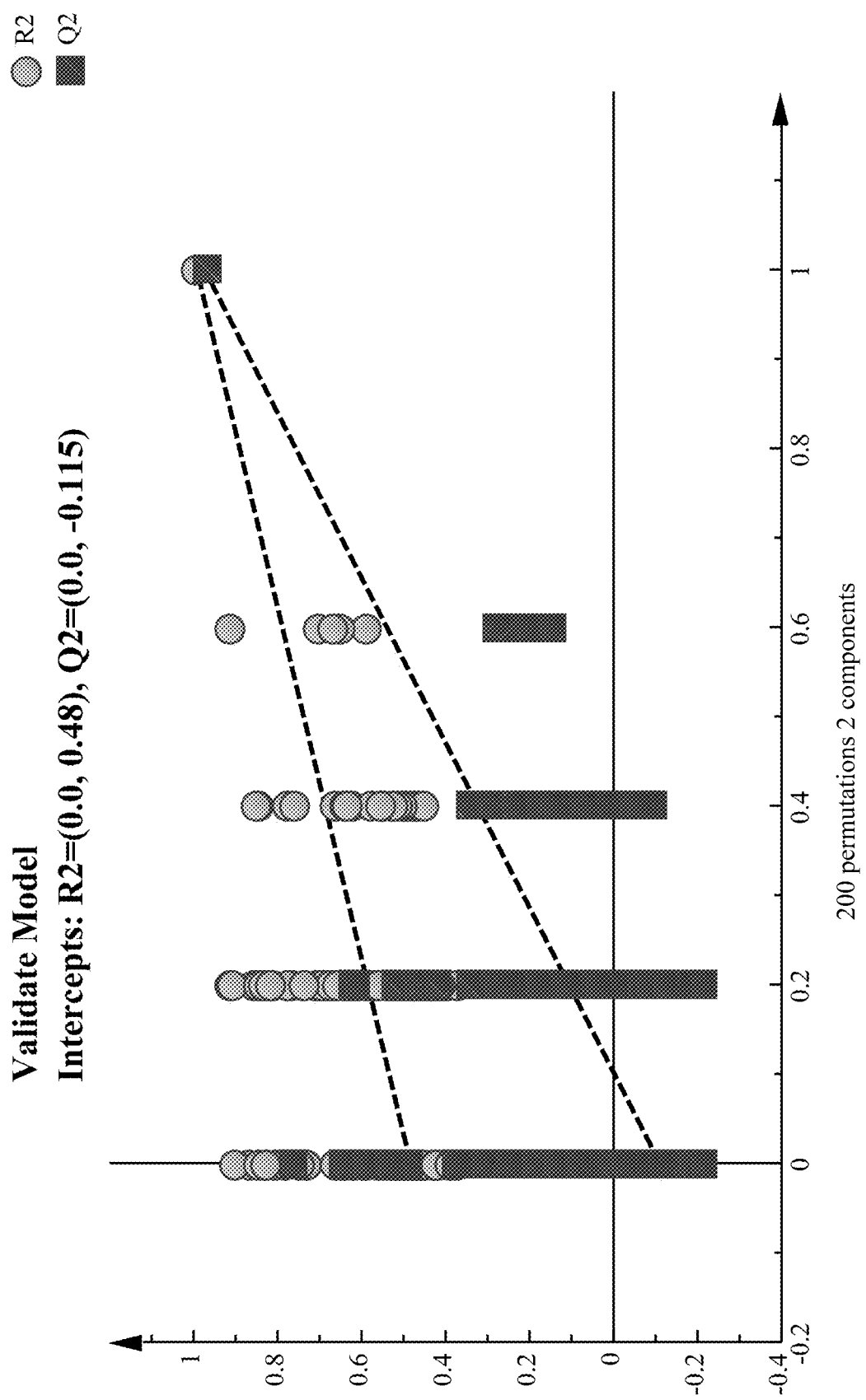
FIG. 19B shows the fitted model and calculated parameters of both the Prco and Orco group (ESI+).
Figure 20A:
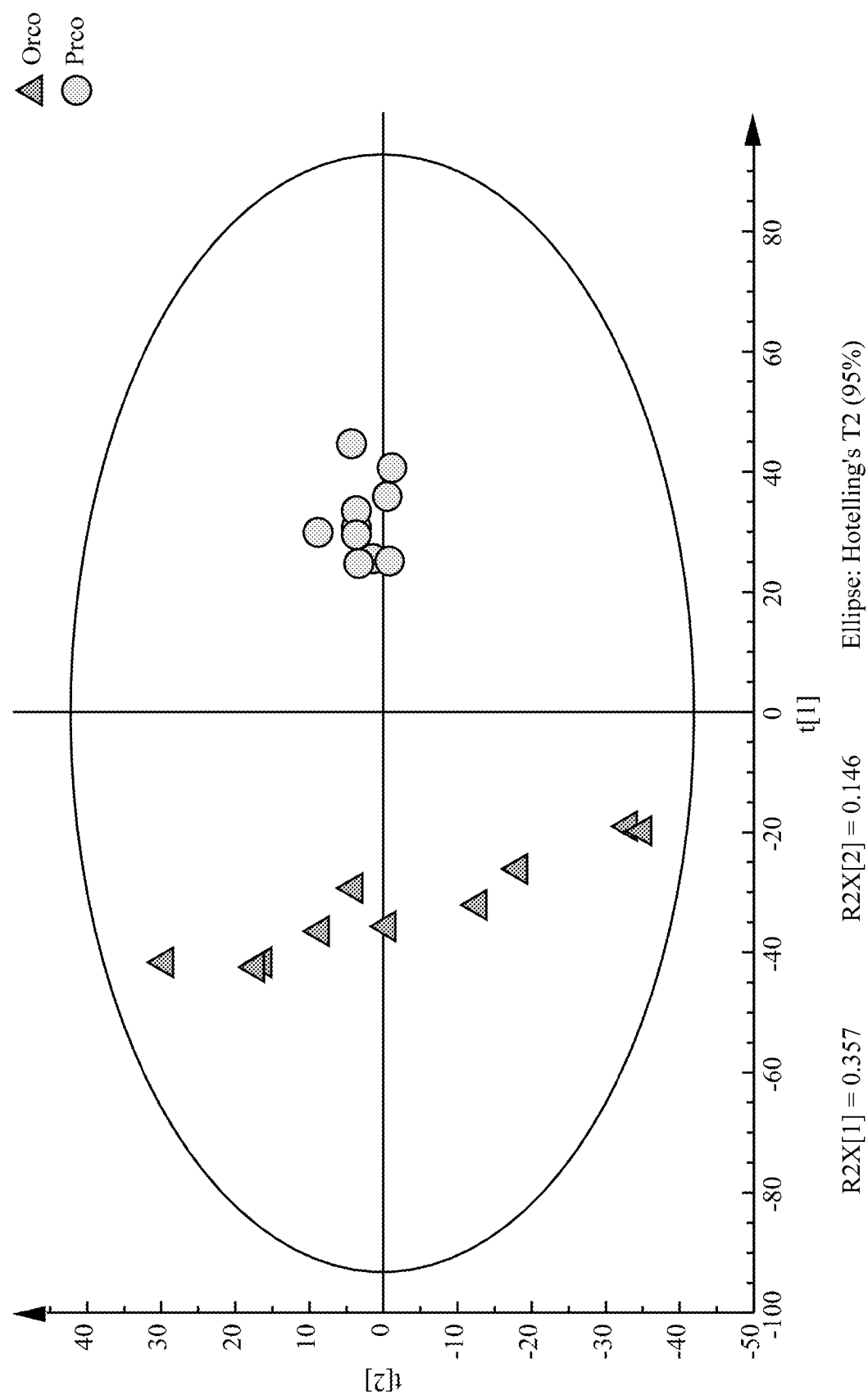
FIG. 20A shows the PLS-DA scores plot of both the Prco and Orco group (ESI−).
Figure 20B:
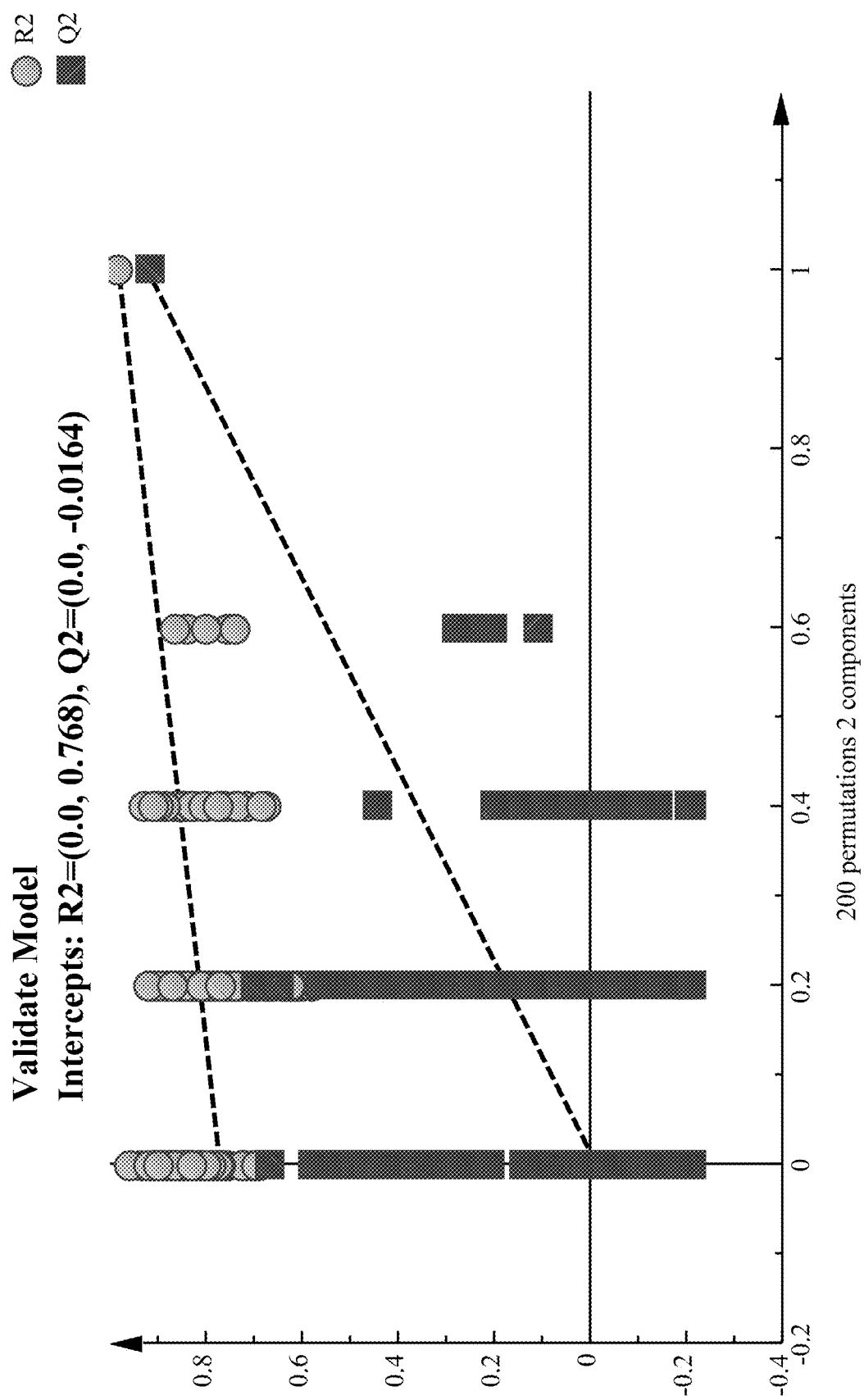
FIG. 20B shows the fitted model and calculated parameters of both the Prco and Orco group (ESI−).

Principal component analysis was conducted on the Prco group (the deacidified coconut oil group) and the Orco group (the original coconut oil group). In this analysis, a total of 2 principal components were obtained in the positive model, with cumulative $R^2X=0.718$ and $Q^2=0.605$. In the negative mode, a total of 2 principal components were obtained, with cumulative $R^2X=0.587$ and $Q^2=0.461$. PCA Scores plot under ESL+ and ESL− modes are shown in FIG. 17 and FIG. 18, respectively.

10.4 PLS-DA Analysis

In order to obtain the ingredient information leading to this significant difference, the supervised multidimensional statistical method, or partial least squares discriminant analysis (PLS-DA) was used to conduct statistical analysis on the two groups of samples.

The model parameters were as follows: in positive mode, there were two principal components, $R^2X=0.713$, $R^2Y=0.988$, and $Q^2=0.97$. In the negative mode, there were two principal components, $R^2X=0.502$, $R^2Y=0.917$, $Q^2=0.919$ (FIGS. 19A-19B, 20A-20B).

The main parameters to determine the quality of the model are $R^2Y$ (which represents the model's interpretation rate) and $Q^2$ (which represents the model's prediction rate). In addition, the model was evaluated to see whether the model is "overfitting". From the model parameters, the model was reliable in explaining the differences between the two groups and searching for different substances, and there was no "overfitting" in the model from the sorting verification diagram.

The "overfitting" of the model reflects the accuracy of the modeling. If the model is not "overfitting", it indicates that the model can describe the sample well and can be used to find the biomarker.

10.5 OPLS-DA Analysis

Figure 21:
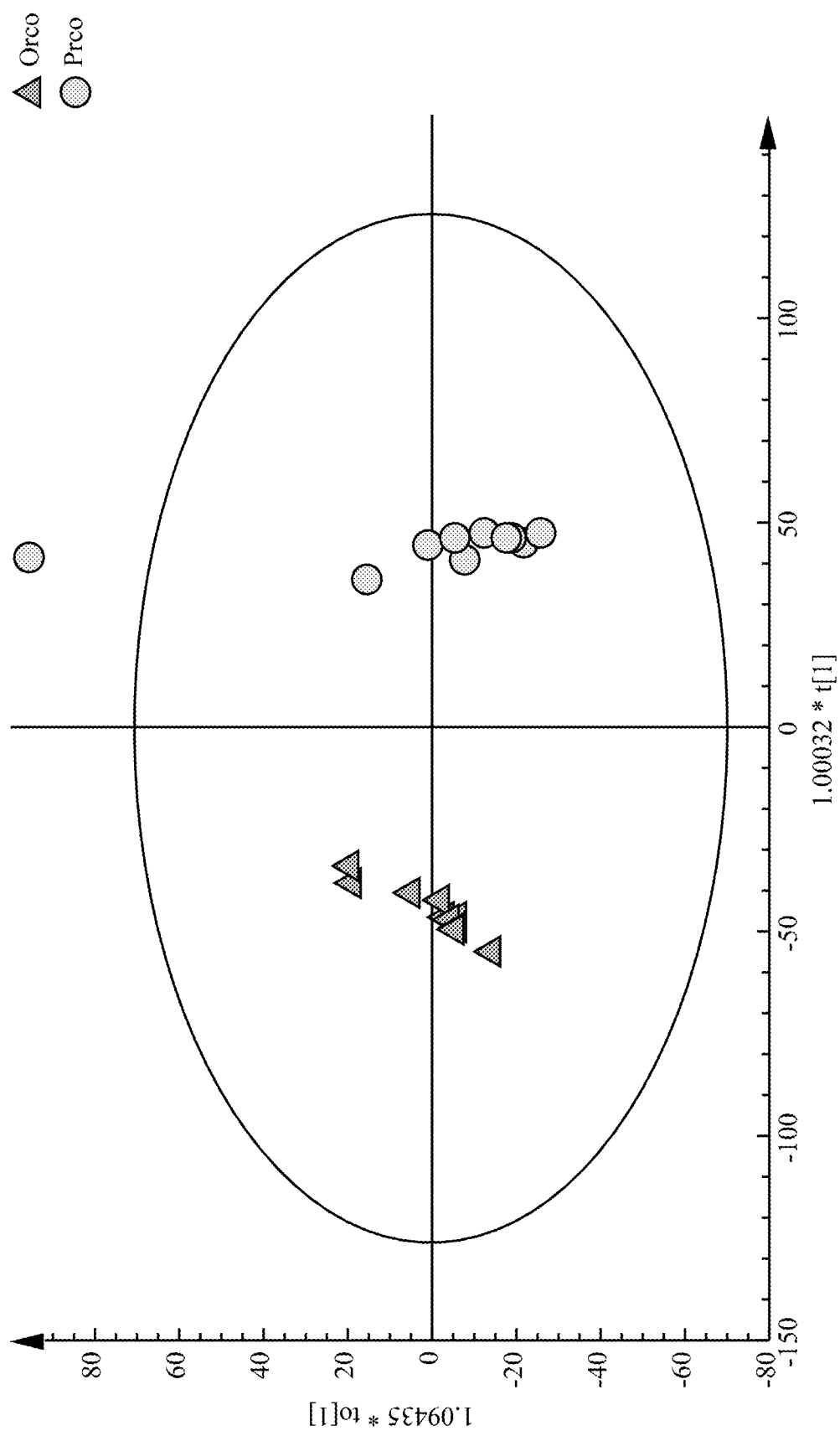
FIG. 21 shows the OPLS-DA scores plot of both the Prco and Orco group (ESI+).
Figure 22:
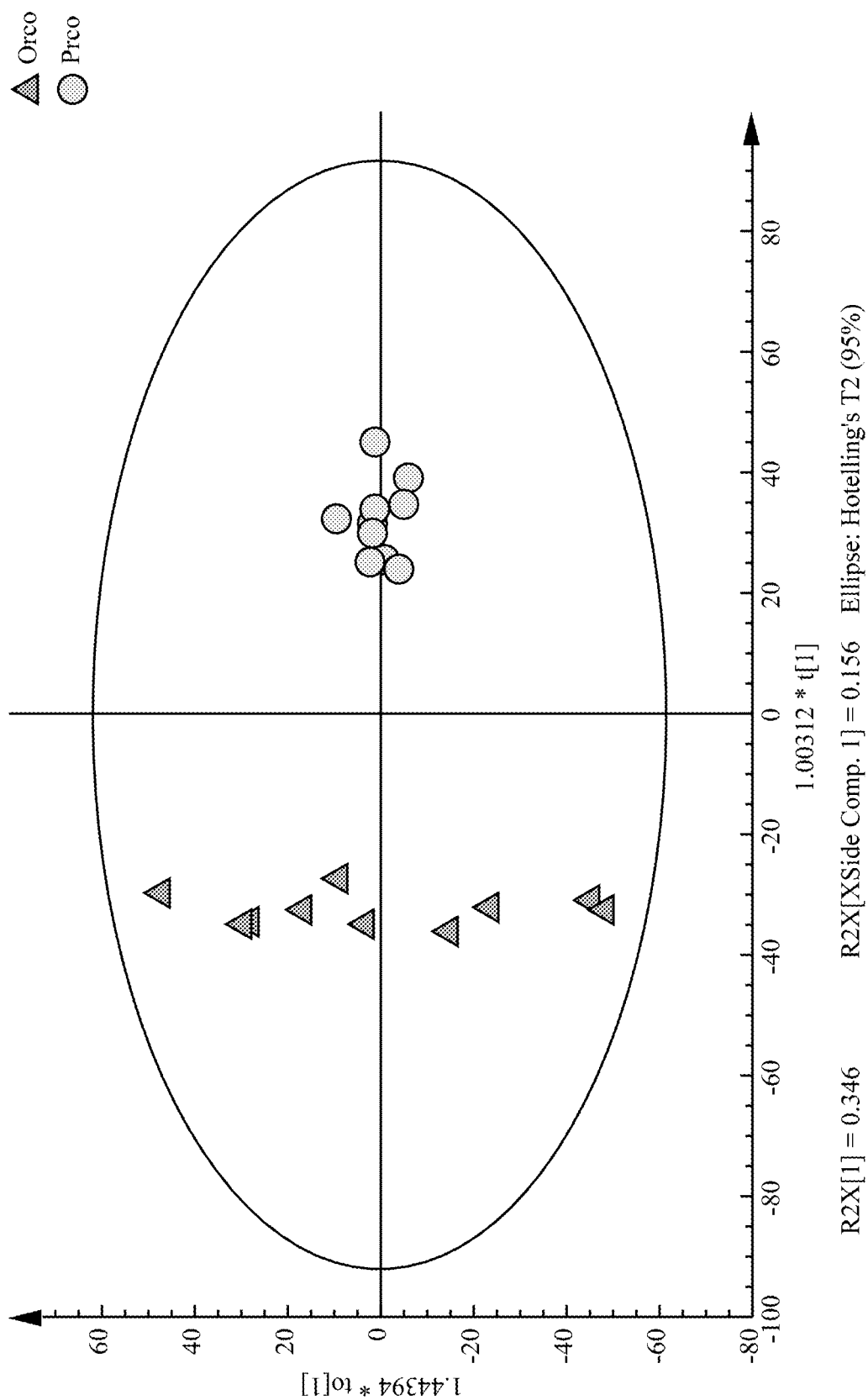
FIG. 22 shows the OPLS-DA scores plot of both the Prco and Orco group (ESI−).

Further, the supervised method OPLS-DA was used. As a result, one principal component and one orthogonal component were obtained in the positive mode, $R^2X=0.713$, $R^2Y=0.988$, and $Q^2=0.973$. In the negative mode, one principal component and one orthogonal component are obtained, $R^2X=0.502$, $R^2Y=0.979$, and $Q^2=0.945$. The model parameter $R^2Y$ represents the model interpretation rate, and $Q^2$ represents the model prediction rate. Their scores are shown in FIGS. 21-22.

10.6 Differential Ingredients Between Groups

Qualitative analysis was conducted by using compound discoverer and finally the information of differential ingredients was obtained. After that, VIP (Variable Importance in the Projection) value and t-test was combined to look for differential expression of ingredients. ingredients with VIP value greater than 1 and p value less than 0.05 were considered as differential.

10.7 Summary

In the positive mode, the contents of 3-hexenoic acid, 5,8-tetradecadienoic acid and Indole in the products as compared to the same amount of original coconut oil sample were significantly reduced (fold change <−7). Cis-9-palmitoleic acid, PA(10:0/21:0) and Stearamide have relatively stable changes. Campest-4-en-3-one and Stigmastentriol contents increased significantly (fold change >7), In general, steroidal lipids (Stigmasterol, Stigmast-22-ene-3,6-dione, Stigmastentriol) and vitamins (ubiquinone-4, Vitamin D3) increased in the products. Amino acids (isolecucine, valine, glutamate, beta-alanine) were reduced after processing.

In the negative mode, the content of sucrose, citric acid decreased by about 7 times, and the concentration of Piperochromenoic acid, LysoPA(a-25:0/0:0) and LysoPA(24:0/0:0) was significantly increased (fold change>5). In general, sucrose, mannitol, sucrose-6-glucose and glucose are lower in the product than in the original coconut oil sample (See FIGS. 43-44 for details).

Example 11: Lipidomics Analysis of Samples 11.1 Sample Preparation, Instrumental Parameters and Data Analysis A total of 20 coconut oil samples (divided into two groups: the product group (deacidified coconut oil) and the stock solution group (original coconut oil)) were tested by LC-MS with positive and negative ion modes, and compared between groups according to the test data.

The samples were dissolved in 25° C. water bath pot and transferred to a 10 mL centrifuge tube. Next, 1.5 mL chloroform/methanol (2/1, v/v) solution was added to 100 µL samples and vortexed for 1 minute. Next, the organic phase (800 µL) was transferred to a clean test tube, dried with nitrogen gas ($N_2$), and then dissolved with 200 µL isopropanol/methanol (1/1, v/v) for 1 minute. Next, 10 µL LPC (12:0) with concentration of 125 µg/mL and 10 µL TG internal standard with concentration of 125 µg/mL were added to the tube and vortexed for 30 seconds. Next, supernatant (200 µL) from the tube was transferred to a vial for inspection.

LC-MS instrument platform (Thermo, Ultimate 3000LC, Q Exactive) and chromatographic column Hyper gold C18 (100×2.1 mm 1.9 µm) were used in chromatographic separation under conditions of the follows: column temperature: column temperature: 50° C.; Flow rate: 0.3 mL/min; mobile phase composition A: ACN: water (60:40, V/V), including 10 mmol/L ammonium acetate, B: ACN: Isopropanol (10:90, V/V), including 10 mmol/L ammonium acetate; injection volume: 5 µL; automatic sampler temperature 10° C.

Mobile phase gradient elution procedure is shown in Table 14.

TABLE 14

| Mobile phase gradient elution procedure | | |
|---|---|---|
| Time (min) | A (%) | B (%) |
| 0 | 70 | 30 |
| 10.5 | 0 | 100 |
| 12.50 | 0 | 100 |
| 12.51 | 70 | 30 |
| 16 | 70 | 30 |

Mass spectrometry analysis was performed using the following parameters: ESI+: Sheath gas velocity: 35 arb; Auxiliary gas velocity: 15 arb; Purge velocity: 1 arb; Electrospray voltage: 3000 V; Capillary temperature: 350° C.; Gasification temperature: 350° C. S-lens RF Level, 50%. ESI−: Sheath gas velocity: 35 arb; Auxiliary gas velocity: 15 arb; Purge velocity: 1 arb; Electrospray voltage: 2800 V; Capillary temperature: 350° C.; Gasification temperature: 350° C. S-lens RF Level, 50%. Scan mode: Full Scan (ESI+: m/z 250~1500; ESI−: m/z 200~1500) and data-dependent second-order mass spectrometry scanning (dd-ms2, TopN=10); Resolution: 70,000 (MS1) & 17,500 (MS2). Collision mode: high energy collision dissociation (HCD).

The data was analyzed by feature extraction and preprocessed with Lipid Search software (Thermo), and then normalized and edited into two-dimensional data matrix by Excel 2010 software, including LipidIon, Class, Fatty acid chains (Fatty Acid, FA1,FA2,FA3), CalcMz, IonFormula, Retention time (RT) and peak intensity. The data after editing were analyzed by Multivariate Analysis (MVA) using SIMCA-P software (Umetrics AB, Umea, Sweden).

11.2 Chromatogram

Figure 23:
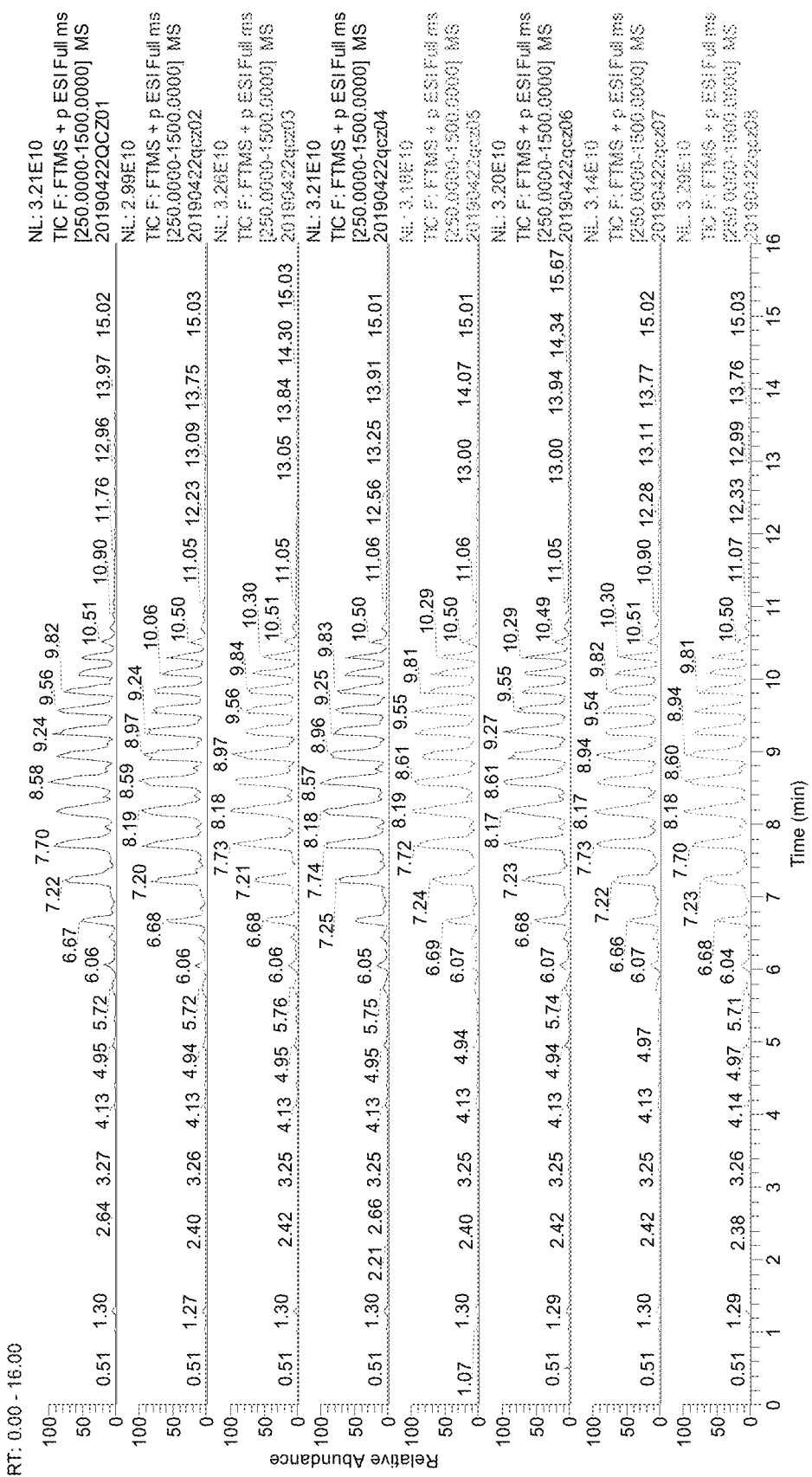
FIG. 23 shows the total ion chromatogram of QC (ESL+).
Figure 24:
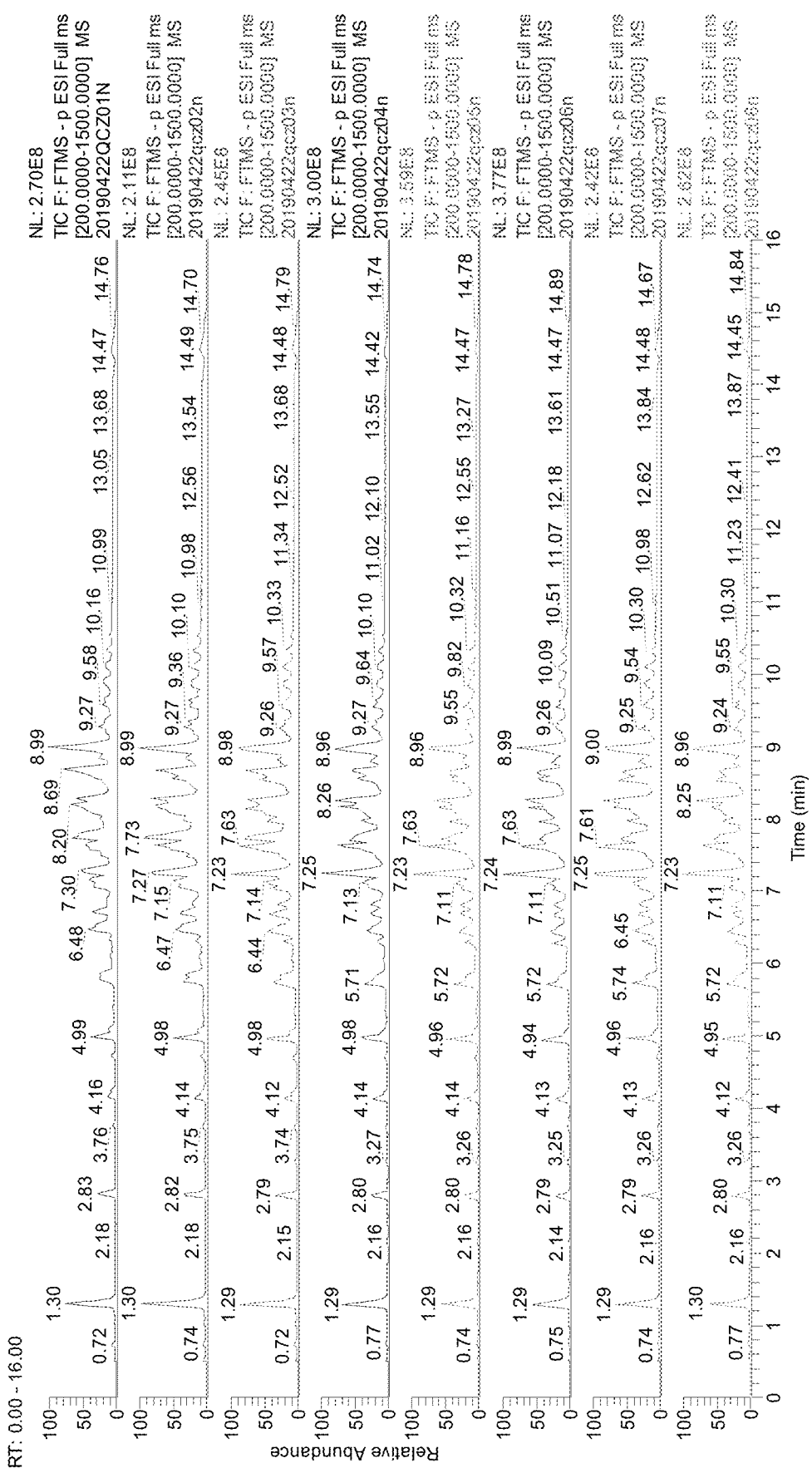
FIG. 24 shows the total ion chromatogram of QC (ESL−).
Figure 25:
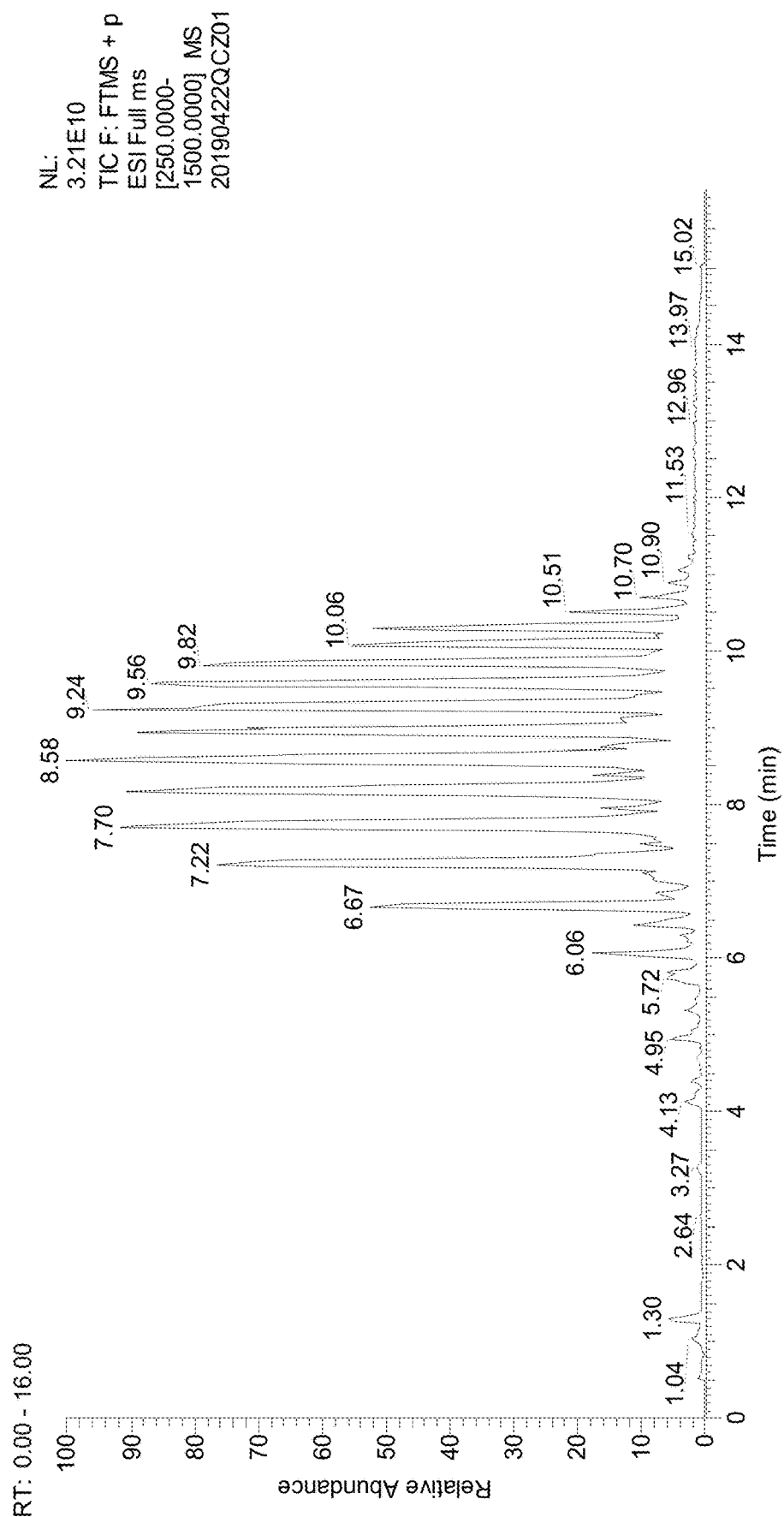
FIG. 25 shows an exemplary total ion chromatogram of the QC group (ECL+).
Figure 26:
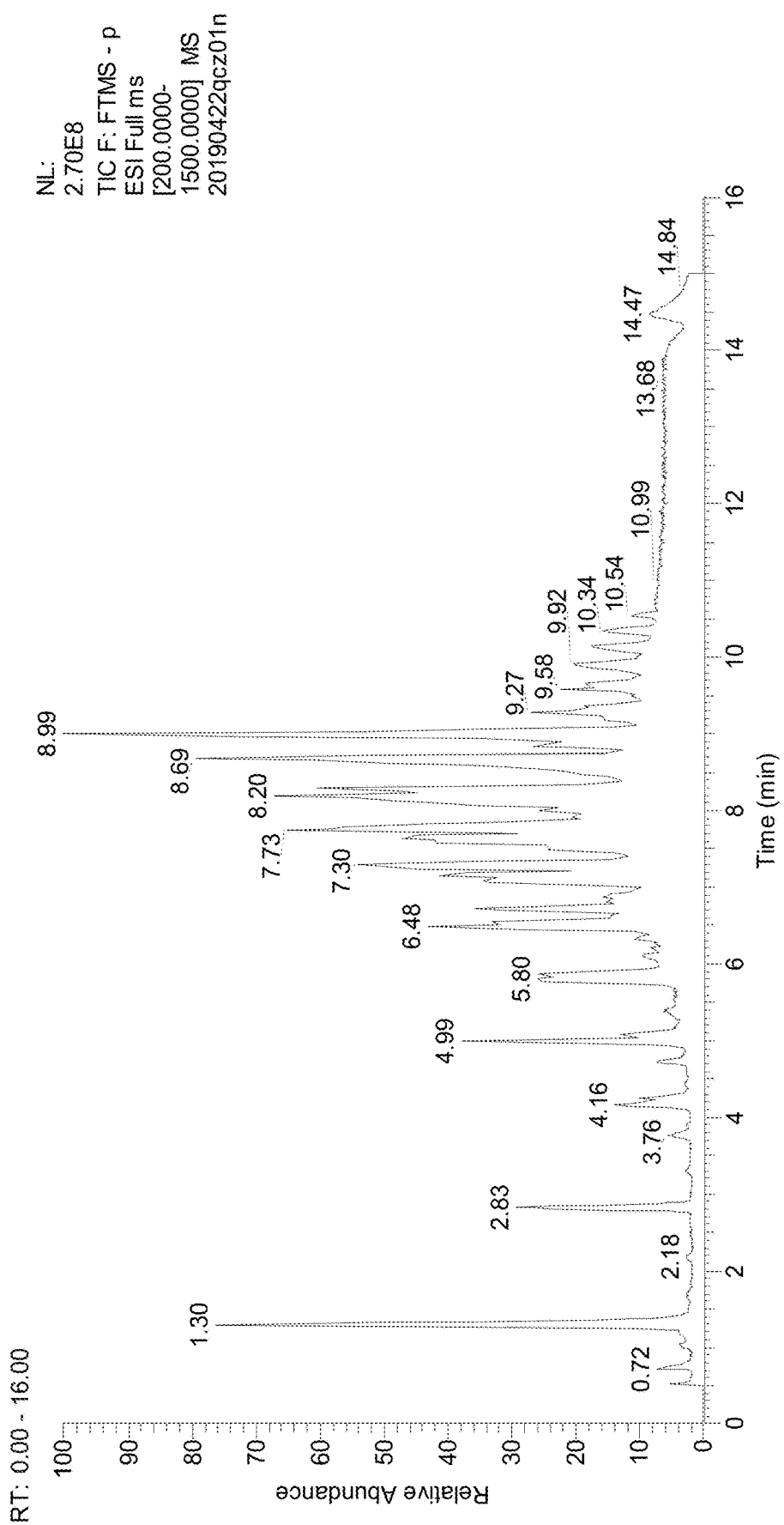
FIG. 26 shows an exemplary total ion chromatogram of the QC group (ECL−).
Figure 27:
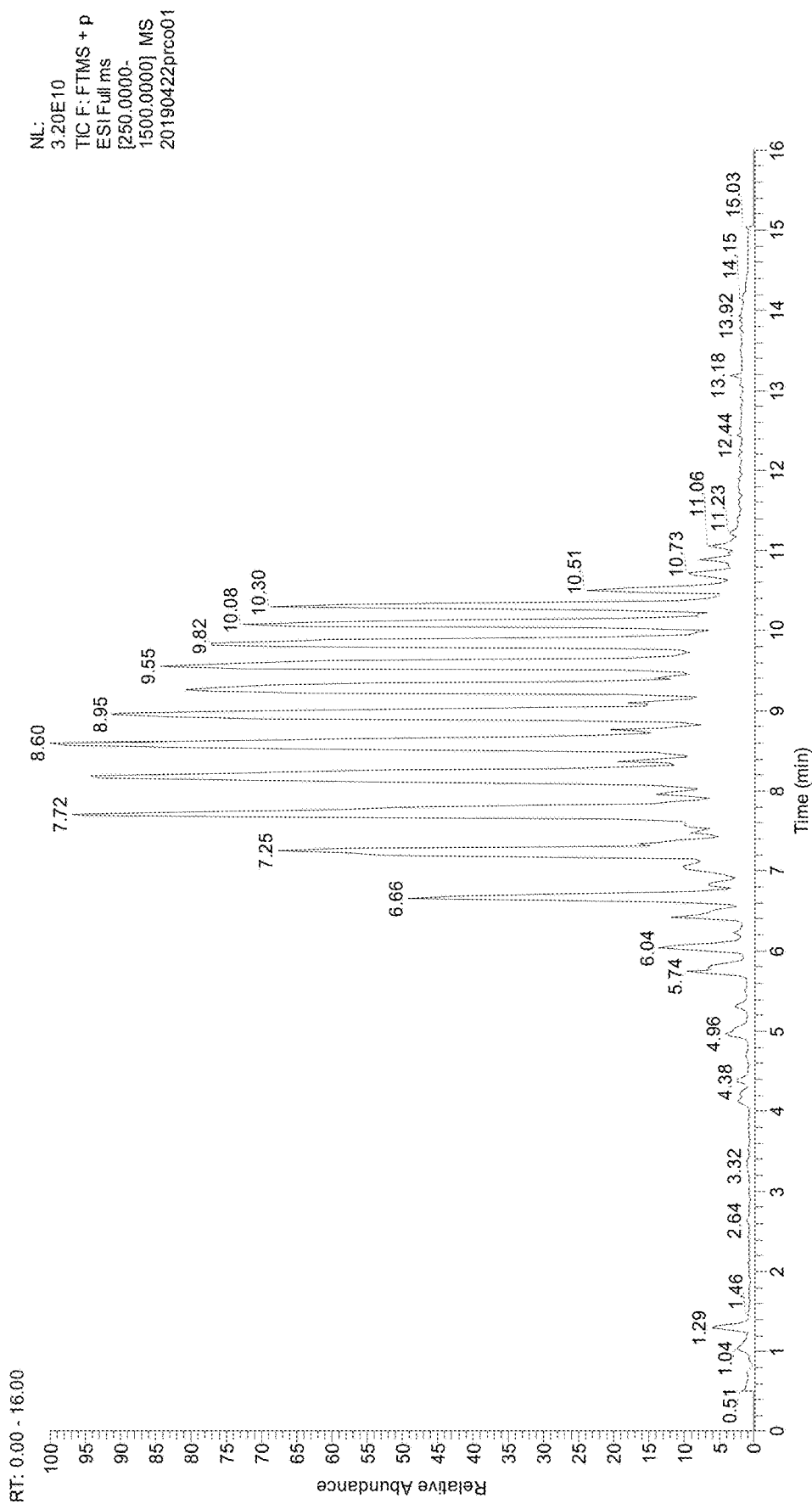
FIG. 27 shows an exemplary total ion chromatogram of the product group (ECL+).
Figure 28:
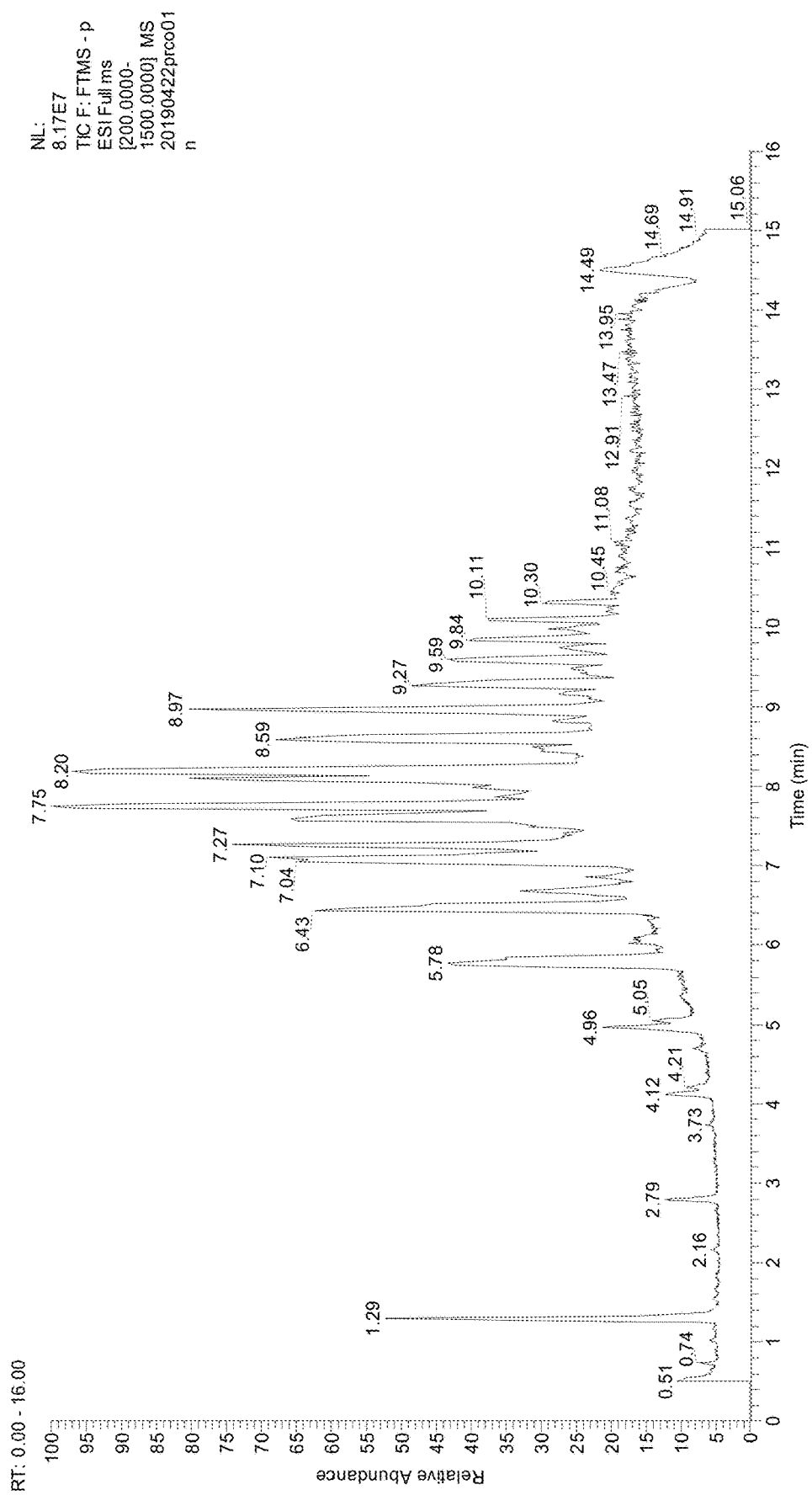
FIG. 28 shows an exemplary total ion chromatogram of the product group (ECL−).
Figure 29:
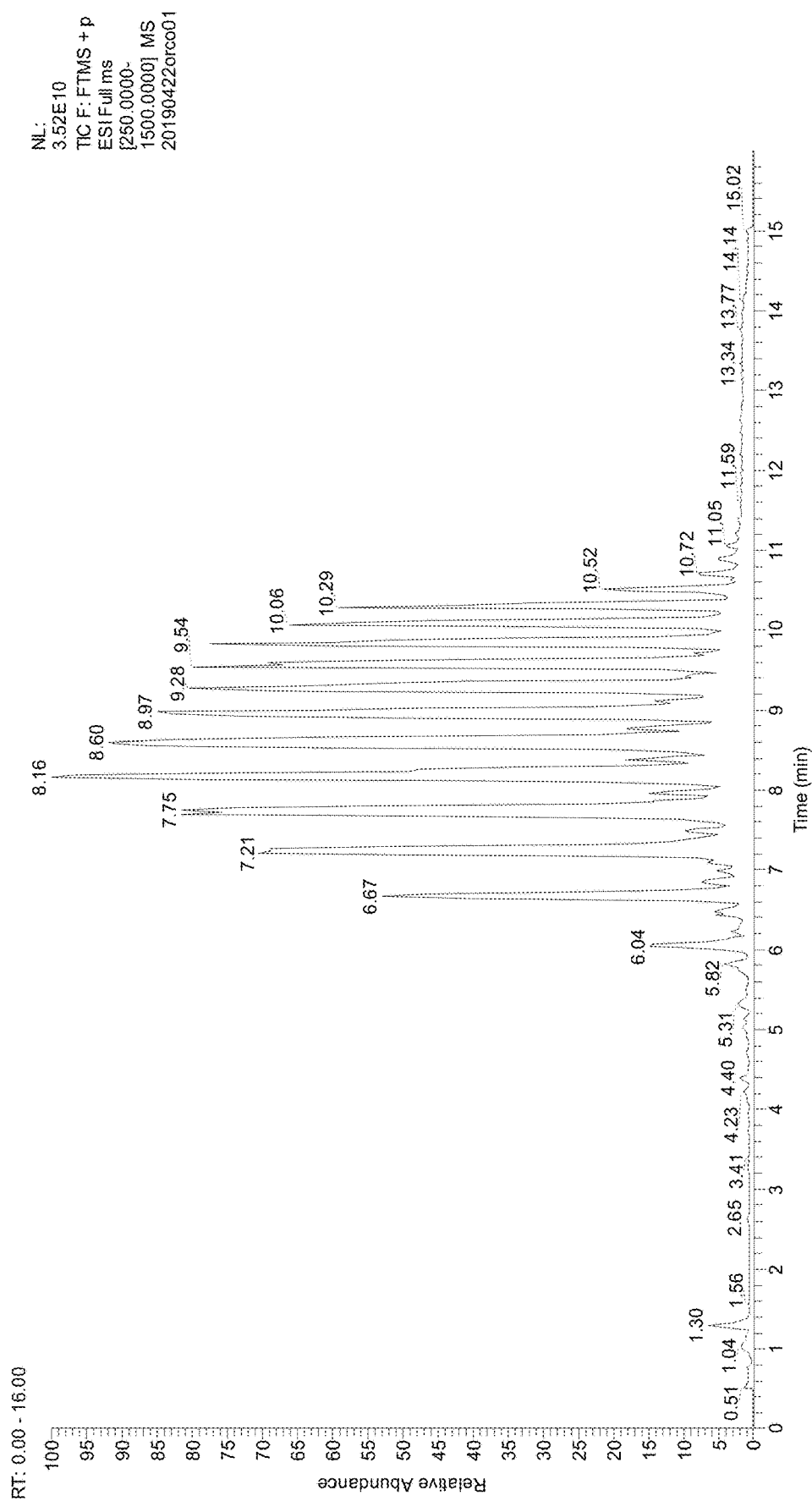
FIG. 29 shows an exemplary total ion chromatogram of the stock solution group (ECL+).
Figure 30:
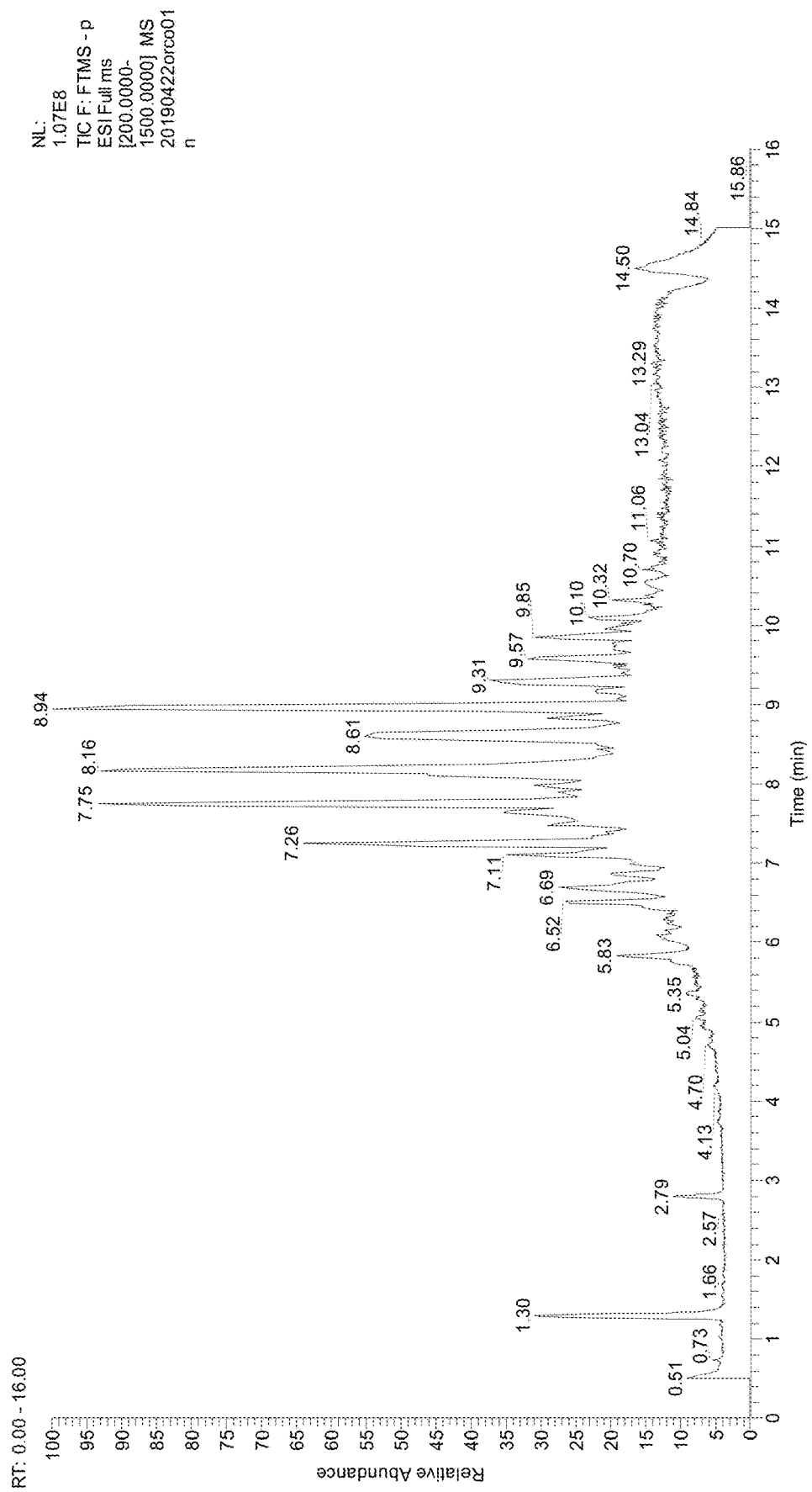
FIG. 30 shows an exemplary total ion chromatogram of the stock solution group (ECL−).

The total ion chromatogram (TIC) of QC samples was overlapped, as shown in FIGS. 23-24, which shows that the retention time reproducibility of the instrument was good and the instrument was stable, so the results of instrument analysis and data have high reliability. A sample of TIC (FIGS. 25-30) for each group of samples and QC is listed separately.

QC is the mixture of different and equal samples after sample extraction. A small amount of QC was injected after analyzing a certain number of samples. The reliability of the instrument can be monitored through the overlapping of QC chromatogram. ESI+ represents the positive ion detection mode, that is, in the detection process, the mass analyzer only scans the positive ion and filters out the negative ion, so as to obtain the information of positive ion. ESI− represents the mode of negative ion detection, that is, during the detection process, the mass analyzer only scans negative charge ions and filters out positive charge ions, so as to obtain information of negative charge ions.

11.3 PCA Analysis of all Samples

Principal component analysis (PCA) was performed to analyze the overall differences between groups of samples and the variation between samples. Before using SMICA-P software for PCA analysis, the dataset was normalized in order to obtain more reliable results.

Figure 31:
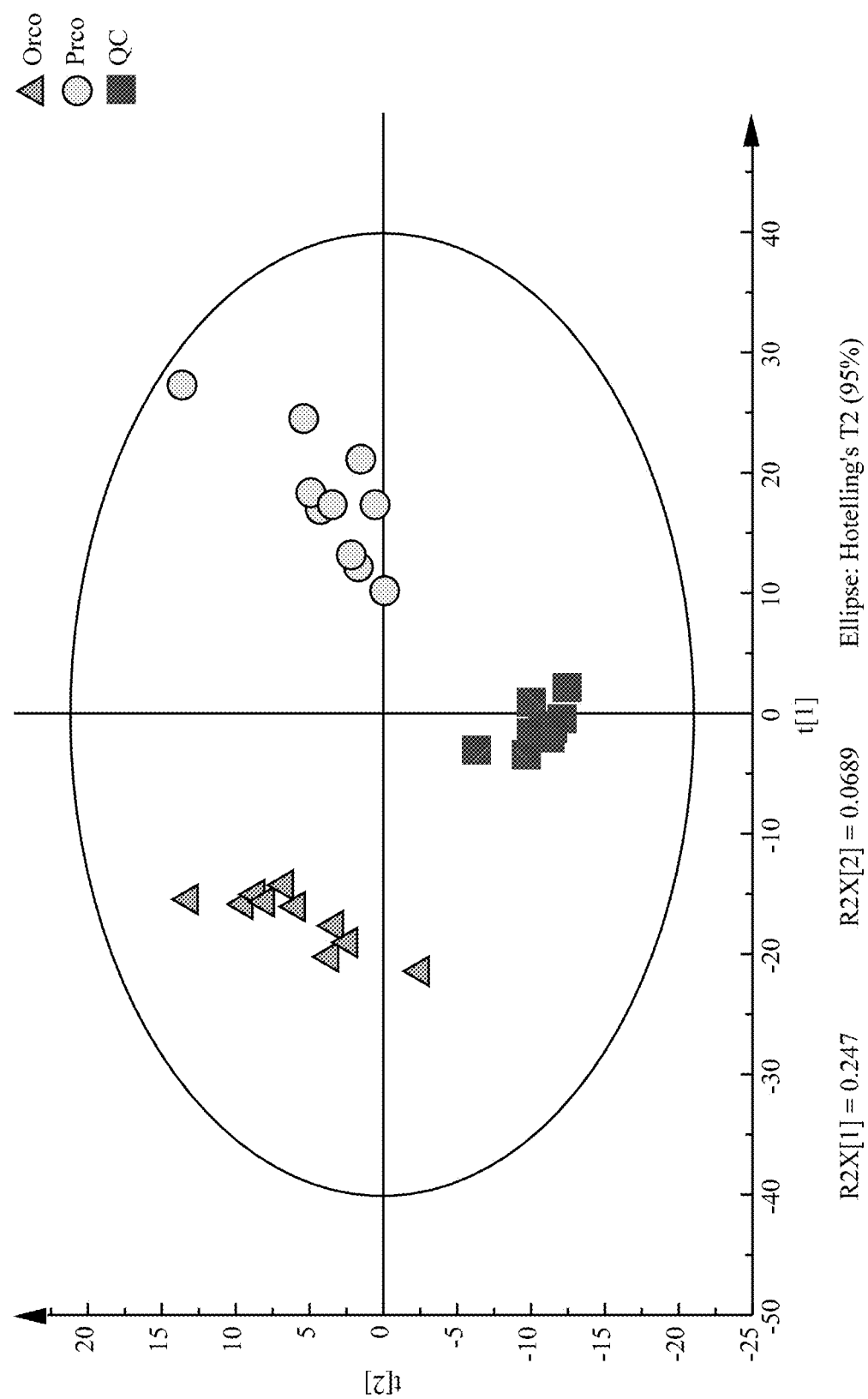
FIG. 31 shows the PCA score plot of all samples (ESI+). Orco is the stock solution group; Prco is the product group; and QC is the QC group.
Figure 32:
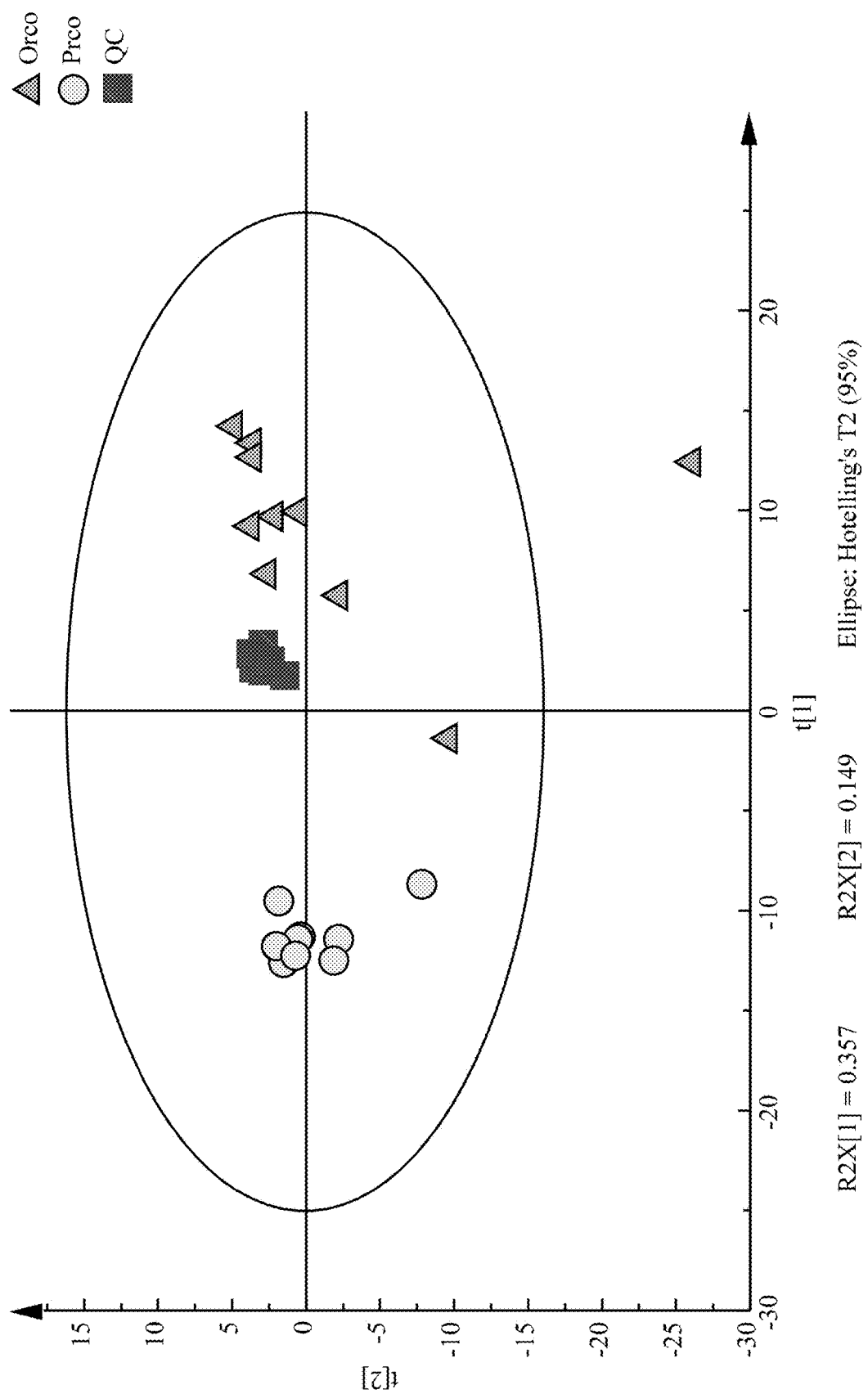
FIG. 32 shows the PCA score plot of all samples (ESI−). Orco is the stock solution group; Prco is the product group; and QC is the QC group.

In order to distinguish whether there are differences between the two groups, we used the PCA modeling method to analyze the samples. In this analysis, a total of two principal components were obtained in the positive mode, with cumulative $R^2X=0.316$ and $Q^2=0.198$. In the negative mode, a total of 3 principal components were obtained, with cumulative $R^2X=0.605$ and $Q^2=0.32$. PCA Scores plot under ESI+ and ESI-modes are shown in FIG. 31 and FIG. 32, respectively.

Figure 33:
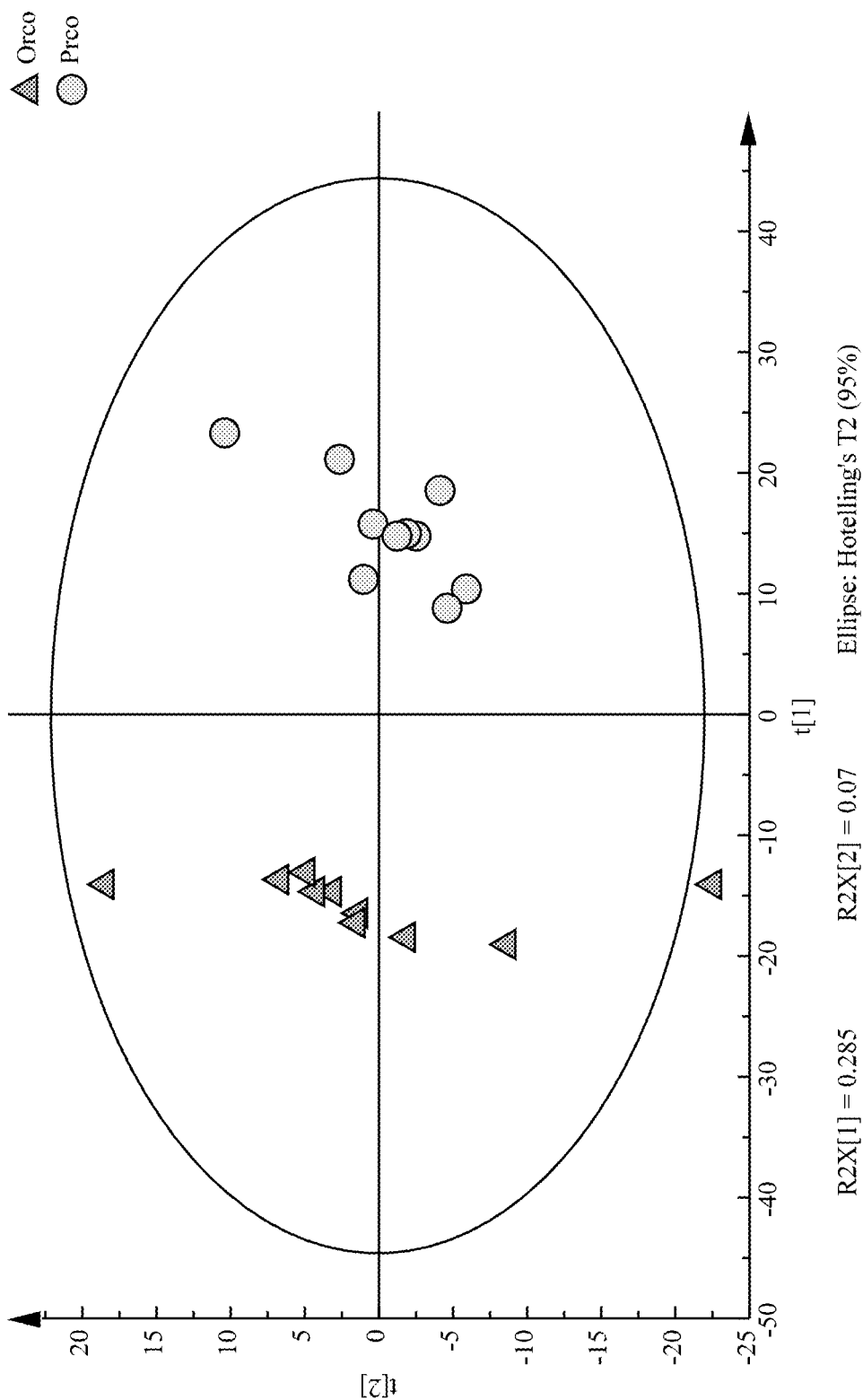
FIG. 33 shows the PCA score plot of both the Prco and Orco groups (ESI+). Orco is the stock solution group; Prco is the product group.
Figure 34:
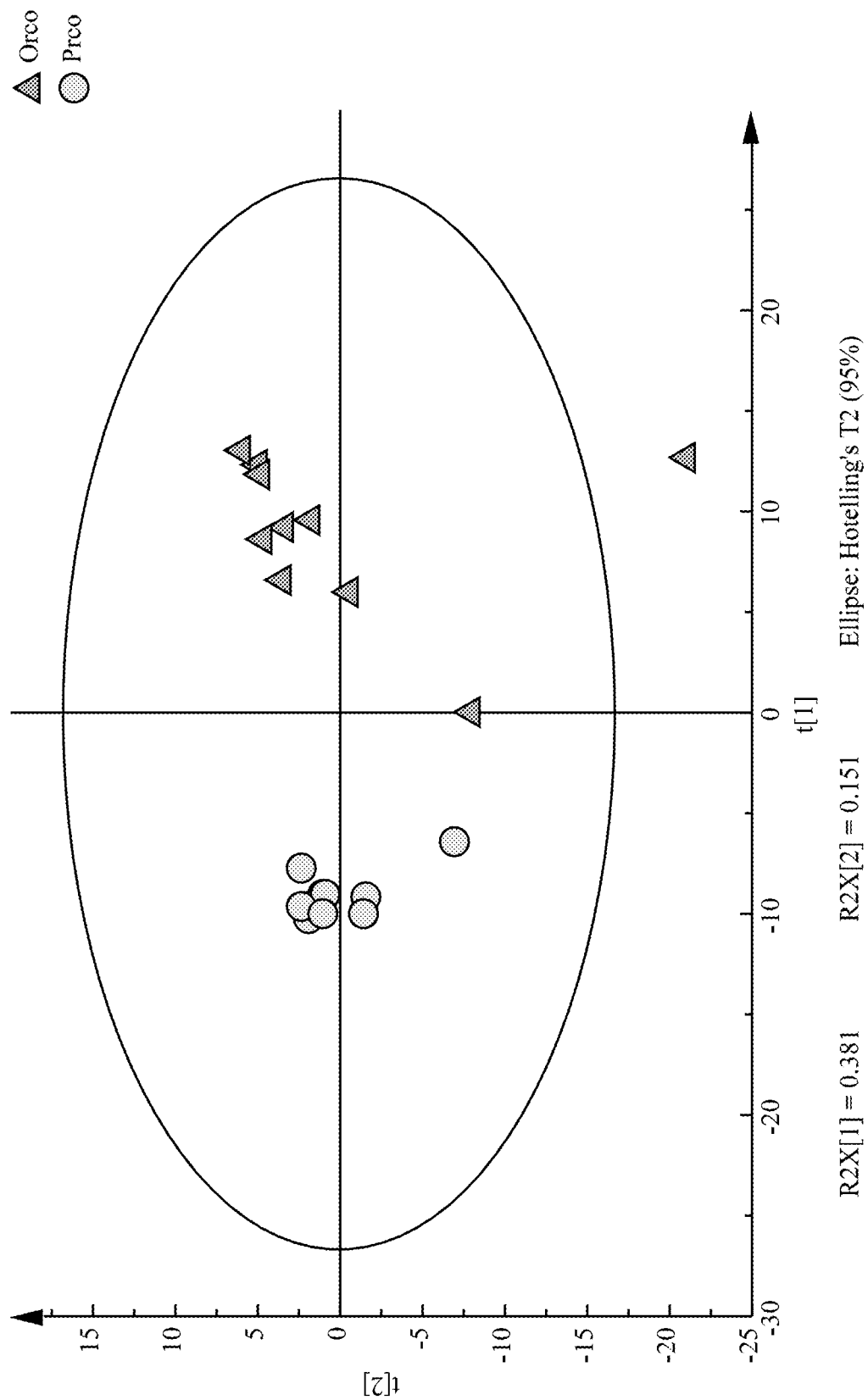
FIG. 34 shows the PCA score plot of both the Prco and Orco groups (ESI−). Orco is the stock solution group; Prco is the product group.
Figure 35A:
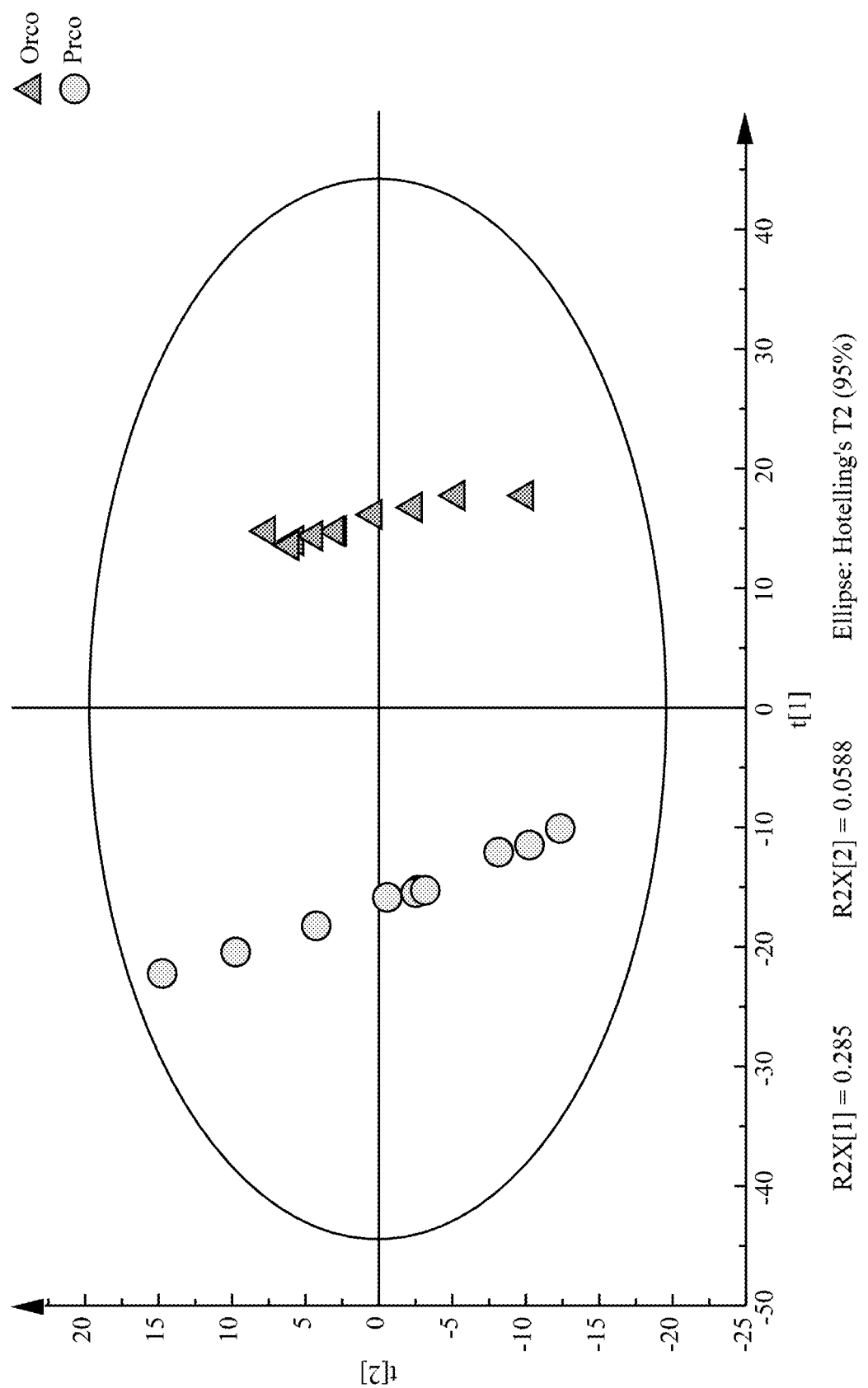
FIG. 35A shows the PLS-DA score plot of both the Prco and Orco group (ESI+). Orco is the stock solution group; Prco is the product group.
Figure 35B:
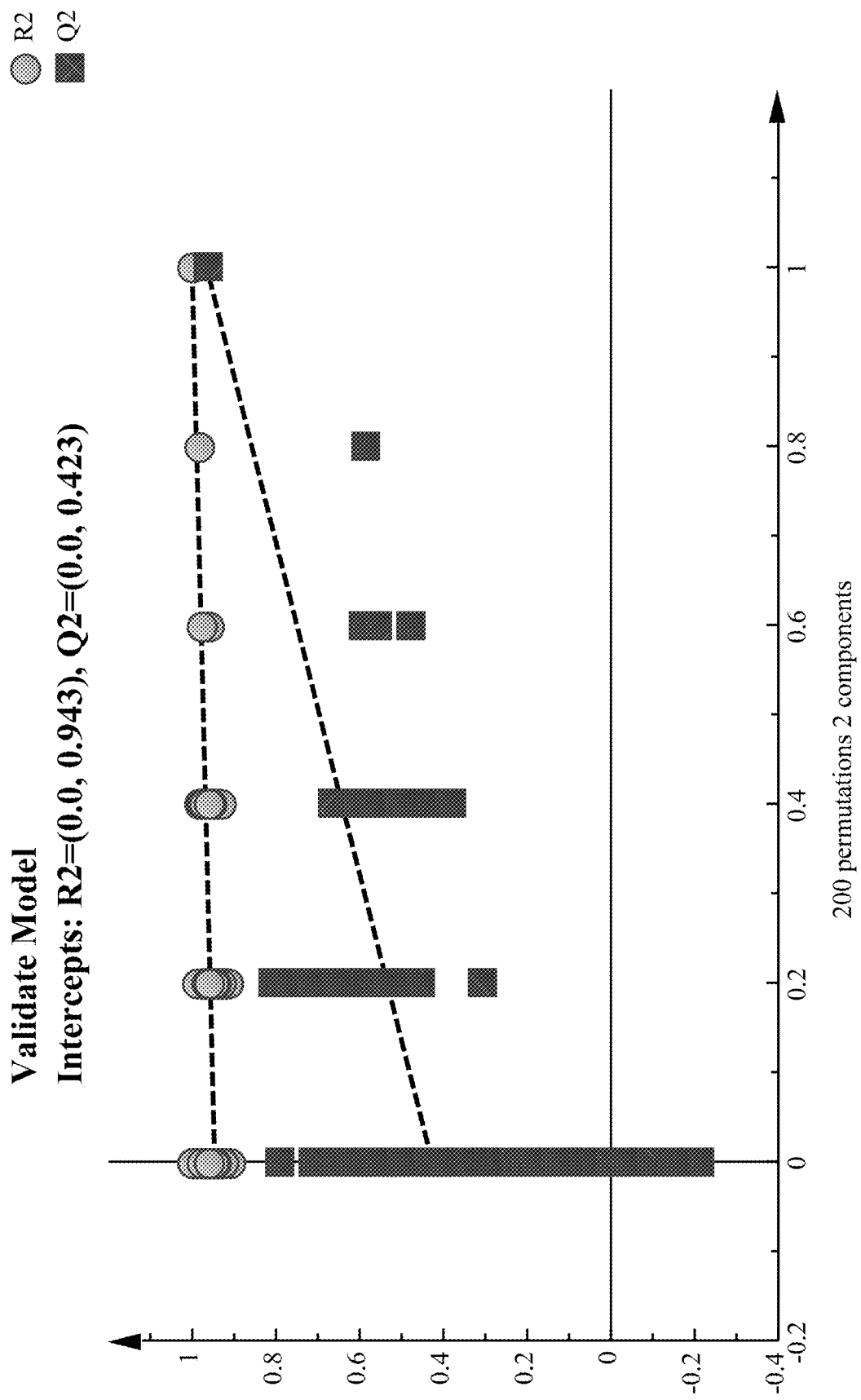
FIG. 35B shows the fitted model and calculated parameters of both the Prco and Orco group (ESI+).
Figure 36A:
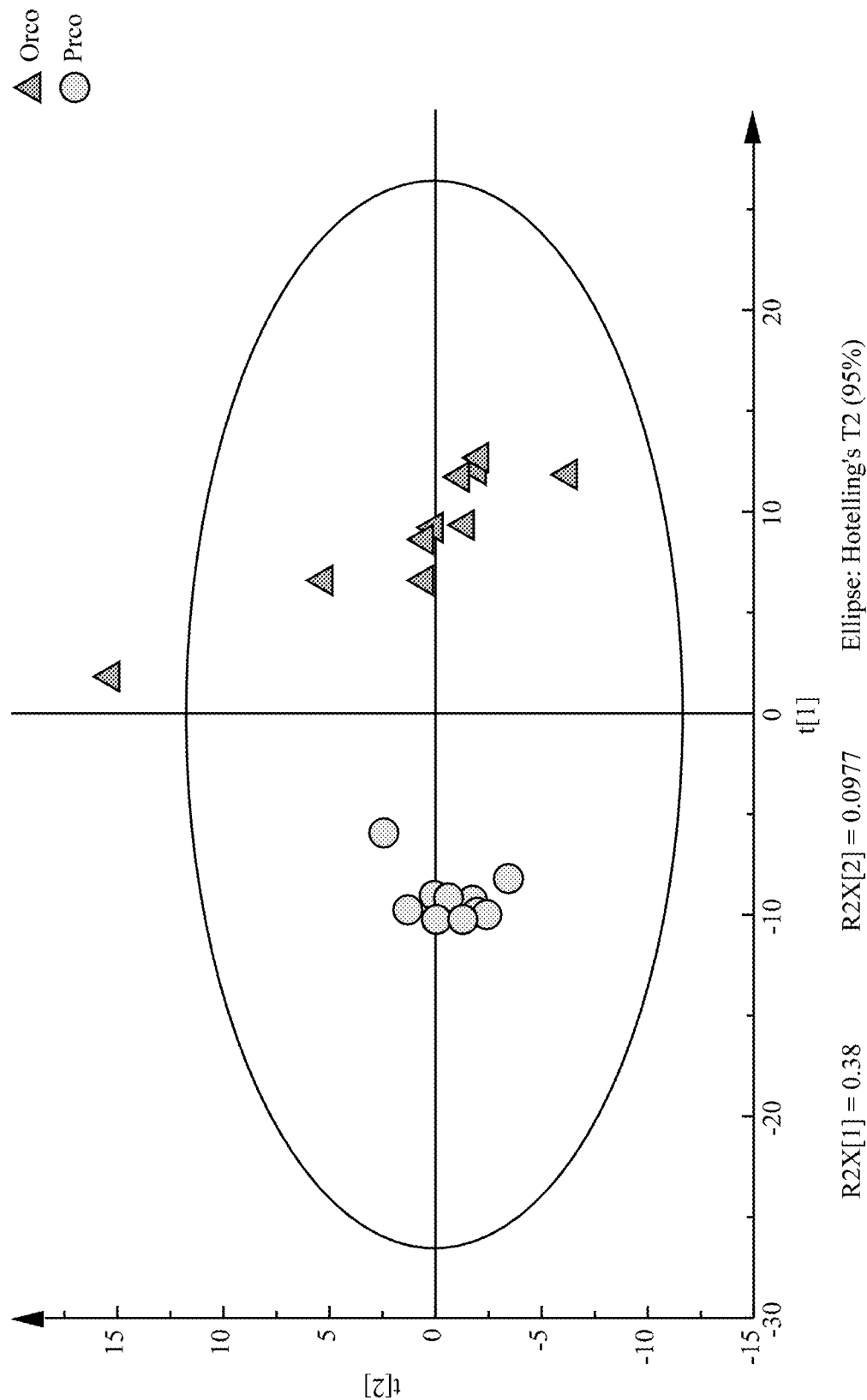
FIG. 36A shows the PLS-DA score plot of both the Prco and Orco group (ESI−). Orco is the stock solution group; Prco is the product group.
Figure 36B:
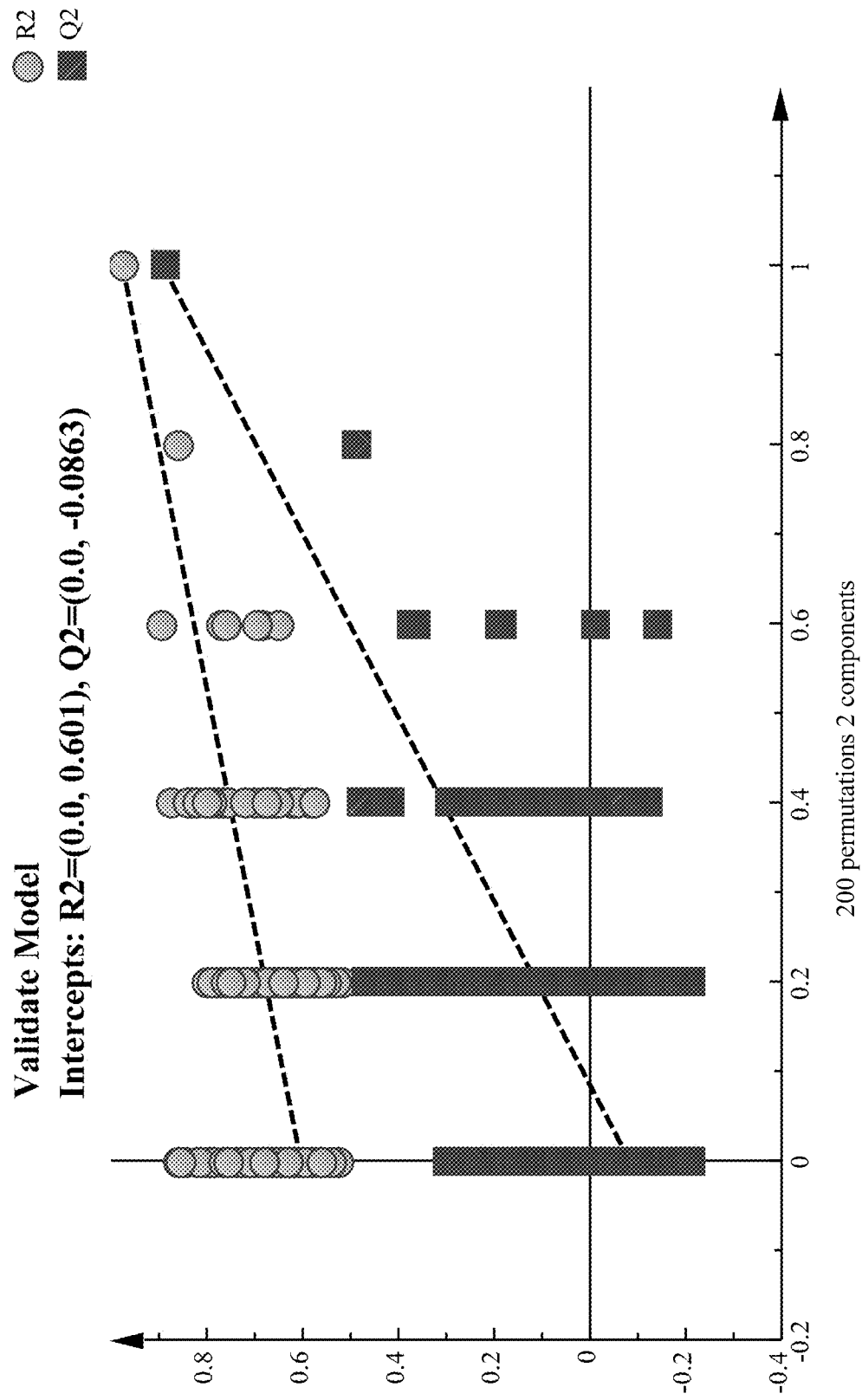
FIG. 36B shows the fitted model and calculated parameters of both the Prco and Orco group (ESI−).

Principal component analysis was conducted on Prco group (the product group) and the Orco group (the original coconut oil group). In this analysis, a total of 2 principal components were obtained in the positive model, with cumulative $R^2X=0.355$ and $Q^2=0.16$. In the negative mode, a total of 3 principal components were obtained, with cumulative $R^2X=0.644$ and $Q^2=0.347$. PCA Scores plot under ESI+ and ESI-modes are shown in FIG. 33 and FIG. 34, respectively.

11.4 PLS-DA Analysis

In order to obtain the ingredient information leading to this significant difference, the supervised multidimensional statistical method, or partial least squares discriminant analysis (PLS-DA) was used.

The model parameters are as follows: in positive mode, there are two principal components, $R^2X=0.344$, $R^2Y=0.998$, and $Q2=0.962$. In the negative mode, $R^2X=0.478$, $R^2Y=0.973$, $Q2=0.889$ (FIGS. 35A-35B, and 36A-36B).

The main parameters to determine the quality of the modeling are $R^2Y$ (which represents the model's interpretation rate) and $Q^2$ (which represents the model's prediction rate). In addition, whether the model is "overfitting" was also assessed. From the model parameters, the model is reliable in explaining the differences between the two groups and searching for different substances, and there is no "overfitting" in the modeling from the verification diagram.

The "overfitting" of the model reflects the accuracy of the model construction. If the model is not "overfitting", it indicates that the model can describe the sample well and can be used to find the most relevant biomarker.

11.5 OPLS-DA Analysis

Figure 37:
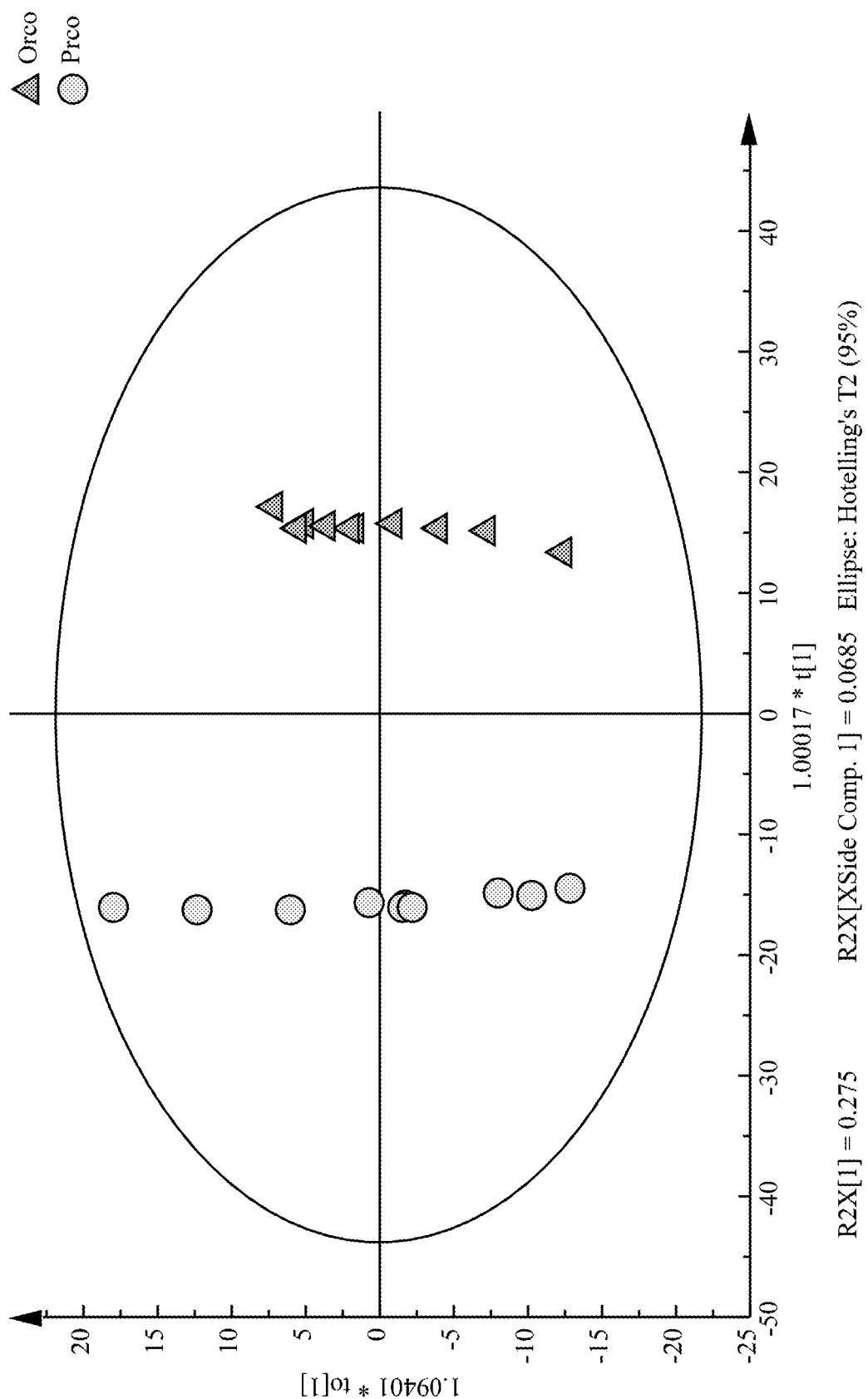
FIG. 37 shows the OPLS-DA score plot of both the Prco and Orco group (ESI+). Orco is the stock solution group; Prco is the product group.
Figure 38:
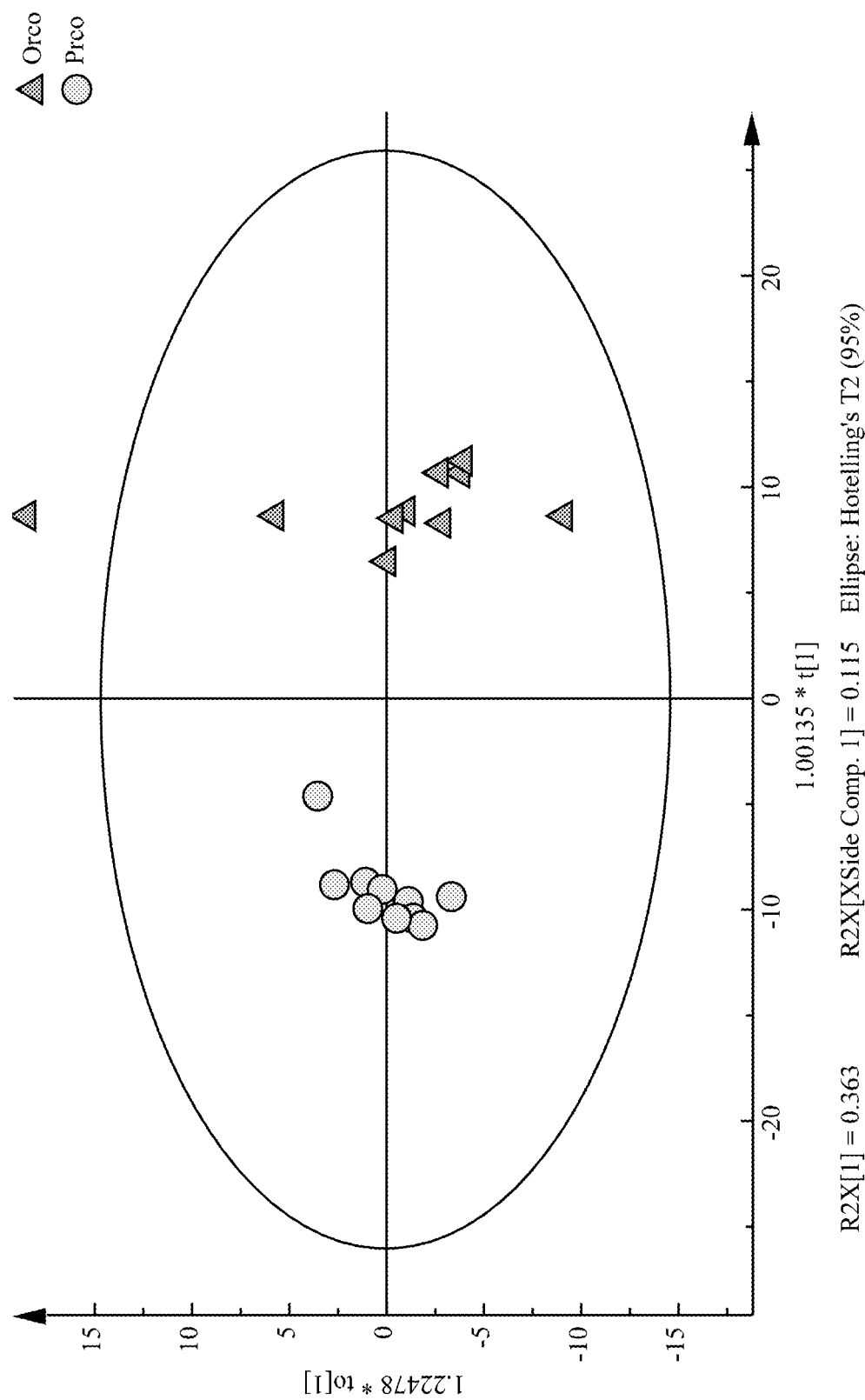
FIG. 38 shows the OPLS-DA score plot of both the Prco and Orco group (ESI−). Orco is the stock solution group; Prco is the product group.
Figure 39:
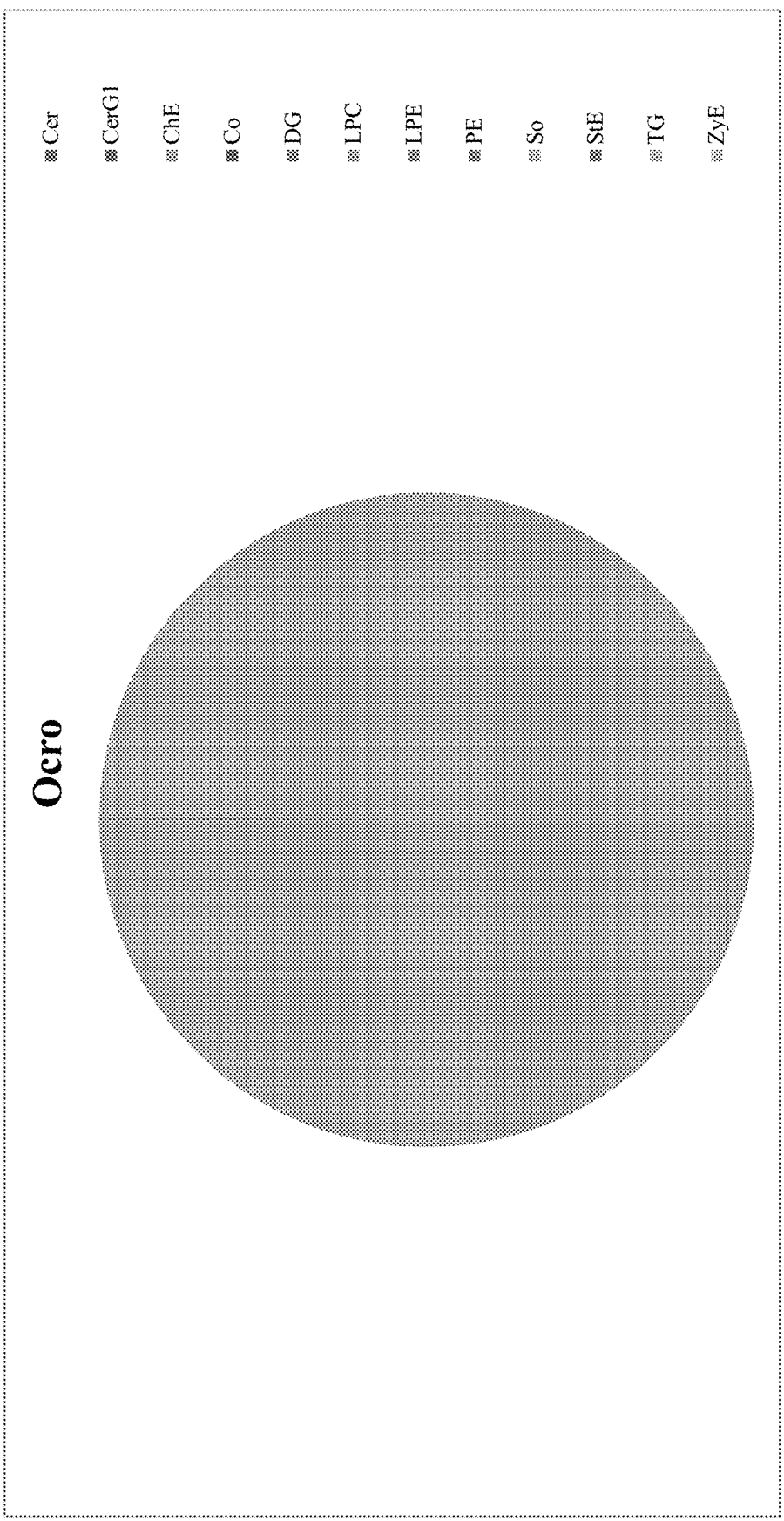
FIG. 39 is a pie graph showing the percentage of lipid classes (ESI+) in the stock solution group. Orco is the stock solution group.
Figure 40:
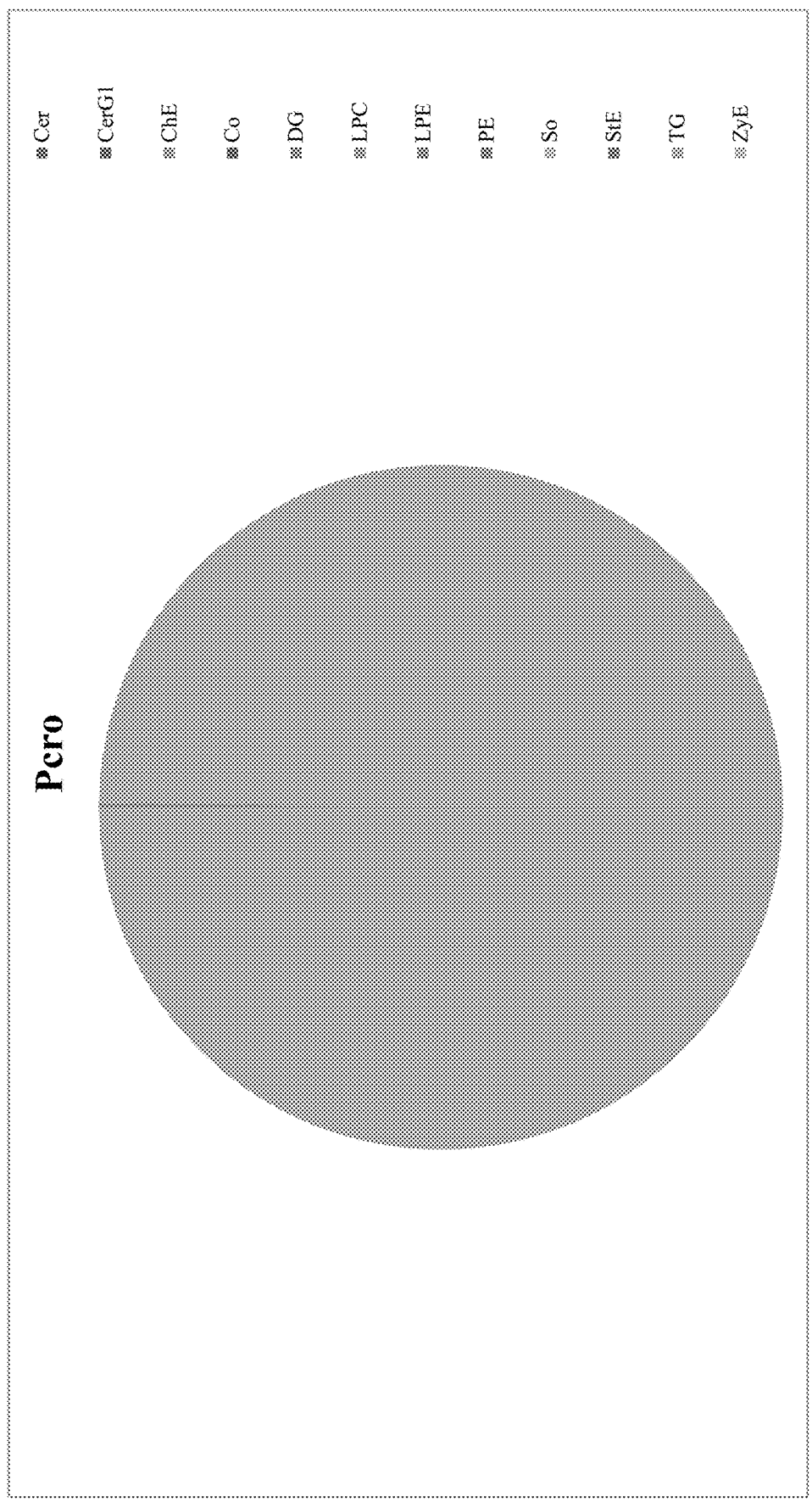
FIG. 40 is a pie graph showing the percentage of lipid classes (ESI+) in the product group. Pcro is the product group.
Figure 41:
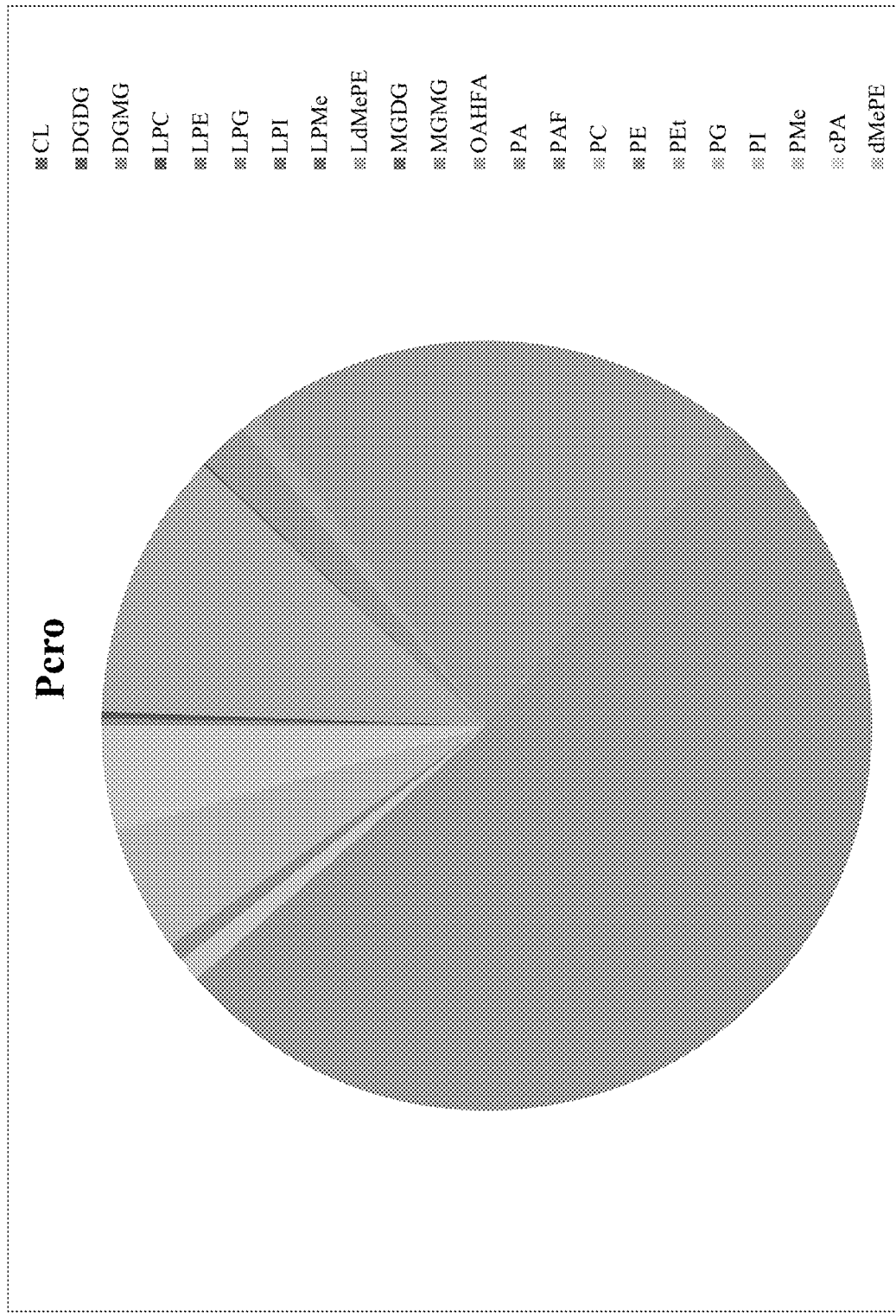
FIG. 41 is a pie graph showing the percentage of lipid classes (ESI−) in the product group. Pcro is the product group.
Figure 42:
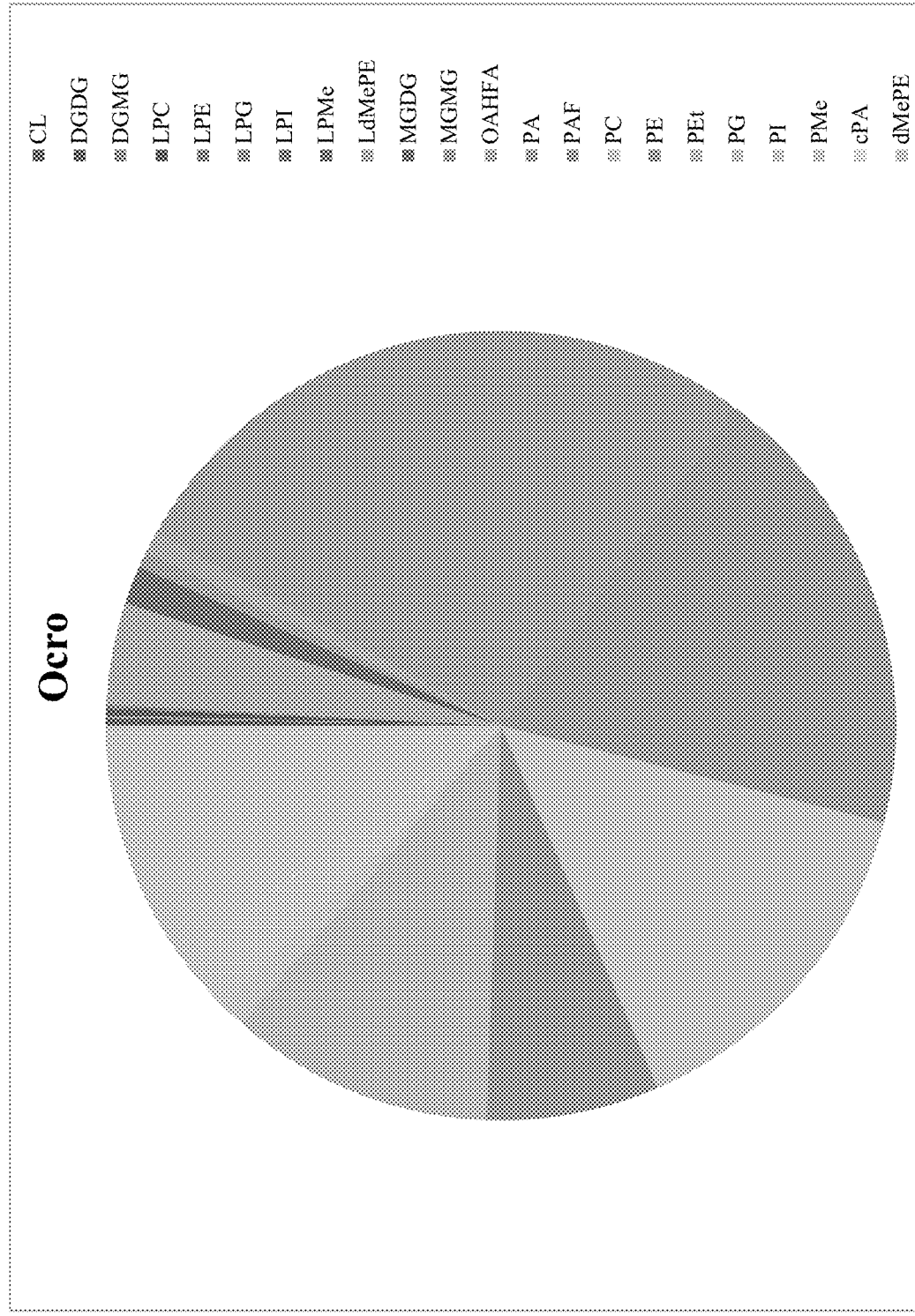
FIG. 42 is a pie graph showing the percentage of lipid classes (ESI−) in the stock solution group. Orco is the stock solution group.

Further, the supervised method OPLS-DA was used. As a result, one principal component and one orthogonal component were obtained in the positive mode, $R^2X=0.344$, $R^2Y=0.998$, and $Q^2=0.962$. In the negative mode, one principal component and one orthogonal component were obtained, $R^2X=0.478$, $R^2Y=0.973$, and $Q^2=0.875$. The model parameter $R^2Y$ represents the model interpretation rate, and $Q^2$ represents the model prediction rate. Their scores are shown in FIGS. 37-38.

11.6 Differential Lipids Between Groups

Qualitative analysis was conducted by using Lipid search, and finally the information of differential ingredients was obtained, including the types of differential lipids, the change in the chain length of each molecule of differential lipids and the number of unsaturated bonds. After that, VIP value and t-test was combined to look for differential expression of lipid ingredients. Lipids with VIP value greater than 1 and p value less than 0.05 were considered as differential lipids. The data of different ingredients are shown in FIGS. 45-46.

11.7 Summary

In this project, 12 classes of lipids were detected at ESI+ in product samples, which are cer (Ceramides, 0.00256864604914964%), CerG1(Simple Glc series, 0.000121562094094825%), ChE(Cholesteryl Ester, 0.000027195581262643%), Co(Coenzyme, 0.000165799851752065%), DG(diglyceride, 0.204618368597593%), LPC (lysophosphatidylcholine, 0.000691245372867429%), LPE (lysophosphatidylethanolamine, 4.39688799919827E-06%), PE(phosphatidylethanolamine, 0.0000221371777288954%), So(Sphingoshine, 0.00800073222443555%), StE(Stigmasteryl ester, 6.13493501356116E-06%), TG (tri-glyceride, 99.7836547325718%), ZyE(zymosteryl, 0.0000119048656356883%). In Orco sample, 11 classes of lipids were detected, which are cer (Ceramides, 0.00305724291322289%), CerG1(Simple Glc series, 0.000296999634909488%), ChE(Cholesteryl Ester, 0.000007562648073146%), Co(Coenzyme, 0.00106715223387679%), DG(cdiglyceride, 0.1020919259929773%), LPC (lysophosphatidylcholine, 0.00192954289175979%), LPE (lysophosphatidylethanolamine, 0.000206199217706794%), PE(phosphatidylethanolamine, 0.000994781308036394%), So(Sphingoshine, 0.007782457246644204%), TG(triglyceride, 99.8825339050066%), ZyE(zymosteryl, 0.00000322309694142598%).

At ESI– mode, 21 classes of lipids were detected, which are DGDG(Digalactosyldiacylglycerol, 0.00337850020676684%), DGMG(Digalactosylmonoacylglycerol, 0.283485348778992%), LPC(lysophosphatidylcholine, 0.278254986476203%), LPE(lysophosphatidylethanolamine, 0.00556230615677608%), LPG(lysophosphatidylglycerol, 0.00243740463723581%), LPI(lysophosphatidylinositol, 0.00152071252159812%), LPMe(lysophosphatidylmethanol, 0.0246170259125403%), LdMePE(lysodimethylphosphatidylethanolamine, 0.0246170259125403%), MGDG (Monogalactosyldiacylglycerol, 0.119679045099086%), MGMG(Monogalactosylmonoacylglycerol, 2.12694214959191%), OAHFA((O-acyl)-1-hydroxy fatty acid, 0.815004998839083%), PA(phosphatidic acid, 21.2775572879869%), PAF(platelet-activating factor, 52.3844436814582%), PC(phosphatidylcholine, 0.996419719716529%), PE(phosphatidylethanolamine, 0.769816735887086%), PEt(phosphatidylethanol, 5.23724828345888%), PG(phosphatidylglycerol, 0.150818577744567%), PI(phosphatidylinositol, 0.224349306155231%), PMe(phosphatidylmethanol, 4.04027226374681%), cPA (cyclic phosphatidic acid, 0.000121119001517959%), dMePE(dimethylphosphatidylethanolamine, 0.009913724165893%).

In Orco samples, 22 classes of lipids were detected, which are CL (Cardiolipin, 0.0205841044276305%) DGDG(Digalactosyldiacylglycerol, 0.291159900494563%), DGMG(Digalactosylmonoacylglycerol, 0.0960936390316132%), LPC (lysophosphatidylcholine, 0.303192132840516%), LPE (lysophosphatidylethanolamine, 0.104579947187398%), LPG(lysophosphatidylglycerol, 0.00534666996716351%), LPI(lysophosphatidylinositol, 0.04437820666618173%), LPMe(lysophosphatidylmethanol, 0.00138869574447737%), LdMePE(lysodimethylphosphatidylethanolamine, 4.15813005466302%), MGDG(Monogalactosyldiacylglycerol, 1.57435383259576%), MGMG(Monogalactosylmonoacylglycerol, 0.662589282973412%), OAHFA((O-acyl)-1-hydroxy fatty acid, 0.864712469689971%), PA(phosphatidic acid, 26.935329672718%), PAF(platelet-activating factor, 18.8938270646209%), PC(phosphatidylcholine, 14.5455100823086%), PE(phosphatidylethanolamine, 7.08341135985417%), PEt(phosphatidylethanol, 10.8236884649902%), PG(phosphatidylglycerol, 0.934358404427319%), PI(phosphatidylinositol, 2.67410886686788%), PMe(phosphatidylmethanol, 9.83226175604876%), cPA(cyclic phosphatidic acid, 0.00785180275211569%), dMePE(dimethylphosphatidylethanolamine, 0.1431435891348811%).

At ESI+ mode, after been processed, the percentage of 5 classes (LPE, PE, Co, LPC, CerG1) descended of lipids in Orco samples; meanwhile 3 lipids (Cer, TG, So) kept stable; while 4 lipid classes (DG, ChE, ZyE and StE) increased significantly. At ESI− mode, after been processed, the percentage of 13 classes (DGDG, cPA, LPI, LPE, PC, dMePE, MGDG, PI, PE, PG, PMe, LPG and PEO descended of lipids in Orco samples; meanwhile 3 lipids (PA, LPC and OAHFA) kept stable; while 6 lipid classes (LdMePE, PAF, DGMG, MGMG, LPMe and CL) increased significantly.

The percentage of lipid classes in the product sample (deacidified coconut oil) at ESI+ and ESI− modes are shown in Tables 15-16 and FIGS. 39-42. Detailed lists of each lipid class at ESI+ and ESI− modes are shown in FIGS. 45-46.

TABLE 15

Percentage of lipid classes in product sample (ESI+)

| Class | Pcro | Ocro | Proc/Orco | Fold change |
| --- | --- | --- | --- | --- |
| LPE | 0.00000% | 0.0002062% | 0.02 | −5.55 |
| PE | 0.00002% | 0.0009948% | 0.02 | −5.49 |
| Co | 0.00017% | 0.0010672% | 0.16 | −2.69 |
| LPC | 0.00069% | 0.0019295% | 0.36 | −1.48 |
| CerG1 | 0.00012% | 0.0002970% | 0.41 | −1.29 |
| Cer | 0.00257% | 0.0030572% | 0.84 | −0.25 |
| TG | 99.78365% | 99.8825339% | 1.00 | 0.00 |
| So | 0.00800% | 0.0077825% | 1.03 | 0.04 |
| DG | 0.20462% | 0.1020919% | 2.00 | 1.00 |
| ChE | 0.00003% | 0.0000076% | 3.60 | 1.85 |
| ZyE | 0.00012% | 0.0000322% | 3.69 | 1.89 |
| StE | 0.00001% | 0.0000000% | — | — |

TABLE 16

Percentage of lipid classes in product sample (ESI−)

| Class | Pcro | Oreo | Prco/Orco | Fold change |
| --- | --- | --- | --- | --- |
| DGDG | 0.00% | 0.291% | 0.011604 | −6.42928 |
| cPA | 0.00% | 0.008% | 0.015435 | −6.01768 |
| LPI | 0.00% | 0.044% | 0.034267 | −4.86703 |
| LPE | 0.01% | 0.105% | 0.053187 | −4.23278 |
| PC | 1.00% | 14.546% | 0.068504 | −3.86768 |
| dMePE | 0.01% | 0.143% | 0.069257 | −3.85189 |
| MGDG | 0.12% | 1.574% | 0.076018 | −3.71752 |
| PI | 0.22% | 2.674% | 0.083897 | −3.57524 |
| PE | 0.77% | 7.083% | 0.108679 | −3.20186 |
| PG | 0.15% | 0.934% | 0.161414 | −2.63116 |
| PMe | 4.04% | 9.832% | 0.41092 | −1.28307 |
| LPG | 0.00% | 0.005% | 0.455873 | −1.13329 |
| PEt | 5.24% | 10.824% | 0.483869 | −1.04731 |
| PA | 21.28% | 26.935% | 0.78995 | −0.34017 |
| LPC | 0.28% | 0.303% | 0.917751 | −0.12382 |
| OAHFA | 0.82% | 0.865% | 0.942516 | −0.08541 |
| LdMePE | 11.25% | 4.158% | 2.7051 | 1.435682 |
| PAF | 52.38% | 18.894% | 2.772569 | 1.471223 |
| DGMG | 0.28% | 0.096% | 2.950095 | 1.560761 |
| MGMG | 2.13% | 0.663% | 3.210046 | 1.682594 |
| LPMe | 0.02% | 0.001% | 17.72672 | 4.147854 |
| CL | 0.00% | 0.021% | 0 | — |

Human meibum samples (eyelid samples) were also analyzed. 11 classes of lipids in both product samples and eyelid samples were detected at ESI+ mode, which are DG(diglyceride), TG(triglyceride), So(Sphingoshine), LPC(lysophosphatidylcholine), Cer(Ceramides), ZyE(zymosteryl), LPE (lysophosphatidylethanolamine), CerG1(Simple Glc series), ChE(Cholesteryl Ester), PE(phosphatidylethanolamine) and StE(Stigmasteryl ester). At ESI− mode, 22 classes of lipids in both product samples and eyelid samples were detected, which are PE(phosphatidylethanolamine), PEt(phosphatidylethanol), MGMG(Monogalactosyldiacylglycerol), cPA(cyclic phosphatidic acid), PE(phosphatidylethanolamine), PI(phosphatidylinositol), DGDG(Digalactosyldiacylglycerol), MGDG(Monogalactosyldiacylglycerol), LdMePE(lysodimethylphosphatidylethanolamine), LPE(lysophosphatidylethanolamine), LPI(lysophosphatidylinositol), LPC (lysophosphatidylcholine), LPMe(lysophosphatidylmethano), LPG(lysophosphatidylglycerol), PG(phosphatidylglycerol), OAHFA((O-acyl)-1-hydroxy fatty acid), PA(phosphatidic acid), dMePE(dimethylphosphatidylethanolamine), PC(phosphatidylcholine), DGMG(Digalactosylmonoacylglycerol), PMe(phosphatidylmethanol) and PAF (platelet-activating factor).

Example 12: Cyclosporin Solubility Test

Solubility of cyclosporine by different organic solvents was tested. The experiment was performed as follows.

Figures 50A, 50B, 50C:
FIG. 50A shows a glass tube containing cyclosporine dissolved in deacidified coconut oil at a concentration of 0.25%.
FIG. 50B shows a glass tube containing cyclosporine dissolved in DMSO at a concentration of 2.5%.
FIG. 50C shows a glass tube containing cyclosporine dissolved in olive oil at a concentration of 2.5%.

Cyclosporin (3.0 mg, white solid powder) was added to 1.2 mL of deacidified coconut oil. After incubation in 42° C. water bath, the white solid powder was dissolved as turbid liquid. Next, the solution was mixed by shaking and then put in 42° C. water bath for 10 minutes, followed by sonication for 15 minutes. As shown in FIG. 50A, cyclosporine was dissolved in the sample.

Cyclosporin (25 mg) was added to 1.0 mL of DMSO (clear and transparent liquid). The solution was mixed by shaking, followed by sonication for 15 minutes. As shown in FIG. 50B, cyclosporine was dissolved in DMSO at a concentration of 2.5% as clear and transparent liquid. In addition, cyclosporin (50 mg) was added to 1.0 mL of DMSO (clear and transparent liquid). The solution was mixed by shaking, followed by sonication for 15 minutes. As a result, cyclosporine was dissolved in DMSO at a concentration of 5% as clear and transparent liquid.

Cyclosporin (25 mg) was added to 1.0 mL of olive oil (yellow transparent liquid). The solution was mixed by shaking, followed by sonication for 15 minutes. As shown in FIG. 50C, cyclosporine was dissolved in olive oil at a concentration of 2.5% as clear and transparent liquid. In addition, cyclosporin (50 mg) was added to 1.0 mL of olive oil (yellow transparent liquid). The solution was mixed by shaking, followed by sonication for 15 minutes. As a result, cyclosporine was dissolved in olive oil at a concentration of 5% as clear and transparent liquid.

Figures 52A, 52B:
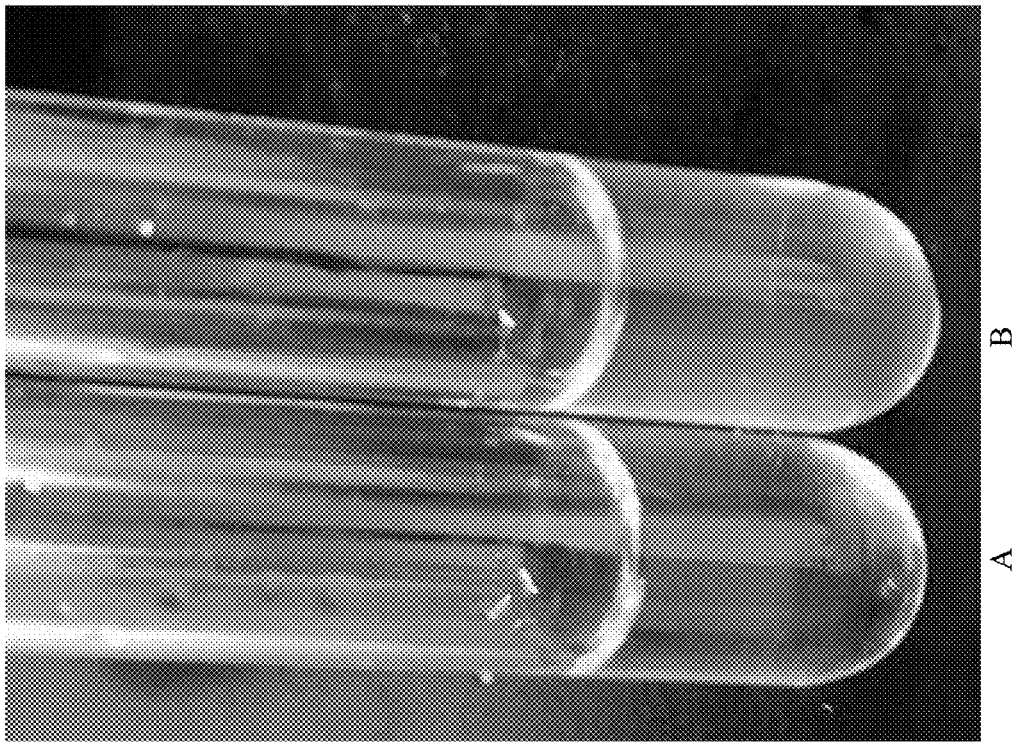
FIG. 52A shows a glass tube containing cyclosporine-DMSO solution (5%) mixed with deacidified coconut oil with a volume ratio of 1:19.
FIG. 52B shows a glass tube containing cyclosporine-olive oil solution (5%) mixed with deacidified coconut oil with a volume ratio of 1:19.
Figures 51A, 51B:
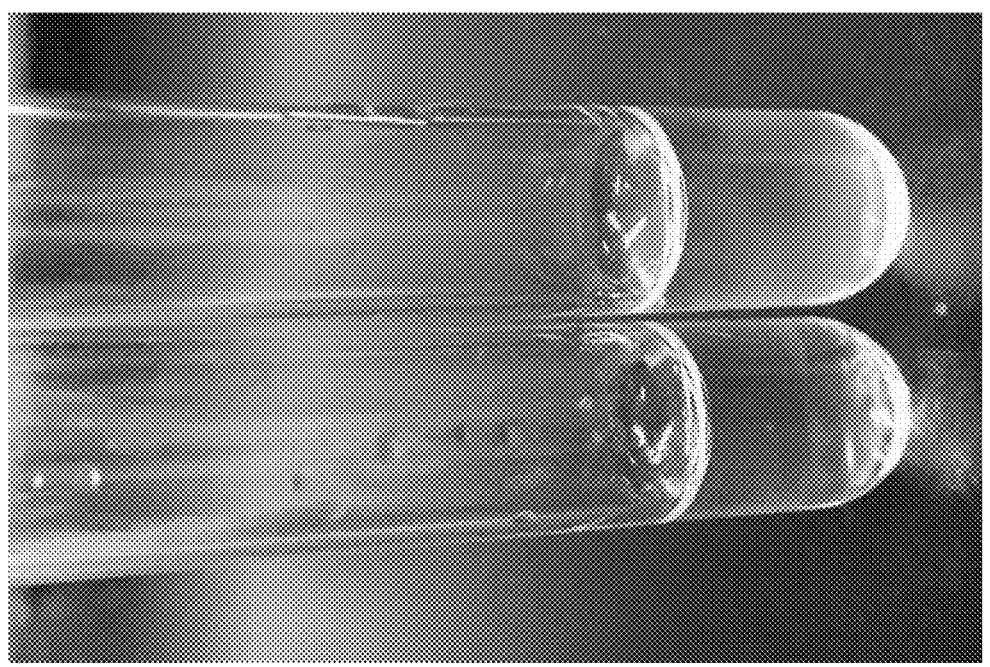
FIG. 51A shows a glass tube containing cyclosporine-DMSO solution (2.5%) mixed with deacidified coconut oil with a volume ratio of 1:9.
FIG. 51B shows a glass tube containing cyclosporine-olive oil solution (2.5%) mixed with deacidified coconut oil with a volume ratio of 1:9.

Cyclosporine-DMSO solution (100 µl, 2.5% as described above) was added to 900 deacidified coconut oil. The solution was mixed by shaking, followed by incubation in 42° C. water bath for 10 minutes. The obtained solution was clear and transparent as shown in FIG. 51A. In addition, cyclosporine-DMSO solution (50 µl, 5% as described above) was added to 950 µl deacidified coconut oil. The solution was mixed by shaking, followed by incubation in 42° C. water bath for 10 minutes. The obtained solution was clear and transparent as shown in FIG. 52A.

Cyclosporine-olive oil solution (100 µl, 2.5% as described above) was added to 900 µl deacidified coconut oil. The solution was mixed by shaking, followed by incubation in 42° C. water bath for 10 minutes. The obtained solution was clear and transparent as shown in FIG. 51B. In addition, cyclosporine-DMSO solution (50 µl, 5% as described above) was added to 950 µl deacidified coconut oil. The solution was mixed by shaking, followed by incubation in 42° C. water bath for 20 minutes. The obtained solution was clear and transparent as shown in FIG. 52B.

Figures 53A, 53B, 53C, 53D:
FIG. 53A shows a centrifuge tube containing cyclosporine dissolved in deacidified coconut oil.
FIG. 53B shows a centrifuge tube containing cyclosporine dissolved in deacidified coconut oil.
FIG. 53C shows a centrifuge tube containing cyclosporine dissolved in DMSO/deacidified coconut oil mixed solution.
FIG. 53D shows a centrifuge tube containing cyclosporine dissolved in DMSO/deacidified coconut oil mixed solution.

Cyclosporine (125 mg) was added to 5 ml of deacidified coconut oil. The solution was mixed by shaking, then incubated in 42° C. water bath for 10 minutes, followed by sonication for 15 minutes. Next, the sonicated solution was sterilized with a 0.22 μm PVDF filter and 2.5 ml of the filter-sterilized solution was mixed with 22.5 ml deacidified coconut oil in a 50 ml sterile centrifuge tube. The obtained solution was light yellow and transparent as shown in FIGS. 53A-53B.

Cyclosporine (125 mg) was added to 5 ml of a mixed solution that contains DMSO and deacidified coconut oil with a volume ratio of 1:19 (250 μl DMSO mixed with 4.75 ml deacidified coconut oil). The solution was mixed by shaking, then incubated in 42° C. water bath for 10 minutes, followed by sonication for 15 minutes. Next, the sonicated solution was sterilized with a 0.22 μm PVDF filter and 2.5 ml of the filter-sterilized solution was mixed with 22.5 ml deacidified coconut oil in a 50 ml sterile centrifuge tube. The obtained solution was light yellow and transparent as shown in FIGS. 53C-53D.

The experiments above showed that cyclosporine can be dissolved in deacidified coconut oil.

Example 13: Clinical Usage of Deacidified Coconut Oil for Treating Eye Diseases or Disorders The deacidified coconut oil was initially developed for treating the dry eye disorder. As the research continued, it was determined that the deacidified coconut oil can also be used to treat asthenopia, impaired vision, blurred vision, photophobia, astigmatism, and blepharitis. As shown in the following cases, the deacidified coconut oil was successfully administered to three patients with positive outcomes.

The first patient is male, and was born in 1966. In 2007, he was diagnosed having dry eye disorder after a surgery to remove trichiasis. The patient was administered carboxypropyl methylcellulose and polyacrylid acid (PAA, or Carbomer). The treatment was not effective. In 2012, the patient had a sensation of dryness, foreign body sensation, and pain in eyes. He also had vision loss and insomnia. In 2013-2014, the patient developed additional eye symptoms including astigmatism, blepharitis, anxiety and body weight loss (e.g., about 10 kilograms). In 2015, the patient used the deacidified coconut oil as described herein as eye drops, placed the thermal pad as described herein on the eyes, and took herb composition as described herein. The treatments alleviated the overall symptoms, and the foreign matter sensation disappeared. In 2019, the symptoms of dry eye disorder including pain, dryness, redness, foreign matter sensation and insomnia were gone. In addition, symptoms such as repetitive visual fatigue, decreased vision, blurred vision, photophobia, sensitivity to wind, astigmatism, and eyelid inflammation disappeared. The patient's overall vision condition improved relative to that in 2015. The eyeglass prescription for both eyes decreased by 1.50-2.00. Three ocular surface inspection reports issued by an eye doctor are summarized in FIG. 54. According to the reports, the non-invasive Keratograph tear breakup time (NIKBUT) increased from 2017 to 2019 for both eyes, indicating in a reduction of the eye dryness levels. In addition, the meibography of the upper and lower eyelids, as determined by Meibo-scan, showed improved Meibomian gland integrity.

The second patient was born in 1971, female. In August 2018, she was diagnosed of having dry eye disorder by an ophthalmologist, and administered Levofloxacin Eye Drops, Tobramycin Eye Drops, Recombinant Bovine Basic Fibroblast Growth Factor Eye Drops and Hycosan Eye Drops. No significant improvement was observed. In 2014, the patient had difficulty in opening eyes. In October 2014, the patient received 30 traditional physical therapies for 10 consecutive months. Both eyes were treated with lacrimal duct embolism, which dropped off after the treatment. The physical therapies alleviated eye dryness but the patient still had difficulty in opening eyes. In 2015, the patient received Intense Pulsed Light (IPL) treatment for a total of three times. Additional treatments include: Hycosan Eye Drops, Ofloxacin Eye Drops, Gatifloxacin gel, sodium hyaluronate Eye Drops, polyacrylid acid (PAA, or Carbomer), and carboxymethylcellulose sodium Eye Drops. Eye dryness was improved. In 2017, the patient had the second lacrimal duct embolism treatment, which dropped off after a year. In May 2018, the patient received 8 treatments for dry eye disorder including acupuncture, Chinese traditional medicine and physical therapy. After the treatments, the difficulty in opening eyes improved, but the patient still had a sensation of dryness, foreign matter sensation and occasional photophobia. In October 2018, the patient was treated by the deacidified coconut oil as described herein as eye drops. The foreign matter sensation was alleviated. The patient also used the thermal pad as described herein on the eyes for one year. Afterwards, visual fatigue, foreign matter sensation and dryness were relieved. Two ocular surface inspection reports issued by an eye doctor are summarized in FIG. 55. According to the reports, the meibography of the upper and lower eyelids showed improved Meibomian gland integrity, as determined by Meibo-scan.

The third patient was born in 1970, female. The patient had a sensation of dryness, presbyopia in both eyes with occasional blurred vision. Eyeglass prescription for both eyes increased by about 2.00 in three years. In 2019, the patient used the deacidified coconut oil as described herein as eye drops, and used the thermal pad as described herein on the eyes. After the treatments, dryness and blurred vision disappeared. The overall vision condition was also significantly improved.

In view of the above clinical results, it has been determined that the deacidified coconut oil samples as described herein can also treat ocular surface diseases, eyestrain, decreased vision, blurred vision, photophobia, astigmatism, and eyelid inflammation.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of treating or alleviating symptoms of a dry eye disorder, asthenopia, impaired vision, blurred vision, photophobia, astigmatism, or blepharitis, comprising
   identifying a subject as having the dry eye disorder, asthenopia, impaired vision, blurred vision, photophobia, astigmatism, or blepharitis; and
   administering to the subject an effective amount of a pharmaceutical composition consisting essentially of deacidified coconut oil or a pharmaceutical composition consisting essentially of deacidified coconut oil and cyclosporine.

2. The method of claim 1, wherein the subject has a dry eye disorder.

3. The method of claim 1, wherein the deacidified coconut oil does not have a detectable amount of cardiolipin (CL) or digalactosyldiacylglycerol (DGDG).

4. The method of claim 1, wherein the pharmaceutical composition consisting essentially of deacidified coconut oil.

5. The method of claim 4, wherein the subject has a dry eye disorder.

6. The method of claim 4, wherein the deacidified coconut oil does not have a detectable amount of cardiolipin (CL) or digalactosyldiacylglycerol (DGDG).

7. The method of claim 4, further comprising administering an effective amount of cyclosporine to the subject.

8. The method of claim 5, wherein the pharmaceutical composition consists of deacidified coconut oil.

9. The method of claim 1, wherein the pharmaceutical composition consists essentially of deacidified coconut oil and cyclosporine.

10. The method of claim 9, wherein the subject has a dry eye disorder.

11. The method of claim 9, wherein the deacidified coconut oil does not have a detectable amount of cardiolipin (CL) or digalactosyldiacylglycerol (DGDG).

12. The method of claim 1, wherein the pharmaceutical composition consists of deacidified coconut oil.

13. The method of claim 1, wherein the pharmaceutical composition consists of deacidified coconut oil and cyclosporine.

14. A method of treating or alleviating symptoms of a dry eye disorder, asthenopia, impaired vision, blurred vision, photophobia, astigmatism, or blepharitis, comprising
    identifying a subject as having the dry eye disorder, asthenopia, impaired vision, blurred vision, photophobia, astigmatism, or blepharitis; and
    administering to the subject an effective amount of a pharmaceutical composition comprising deacidified coconut oil, wherein the deacidified coconut oil is made by a process comprising the following steps:
    providing coconut oil;
    mixing the coconut oil with a basic solution, thereby obtaining a mixture comprising a water phase and an oil phase;
    separating the water phase and the oil phase from the mixture; and
    collecting deacidified coconut oil from the oil phase.

15. The method of claim 14, wherein the subject has a dry eye disorder.

16. The method of claim 14, further comprising administering an effective amount of cyclosporine to the subject.

17. A method of treating or alleviating symptoms of a dry eye disorder, asthenopia, impaired vision, blurred vision, photophobia, astigmatism, or blepharitis, comprising
    identifying a subject as having the dry eye disorder, asthenopia, impaired vision, blurred vision, photophobia, astigmatism, or blepharitis; and
    administering to the subject an effective amount of a pharmaceutical composition comprising deacidified coconut oil, wherein prior to administering the pharmaceutical composition to the subject, artificial tear eye drops are administered to the subject.

18. The method of claim 17, wherein the subject has a dry eye disorder.

19. The method of claim 17, further comprising administering an effective amount of cyclosporine to the subject.

20. The method of claim 17, wherein the deacidified coconut oil does not have a detectable amount of cardiolipin (CL) or digalactosyldiacylglycerol (DGDG).

* * * * *

UNITED STATES PATENT AND TRADEMARK OFFICE
CERTIFICATE OF CORRECTION

PATENT NO. : 10,933,111 B2  
APPLICATION NO. : 16/810674  
DATED : March 2, 2021  
INVENTOR(S) : Dan Yang Page 1 of 1

It is certified that error appears in the above-identified patent and that said Letters Patent is hereby corrected as shown below:

On the Title Page

Column 1 Item (63) (Related U.S. Application Data): please delete "Continuation" and insert therefor
-- Continuation-in-Part --

Signed and Sealed this
Eleventh Day of May, 2021

Drew Hirshfeld
*Performing the Functions and Duties of the
Under Secretary of Commerce for Intellectual Property and
Director of the United States Patent and Trademark Office*